US011779659B2

(12) United States Patent
Sahin et al.

(10) Patent No.: US 11,779,659 B2
(45) Date of Patent: *Oct. 10, 2023

(54) RNA CONSTRUCTS AND USES THEREOF

(71) Applicant: BioNTech SE, Mainz (DE)

(72) Inventors: Ugur Sahin, Mainz (DE); Gábor Boros, Mainz (DE); Azita Josefine Mahiny, Mainz (DE); Jonas Reinholz, Mainz (DE); Katalin Karikó, Rydal, PA (US)

(73) Assignee: BioNTech SE, Mainz (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/565,842

(22) Filed: Dec. 30, 2021

(65) Prior Publication Data

US 2022/0249704 A1 Aug. 11, 2022

Related U.S. Application Data

(63) Continuation of application No. PCT/EP2021/060508, filed on Apr. 22, 2021.

(30) Foreign Application Priority Data

| | | |
|---|---|---|
| Apr. 22, 2020 | (WO) | PCT/EP2020/061239 |
| Jun. 18, 2020 | (WO) | PCT/EP2020/066968 |
| Jun. 26, 2020 | (WO) | PCT/EP2020/068174 |
| Jul. 13, 2020 | (WO) | PCT/EP2020/069805 |
| Jul. 31, 2020 | (WO) | PCT/EP2020/071733 |
| Aug. 3, 2020 | (WO) | PCT/EP2020/071839 |
| Aug. 24, 2020 | (WO) | PCT/EP2020/073668 |
| Nov. 9, 2020 | (WO) | PCT/EP2020/081544 |
| Nov. 12, 2020 | (WO) | PCT/EP2020/081981 |
| Nov. 18, 2020 | (WO) | PCT/EP2020/082601 |
| Nov. 20, 2020 | (WO) | PCT/EP2020/082989 |
| Nov. 25, 2020 | (WO) | PCT/EP2020/083435 |
| Dec. 2, 2020 | (WO) | PCT/EP2020/084342 |
| Dec. 8, 2020 | (WO) | PCT/EP2020/085145 |
| Dec. 10, 2020 | (WO) | PCT/EP2020/085653 |
| Dec. 23, 2020 | (WO) | PCT/EP2020/087844 |
| Jan. 4, 2021 | (WO) | PCT/EP2021/050027 |
| Jan. 15, 2021 | (WO) | PCT/EP2021/050874 |
| Jan. 15, 2021 | (WO) | PCT/EP2021/050875 |
| Jan. 26, 2021 | (WO) | PCT/EP2021/052572 |
| Feb. 4, 2021 | (WO) | PCT/EP2021/052716 |
| Feb. 24, 2021 | (WO) | PCT/EP2021/054622 |
| Apr. 16, 2021 | (WO) | PCT/EP2021/059947 |

(51) Int. Cl.

| | |
|---|---|
| ***A61K 48/00*** | (2006.01) |
| ***A61P 35/00*** | (2006.01) |
| ***A61K 31/7088*** | (2006.01) |
| ***A61K 39/00*** | (2006.01) |
| ***A61K 39/12*** | (2006.01) |
| ***A61K 9/127*** | (2006.01) |
| ***A61K 39/215*** | (2006.01) |

(Continued)

(52) U.S. Cl.

CPC ........ *A61K 48/0066* (2013.01); *A61K 9/0019* (2013.01); *A61K 9/1271* (2013.01); *A61K 9/5123* (2013.01); *A61K 9/5146* (2013.01); *A61K 31/7088* (2013.01); *A61K 31/711* (2013.01); *A61K 31/712* (2013.01); *A61K 31/7105* (2013.01); *A61K 31/7115* (2013.01); *A61K 39/0011* (2013.01); *A61K 39/12* (2013.01); *A61K 39/215* (2013.01); *A61K 48/0033* (2013.01); *A61P 31/14* (2018.01); *A61P 35/00* (2018.01); *B82Y 5/00* (2013.01); *C12N 7/00* (2013.01); *C12N 15/11* (2013.01); *C12N 15/67* (2013.01); *C12N 15/88* (2013.01); *C12P 19/34* (2013.01); *A61K 38/00* (2013.01); *A61K 2039/53* (2013.01); *A61K 2039/54* (2013.01); *A61K 2039/545* (2013.01); *A61K 2039/55555* (2013.01); *C12N 2770/18022* (2013.01); *C12N 2770/18034* (2013.01); *C12N 2770/18071* (2013.01); *C12N 2770/20034* (2013.01); *C12N 2840/00* (2013.01)

(58) Field of Classification Search

None

See application file for complete search history.

(56) References Cited

U.S. PATENT DOCUMENTS

| | | | |
|---|---|---|---|
| 4,898,278 | A | 2/1990 | Leoncavallo et al. |
| 6,381,981 | B1 | 5/2002 | Yaddgo et al. |

(Continued)

FOREIGN PATENT DOCUMENTS

| | | | |
|---|---|---|---|
| AU | 2015210364 | A1 | 8/2015 |
| AU | 2019264591 | A1 | 12/2019 |

(Continued)

OTHER PUBLICATIONS

Andries, O et al., N(I)-methylpseudouridine-incorporated mRNA outperforms pseudouridineincorporated mRNA by providing enhanced protein expression and reduced immunogenicity in mammalian cell lines and mice, J Control Release, 217:337-44 (2015).

(Continued)

*Primary Examiner* — Michael D Burkhart

(74) *Attorney, Agent, or Firm* — Choate, Hall & Stewart LLP; Brenda Herschbach Jarrell; Nicholas J. Pace

(57) ABSTRACT

Disclosed herein are RNA polynucleotides comprising a 5' Cap, a 5' UTR comprising a cap proximal sequence disclosed herein, and a sequence encoding a payload. Also disclosed herein are compositions and medical preparations comprising the same, and methods of making and using the same.

22 Claims, 23 Drawing Sheets

Specification includes a Sequence Listing.

(51) Int. Cl.

| | |
|---|---|
| ***C12N 7/00*** | (2006.01) |
| ***A61P 31/14*** | (2006.01) |
| ***A61K 9/00*** | (2006.01) |
| ***A61K 9/51*** | (2006.01) |
| ***A61K 31/7105*** | (2006.01) |
| ***A61K 31/7115*** | (2006.01) |
| ***A61K 31/712*** | (2006.01) |
| ***B82Y 5/00*** | (2011.01) |
| ***C12N 15/11*** | (2006.01) |
| ***C12N 15/67*** | (2006.01) |
| ***C12N 15/88*** | (2006.01) |
| ***C12P 19/34*** | (2006.01) |
| ***A61K 31/711*** | (2006.01) |
| *A61K 38/00* | (2006.01) |

(56) References Cited

U.S. PATENT DOCUMENTS

| | | | |
|---|---|---|---|
| 7,736,850 | B2 | 6/2010 | Van Der Werf et al. |
| 7,901,708 | B2 | 3/2011 | MacLachlan et al. |
| 8,058,069 | B2 | 11/2011 | Yaworski et al. |
| 8,153,773 | B2 | 4/2012 | Jemielity et al. |
| 8,278,036 | B2 | 10/2012 | Kariko et al. |
| 8,329,070 | B2 | 12/2012 | MacLachlan et al. |
| 8,691,966 | B2 | 4/2014 | Kariko et al. |
| 8,710,200 | B2 | 4/2014 | Schrum et al. |
| 8,748,089 | B2 | 6/2014 | Kariko et al. |
| 8,754,062 | B2 | 6/2014 | de Fougerolles et al. |
| 8,822,663 | B2 | 9/2014 | Schrum et al. |
| 8,835,108 | B2 | 9/2014 | Kariko et al. |
| 8,999,380 | B2 | 4/2015 | Bancel et al. |
| 9,220,755 | B2 | 12/2015 | Chakraborty et al. |
| 9,221,891 | B2 | 12/2015 | Bancel et al. |
| 9,283,287 | B2 | 3/2016 | Chakraborty et al. |
| 9,295,717 | B2 | 3/2016 | Sahin et al. |
| 9,303,079 | B2 | 4/2016 | Chakraborty et al. |
| 9,334,328 | B2 | 5/2016 | Schrum et al. |
| 9,364,435 | B2 | 6/2016 | Yaworski et al. |
| 9,428,535 | B2 | 8/2016 | De Fougerolles et al. |
| 9,464,124 | B2 | 10/2016 | Bancel et al. |
| 9,476,055 | B2 | 10/2016 | Sahin et al. |
| 9,492,386 | B2 | 11/2016 | MacLachlan et al. |
| 9,504,651 | B2 | 11/2016 | MacLachlan et al. |
| 9,512,456 | B2 | 12/2016 | Wang et al. |
| 9,533,047 | B2 | 1/2017 | de Fougerolles et al. |
| 9,597,380 | B2 | 3/2017 | Chakraborty et al. |
| 9,657,295 | B2 | 5/2017 | Schrum et al. |
| 9,669,089 | B2 | 6/2017 | Thess et al. |
| 9,737,619 | B2 | 8/2017 | Ansell et al. |
| 9,738,593 | B2 | 8/2017 | Ansell et al. |
| 9,750,824 | B2 | 9/2017 | Kariko et al. |
| 9,850,269 | B2 | 12/2017 | DeRosa et al. |
| 9,868,691 | B2 | 1/2018 | Benenato |
| 9,868,692 | B2 | 1/2018 | Benenato |
| 9,872,900 | B2 | 1/2018 | Ciaramella et al. |
| 9,957,499 | B2 | 5/2018 | Heartlein et al. |
| 9,970,047 | B2 | 5/2018 | Heartlein et al. |
| 10,022,435 | B2 | 7/2018 | Ciaramella et al. |
| 10,064,934 | B2 | 9/2018 | Ciaramella et al. |
| 10,064,935 | B2 | 9/2018 | Ciaramella et al. |
| 10,064,959 | B2 | 9/2018 | Schrum et al. |
| 10,106,490 | B2 | 10/2018 | Du |
| 10,106,800 | B2 | 10/2018 | Sahin et al. |
| 10,124,055 | B2 | 11/2018 | Ciaramella et al. |
| 10,166,298 | B2 | 1/2019 | Ansell et al. |
| 10,207,010 | B2 | 2/2019 | Besin et al. |
| 10,232,055 | B2 | 3/2019 | Kariko et al. |
| 10,238,754 | B2 | 3/2019 | Guild et al. |
| 10,266,485 | B2 | 4/2019 | Benenato |
| 10,272,150 | B2 | 4/2019 | Ciaramella et al. |
| 10,273,269 | B2 | 4/2019 | Ciaramella |
| 10,286,086 | B2 | 5/2019 | Roy et al. |
| 10,350,303 | B1 | 7/2019 | Guild et al. |
| 10,385,088 | B2 | 8/2019 | Fraley et al. |
| 10,413,618 | B2 | 9/2019 | Guild et al. |
| 10,442,756 | B2 | 10/2019 | Benenato et al. |
| 10,449,244 | B2 | 10/2019 | Ciaramella et al. |
| 10,465,190 | B1 | 11/2019 | Chen et al. |
| 10,493,143 | B2 | 12/2019 | Ciaramella et al. |
| 10,493,167 | B2 | 12/2019 | de Fougerolles et al. |
| 10,494,399 | B2 | 12/2019 | Hogrefe et al. |
| 10,519,189 | B2 | 12/2019 | Hogrefe et al. |
| 10,543,269 | B2 | 1/2020 | Ciaramella et al. |
| 10,577,403 | B2 | 3/2020 | De Fougerolles et al. |
| 10,583,203 | B2 | 3/2020 | De Fougerolles et al. |
| 10,648,017 | B2 | 5/2020 | Wochner |
| 10,653,712 | B2 | 5/2020 | Hoge et al. |
| 10,653,767 | B2 | 5/2020 | Ciaramella et al. |
| 10,695,419 | B2 | 6/2020 | Ciaramella et al. |
| 10,702,599 | B2 | 7/2020 | Ciaramella et al. |
| 10,702,600 | B1 | 7/2020 | Ciaramella et al. |
| 10,703,789 | B2 | 7/2020 | De Fougerolles et al. |
| 10,709,779 | B2 | 7/2020 | Ciaramella et al. |
| 10,717,982 | B2 | 7/2020 | Eberle et al. |
| 10,723,692 | B2 | 7/2020 | Ansell et al. |
| 10,738,306 | B2 | 8/2020 | Thess |
| 10,760,070 | B2 | 9/2020 | Funkner et al. |
| 10,772,975 | B2 | 9/2020 | Bancel et al. |
| 10,808,242 | B2 | 10/2020 | Kariko et al. |
| 10,857,105 | B2 | 12/2020 | Benenato et al. |
| 10,912,826 | B2 | 2/2021 | Thess et al. |
| 10,913,768 | B2 | 2/2021 | Hogrefe et al. |
| 10,925,935 | B2 | 2/2021 | Chakraborty et al. |
| 10,925,958 | B2 | 2/2021 | Ciaramella |
| 11,040,112 | B2 | 6/2021 | Ansell et al. |
| 11,045,540 | B2 | 6/2021 | Ciaramella |
| 11,241,493 | B2 | 2/2022 | Rauch et al. |
| 11,547,673 | B1 | 1/2023 | Sahin et al. |
| 2003/0194759 | A1 | 10/2003 | Darzynkiewiz et al. |
| 2005/0002953 | A1 | 1/2005 | Herold |
| 2005/0095582 | A1 | 5/2005 | Gillim-Ross et al. |
| 2005/0249742 | A1 | 11/2005 | Ruprecht et al. |
| 2009/0093433 | A1 | 4/2009 | Woolf et al. |
| 2009/0286852 | A1 | 11/2009 | Kariko et al. |
| 2010/0017904 | A1 | 1/2010 | Abad et al. |
| 2011/0300205 | A1 | 12/2011 | Geall et al. |
| 2012/0082693 | A1 | 4/2012 | Van Der Werf et al. |
| 2012/0101148 | A1 | 4/2012 | Aking et al. |
| 2013/0102034 | A1 | 4/2013 | Schrum |
| 2013/0115272 | A1 | 5/2013 | de Fougerolles et al. |
| 2013/0236974 | A1 | 9/2013 | de Fougerolles |
| 2013/0245103 | A1 | 9/2013 | de Fougerolles et al. |
| 2013/0259923 | A1 | 10/2013 | Bancel et al. |
| 2013/0266640 | A1 | 10/2013 | de Fougerolles et al. |
| 2014/0147432 | A1 | 5/2014 | Bancel et al. |
| 2014/0148502 | A1 | 5/2014 | Bancel et al. |
| 2014/0193482 | A1 | 7/2014 | Bancel et al. |
| 2014/0206752 | A1 | 7/2014 | Afeyan et al. |
| 2014/0308304 | A1 | 10/2014 | Manoharan et al. |
| 2014/0378538 | A1 | 12/2014 | Bancel |
| 2015/0051268 | A1 | 2/2015 | Bancel et al. |
| 2015/0056253 | A1 | 2/2015 | Bancel et al. |
| 2015/0141499 | A1 | 5/2015 | Bancel et al. |
| 2015/0265698 | A1 | 9/2015 | Pushko et al. |
| 2015/0307542 | A1 | 10/2015 | Roy et al. |
| 2015/0315541 | A1 | 11/2015 | Bancel et al. |
| 2015/0376115 | A1 | 12/2015 | Ansell et al. |
| 2016/0022580 | A1 | 1/2016 | Ramsay et al. |
| 2016/0024140 | A1 | 1/2016 | Issa et al. |
| 2016/0024141 | A1 | 1/2016 | Issa et al. |
| 2016/0032273 | A1 | 2/2016 | Shahrokh et al. |
| 2016/0038612 | A1 | 2/2016 | Hoge et al. |
| 2016/0235864 | A1 | 8/2016 | Schlake et al. |
| 2016/0243221 | A1 | 8/2016 | Hoge et al. |
| 2016/0317647 | A1 | 11/2016 | Ciaramella et al. |
| 2017/0043037 | A1 | 2/2017 | Kariko et al. |
| 2017/0056528 | A1 | 3/2017 | De Fougerolles et al. |
| 2017/0130255 | A1 | 5/2017 | Wang et al. |
| 2017/0166905 | A1 | 6/2017 | Eberle et al. |
| 2017/0202979 | A1 | 7/2017 | Chakraborty et al. |
| 2017/0204152 | A1 | 7/2017 | Nelson et al. |
| 2017/0362627 | A1 | 12/2017 | Reynders, III et al. |
| 2018/0000953 | A1 | 1/2018 | Almarsson et al. |

(56) References Cited

U.S. PATENT DOCUMENTS

2018/0002393 A1 1/2018 Bancel et al.
2018/0086816 A1 3/2018 Hoge et al.
2018/0112221 A1 4/2018 Schrum et al.
2018/0161422 A1 6/2018 Thess et al.
2018/0237766 A1 8/2018 Heartlein et al.
2018/0237849 A1 8/2018 Thompson
2018/0243225 A1 8/2018 Ciaramella
2018/0243230 A1 8/2018 Smith
2018/0256628 A1 9/2018 Hoge et al.
2018/0256750 A1 9/2018 Butora et al.
2018/0271795 A1 9/2018 Martini et al.
2018/0271970 A1 9/2018 Ciaramella et al.
2018/0273576 A1 9/2018 Hogrefe et al.
2018/0273977 A1 9/2018 Mousavi et al.
2018/0274009 A1 9/2018 Marquardt et al.
2018/0291425 A1 10/2018 Heartlein et al.
2018/0303925 A1 10/2018 Weissman et al.
2018/0303929 A1 10/2018 Ciaramella et al.
2018/0311336 A1 11/2018 Ciaramella et al.
2018/0311343 A1 11/2018 Huang et al.
2018/0318409 A1 11/2018 Valiante et al.
2018/0318446 A1 11/2018 Bancel et al.
2018/0353618 A1 12/2018 Burkhardt et al.
2018/0369374 A1 12/2018 Frederick et al.
2018/0369419 A1 12/2018 Benenato et al.
2018/0371047 A1 12/2018 Ticho et al.
2019/0000959 A1 1/2019 Ciaramella et al.
2019/0002890 A1 1/2019 Martini et al.
2019/0008938 A1 1/2019 Ciaramella et al.
2019/0008948 A1 1/2019 Ciaramella et al.
2019/0015501 A1 1/2019 Ciaramella et al.
2019/0030129 A1 1/2019 Schrum et al.
2019/0060458 A1 2/2019 De Fougerolles et al.
2019/0062762 A1 2/2019 Sahin et al.
2019/0071682 A1 3/2019 Orlandini Von Niessen et al.
2019/0078087 A1 3/2019 Butora et al.
2019/0085368 A1 3/2019 Bancel et al.
2019/0100748 A1 4/2019 Issa et al.
2019/0144480 A1 5/2019 DeRosa et al.
2019/0153428 A1 5/2019 Kariko et al.
2019/0160185 A1 5/2019 Schrum et al.
2019/0167811 A1 6/2019 Benenato et al.
2019/0175517 A1 6/2019 Martini et al.
2019/0175727 A1 6/2019 Huang et al.
2019/0192646 A1 6/2019 Cohen et al.
2019/0192653 A1 6/2019 Hoge et al.
2019/0211368 A1 7/2019 Butora et al.
2019/0216951 A1 7/2019 Baumhof
2019/0218546 A1 7/2019 Butora et al.
2019/0225644 A1 7/2019 Butora et al.
2019/0240317 A1 8/2019 Ciaramella et al.
2019/0241633 A1 8/2019 Fotin-Mleczek et al.
2019/0247417 A1 8/2019 Hoge et al.
2019/0255194 A1 8/2019 Roy et al.
2019/0275170 A1 9/2019 Benenato et al.
2019/0298657 A1 10/2019 Martini et al.
2019/0298658 A1 10/2019 Benenato et al.
2019/0300906 A1 10/2019 Martini et al.
2019/0314291 A1 10/2019 Besin et al.
2019/0314292 A1 10/2019 Benenato et al.
2019/0314524 A1 10/2019 Ansell et al.
2019/0336452 A1 11/2019 Brader
2019/0336595 A1 11/2019 Ciaramella
2019/0351040 A1 11/2019 Valiante et al.
2019/0351048 A1 11/2019 Rauch
2019/0382774 A1 12/2019 Hoge et al.
2019/0390181 A1 12/2019 Benenato et al.
2020/0010528 A1 1/2020 Seidel, III et al.
2020/0030432 A1 1/2020 Ciaramella et al.
2020/0030460 A1 1/2020 Kariko et al.
2020/0032274 A1 1/2020 Mauger et al.
2020/0038499 A1 2/2020 Narayanan et al.
2020/0054737 A1 2/2020 Ciaramella et al.
2020/0060971 A1 2/2020 Eber et al.
2020/0061185 A1 2/2020 Graham et al.
2020/0069599 A1 3/2020 Smith et al.
2020/0069793 A1 3/2020 Ciaramella
2020/0069794 A1 3/2020 Ciaramella et al.
2020/0071689 A1 3/2020 Miracco
2020/0085916 A1 3/2020 Martini et al.
2020/0109420 A1 4/2020 Brito et al.
2020/0113832 A1 4/2020 Yaworski et al.
2020/0121809 A1 4/2020 Hope et al.
2020/0123100 A1 4/2020 Benenato et al.
2020/0129445 A1 4/2020 Patel et al.
2020/0129608 A1 4/2020 Ciaramella et al.
2020/0129615 A1 4/2020 Ciaramella et al.
2020/0147176 A1 5/2020 Gieseke et al.
2020/0155706 A1 5/2020 De Fougerolles et al.
2020/0163878 A1 5/2020 Baumhof et al.
2020/0164038 A1 5/2020 De Fougerolles et al.
2020/0206362 A1 7/2020 Besin et al.
2020/0208145 A1 7/2020 Moore et al.
2020/0247861 A1 8/2020 De Fougerolles et al.
2020/0254086 A1 8/2020 Hoge et al.
2020/0268664 A1 8/2020 MacLachlan et al.
2020/0282046 A1 9/2020 Ciaramella et al.
2020/0282047 A1 9/2020 Ciaramella et al.
2020/0332293 A1 10/2020 Thess
2020/0338214 A1 10/2020 Guild et al.
2020/0354423 A1 11/2020 De Fougerolles et al.
2020/0383922 A1 12/2020 Ketterer et al.
2020/0392518 A1 12/2020 Eberle et al.
2020/0399629 A1 12/2020 Kariko et al.
2020/0405844 A1 12/2020 Ciaramella et al.
2021/0023199 A1 1/2021 Kallen et al.
2021/0030683 A1 2/2021 Eber et al.
2021/0030866 A1 2/2021 Kallen et al.
2021/0040473 A1 2/2021 Funkner et al.
2021/0046173 A1 2/2021 Ciaramella et al.
2021/0060175 A1 3/2021 Fotin-Mleczek et al.
2021/0077634 A1 3/2021 De Fougerolles et al.
2021/0107861 A1 4/2021 Ansell et al.
2021/0128716 A1 5/2021 Thess et al.
2021/0187097 A1 6/2021 Ciaramella et al.
2021/0217484 A1 7/2021 Giessel et al.
2021/0220467 A1 7/2021 Ciaramella et al.
2021/0228707 A1 7/2021 Metkar et al.
2021/0228708 A1 7/2021 Smith et al.
2021/0251898 A1 8/2021 Baumhof et al.
2021/0261597 A1 8/2021 Hogrefe et al.
2021/0290756 A1 9/2021 Sullivan et al.
2021/0299244 A1 9/2021 Mosharraf et al.
2021/0299278 A1 9/2021 Bancel et al.
2021/0371452 A1 12/2021 Hogrefe et al.
2021/0379181 A1 12/2021 Rauch et al.
2021/0388032 A1 12/2021 Langedijk et al.
2022/0016234 A1 1/2022 Rice et al.
2022/0040285 A1 2/2022 Weissman et al.
2022/0040292 A1 2/2022 Tang et al.
2022/0072155 A1 3/2022 Ansell et al.
2022/0105201 A1 4/2022 Guild et al.
2022/0193226 A1 6/2022 Rauch et al.
2022/0202930 A1 6/2022 Roth et al.
2022/0211838 A1 7/2022 Oostvogels et al.
2022/0211841 A1 7/2022 Oostvogels et al.
2022/0218815 A1 7/2022 Rauch et al.
2022/0218816 A1 7/2022 Ying
2022/0273820 A1 9/2022 Sahin et al.
2023/0073461 A1 3/2023 Sahin et al.
2023/0075979 A1 3/2023 Sahin et al.

FOREIGN PATENT DOCUMENTS

AU 2016253972 B2 1/2020
AU 2015280499 B2 3/2020
CN 110167587 A 8/2019
CN 106795096 B 5/2020
CN 112226445 A 1/2021
CN 113186203 A 7/2021
DE 20 2021 003 575 U1 1/2022
EP 1392341 B1 3/2005
EP 1857122 B1 12/2010
EP 2691101 A2 2/2014

(56) References Cited

FOREIGN PATENT DOCUMENTS

| | | | |
|---|---|---|---|
| EP | 2791160 | A1 | 10/2014 |
| EP | 2833892 | A2 | 2/2015 |
| EP | 2833894 | A1 | 2/2015 |
| EP | 1685844 | B1 | 3/2015 |
| EP | 3134131 | A1 | 3/2017 |
| EP | 3160938 | A1 | 5/2017 |
| EP | 3169693 | A1 | 5/2017 |
| EP | 2958588 | B1 | 8/2017 |
| EP | 3218508 | A1 | 9/2017 |
| EP | 2506857 | B1 | 2/2018 |
| EP | 3289083 | A1 | 3/2018 |
| EP | 2971102 | B1 | 6/2018 |
| EP | 3334828 | A1 | 6/2018 |
| EP | 3350157 | A2 | 7/2018 |
| EP | 3350333 | A2 | 7/2018 |
| EP | 3362460 | A1 | 8/2018 |
| EP | 3362461 | A1 | 8/2018 |
| EP | 3364949 | A1 | 8/2018 |
| EP | 3364983 | A2 | 8/2018 |
| EP | 3036330 | B1 | 9/2018 |
| EP | 3368507 | A1 | 9/2018 |
| EP | 3386484 | A1 | 10/2018 |
| EP | 3394030 | A1 | 10/2018 |
| EP | 2970955 | B1 | 11/2018 |
| EP | 2763701 | B1 | 12/2018 |
| EP | 3090060 | B1 | 2/2019 |
| EP | 3452101 | A2 | 3/2019 |
| EP | 3318248 | B1 | 4/2019 |
| EP | 3468537 | A1 | 4/2019 |
| EP | 2717893 | B1 | 5/2019 |
| EP | 3260541 | B1 | 5/2019 |
| EP | 3292873 | B1 | 5/2019 |
| EP | 3501550 | A1 | 6/2019 |
| EP | 1797886 | B1 | 7/2019 |
| EP | 3505176 | A1 | 7/2019 |
| EP | 3512944 | A1 | 7/2019 |
| EP | 3134506 | B1 | 8/2019 |
| EP | 3520820 | A1 | 8/2019 |
| EP | 3520821 | A1 | 8/2019 |
| EP | 3532070 | A1 | 9/2019 |
| EP | 3538067 | A1 | 9/2019 |
| EP | 3540060 | A1 | 9/2019 |
| EP | 3577221 | A1 | 12/2019 |
| EP | 3578200 | A1 | 12/2019 |
| EP | 3578205 | A1 | 12/2019 |
| EP | 3578659 | A1 | 12/2019 |
| EP | 3586861 | A1 | 1/2020 |
| EP | 3590949 | A1 | 1/2020 |
| EP | 3595676 | A1 | 1/2020 |
| EP | 3595727 | A1 | 1/2020 |
| EP | 3596041 | A1 | 1/2020 |
| EP | 3596042 | A1 | 1/2020 |
| EP | 3607074 | A1 | 2/2020 |
| EP | 3492109 | B1 | 3/2020 |
| EP | 3625345 | A1 | 3/2020 |
| EP | 3638215 | A1 | 4/2020 |
| EP | 3062798 | B1 | 5/2020 |
| EP | 3668522 | A2 | 6/2020 |
| EP | 3682905 | A1 | 7/2020 |
| EP | 3886897 | A1 | 10/2021 |
| EP | 3901260 | A1 | 10/2021 |
| EP | 3901261 | A1 | 10/2021 |
| EP | 3718565 | B1 | 4/2022 |
| JP | H10-113117 | A | 5/1998 |
| JP | 6594421 | B2 | 10/2019 |
| TW | 200515917 | A | 5/2005 |
| WO | WO-1998/051278 | A2 | 11/1998 |
| WO | WO-1999/14346 | A2 | 3/1999 |
| WO | WO-02/098443 | A2 | 12/2002 |
| WO | WO-2004/002453 | A1 | 1/2004 |
| WO | WO-2004/004743 | A1 | 1/2004 |
| WO | WO-2004/096842 | A2 | 11/2004 |
| WO | WO-2006/138380 | A2 | 12/2006 |
| WO | WO-2007/024708 | A2 | 3/2007 |
| WO | WO-2007/036366 | A2 | 4/2007 |
| WO | WO-2008/016473 | A2 | 2/2008 |
| WO | WO-2008/027942 | A2 | 3/2008 |
| WO | WO-2008/052770 | A2 | 5/2008 |
| WO | WO-2008/157688 | A2 | 12/2008 |
| WO | WO-2009/127060 | A1 | 10/2009 |
| WO | WO-2009/149253 | A2 | 12/2009 |
| WO | WO-2011/015347 | A1 | 2/2011 |
| WO | WO-2011/068810 | A1 | 6/2011 |
| WO | WO-2012/019168 | A2 | 2/2012 |
| WO | WO-2012/045075 | A1 | 4/2012 |
| WO | WO-2012/135805 | A2 | 10/2012 |
| WO | WO-2012/170930 | A1 | 12/2012 |
| WO | WO-2013/052523 | A1 | 4/2013 |
| WO | WO-2013/090648 | A1 | 6/2013 |
| WO | WO-2013/143699 | A1 | 10/2013 |
| WO | WO-2013/151668 | A2 | 10/2013 |
| WO | WO-2013/151671 | A1 | 10/2013 |
| WO | WO-2013/151672 | A2 | 10/2013 |
| WO | WO-2013/151736 | A2 | 10/2013 |
| WO | WO-2014/089239 | A1 | 6/2014 |
| WO | WO-2014/127917 | A1 | 8/2014 |
| WO | WO-2014/144711 | A1 | 9/2014 |
| WO | WO-2014/152659 | A1 | 9/2014 |
| WO | WO-2014/152966 | A1 | 9/2014 |
| WO | WO-2014/159813 | A1 | 10/2014 |
| WO | WO-2014/164253 | A1 | 10/2014 |
| WO | WO-2015/005253 | A1 | 1/2015 |
| WO | WO-2015/024667 | A1 | 2/2015 |
| WO | WO-2015/062738 | A1 | 5/2015 |
| WO | WO-2015/101416 | A1 | 7/2015 |
| WO | WO-2015/130584 | A2 | 9/2015 |
| WO | WO-2015/164674 | A1 | 10/2015 |
| WO | WO-2015/164773 | A1 | 10/2015 |
| WO | WO-2015/199952 | A1 | 12/2015 |
| WO | WO-2016/005004 | A1 | 1/2016 |
| WO | WO-2016/005324 | A1 | 1/2016 |
| WO | WO-2016/010840 | A1 | 1/2016 |
| WO | WO-2016/011226 | A1 | 1/2016 |
| WO | WO-2016/045732 | A1 | 3/2016 |
| WO | WO-2016/077123 | A1 | 5/2016 |
| WO | WO-2016/091391 | A1 | 6/2016 |
| WO | WO-2016/164762 | A1 | 10/2016 |
| WO | WO-2016/165831 | A1 | 10/2016 |
| WO | WO-2016/176330 | A1 | 11/2016 |
| WO | WO-2016/180430 | A1 | 11/2016 |
| WO | WO-2016/184575 | A1 | 11/2016 |
| WO | WO-2016/184576 | A2 | 11/2016 |
| WO | WO-2016/193206 | A1 | 12/2016 |
| WO | WO-2016/201377 | A1 | 12/2016 |
| WO | WO-2017/015457 | A1 | 1/2017 |
| WO | WO-2017/025447 | A1 | 2/2017 |
| WO | WO-2017/036889 | A1 | 3/2017 |
| WO | WO-2017/049245 | A2 | 3/2017 |
| WO | WO-2017/049275 | A2 | 3/2017 |
| WO | WO-2017/053297 | A1 | 3/2017 |
| WO | WO-2017/059902 | A1 | 4/2017 |
| WO | WO-2017/060314 | A2 | 4/2017 |
| WO | WO-2017/066781 | A1 | 4/2017 |
| WO | WO-2017/066789 | A1 | 4/2017 |
| WO | WO-2017/066793 | A1 | 4/2017 |
| WO | WO-2017/070601 | A1 | 4/2017 |
| WO | WO-2017/070618 | A1 | 4/2017 |
| WO | WO-2017/070626 | A2 | 4/2017 |
| WO | WO-2017/075531 | A1 | 5/2017 |
| WO | WO-2017/099823 | A1 | 6/2017 |
| WO | WO-2017/112865 | A1 | 6/2017 |
| WO | WO-2017/127750 | A1 | 7/2017 |
| WO | WO-2017/191274 | A2 | 11/2017 |
| WO | WO-2017/201333 | A1 | 11/2017 |
| WO | WO-2017/218704 | A1 | 12/2017 |
| WO | WO-2018/053209 | A1 | 3/2018 |
| WO | WO-2018/075827 | A1 | 4/2018 |
| WO | WO-2018/078053 | A1 | 5/2018 |
| WO | WO-2018/081459 | A1 | 5/2018 |
| WO | WO-2018/081462 | A1 | 5/2018 |
| WO | WO-2018/081480 | A1 | 5/2018 |
| WO | WO-2018/089540 | A1 | 5/2018 |
| WO | WO-2018/089851 | A2 | 5/2018 |
| WO | WO-2018/115527 | A2 | 6/2018 |

(56) References Cited

FOREIGN PATENT DOCUMENTS

| | | | | |
|---|---|---|---|---|
| WO | WO-2018/144778 A1 | 8/2018 | | |
| WO | WO-2018/157009 A1 | 8/2018 | | |
| WO | WO-2018/170245 A1 | 9/2018 | | |
| WO | WO-2018/170306 A1 | 9/2018 | | |
| WO | WO-2018/170322 A1 | 9/2018 | | |
| WO | WO-2018/170336 A1 | 9/2018 | | |
| WO | WO-2018/170347 A1 | 9/2018 | | |
| WO | WO-2018/187590 A1 | 10/2018 | | |
| WO | WO-2018/213789 A1 | 11/2018 | | |
| WO | WO-2018/232355 A1 | 12/2018 | | |
| WO | WO-2018/232357 A1 | 12/2018 | | |
| WO | WO-2019/035998 A1 | 2/2019 | | |
| WO | WO-2019/036670 A2 | 2/2019 | | |
| WO | WO-2019/036683 A1 | 2/2019 | | |
| WO | WO-2019/036685 A1 | 2/2019 | | |
| WO | WO-2019/092002 A1 | 5/2019 | | |
| WO | WO-2019/092437 A1 | 5/2019 | | |
| WO | WO-2019/148101 A1 | 8/2019 | | |
| WO | WO-2019/209914 A2 | 10/2019 | | |
| WO | WO-2019/232097 A1 | 12/2019 | | |
| WO | WO-2020/006242 A1 | 1/2020 | | |
| WO | WO-2020/056370 A1 | 3/2020 | | |
| WO | WO-2020/061284 A1 | 3/2020 | | |
| WO | WO-2020/061295 A1 | 3/2020 | | |
| WO | WO-2020/061367 A1 | 3/2020 | | |
| WO | WO-2020/061457 A1 | 3/2020 | | |
| WO | PCT/EP2020/061239 | 4/2020 | | |
| WO | WO-2020/097291 A1 | 5/2020 | | |
| WO | PCT/EP2020/066968 | 6/2020 | | |
| WO | PCT/EP2020/068174 | 6/2020 | | |
| WO | PCT/EP2020/069805 | 7/2020 | | |
| WO | PCT/EP2020/071733 | 7/2020 | | |
| WO | WO-2020150152 A1 * | 7/2020 | ......... | A61K 39/0011 |
| WO | PCT/EP2020/071839 | 8/2020 | | |
| WO | PCT/EP2020/073668 | 8/2020 | | |
| WO | WO-2020/160397 A1 | 8/2020 | | |
| WO | WO-2020/190750 A1 | 9/2020 | | |
| WO | WO-2020/198337 A1 | 10/2020 | | |
| WO | PCT/EP2020/081544 | 11/2020 | | |
| WO | PCT/EP2020/081981 | 11/2020 | | |
| WO | PCT/EP2020/082601 | 11/2020 | | |
| WO | PCT/EP2020/082989 | 11/2020 | | |
| WO | PCT/EP2020/083435 | 11/2020 | | |
| WO | PCT/EP2020/084342 | 12/2020 | | |
| WO | PCT/EP2020/085145 | 12/2020 | | |
| WO | PCT/EP2020/085653 | 12/2020 | | |
| WO | PCT/EP2020/087844 | 12/2020 | | |
| WO | WO-2020/263985 A1 | 12/2020 | | |
| WO | PCT/EP2021/050027 | 1/2021 | | |
| WO | PCT/EP2021/050874 | 1/2021 | | |
| WO | PCT/EP2021/050875 | 1/2021 | | |
| WO | PCT/EP2021/051772 | 1/2021 | | |
| WO | PCT/EP2021/052572 | 2/2021 | | |
| WO | PCT/EP2021/052716 | 2/2021 | | |
| WO | PCT/EP2021/054622 | 2/2021 | | |
| WO | WO-2021/030701 A1 | 2/2021 | | |
| WO | WO-2021/050864 A1 | 3/2021 | | |
| WO | WO-2021/055811 A1 | 3/2021 | | |
| WO | PCT/EP2021/059947 | 4/2021 | | |
| WO | WO-2021/147025 A1 | 7/2021 | | |
| WO | WO-2021/154763 A1 | 8/2021 | | |
| WO | WO-2021/155243 A1 | 8/2021 | | |
| WO | WO-2021/155760 A1 | 8/2021 | | |
| WO | WO-2021/156267 A1 | 8/2021 | | |
| WO | WO-2021/159040 A2 | 8/2021 | | |
| WO | WO-2021/159118 A2 | 8/2021 | | |
| WO | WO-2021/159130 A2 | 8/2021 | | |
| WO | WO-2021/159985 A1 | 8/2021 | | |
| WO | WO-2021/160346 A1 | 8/2021 | | |
| WO | WO-2021/165667 A1 | 8/2021 | | |
| WO | WO-2021/181100 A1 | 9/2021 | | |
| WO | WO-2021/188906 A1 | 9/2021 | | |
| WO | WO-2021/188969 A2 | 9/2021 | | |
| WO | WO-2021/194826 A2 | 9/2021 | | |
| WO | WO-2021/198706 A2 | 10/2021 | | |
| WO | WO-2021/202599 A2 | 10/2021 | | |
| WO | WO-2021/202772 A1 | 10/2021 | | |
| WO | WO-2021/204179 A1 | 10/2021 | | |
| WO | WO-2021/210686 A1 | 10/2021 | | |
| WO | WO-2021/211688 A1 | 10/2021 | | |
| WO | WO-2021/211748 A1 | 10/2021 | | |
| WO | WO-2021/213924 A1 | 10/2021 | | |
| WO | WO-2021/213945 A1 | 10/2021 | | |
| WO | WO-2021/214204 A1 | 10/2021 | | |
| WO | WO-2021/216729 A1 | 10/2021 | | |
| WO | WO-2021/220319 A1 | 11/2021 | | |
| WO | WO-2021/222304 A1 | 11/2021 | | |
| WO | WO-2021/226436 A1 | 11/2021 | | |
| WO | WO-2021/231560 A1 | 11/2021 | | |
| WO | WO-2021/231929 A1 | 11/2021 | | |
| WO | WO-2021/231963 A1 | 11/2021 | | |
| WO | WO-2021/239880 A1 | 12/2021 | | |
| WO | WO-2022/009121 A1 | 1/2022 | | |
| WO | WO-2022/011092 A1 | 1/2022 | | |
| WO | WO-2022/011332 A2 | 1/2022 | | |

OTHER PUBLICATIONS

Bouloy, M. et al., Both the 7-methyl and the 2'-0-methyl groups in the CAP of mRNA strongly influence its ability to act as primer for influenza virus RNA transcription, Proceedings of The National Academy of Sciences of the USA, 77(7):3952-3956 (1980).

Cullis, P. and Hope, M., Lipid Nanoparticle Systems for Enabling Gene Therapies, Mol Ther, 25(7):1467-1475 (2017).

Furuichi, Y. and Shatkin, A., Viral and cellular mRNA capping: past and prospects, Adv Virus Res, 55:135-84 (2000).

Furuichi, Yasuhiro, Caps on Eukaryotic mRNAs, John Wiley & Sons, pp. 1-12 (Jul. 2014).

Gallie, Daniel R., The cap and poly(A) tail function synergistically to regulate mRNA translational efficiency, Genes Dev, 5(11):2108-16 (1991).

Gebre, M. S. et al., Optimization of Non-Coding Regions Improves Protective Efficacy of an mRNA SARS-CoV-2 Vaccine in Nonhuman Primates, bioRxiv, 36 pages (2021).

Habjan, M. et al., Sequestration by IFIT1 impairs translation of 2'0-unmethylated capped RNA, PLOS Pathogens, 9(10):e1003663 (2013).

Hassett, K. et al., Optimization of Lipid Nanoparticles for Intramuscular Administration of mRNA Vaccines, Mol Ther Nucleic Acids, 15:1-11 (2019).

Huang, Q. et al., A single-dose mRNA vaccine provides a long-term protection for hACE2 transgenic mice from SARS-CoV-2, Nat. Comm., 12(776):1-10 (2021).

Hyde, J. L. et al., A viral RNA structural element alters host recognition of nonself RNA, Science, 343(6172):783-787 (2014).

Hyde, J. L. et al., Supplementary Information, Science, 343(6172):783-787 (2014).

International Search Report for PCT/EP2021/060508, 7 pages (dated Aug. 5, 2021).

Ivens, I. et al., PEGylated Biopharmaceuticals: Current Experience and Considerations for Nonclinical Development, Toxicol Pathol., 43(7):959-83 (2015).

Jackson, N. A. C. et al., The promise of mRNA vaccines: a biotech and industrial perspective, NPJ Vaccines, 5(11):1-6 (2020).

Kauffman, K. et al., Materials for non-viral intracellular delivery of messenger RNA therapeutics, J Control Release, 240:227-234 (2016).

Kozma, G. T. et al., Pseudo-anaphylaxis to Polyethylene Glycol (PEG)-Coated Liposomes: Roles of Anti-PEG IgM and Complement Activation in a Porcine Model of Human Infusion Reactions, ACS Nano, 13:9315-9324 (2019).

Kurimoto, S. et al., PEG-OligoRNA Hybridization of mRNA for Developing Sterically Stable Lipid Nanoparticles toward In Vivo Administration, Molecules, 24(7):1303, 16 pages (2019).

Laczkó, D. et al., A Single Immunization with Nucleoside-Modified mRNA Vaccines Elicits Strong Cellular and Humoral Immune Responses against SARS-CoV-2 in Mice, Immunity, 53(4):724-732 (2020).

McCown, P. J. et al., Naturally occurring modified ribonucleosides, Wires RNA, 11(e1595):1-71 (2020).

(56) References Cited

OTHER PUBLICATIONS

Pardi, N. et al., Characterization of HIV-1 Nucleoside-Modified mRNA Vaccines in Rabbits and Rhesus Macaques, Molecular Therapy: Nucleic Acids, 15:36-47 (2019).
Pardi, N. et al., mRNA vaccines—a new era in vaccinology, Nat Rev Drug Discov, 17(4):261-279 (2018).
Pardi, N. et al., Nucleoside-modified mRNA immunization elicits influenza virus hemagglutinin stalk-specific antibodies, Nat Commun., 22;9(1):3361 (2018).
Pardi, N. et al., Zika virus protection by a single low-dose nucleoside-modified mRNA vaccination, Nature, 543(7644):248-251 (2017).
Pardi, Norbert, COVID-19 Symposium: Nucleoside-modified mRNA Vaccines Against SARS-CoV-2, Penn Medicine, 10 pages (2020).
Ramanathan, A. et al., mRNA capping: biological functions and applications, Nucleic Acids Research, 44(16) 7511-7526 (2016).
Reichmuth, A. et al., mRNA vaccine delivery using lipid nanoparticles, Ther. Deliv., 7(5):319-334 (2016).
Sahin, U. et al., mRNA-based therapeutics—developing a new class of drugs, Nat Rev Drug Discov., 13(10):759-80 (2014).
Schlake, T. et al., Developing mRNA-vaccine technologies, RNA Biol, 9(11):1319-30 (2012).
Written Opinion for PCT/EP2021/060508, 11 pages (dated Aug. 5, 2021).
Xia, X., Detailed Dissection and Critical Evaluation of the Pfizer/BioNTech and Moderna mRNA Vaccines, Vaccines, 9(734):1-19 (2021).
Zeng, C. et al., Leveraging mRNAs sequences to express SARS-CoV-2 antigens in vivo, bioRxiv, 16 pages (2020), Retrieved from the Internet: URL:https://www.biorxiv.org/content/10.1101/2020.04.01.019877vl.full.pdf.
Zeng, C. et al., Leveraging mRNAs sequences to express SARS-CoV-2 antigens in vivo, Supplementary Information, bioRxiv, 13 pages (2020).
Zhao, L. et al., Nanoparticle vaccines, Vaccine, 32(3):327-37 (2014).
U.S. Appl. No. 17/233,396, filed Apr. 16, 2021, Allowed, Issue Fee paid.
U.S. Appl. No. 17/698,829, filed Mar. 18, 2022, Pending.
U.S. Appl. No. 17/699,035, filed Mar. 18, 2022, Pending.
[No Author Listed], Assessment Report—Comirnaty, 140 pages Jan. 19, 2021.
CureVac's COVID-19 vaccine (CVnCoV): Withdrawal from the rolling review process, Oct. 12, 2021, European Medical Agency (EMA), ema.europa.eu/en/medicines/human/withdrawn-applications/curevacs-covid-19-vaccine-cvncov, 3 pages.
Den Dunnon, J.T. and Antonarakis, S.E., Nomenclature for the description of sequence variations, Human Genet., 109(1):121-124 (2001).
International Nonproprietary Names for Pharmaceutical Substances (INN), WHO Drug Information, vol. 33, No. 3, 139 pages, (2019).
Jeong, D. et al., Assemblies-of-putative-SARS-CoV2-spike-encoding-mRNA-sequences-for-vaccines-BNT-162b2-and-mRNA-1273, 4 pages (2021).
Orlandini Von Niessen, A. G. et al., Improving mRNA-Based Therapeautic Gene Delivery by Expression-Augmenting 3' UTRs Identified by Cellular Library Screening, Molecular Therapy Original Article, 27(4):824-836 (2019).
Sinopeg Data Sheet, 10 pages (2022).
WHO Drug Information 2021, vol. 35, 2 [full issue], WHO Drug Information 35(2):270-605 (2021).
Grudezen, E. et al., Differential Inhibition of mRNA Degradation Pathways by Novel Cap Analogs, The Journal of Biological Chemistry, 281(4):1857-1867 (2006).
Iadevaia, V. et al., All translation elongation factors and the e, f, and h subunits of translation initiation factor 3 are encoded by 5'-terminal oligopyrimidine (TOP) mRNAs, RNA, 14:1730-1736 (2008).
Ishikawa, M. et al., Preparation of eukaryotic mRNA having differently methylated adenosine at the 5'-terminus and the effect of the methyl group in translation, Nucleic Acids Symposium Series, Oxford, 53:129-130 (2009).
Koukhareva I. I. and Lebedev, A. V., Chemical Route to the Capped RNAs, Nucloesides, Nucleotides and Nucleic Acids, 23(10:1667-1780 (2004).
Kuhn, A. et al., Phosphorothioate cap analogs increase stability and translational efficiency of RNA vaccines in immature dentritic cells and induce superior immune responses in vivo, Gene Therapy, 17:961-971 (2010).
Limbach, P. A. et al., Summary: the modified nucleosides of RNA, Nucleic Acids Research, 22(12):2183-2196 (1994).
Selisko, B. et al., Biochemical characterization of the (nucleoside-2'O)-methyltransferase activity of dengue virus protein NS5 using purified capped RNA oligonucleotides (7Me)GpppAC(n) and GpppAC(n), Journal of General Virology, 91(Pt1):112-121 (2010).

* cited by examiner

Complementarity of Lig3 to the translation start site of the 5'UTR and to the I-element of the 3'UTR $(m_2^{7,3'-O})Gppp(m^{2'-O})ApG$ m1-pseudouridine triphosphate enzymatic cap0

$(m^7)$GpppG..

enzymatic cap1

$(m^7)$Gppp$(m^{2'}$-O$)$G..

$(m_2^{7,3'-O})Gppp(m^{2'-O})GpG$ $(m^7)Gppp(m^{2'-O})ApG$ $(m_2{}^{7,3'\text{-}O})Gppp(m_2{}^{6,2'\text{-}O})ApG$ $(m_2{}^{7,3'\text{-}O})Gppp(m^{2'\text{-}O})Ap\ (m^{2'\text{-}O})GpG$ $(m_2^{7,3'-O})Gppp(m_2^{6,2'-O})ApG$ $(m_2^{7,3'-O})Gppp(m^{2'-O})Ap(m^{2'-O})GpG$ $(m_2^{7,2'-O})GppSpG$

RNA CONSTRUCTS AND USES THEREOF

CROSS-REFERENCE TO RELATED APPLICATIONS

This application is a continuation of PCT Application No. PCT/EP2021/060508, filed Apr. 22, 2021, which claims foreign priority to International Patent Application Nos. PCT/EP2021/059947, filed on Apr. 16, 2021, PCT/EP2021/054622, filed on Feb. 24, 2021, PCT/EP2021/052716, filed on Feb. 4, 2021, PCT/EP2021/052572, filed on Feb. 3, 2021, PCT/EP2021/051772, filed on Jan. 26, 2021, PCT/EP2021/050874, filed on Jan. 15, 2021, PCT/EP2021/050875, filed on Jan. 15, 2021, PCT/EP2021/050027, filed on Jan. 4, 2021, PCT/EP2020/087844, filed on Dec. 23, 2020, PCT/EP2020/085653, filed on Dec. 10, 2020, PCT/EP2020/085145, filed on Dec. 8, 2020, PCT/EP2020/084342, filed on Dec. 2, 2020, PCT/EP2020/083435, filed on Nov. 25, 2020, PCT/EP2020/082989, filed on Nov. 20, 2020, PCT/EP2020/082601, filed on Nov. 18, 2020, PCT/EP2020/081981, filed on Nov. 12, 2020, PCT/EP2020/081544, filed on Nov. 9, 2020, PCT/EP2020/073668, filed on Aug. 24, 2020, PCT/EP2020/071839, filed on Aug. 3, 2020, PCT/EP2020/071733, filed on Jul. 31, 2020, PCT/EP2020/069805, filed on Jul. 13, 2020, PCT/EP2020/068174, filed on Jun. 26, 2020, PCT/EP2020/066968, filed on Jun. 18, 2020, PCT/EP2020/061239, filed on Apr. 22, 2020, the disclosures of each of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Apr. 20, 2022, is named 2013237-0218_SL.txt and is 152,913 bytes in size.

BACKGROUND

Use of RNA polynucleotides as therapeutics is a new and emerging field.

SUMMARY

The present disclosure identifies certain challenges that can be associated with RNA therapeutics.

For example, in some embodiments, the present disclosure identifies the source of certain problems that can be encountered with expression of polypeptides encoded by RNA therapeutics. Among other things, the present disclosure provides technologies for improving translation efficiency of an RNA encoding a payload, and/or expression of a polypeptide payload encoded by an RNA. In some embodiments, translation efficiency and/or expression of an RNA-encoded payload can be improved with an RNA polynucleotide comprising: a Cap1 structure (e.g., a $m_2^{7,3'-O}$Gppp($m_1^{2'-O}$)ApG cap); a 5' UTR comprising a cap proximal sequence disclosed herein, and a sequence encoding a payload. Without wishing to be bound by theory, the present disclosure proposes that improved translation efficiency and/or polypeptide payload expression can be achieved through preferential binding of eukaryotic translation initiation factor 4E (eIF4E), rather than IFN-induced protein with tetratricopeptide repeats-1 (IFIT1) to an RNA comprising a Cap1 structure, e.g., a $m_2^{7,3'-O}$Gppp($m_1^{2'-O}$)ApG cap, and/or a 5' UTR comprising a cap proximal sequence disclosed herein. For example, in some embodiments, it is proposed that eIF4E may compete with IFIT1 for binding to an RNA polynucleotide based on a 5' cap structure. Among other things, the present disclosure provides certain technologies that may favor eIF4E binding, at least relative to IFIT1 binding, and/or may otherwise enhance translation.

In some embodiments, the present disclosure teaches that identity of particular sequence(s) proximal to a 5' cap (e.g., a 5' Cap1 structure) can influence translation efficiency of an associated payload. Without wishing to be bound by any particular theory, the present disclosure proposes that eIF4E competes with IFIT1 for binding to an RNA polynucleotide based on the identity of one or more nucleotides downstream of a 5' cap, e.g., a cap proximal sequence as disclosed herein. In some embodiments, the present disclosure demonstrates that an AGAAU or an AGCAC sequence downstream of a 5' cap (e.g., a 5' Cap 1 structure) can improve translation. The present disclosure proposes that presence of such sequence (e.g., AGAAU or an AGCAC can increase eIF4E binding, at least relative to IFIT1.

Alternatively or additionally, the present disclosure documents certain advantages of avoiding (e.g., ensuring that absence of) a self-hybridizing sequence (which may, in some instances, be referred to as a self-complementary sequence) in an RNA polynucleotide encoding a payload, For example, the present disclosure demonstrates that such absence can improve, and/or be required for, translation (e.g., translation efficiency) of an associated (e.g., RNA-encoded) payload, and/or otherwise for expression of a polypeptide encoded thereby. Without wishing to be bound by theory, it is believed that a self-hybridizing sequence (and in particular a sequence that hybridizes with sequences within or comprising one or more of a Kozak sequence, a 5' UTR element, and/or a 3' UTR element) interfere with one or more aspects of translation. For example, in some embodiments, it is proposed that such self-hybridization may inhibit binding of transcription and/or translation factors to an RNA polynucleotide by self-hybridizing to a complementary sequence in said RNA polynucleotide.

Still further alternatively or additionally, in some embodiments, the present disclosure defines particular lipid components, and/or ratios thereof, that may be especially useful or effective in delivering nucleic acids, and in particular RNAs (e.g., therapeutic RNAs or other RNAs encoding a polypeptide) upon administration (e.g., by injection, such as by intramuscular injection or by intravenous injection) to a subject. For example, in some embodiments, the present disclosure demonstrates that lipid ALC-0315 is unusually and particularly useful for delivery as described herein.

Disclosed herein, inter alia, is a composition or medical preparation comprising an RNA polynucleotide, comprising: (i) a 5' cap that is or comprises a cap1 structure, e.g., as disclosed herein; (ii) a 5' UTR sequence comprising a cap proximal sequence, e.g., as disclosed herein; and (iii) a sequence encoding a payload. Also disclosed herein are methods of making and using the same to, e.g., induce an immune response in a subject.

Provided herein is a composition or medical preparation comprising an RNA polynucleotide comprising:

a 5' cap comprising a Cap1 structure; a cap proximal sequence comprising positions +1, +2, +3, +4, and +5 of the RNA polynucleotide; and a sequence encoding a payload, wherein:

(i) the Cap1 structure comprises m7G(5')ppp(5')(2'OMeN$_1$)pN$_2$, wherein N$_1$ is position +1 of the RNA polynucleotide, and N$_2$ is position +2 of the RNA polynucleotide, and wherein N$_1$ and N$_2$ are each independently chosen from: A, C, G, or U; and (ii) the cap proximal sequence comprises N$_1$ and N$_2$ of the Cap1 structure, and:

(a) a sequence selected from the group consisting of: $A_3A_4X_5$ (SEQ ID NO: 1); $C_3A_4X_5$ (SEQ ID NO: 2); $A_3C_4A_5$ (SEQ ID NO: 3) and $A_3U_4G_5$ (SEQ ID NO: 4); or (b) a sequence comprising: $X_3Y_4X_5$ (SEQ ID NO: 7);

wherein $X_3$ (nucleotide X at position +3 in SEQ ID NO: 7) or $X_5$ (nucleotide X at position +5 in SEQ ID NO: 1 or SEQ ID NO: 2) is each independently chosen from A, G, C, or U; and wherein $Y_4$ (nucleotide Y at position +4 in SEQ ID NO: 7) is not C.

This disclosure also provides a composition or medical preparation comprising an RNA polynucleotide comprising: a 5' cap; a cap proximal sequence comprising positions +1, +2, +3, +4, and +5 of an RNA polynucleotide; and a sequence encoding a payload, wherein:

(i) the 5' cap comprises a Cap1 structure comprising G*ppp($m_1^{2'-O}$)N$_1$pN$_2$, wherein: N1 is position +1 of the RNA polynucleotide, and N$_2$ is position +2 of the RNA polynucleotide, and wherein N$_1$ and N$_2$ are each independently chosen from: A, C, G, or U; and G* comprises the following structure:

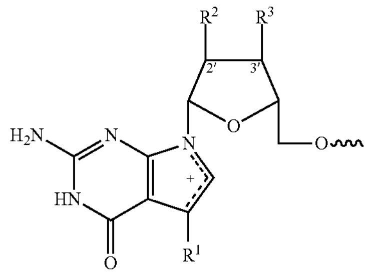

wherein ∿∿∿ represents the bond by which G* is bound to the first phosphor atom of the ppp group, $R^1$ is $CH_3$, $R^2$ is OH or O—$CH_3$, and $R^3$ is O—$CH_3$; and (ii) the cap proximal sequence comprises N$_1$ and N$_2$ of the Cap1 structure, and:

(a) a sequence selected from the group consisting of: $A_3A_4X_5$ (SEQ ID NO: 1); $C_3A_4X_5$ (SEQ ID NO: 2); $A_3C_4A_5$ (SEQ ID NO: 3) and $A_3U_4G_5$ (SEQ ID NO: 4); or (b) a sequence comprising: $X_3Y_4X_5$ (SEQ ID NO: 7);

wherein $X_3$ (nucleotide X at position +3 in SEQ ID NO: 7) or $X_5$ (nucleotide X at position +5 in SEQ ID NO: 1 or SEQ ID NO: 2) is each independently chosen from A, G, C, or U; and wherein $Y_4$ (nucleotide Y at position +4 in SEQ ID NO: 7) is not C.

Also provided herein is a composition or medical preparation comprising an RNA polynucleotide comprising:

a 5' cap comprising a Cap1 structure; a cap proximal sequence comprising positions +1, +2, +3, +4, and +5 of the RNA polynucleotide; and a sequence encoding a payload, wherein:

(i) the Cap1 structure comprises m7(3'OMeG)(5')ppp(5')(2'OMeA$_1$)pG$_2$, wherein A$_1$ is position +1 of the RNA polynucleotide, and G$_2$ is position +2 of the RNA polynucleotide; and (ii) the cap proximal sequence comprises A$_1$ and G$_2$ of the Cap1 structure, and a sequence comprising: $A_3A_4U_5$ (SEQ ID NO: 5) at positions +3, +4 and +5 respectively of the RNA polynucleotide.

This disclosure provides a composition or medical preparation comprising a capped RNA polynucleotide encoding a gene product, which RNA polynucleotide comprises the formula:

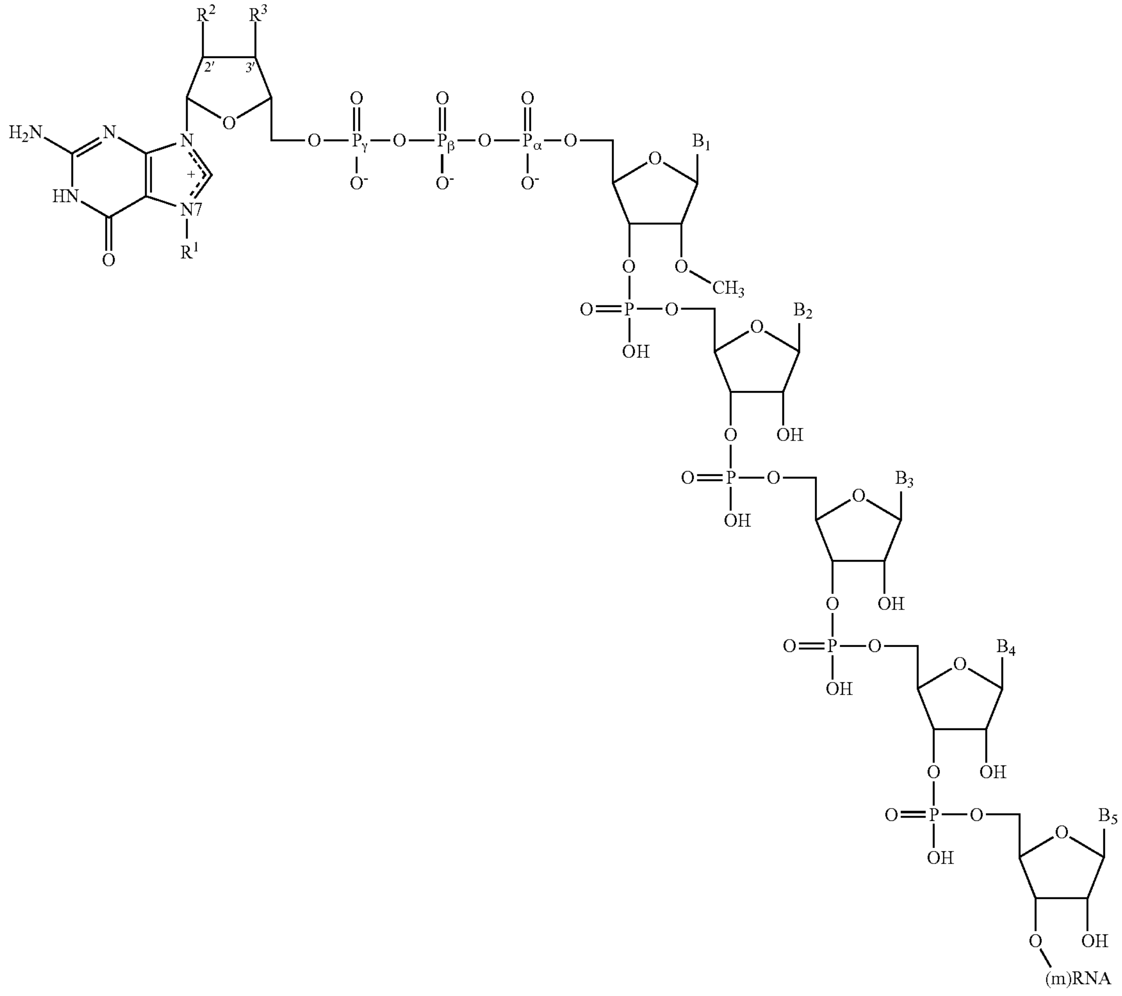

wherein $R^1$ is $CH_3$, $R^2$ is OH or O—$CH_3$, and $R^3$ is O—$CH_3$, wherein $B_1$ is any nucleobase, preferably A; $B_2$ is any nucleobase, preferably G; $B_3$ is any nucleobase, preferably A or C; $B_4$ is any nucleobase; and $B_5$ is any nucleobase, and wherein, when the RNA polynucleotide is administered to a subject, the levels of expression of the encoded gene product at about 6 hours after administration and at about 48 hours after administration do not differ by more than 5-fold.

Provided herein is a pharmaceutical composition comprising an RNA polynucleotide disclosed herein. In some embodiments, a pharmaceutical composition comprises a composition or a medical preparation disclosed herein.

Also provided herein is a method of manufacturing a pharmaceutical composition, e.g., comprising an RNA polynucleotide disclosed herein, by combining an RNA polynucleotide with lipids to form lipid nanoparticles that encapsulate said RNA.

This disclosure provides a nucleic acid template suitable to produce a cap1-capped RNA, in which the first five nucleotides transcribed from the template strand of the nucleic acid template comprise the sequence $N_1pN_2pN_3pN_4pN_5$, wherein $N_1$ is any nucleotide, preferably T; $N_2$ is any nucleotide, preferably C; $N_3$ is any nucleotide, preferably T or G; $N_4$ is any nucleotide; and $N_5$ is any nucleotide. In some embodiments, a DNA template comprises: a 5' UTR, a sequence encoding a payload, a 3' UTR and a polyA sequence.

Provided herein is an vitro transcription reaction comprising:

(i) a template DNA comprising a polynucleotide sequence complementary to an RNA polynucleotide sequence disclosed herein;

(ii) a polymerase; and (iii) an RNA polynucleotide.

Also provided herein is an RNA polynucleotide isolated from an in vitro transcription reaction provided.

This disclosure provides, a method for producing a capped RNA comprising, transcribing a nucleic acid template in the presence of a cap structure, wherein the cap structure comprises $G^*ppp(m_1^{2'-O})N_1pN_2$, wherein $N_1$ is complementary to position +1 of the nucleic acid template and $N_2$ is complementary to position +2 of the nucleic acid template, and $N_1$ and $N_2$ are independently chosen from A, C, G or U, wherein position +3 of the nucleic acid template is any nucleotide, preferably T or G; position +4 of the nucleic acid template is any nucleotide; and position +5 of the nucleic acid template is any nucleotide, wherein G* comprises the following structure:

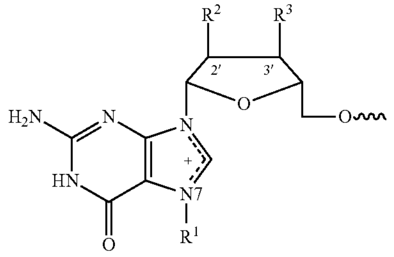

wherein  represents the bond by which G* is bound to the first phosphor atom of the ppp group, $R^1$ is $CH_3$, $R^2$ is OH or O—$CH_3$, and $R^3$ is O—$CH_3$.

Also provided herein is a composition comprising a DNA polynucleotide comprising a sequence complementary to an RNA polynucleotide sequence provided. In some embodiments, a DNA polynucleotide disclosed herein can be used to transcribe an RNA polynucleotide disclosed herein.

This disclosure provides, a method comprising: administering to a subject, a pharmaceutical composition comprising an RNA polynucleotide disclosed herein formulated in a lipid nanoparticle (LNP) or a lipoplex (LPX) particle, e.g., as disclosed herein.

Also provided herein is a method of inducing an immune response in a subject, comprising administering to a subject, a pharmaceutical composition comprising an RNA polynucleotide disclosed herein formulated in a lipid nanoparticle (LNP) or a lipoplex (LPX) particle, e.g., as disclosed herein Provided herein is a method of vaccination of a subject by administering a pharmaceutical composition comprising an RNA polynucleotide disclosed herein formulated in a lipid nanoparticle (LNP) or a lipoplex (LPX) particle, e.g., as disclosed herein.

This disclosure provides, a method of decreasing interaction with IFIT1 of an RNA polynucleotide that comprises a 5' cap and a cap proximal sequence comprising positions +1, +2, +3, +4, and +5 of the RNA polynucleotide, the method comprising a step of:

providing a variant of an RNA polynucleotide that differs from a parental RNA polynucleotide by substitution of one or more residues within a cap proximal sequence, and determining that interaction of a variant with IFIT1 is decreased relative to that of a parental RNA polynucleotide.

Also provided herein is a method of producing a polypeptide comprising a step of:

providing an RNA polynucleotide that comprises a 5' cap, a cap proximal sequence that comprises positions +1, +2, +3, +4, and +5 of the RNA polynucleotide, and a sequence encoding a payload;

wherein an RNA polynucleotide is characterized in that when assessed in an organism administered an RNA polynucleotide or a composition comprising the same, elevated expression and/or increased duration of expression of a payload is observed relative to an appropriate reference comparator.

Provided herein is a method of increasing translatability of an RNA polynucleotide that comprises a 5' cap, a cap proximal sequence that comprises positions +1, +2, +3, +4, and +5 of the RNA polynucleotide and a sequence encoding a payload, the method comprising a step of:

providing a variant of an RNA polynucleotide that differs from a parental RNA polynucleotide by substitution of one or more residues within a cap proximal sequence; and determining that expression of a variant is increased relative to that of a parental RNA polynucleotide.

Provided herein is a therapeutic RNA comprising a 5' cap that includes a Cap1 structure, a cap proximal sequence and a sequence encoding a payload, the improvement that comprises: including one or more of the following residues in a cap proximal sequence: X at position +1 of an RNA polynucleotide, X at position +2 of an RNA polynucleotide, A at position +3 of an RNA polynucleotide, A at position +4 of an RNA polynucleotide, and X at position +5 of an RNA polynucleotide, demonstrated to increase expression of an RNA when administered to a subject in an LNP formulation. In some embodiments, X is chosen from A, C, G or U.

This disclosed provides, a therapeutic RNA comprising a 5' cap that includes a Cap1 structure, a cap proximal sequence and a sequence encoding a payload, the improvement that comprises: including one or more of the following residues in a cap proximal sequence: X at position +1 of an RNA polynucleotide, X at position +2 of an RNA polynucleotide, C at position +3 of an RNA polynucleotide, A at position +4 of an RNA polynucleotide, and X at position +5 of an RNA polynucleotide, demonstrated to increase expression of an RNA when administered to a subject in an LNP formulation. In some embodiments, X is chosen from A, C, G or U.

Also provided herein is therapeutic RNA comprising a 5' cap that includes a Cap1 structure, a cap proximal sequence and a sequence encoding a payload, the improvement that comprises: including one or more of the following residues in a cap proximal sequence: A at position +1 of an RNA polynucleotide, G at position +2 of an RNA polynucleotide, A at position +3 of an RNA polynucleotide, A at position +4 of an RNA polynucleotide, and U at position +5 of an RNA polynucleotide, demonstrated to increase expression of an RNA when administered to a subject in an LNP formulation.

This disclosure provides, a method of increasing translation of an RNA polynucleotide comprising a 5' cap that includes a Cap1 structure, a cap proximal sequence and a sequence encoding a payload, the improvement that comprises: including one or more of the following residues in a cap proximal sequence: X at position +1 of an RNA polynucleotide, X at position +2 of an RNA polynucleotide, A at position +3 of an RNA polynucleotide, A at position +4 of an RNA polynucleotide, and X at position +5 of an RNA polynucleotide. In some embodiments, X is chosen from A, C, G or U.

Provided herein is a method of increasing translation of an RNA polynucleotide comprising a 5' cap that includes a Cap1 structure, a cap proximal sequence and a sequence encoding a payload, the improvement that comprises: including one or more of the following residues in a cap proximal sequence: X at position +1 of an RNA polynucleotide, X at position +2 of an RNA polynucleotide, C at position +3 of an RNA polynucleotide, A at position +4 of an RNA polynucleotide, and X at position +5 of an RNA polynucleotide. In some embodiments, X is chosen from A, C, G or U.

Also provided herein is a method of increasing translation of an RNA polynucleotide comprising a 5' cap that includes a Cap1 structure, a cap proximal sequence and a sequence encoding a payload, the improvement that comprises: including one or more of the following residues in a cap proximal sequence: A at position +1 of an RNA polynucleotide, G at position +2 of an RNA polynucleotide, A at position +3 of an RNA polynucleotide, A at position +4 of an RNA polynucleotide, and U at position +5 of an RNA polynucleotide.

Also provided herein is a method of providing a framework for an RNA polynucleotide that comprises a 5' cap, a cap proximal sequence, and a payload sequence, the method comprising a step of:

assessing at least two variants of an RNA polynucleotide, wherein:

each variant includes a same 5' cap and payload sequence; and the variants differ from one another at one or more specific residues of a cap proximal sequence;

wherein the assessing comprises determining expression levels and/or duration of expression of a payload sequence; and selecting at least one combination of 5' cap and a cap proximal sequence that displays elevated expression relative to at least one other combination.

BRIEF DESCRIPTION OF THE DRAWING

FIG. 2A discloses SEQ ID NOs: 43-44, respectively, in order of appearance. FIG. 2B discloses SEQ ID NOs: 45 and 44, respectively, in order of appearance. FIG. 2C discloses SEQ ID NOs: 46-47, respectively, in order of appearance.

FIG. 4 discloses SEQ ID NOs: 5, 3, 4 and 6 respectively, in order of appearance.

CERTAIN DEFINITIONS

Figure 1:
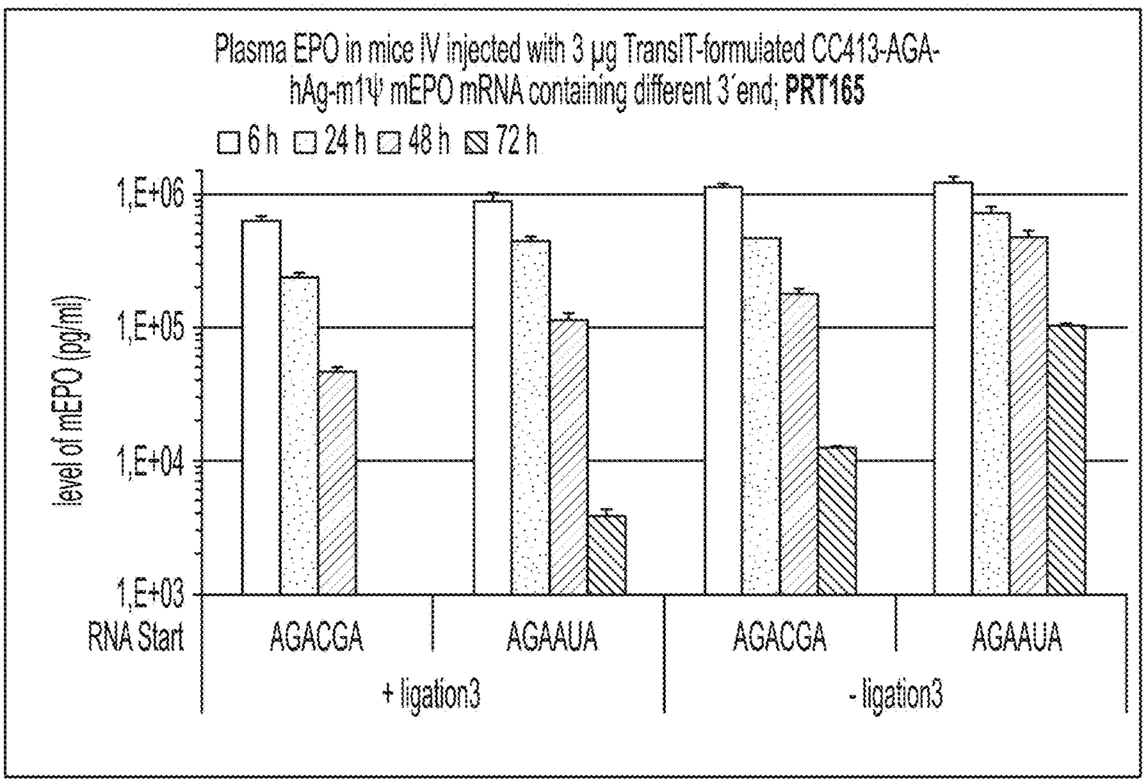
FIG. 1 demonstrates plasma levels of EPO at 6, 24, 48 and 72 hours after intravenous administration of mice with murine EPO (mEPO) mRNA constructs with or without a Lig3 presence in the 3'UTR sequence. Blood was collected 6, 24, 48 and 72 hours after administration and samples were analyzed for mEPO levels via ELISA.

Although the present disclosure is described in detail below, it is to be understood that this disclosure is not limited to the particular methodologies, protocols and reagents described herein as these may vary. It is also to be understood that the terminology used herein is for the purpose of describing particular embodiments only, and is not intended to limit the scope of the present disclosure which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present disclosure will employ, unless otherwise indicated, conventional methods of chemistry, biochemistry, cell biology, immunology, and recombinant DNA techniques which are explained in the literature in the field (cf., e.g., Molecular Cloning: A Laboratory Manual, 2nd Edition, J. Sambrook et al. eds., Cold Spring Harbor Laboratory Press, Cold Spring Harbor 1989).

In the following, the elements of the present disclosure will be described. These elements are listed with specific embodiments, however, it should be understood that they may be combined in any manner and in any number to create additional embodiments. The variously described examples and embodiments should not be construed to limit the present disclosure to only the explicitly described embodiments. This description should be understood to disclose and encompass embodiments which combine the explicitly described embodiments with any number of the disclosed elements. Furthermore, any permutations and combinations of all described elements should be considered disclosed by this description unless the context indicates otherwise. The term "about" means approximately or nearly, and in the context of a numerical value or range set forth herein in some embodiments means±20%, ±10%, ±5%, or ±3% of the numerical value or range recited or claimed.

The terms "a" and "an" and "the" and similar reference used in the context of describing the disclosure (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it was individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the disclosure and does not pose a limitation on the scope of the claims. No language in the specification should be construed as indicating any non-claimed element essential to the practice of the disclosure.

Unless expressly specified otherwise, the term "comprising" is used in the context of the present document to indicate that further members may optionally be present in addition to the members of the list introduced by "comprising". It is, however, contemplated as a specific embodiment of the present disclosure that the term "comprising" encompasses the possibility of no further members being present, i.e., for the purpose of this embodiment "comprising" is to be understood as having the meaning of "consisting of" or "consisting essentially of".

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the present disclosure was not entitled to antedate such disclosure.

In the following, definitions will be provided which apply to all aspects of the present disclosure. The following terms have the following meanings unless otherwise indicated. Any undefined terms have their art recognized meanings.

Agent: As used herein, the term "agent", may refer to a physical entity or phenomenon. In some embodiments, an agent may be characterized by a particular feature and/or effect. In some embodiments, an agent may be a compound, molecule, or entity of any chemical class including, for example, a small molecule, polypeptide, nucleic acid, saccharide, lipid, metal, or a combination or complex thereof. In some embodiments, the term "agent" may refer to a compound, molecule, or entity that comprises a polymer. In some embodiments, the term may refer to a compound or entity that comprises one or more polymeric moieties. In some embodiments, the term "agent" may refer to a compound, molecule, or entity that is substantially free of a particular polymer or polymeric moiety. In some embodiments, the term may refer to a compound, molecule, or entity that lacks or is substantially free of any polymer or polymeric moiety.

Amino acid: in its broadest sense, as used herein, the term "amino acid" refers to a compound and/or substance that can be, is, or has been incorporated into a polypeptide chain, e.g., through formation of one or more peptide bonds. In some embodiments, an amino acid has the general structure $H_2N—C(H)(R)—COOH$. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, pegylation, glycosylation, phosphorylation, and/or substitution (e.g., of the amino group, the carboxylic acid group, one or more protons, and/or the hydroxyl group) as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" may be used to refer to a free amino acid; in some embodiments it may be used to refer to an amino acid residue of a polypeptide.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Antibody agent: As used herein, the term "antibody agent" refers to an agent that specifically binds to a particular antigen. In some embodiments, the term encompasses a polypeptide or polypeptide complex that includes immunoglobulin structural elements sufficient to confer specific binding. For example, in some embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent in or comprises a polypeptide whose amino acid sequence includes structural elements recognized by those skilled in the art to correspond to CDRs1, 2, and 3 of an antibody variable domain; in some such embodiments, an antibody agent in or comprises a polypeptide or set of polypeptides whose amino acid sequence(s) together include structural elements recognized by those skilled in the art to correspond to both heavy chain and light chain variable region CDRs, e.g., heavy chain CDRs 1, 2, and/or 3 and light chain CDRs 1, 2, and/or 3. In some embodiments, an antibody agent is a polypeptide protein having a binding domain which is homologous or largely homologous to an immunoglobulin-binding domain. In some embodiments, an antibody agent may be or comprise a polyclonal antibody preparation. In some embodiments, an antibody agent may be or comprise a monoclonal antibody preparation. In some embodiments, an antibody agent may include one or more constant region sequences that are characteristic of a particular organism, such as a camel, human, mouse, primate, rabbit, rat; in many embodiments, an antibody agent may include one or more constant region sequences that are characteristic of a human. In some embodiments, an antibody agent may include one or more sequence elements that would be recognized by one skilled in the art as a humanized sequence, a primatized sequence, a chimeric sequence, etc. In some embodiments, an antibody agent may be a canonical antibody (e.g., may comprise two heavy chains and two light chains). In some embodiments, an antibody agent may be in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof, single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.].

Associated: Two events or entities are "associated" with one another, as that term is used herein, if the presence, level, degree, type and/or form of one is correlated with that of the other. For example, a particular entity (e.g., polypeptide, genetic signature, metabolite, microbe, etc) is considered to be associated with a particular disease, disorder, or condition, if its presence, level and/or form correlates with incidence of, susceptibility to, severity of, stage of, etc the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell). Binding between two entities may be considered "specific" if, under the conditions assessed, the relevant entities are more likely to associate with one another than with other available binding partners.

Biological Sample: As used herein, the term "biological sample" typically refers to a sample obtained or derived from a biological source (e.g., a tissue or organism or cell culture) of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Combination therapy: As used herein, the term "combination therapy" refers to those situations in which a subject is simultaneously exposed to two or more therapeutic regimens (e.g., two or more therapeutic agents). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s)

or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

Comparable: As used herein, the term "comparable" refers to two or more agents, entities, situations, sets of conditions, etc., that may not be identical to one another but that are sufficiently similar to permit comparison there between so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Corresponding to: As used herein, the term "corresponding to" refers to a relationship between two or more entities. For example, the term "corresponding to" may be used to designate the position/identity of a structural element in a compound or composition relative to another compound or composition (e.g., to an appropriate reference compound or composition). For example, in some embodiments, a monomeric residue in a polymer (e.g., an amino acid residue in a polypeptide or a nucleic acid residue in a polynucleotide) may be identified as "corresponding to" a residue in an appropriate reference polymer. For example, those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the $190^{th}$ amino acid in a particular amino acid chain but rather corresponds to the residue found at 190 in the reference polypeptide; those of ordinary skill in the art readily appreciate how to identify "corresponding" amino acids. For example, those skilled in the art will be aware of various sequence alignment strategies, including software programs such as, for example, BLAST, CS-BLAST, CUSASW++, DIAMOND, FASTA, GGSEARCH/GLSEARCH, Genoogle, HMMER, HHpred/HHsearch, IDF, Infernal, KLAST, USEARCH, parasail, PSI-BLAST, PSI-Search, ScalaBLAST, Sequilab, SAM, SSEARCH, SWAPHI, SWAPHI-LS, SWIMM, or SWIPE that can be utilized, for example, to identify "corresponding" residues in polypeptides and/or nucleic acids in accordance with the present disclosure. Those of skill in the art will also appreciate that, in some instances, the term "corresponding to" may be used to describe an event or entity that shares a relevant similarity with another event or entity (e.g., an appropriate reference event or entity). To give but one example, a gene or protein in one organism may be described as "corresponding to" a gene or protein from another organism in order to indicate, in some embodiments, that it plays an analogous role or performs an analogous function and/or that it shows a particular degree of sequence identity or homology, or shares a particular characteristic sequence element.

Designed: As used herein, the term "designed" refers to an agent (i) whose structure is or was selected by the hand of man; (ii) that is produced by a process requiring the hand of man; and/or (iii) that is distinct from natural substances and other known agents.

Dosing regimen: Those skilled in the art will appreciate that the term "dosing regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Engineered: In general, the term "engineered" refers to the aspect of having been manipulated by the hand of man. For example, a polynucleotide is considered to be "engineered" when two or more sequences that are not linked together in that order in nature are manipulated by the hand of man to be directly linked to one another in the engineered polynucleotide and/or when a particular residue in a polynucleotide is non-naturally occurring and/or is caused through action of the hand of man to be linked with an entity or moiety with which it is not linked in nature.

Epitope: as used herein, the term "epitope" refers to a moiety that is specifically recognized by an immunoglobulin (e.g., antibody or receptor) binding component. In some embodiments, an epitope is comprised of a plurality of chemical atoms or groups on an antigen. In some embodiments, such chemical atoms or groups are surface-exposed when the antigen adopts a relevant three-dimensional conformation. In some embodiments, such chemical atoms or groups are physically near to each other in space when the antigen adopts such a conformation. In some embodiments, at least some such chemical atoms are groups are physically separated from one another when the antigen adopts an alternative conformation (e.g., is linearized).

Expression: As used herein, the term "expression" of a nucleic acid sequence refers to the generation of any gene product from the nucleic acid sequence. In some embodiments, a gene product can be a transcript. In some embodiments, a gene product can be a polypeptide. In some embodiments, expression of a nucleic acid sequence involves one or more of the following: (1) production of an RNA template from a DNA sequence (e.g., by transcription); (2) processing of an RNA transcript (e.g., by splicing, editing, etc); (3) translation of an RNA into a polypeptide or protein; and/or (4) post-translational modification of a polypeptide or protein.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for parenteral administration, for example, by subcutaneous, intramuscular, intravenous or epidural injection as, for example, a sterile solution or suspension, or sustained-release formulation.

Polypeptide: As used herein refers to a polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, pegylation, etc., including combinations thereof. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may be or comprise a stapled polypeptide. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class or family. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that may in some embodiments be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a relevant polypeptide may comprise or consist of a fragment of a parent polypeptide.

Prevent or prevention: as used herein when used in connection with the occurrence of a disease, disorder, and/or condition, refers to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Risk: as will be understood from context, "risk" of a disease, disorder, and/or condition refers to a likelihood that a particular individual will develop the disease, disorder, and/or condition. In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event. In some embodiments a reference sample or group of reference samples are from individuals comparable to a particular individual. In some embodiments, relative risk is 0, 1, 2, 3, 4, 5, 6, 7, 8, 9, 10, or more. In some embodiments, risk may reflect one or more genetic attributes, e.g., which may predispose an individual toward development (or not) of a particular disease, disorder and/or condition. In some embodiments, risk may reflect one or more epigenetic events or attributes and/or one or more lifestyle or environmental events or attributes.

Susceptible to: An individual who is "susceptible to" a disease, disorder, and/or condition is one who has a higher risk of developing the disease, disorder, and/or condition than does a member of the general public. In some embodiments, an individual who is susceptible to a disease, disorder and/or condition may not have been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Vaccination: As used herein, the term "vaccination" refers to the administration of a composition intended to generate an immune response, for example to a disease-associated (e.g., disease-causing) agent. In some embodiments, vaccination can be administered before, during, and/or after exposure to a disease-associated agent, and in certain embodiments, before, during, and/or shortly after exposure to the agent. In some embodiments, vaccination includes multiple administrations, appropriately spaced in time, of a vaccine composition. In some embodiments, vaccination generates an immune response to an infectious agent. In some embodiments, vaccination generates an immune response to a tumor; in some such embodiments, vaccination is "personalized" in that it is partly or wholly directed to epitope(s) (e.g., which may be or include one or more neoepitopes) determined to be present in a particular individual's tumors.

Variant: As used herein in the context of molecules, e.g., nucleic acids, proteins, or small molecules, the term "variant" refers to a molecule that shows significant structural identity with a reference molecule but differs structurally from the reference molecule, e.g., in the presence or absence or in the level of one or more chemical moieties as compared to the reference entity. In some embodiments, a variant also differs functionally from its reference molecule. In general, whether a particular molecule is properly considered to be a "variant" of a reference molecule is based on its degree of structural identity with the reference molecule. As will be appreciated by those skilled in the art, any biological or chemical reference molecule has certain characteristic structural elements. A variant, by definition, is a distinct molecule that shares one or more such characteristic structural elements but differs in at least one aspect from the reference molecule. In some embodiments, a variant polypeptide or nucleic acid may differ from a reference polypeptide or nucleic acid as a result of one or more differences in amino acid or nucleotide sequence and/or one or more differences in chemical moieties (e.g., carbohydrates, lipids, phosphate groups) that are covalently components of the polypeptide or nucleic acid (e.g., that are attached to the polypeptide or nucleic acid backbone). In some embodiments, a variant polypeptide or nucleic acid shows an overall sequence identity with a reference polypeptide or nucleic acid that is at least 85%, 86%, 87%, 88%, 89%, 90%, 91%, 92%, 93%, 94%, 95%, 96%, 97%, or 99%. In some embodiments, a variant polypeptide or nucleic acid does not share at least one characteristic sequence element with a reference polypeptide or nucleic acid. In some embodiments, a reference polypeptide or nucleic acid has one or more biological activities. In some embodiments, a variant polypeptide or nucleic acid shares one or more of the biological activities of the reference polypeptide or nucleic acid. In some embodiments, a variant polypeptide or nucleic acid lacks one or more of the biological activities of the reference polypeptide or nucleic acid. In some embodiments, a variant polypeptide or nucleic acid shows a reduced level of one or more biological activities as compared to the reference polypeptide or nucleic acid. In some embodiments, a polypeptide or nucleic acid of interest is considered to be a "variant" of a reference polypeptide or nucleic acid if it has an amino acid or nucleotide sequence that is identical to that of the reference but for a small number of sequence alterations at particular positions. Typically, fewer than about 20%, about 15%, about 10%, about 9%, about 8%, about 7%, about 6%, about 5%, about 4%, about 3%, or about 2% of the residues in a variant are substituted, inserted, or deleted, as compared to the reference. In some embodiments, a variant polypeptide or nucleic acid comprises about 10, about 9, about 8, about 7, about 6, about 5, about 4, about 3, about 2, or about 1 substituted residues as compared to a reference. Often, a variant polypeptide or nucleic acid comprises a very small number (e.g., fewer than about 5, about 4, about 3, about 2, or about 1) number of substituted, inserted, or deleted, functional residues (i.e., residues that participate in a particular biological activity) relative to the reference. In some embodiments, a variant polypeptide or nucleic acid comprises not more than about 5, about 4, about 3, about 2, or about 1 addition or deletion, and, in some embodiments, comprises no additions or deletions, as compared to the reference. In some embodiments, a variant polypeptide or nucleic acid comprises fewer than about 25, about 20, about 19, about 18, about 17, about 16, about 15, about 14, about 13, about 10, about 9, about 8, about 7, about 6, and commonly fewer than about 5, about 4, about 3, or about 2 additions or deletions as compared to the reference. In some embodiments, a reference polypeptide or nucleic acid is one found in nature.

DETAILED DESCRIPTION OF CERTAIN EMBODIMENTS

The present disclosure provides, among other things, an RNA polynucleotide comprising (i) a 5' cap that is or comprises a cap1 structure, e.g., as disclosed herein; (ii) a 5' UTR sequence comprising a cap proximal sequence, e.g., as disclosed herein; and (iii) a sequence encoding a payload. Also provided herein are compositions and medical preparations comprising the same, as well as methods of making and using the same. In some embodiments, translation efficiency of an RNA encoding a payload, and/or expression of a payload encoded by an RNA, can be improved with an RNA polynucleotide comprising a 5' cap comprising a Cap1 structure disclosed herein, e.g., $m_2^{7,3'-O}Gppp(m_1^{2'-O})ApG$ cap; a 5' UTR comprising a cap proximal sequence disclosed herein, and a sequence encoding a payload. In some embodiments, absence of a self-hybridizing sequence in an RNA polynucleotide encoding a payload can further improve translation efficiency of an RNA encoding a payload, and/or expression of a payload encoded by an RNA payload.

RNA Polynucleotide

The term "polynucleotide" or "nucleic acid", as used herein, refers to DNA and RNA such as genomic DNA, cDNA, mRNA, recombinantly produced and chemically synthesized molecules. A nucleic acid may be single-stranded or double-stranded. RNA includes in vitro transcribed RNA (IVT RNA) or synthetic RNA. According to the invention, a polynucleotide is preferably isolated.

In some embodiments, nucleic acids may be comprised in a vector. The term "vector" as used herein includes any vectors known to the skilled person including plasmid vectors, cosmid vectors, phage vectors such as lambda phage, viral vectors such as retroviral, adenoviral or baculoviral vectors, or artificial chromosome vectors such as bacterial artificial chromosomes (BAC), yeast artificial chromosomes (YAC), or P1 artificial chromosomes (PAC). In some embodiments, a vector may be an expression vector;

alternatively or additionally, in some embodiments, a vector may be a cloning vector. Those skilled in the art will appreciate that, in some embodiments, an expression vector may be, for example, a plasmid; alternatively or additionally, in some embodiments, an expression vector may be a viral vector. Typically, an expression vector will contain a desired coding sequence and appropriate other sequences necessary for the expression of the operably linked coding sequence in a particular host organism (e.g., bacteria, yeast, plant, insect, or mammal) or in in vitro expression systems. Cloning vectors are generally used to engineer and amplify a certain desired fragment (typically a DNA fragment), and may lack functional sequences needed for expression of the desired fragment(s).

In some embodiments, a nucleic acid as described and/or utilized herein may be or comprise recombinant and/or isolated molecules.

Those skilled in the art, reading the present disclosure, will understand that the term "RNA" typically refers to a nucleic acid molecule which includes ribonucleotide residues. In some embodiments, an RNA contains all or a majority of ribonucleotide residues. As used herein, "ribonucleotide" refers to a nucleotide with a hydroxyl group at the 2'-position of a β-D-ribofuranosyl group. In some embodiments, an RNA may be partly or fully double stranded RNA; in some embodiments, an RNA may comprise two or more distinct nucleic acid strands (e.g., separate molecules) that are partly or fully hybridized with one another. In many embodiments, an RNA is a single strand, which may in some embodiments, self-hybridize or otherwise fold into secondary and/or tertiary structures. In some embodiments, an RNA as described and/or utilized herein does not self-hybridize, at least with respect to certain sequences as described herein. In some embodiments, an RNA may be an isolated RNA such as partially purified RNA, essentially pure RNA, synthetic RNA, recombinantly produced RNA, and/or a modified RNA (where the term "modified" is understood to indicate that one or more residues or other structural elements of the RNA differs from naturally occurring RNA; for example, in some embodiments, a modified RNA differs by the addition, deletion, substitution and/or alteration of one or more nucleotides and/or by one or more moieties or characteristics of a nucleotide—e.g., of a nucleoside or of a backbone structure or linkage). In some embodiments, a modification may be or comprise addition of non-nucleotide material to internal RNA nucleotides or to the end(s) of RNA. It is also contemplated herein that nucleotides in RNA (e.g., in a modified RNA) may be non-standard nucleotides, such as chemically synthesized nucleotides or deoxynucleotides. For the present disclosure, these altered RNAs are considered analogs of naturally-occurring RNA.

In some embodiments of the present disclosure, an RNA is or comprises messenger RNA (mRNA) that relates to an RNA transcript which encodes a polypeptide.

In some embodiments, an RNA disclosed herein comprises: a 5' cap comprising a 5' cap disclosed herein; a 5' untranslated region comprising a cap proximal sequence (5'-UTR), a sequence encoding a payload (e.g., a polypeptide); a 3' untranslated region (3'-UTR); and/or a polyadenylate (PolyA) sequence.

In some embodiments, an RNA disclosed herein comprises the following components in 5' to 3' orientation: a 5' cap comprising a 5' cap disclosed herein; a 5' untranslated region comprising a cap proximal sequence (5'-UTR), a sequence encoding a payload (e.g., a polypeptide); a 3' untranslated region (3'-UTR); and a PolyA sequence.

In some embodiments, an RNA is produced by in vitro transcription or chemical synthesis. In some embodiments, an mRNA is produced by in vitro transcription using a DNA template where DNA refers to a nucleic acid that contains deoxyribonucleotides.

In some embodiments, an RNA disclosed herein is in vitro transcribed RNA (IVT-RNA) and may be obtained by in vitro transcription of an appropriate DNA template. The promoter for controlling transcription can be any promoter for any RNA polymerase. A DNA template for in vitro transcription may be obtained by cloning of a nucleic acid, in particular cDNA, and introducing it into an appropriate vector for in vitro transcription. The cDNA may be obtained by reverse transcription of RNA.

In some embodiments, an RNA is "replicon RNA" or simply a "replicon", in particular "self-replicating RNA" or "self-amplifying RNA". In some embodiments, a replicon or self-replicating RNA is derived from or comprises elements derived from a ssRNA virus, in particular a positive-stranded ssRNA virus such as an alphavirus. Alphaviruses are typical representatives of positive-stranded RNA viruses. Alphaviruses replicate in the cytoplasm of infected cells (for review of the alphaviral life cycle see Jose et al., Future Microbiol., 2009, vol. 4, pp. 837-856). The total genome length of many alphaviruses typically ranges between 11,000 and 12,000 nucleotides, and the genomic RNA typically has a 5'-cap, and a 3' poly(A) tail. The genome of alphaviruses encodes non-structural proteins (involved in transcription, modification and replication of viral RNA and in protein modification) and structural proteins (forming the virus particle). There are typically two open reading frames (ORFs) in the genome. The four non-structural proteins (nsP1-nsP4) are typically encoded together by a first ORF beginning near the 5' terminus of the genome, while alphavirus structural proteins are encoded together by a second ORF which is found downstream of the first ORF and extends near the 3' terminus of the genome. Typically, the first ORF is larger than the second ORF, the ratio being roughly 2:1. In cells infected by an alphavirus, only the nucleic acid sequence encoding non-structural proteins is translated from the genomic RNA, while the genetic information encoding structural proteins is translatable from a subgenomic transcript, which is an RNA polynucleotide that resembles eukaryotic messenger RNA (mRNA; Gould et al., 2010, Antiviral Res., vol. 87 pp. 111-124). Following infection, i.e. at early stages of the viral life cycle, the (+) stranded genomic RNA directly acts like a messenger RNA for the translation of the open reading frame encoding the non-structural poly-protein (nsP1234). Alphavirus-derived vectors have been proposed for delivery of foreign genetic information into target cells or target organisms. In simple approaches, the open reading frame encoding alphaviral structural proteins is replaced by an open reading frame encoding a protein of interest. Alphavirus-based trans-replication systems rely on alphavirus nucleotide sequence elements on two separate nucleic acid molecules: one nucleic acid molecule encodes a viral replicase, and the other nucleic acid molecule is capable of being replicated by said replicase in trans (hence the designation trans-replication system). Trans-replication requires the presence of both these nucleic acid molecules in a given host cell. The nucleic acid molecule capable of being replicated by the replicase in trans must comprise certain alphaviral sequence elements to allow recognition and RNA synthesis by the alphaviral replicase.

In some embodiments, an RNA described herein may have modified nucleosides. In some embodiments, an RNA comprises a modified nucleoside in place of at least one (e.g., every) uridine.

The term “uracil,” as used herein, describes one of the nucleobases that can occur in the nucleic acid of RNA. The structure of uracil is:

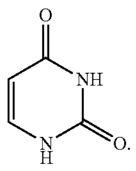

The term “uridine,” as used herein, describes one of the nucleosides that can occur in RNA. The structure of uridine is:

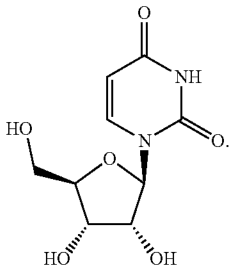 [SMILES: O=c1ccn([C@@H]2O[C@H](CO)[C@@H](O)[C@H]2O)c(=O)[nH]1]

UTP (uridine 5'-triphosphate) has the following structure:

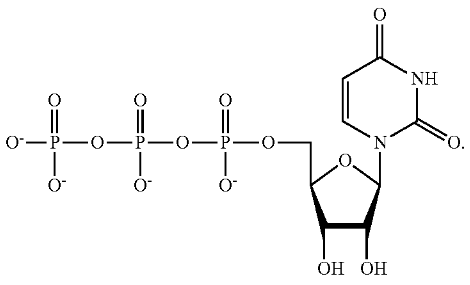

Pseudo-UTP (pseudouridine-5'-triphosphate) has the following structure:

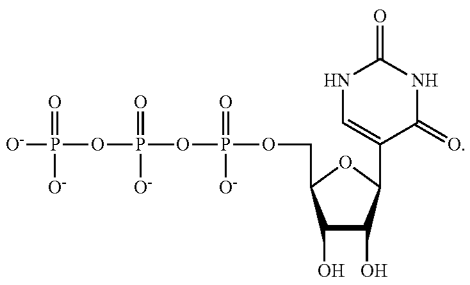

“Pseudouridine” is one example of a modified nucleoside that is an isomer of uridine, where the uracil is attached to the pentose ring via a carbon-carbon bond instead of a nitrogen-carbon glycosidic bond.

Another exemplary modified nucleoside is N1-methylpseudouridine (m1Ψ), which has the structure:

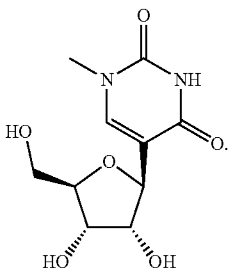 [SMILES: Cn1cc([C@@H]2O[C@H](CO)[C@@H](O)[C@H]2O)c(=O)[nH]c1=O]

N1-methylpseudouridine-5'-triphosphate (m1ΨTP) has the following structure:

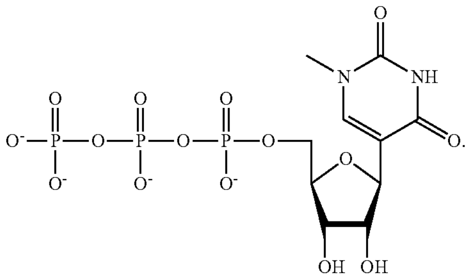

Another exemplary modified nucleoside is 5-methyluridine (m5U), which has the structure:

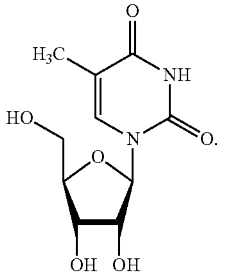

In some embodiments, one or more uridine in an RNA described herein is replaced by a modified nucleoside. In some embodiments, a modified nucleoside is a modified uridine. In some embodiments, an RNA comprises a modified nucleoside in place of at least one uridine. In some embodiments, an RNA comprises a modified nucleoside in place of each uridine.

In some embodiments, a modified nucleoside is independently selected from pseudouridine (Ψ), N1-methylpseudouridine (m1Ψ), and 5-methyluridine (m5U). In some embodiments, a modified nucleoside comprises pseudouridine (Ψ). In some embodiments, a modified nucleoside comprises N1-methyl-pseudouridine (m1Ψ). In some embodiments, a modified nucleoside comprises 5-methyluridine (m5U). In some embodiments, an RNA may comprise more than one type of modified nucleoside, and a modified nucleosides are independently selected from pseudouridine (Ψ), N1-methylpseudouridine (m1Ψ), and 5-methyluridine (m5U). In some embodiments, a modified nucleosides comprise pseudouridine (Ψ) and N1-methylpseudouridine (m1Ψ). In some embodiments, a modified nucleosides comprise pseudouridine (Ψ) and 5-methyluridine (m5U). In some embodiments, a modified nucleosides comprise N1-methylpseudouridine (m1Ψ) and 5-methyluridine (m5U). In some embodiments, a modified nucleosides comprise pseudouridine (Ψ), N1-methylpseudouridine (m1Ψ), and 5-methyluridine (m5U).

In some embodiments, a modified nucleoside replacing one or more, e.g., all, uridine in the RNA may be any one or more of 3-methyl-uridine ($m^3U$), 5-methoxy-uridine ($mo^5U$), 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine ($ho^5U$), 5-aminoallyl-uridine, 5-halo-uridine (e.g., 5-iodo-uridine or 5-bromo-uridine), uridine 5-oxyacetic acid ($cmo^5U$), uridine 5-oxyacetic acid methyl ester ($mcmo^5U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine ($mcm^5U$), 5-methoxycarbonylmethyl-2-thio-uridine ($mcm^5s^2U$), 5-aminomethyl-2-thio-uridine ($nm^5s^2U$), 5-methylaminomethyl-uridine ($mnm^5U$), 1-ethyl-pseudouridine, 5-methylaminomethyl-2-thio-uridine ($mnm^5s^2U$), 5-methylaminomethyl-2-seleno-uridine ($mnm^5se^2U$), 5-carbamoylmethyl-uridine ($ncm^5U$), 5-carboxymethylaminomethyl-uridine ($cmnm^5U$), 5-carboxymethylaminomethyl-2-thio-uridine ($cmnm^5s^2U$), 5-propynyl-uridine, 1-propynyl-pseudouridine, 5-taurinomethyl-uridine ($\tau m^5U$), 1-taurinomethyl-pseudouridine, 5-taurinomethyl-2-thio-uridine (τm5s2U), 1-taurinomethyl-4-thio-pseudouridine), 5-methyl-2-thio-uridine ($m^5s^2U$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine ($acp^3U$), 1-methyl-3-(3-amino-3-carboxypropyl)pseudouridine ($acp^3\psi$), 5-(isopentenylaminomethyl)uridine ($inm^5U$), 5-(isopentenylaminomethyl)-2-thio-uridine ($inm^5s^2U$), α-thio-uridine, 2'-O-methyl-uridine (Um), 5,2'-O-dimethyl-uridine ($m^5Um$), 2'-O-methyl-pseudouridine (ψm), 2-thio-2'-O-methyl-uridine ($s^2Um$), 5-methoxycarbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), 5-(isopentenylaminomethyl)-2'-O-methyl-uridine ($inm^5Um$), 1-thio-uridine, deoxythymidine, 2'-F-ara-uridine, 2'-F-uridine, 2'-OH-ara-uridine, 5-(2-carbomethoxyvinyl) uridine, 5-[3-(1-E-propenylamino)uridine, or any other modified uridine known in the art.

In some embodiments, an RNA comprises other modified nucleosides or comprises further modified nucleosides, e.g., modified cytidine. For example, in some embodiments, in an RNA 5-methylcytidine is substituted partially or completely, preferably completely, for cytidine. In some embodiments, an RNA comprises 5-methylcytidine and one or more selected from pseudouridine (ψ), N1-methyl-pseudouridine (m1ψ), and 5-methyl-uridine (m5U). In some embodiments, an RNA comprises 5-methylcytidine and N1-methyl-pseudouridine (m1ψ). In some embodiments, the RNA comprises 5-methylcytidine in place of each cytidine and N1-methyl-pseudouridine (m1ψ) in place of each uridine.

In some embodiments, an RNA encoding a payload, e.g., a vaccine antigen, is expressed in cells of a subject treated to provide a payload, e.g., vaccine antigen. In some embodiments, the RNA is transiently expressed in cells of the subject. In some embodiments, the RNA is in vitro transcribed RNA. In some embodiments, expression of a payload, e.g., a vaccine antigen is at the cell surface. In some embodiments, a payload, e.g., a vaccine antigen is expressed and presented in the context of MHC. In some embodiments, expression of a payload, e.g., a vaccine antigen is into the extracellular space, i.e., the vaccine antigen is secreted.

In the context of the present disclosure, the term "transcription" relates to a process, wherein the genetic code in a DNA sequence is transcribed into RNA. Subsequently, the RNA may be translated into peptide or protein.

According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". According to the present invention, the RNA used in the present invention preferably is in vitro transcribed RNA (IVT-RNA) and may be obtained by in vitro transcription of an appropriate DNA template. The promoter for controlling transcription can be any promoter for any RNA polymerase. Particular examples of RNA polymerases are the T7, T3, and SP6 RNA polymerases. Preferably, the in vitro transcription according to the invention is controlled by a T7 or SP6 promoter. A DNA template for in vitro transcription may be obtained by cloning of a nucleic acid, in particular cDNA, and introducing it into an appropriate vector for in vitro transcription. The cDNA may be obtained by reverse transcription of RNA.

With respect to RNA, the term "expression" or "translation" relates to the process in the ribosomes of a cell by which a strand of mRNA directs the assembly of a sequence of amino acids to make a peptide or protein.

In some embodiments, after administration of an RNA described herein, e.g., formulated as RNA lipid particles, at least a portion of the RNA is delivered to a target cell. In some embodiments, at least a portion of the RNA is delivered to the cytosol of the target cell. In some embodiments, the RNA is translated by the target cell to produce the peptide or protein it encodes. In some embodiments, the target cell is a spleen cell. In some embodiments, the target cell is an antigen presenting cell such as a professional antigen presenting cell in the spleen. In some embodiments, the target cell is a dendritic cell or macrophage. RNA particles such as RNA lipid particles described herein may be used for delivering RNA to such target cell. Accordingly, the present disclosure also relates to a method for delivering RNA to a target cell in a subject comprising the administration of the RNA particles described herein to the subject. In some embodiments, the RNA is delivered to the cytosol of the target cell. In some embodiments, the RNA is translated by the target cell to produce the peptide or protein encoded by the RNA. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

In some embodiments, nucleic acid compositions described herein, e.g., compositions comprising a lipid nanoparticle encapsulated mRNA are characterized by (e.g., when administered to a subject) sustained expression of an encoded polypeptide. For example, in some embodiments, such compositions are characterized in that, when administered to a human, they achieve detectable polypeptide expression in a biological sample (e.g., serum) from such human and, in some embodiments, such expression persists for a period of time that is at least at least 36 hours or longer, including, e.g., at least 48 hours, at least 60 hours, at least 72 hours, at least 96 hours, at least 120 hours, at least 148 hours, or longer.

In some embodiments, the RNA encoding vaccine antigen to be administered according to the invention is non-immunogenic. RNA encoding immunostimulant may be administered according to the invention to provide an adjuvant effect. The RNA encoding immunostimulant may be standard RNA or non-immunogenic RNA.

The term "non-immunogenic RNA" as used herein refers to RNA that does not induce a response by the immune system upon administration, e.g., to a mammal, or induces a weaker response than would have been induced by the same RNA that differs only in that it has not been subjected to the modifications and treatments that render the non-immunogenic RNA non-immunogenic, i.e., than would have been induced by standard RNA (stdRNA). In one preferred embodiment, non-immunogenic RNA, which is also termed modified RNA (modRNA) herein, is rendered non-immunogenic by incorporating modified nucleosides suppressing RNA-mediated activation of innate immune receptors into the RNA and removing double-stranded RNA (dsRNA).

For rendering the non-immunogenic RNA non-immunogenic by the incorporation of modified nucleosides, any modified nucleoside may be used as long as it lowers or suppresses immunogenicity of the RNA. Particularly preferred are modified nucleosides that suppress RNA-mediated activation of innate immune receptors. In some embodiments, the modified nucleosides comprises a replacement of one or more uridines with a nucleoside comprising a modified nucleobase. In some embodiments, the modified nucleobase is a modified uracil. In some embodiments, the nucleoside comprising a modified nucleobase is selected from the group consisting of 3-methyl-uridine ($m^3U$), 5-methoxy-uridine ($mo^5U$), 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine ($ho^5U$), 5-aminoallyl-uridine, 5-halo-uridine (e.g., 5-iodo-uridine or 5-bromo-uridine), uridine 5-oxyacetic acid ($cmo^5U$), uridine 5-oxyacetic acid methyl ester ($mcmo^5U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine ($mcm^5U$), 5-methoxycarbonylmethyl-2-thio-uridine ($mcm^5s^2U$), 5-aminomethyl-2-thio-uridine ($nm^5s^2U$), 5-methylaminomethyl-uridine ($mnm^5U$), 1-ethyl-pseudouridine, 5-methylaminomethyl-2-thio-uridine ($mnm^5s^2U$), 5-methylaminomethyl-2-seleno-uridine ($mnm^5se^2U$), 5-carbamoylmethyl-uridine ($ncm^5U$), 5-carboxymethylaminomethyl-uridine ($cmnm^5U$), 5-carboxymethylaminomethyl-2-thio-uridine ($cmnm^5s^2U$), 5-propynyl-uridine, 1-propynyl-pseudouridine, 5-taurinomethyl-uridine ($\tau m^5U$), 1-taurinomethyl-pseudouridine, 5-taurinomethyl-2-thio-uridine (τm5s2U), 1-taurinomethyl-4-thio-pseudouridine), 5-methyl-2-thio-uridine ($m^5s^2U$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine ($acp^3U$), 1-methyl-3-(3-amino-3-carboxypropyl)pseudouridine ($acp^3\psi$), 5-(isopentenylaminomethyl)uridine ($inm^5U$), 5-(isopentenylaminomethyl)-2-thio-uridine ($inm^5s^2U$), α-thio-uridine, 2'-O-methyl-uridine (Um), 5,2'-O-dimethyl-uridine ($m^5Um$), 2'-O-methyl-pseudouridine (ψm), 2-thio-2'-O-methyl-uridine ($s^2Um$), 5-methoxycarbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), 5-(isopentenylaminomethyl)-2'-O-methyl-uridine ($inm^5Um$), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)uridine. In one particularly preferred embodiment, the nucleoside comprising a modified nucleobase is pseudouridine (ψ), N1-methyl-pseudouridine (m1ψ) or 5-methyl-uridine (m5U), in particular N1-methyl-pseudouridine.

In some embodiments, the replacement of one or more uridines with a nucleoside comprising a modified nucleobase comprises a replacement of at least 1%, at least 2%, at least 3%, at least 4%, at least 5%, at least 10%, at least 25%, at least 50%, at least 75%, at least 90%, at least 95%, at least 96%, at least 97%, at least 98%, at least 99% or 100% of the uridines. During synthesis of mRNA by in vitro transcription (IVT) using T7 RNA polymerase significant amounts of aberrant products, including double-stranded RNA (dsRNA) are produced due to unconventional activity of the enzyme. dsRNA induces inflammatory cytokines and activates effector enzymes leading to protein synthesis inhibition. dsRNA can be removed from RNA such as IVT RNA, for example, by ion-pair reversed phase HPLC using a non-porous or porous C-18 polystyrene-divinylbenzene (PS-DVB) matrix. Alternatively, an enzymatic based method using *E. coli* RNaseIII that specifically hydrolyzes dsRNA but not ssRNA, thereby eliminating dsRNA contaminants from IVT RNA preparations can be used. Furthermore, dsRNA can be separated from ssRNA by using a cellulose material. In some embodiments, an RNA preparation is contacted with a cellulose material and the ssRNA is separated from the cellulose material under conditions which allow binding of dsRNA to the cellulose material and do not allow binding of ssRNA to the cellulose material.

As the term is used herein, "remove" or "removal" refers to the characteristic of a population of first substances, such as non-immunogenic RNA, being separated from the proximity of a population of second substances, such as dsRNA, wherein the population of first substances is not necessarily devoid of the second substance, and the population of second substances is not necessarily devoid of the first substance. However, a population of first substances characterized by the removal of a population of second substances has a measurably lower content of second substances as compared to the non-separated mixture of first and second substances.

In some embodiments, the removal of dsRNA from non-immunogenic RNA comprises a removal of dsRNA such that less than 10%, less than 5%, less than 4%, less than 3%, less than 2%, less than 1%, less than 0.5%, less than 0.3%, or less than 0.1% of the RNA in the non-immunogenic RNA composition is dsRNA. In some embodiments, the non-immunogenic RNA is free or essentially free of dsRNA. In some embodiments, the non-immunogenic RNA composition comprises a purified preparation of single-stranded nucleoside modified RNA. For example, in some embodiments, the purified preparation of single-stranded nucleoside modified RNA is substantially free of double stranded RNA (dsRNA). In some embodiments, the purified preparation is at least 90%, at least 91%, at least 92%, at least 93%, at least 94%, at least 95%, at least 96%, at least 97%, at least 98%, at least 99%, at least 99.5%, or at least 99.9% single stranded nucleoside modified RNA, relative to all other nucleic acid molecules (DNA, dsRNA, etc.).

In some embodiments, the non-immunogenic RNA is translated in a cell more efficiently than standard RNA with the same sequence. In some embodiments, translation is enhanced by a factor of 2-fold relative to its unmodified counterpart. In some embodiments, translation is enhanced by a 3-fold factor. In some embodiments, translation is enhanced by a 4-fold factor. In some embodiments, translation is enhanced by a 5-fold factor. In some embodiments, translation is enhanced by a 6-fold factor. In some embodiments, translation is enhanced by a 7-fold factor. In some embodiments, translation is enhanced by an 8-fold factor. In some embodiments, translation is enhanced by a 9-fold factor. In some embodiments, translation is enhanced by a 10-fold factor. In some embodiments, translation is enhanced by a 15-fold factor. In some embodiments, translation is enhanced by a 20-fold factor. In some embodiments, translation is enhanced by a 50-fold factor. In some embodiments, translation is enhanced by a 100-fold factor. In some embodiments, translation is enhanced by a 200-fold factor. In some embodiments, translation is enhanced by a 500-fold factor. In some embodiments, translation is enhanced by a 1000-fold factor. In some embodiments, translation is enhanced by a 2000-fold factor. In some embodiments, the factor is 10-1000-fold. In some embodiments, the factor is 10-100-fold. In some embodiments, the factor is 10-200-fold. In some embodiments, the factor is 10-300-fold. In some embodiments, the factor is 10-500-fold. In some embodiments, the factor is 20-1000-fold. In some embodiments, the factor is 30-1000-fold. In some embodiments, the factor is 50-1000-fold. In some embodiments, the factor is 100-1000-fold. In some embodiments, the factor is 200-1000-fold. In some embodiments, translation is enhanced by any other significant amount or range of amounts.

In some embodiments, the non-immunogenic RNA exhibits significantly less innate immunogenicity than standard RNA with the same sequence. In some embodiments, the non-immunogenic RNA exhibits an innate immune response that is 2-fold less than its unmodified counterpart. In some embodiments, innate immunogenicity is reduced by a 3-fold factor. In some embodiments, innate immunogenicity is reduced by a 4-fold factor. In some embodiments, innate immunogenicity is reduced by a 5-fold factor. In some embodiments, innate immunogenicity is reduced by a 6-fold factor. In some embodiments, innate immunogenicity is reduced by a 7-fold factor. In some embodiments, innate immunogenicity is reduced by a 8-fold factor. In some embodiments, innate immunogenicity is reduced by a 9-fold factor. In some embodiments, innate immunogenicity is reduced by a 10-fold factor. In some embodiments, innate immunogenicity is reduced by a 15-fold factor. In some embodiments, innate immunogenicity is reduced by a 20-fold factor. In some embodiments, innate immunogenicity is reduced by a 50-fold factor. In some embodiments, innate immunogenicity is reduced by a 100-fold factor. In some embodiments, innate immunogenicity is reduced by a 200-fold factor. In some embodiments, innate immunogenicity is reduced by a 500-fold factor. In some embodiments, innate immunogenicity is reduced by a 1000-fold factor. In some embodiments, innate immunogenicity is reduced by a 2000-fold factor.

The term "exhibits significantly less innate immunogenicity" refers to a detectable decrease in innate immunogenicity. In some embodiments, the term refers to a decrease such that an effective amount of the non-immunogenic RNA can be administered without triggering a detectable innate immune response. In some embodiments, the term refers to a decrease such that the non-immunogenic RNA can be repeatedly administered without eliciting an innate immune response sufficient to detectably reduce production of the protein encoded by the non-immunogenic RNA. In some embodiments, the decrease is such that the non-immunogenic RNA can be repeatedly administered without eliciting an innate immune response sufficient to eliminate detectable production of the protein encoded by the non-immunogenic RNA. "Immunogenicity" is the ability of a foreign substance, such as RNA, to provoke an immune response in the body of a human or other animal. The innate immune system is the component of the immune system that is relatively unspecific and immediate. It is one of two main components of the vertebrate immune system, along with the adaptive immune system.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence.

As used herein, the terms "linked," "fused", or "fusion" are used interchangeably. These terms refer to the joining together of two or more elements or components or domains.

Codon Optimization

In some embodiments, a payload (e.g., a polypeptide) described herein is encoded by a coding sequence which is codon-optimized and/or the G/C content of which is increased compared to wild type coding sequence. In some embodiments, one or more sequence regions of the coding sequence are codon-optimized and/or increased in the G/C content compared to the corresponding sequence regions of the wild type coding sequence. In some embodiments, codon-optimization and/or increased the G/C content does not change the sequence of the encoded amino acid sequence.

The term "codon-optimized" is understood by those in the art to refer to alteration of codons in the coding region of a nucleic acid molecule to reflect the typical codon usage of a host organism without preferably altering the amino acid sequence encoded by the nucleic acid molecule. Within the context of the present disclosure, coding regions are preferably codon-optimized for optimal expression in a subject to be treated using an RNA polynucleotide described herein. Codon-optimization is based on the finding that the translation efficiency is also determined by a different frequency in the occurrence of tRNAs in cells. Thus, the sequence of RNA may be modified such that codons for which frequently occurring tRNAs are available are inserted in place of "rare codons".

In some embodiments, guanosine/cytidine (G/C) content of a coding region (e.g., of a payload sequence) of an RNA is increased compared to the G/C content of the corresponding coding sequence of a wild type RNA encoding the payload, wherein the amino acid sequence encoded by the RNA is preferably not modified compared to the amino acid sequence encoded by the wild type RNA. This modification of the RNA sequence is based on the fact that the sequence of any RNA region to be translated is important for efficient translation of that mRNA. Sequences having an increased G (guanosine)/C (cytidine) content are more stable than sequences having an increased A (adenosine)/U (uridine) content. In respect to the fact that several codons code for one and the same amino acid (so-called degeneration of the genetic code), the most favourable codons for the stability can be determined (so-called alternative codon usage). Depending on the amino acid to be encoded by the RNA, there are various possibilities for modification of the RNA sequence, compared to its wild type sequence. In particular, codons which contain A and/or U nucleosides can be modified by substituting these codons by other codons, which code for the same amino acids but contain no A and/or U or contain a lower content of A and/or U nucleosides.

In some embodiments, G/C content of a coding region of an RNA described herein is increased by at least 10%, at least 20%, at least 30%, at least 40%, at least 50%, at least 55%, or even more compared to the G/C content of a coding region of a wild type RNA.

5' Cap

RNA capping is well researched and is described, e.g., in Decroly E et al. (2012) *Nature Reviews* 10: 51-65; and in Ramanathan A. et al., (2016) *Nucleic Acids Res;* 44(16): 7511-7526, the entire contents of each of which is hereby incorporated by reference. 5' caps include a Cap-0 (also referred herein as "Cap0"), a Cap-1 (also referred herein as "Cap1"), or Cap-2 (also referred herein as "Cap2"). See, e.g., FIG. 1 of Ramanathan A et al., and FIG. 1 of Decroly E et al.

The term "5'-cap" as used herein refers to a structure found on the 5'-end of an RNA, e.g., mRNA, and generally includes a guanosine nucleotide connected to an RNA, e.g., mRNA, via a 5'- to 5'-triphosphate linkage (also referred to as Gppp or G(5')ppp(5')). In some embodiments, a guanosine nucleoside included in a 5' cap may be modified, for example, by methylation at one or more positions (e.g., at the 7-position) on a base (guanine), and/or by methylation at one or more positions of a ribose. In some embodiments, a guanosine nucleoside included in a 5' cap comprises a 3'O methylation at a ribose (3'OMeG). In some embodiments, a guanosine nucleoside included in a 5' cap comprises methylation at the 7-position of guanine (m7G). In some embodiments, a guanosine nucleoside included in a 5' cap comprises methylation at the 7-position of guanine and a 3' O methylation at a ribose (m7(3'OMeG)).

In some embodiments, providing an RNA with a 5'-cap disclosed herein or a 5'-cap analog may be achieved by in vitro transcription, in which a 5'-cap is co-transcriptionally expressed into an RNA strand, or may be attached to an RNA post-transcriptionally using capping enzymes. In some embodiments, co-transcriptional capping with a cap disclosed herein, e.g., with a cap1 or a cap1 analog, improves the capping efficiency of an RNA compared to co-transcriptional capping with an appropriate reference comparator. In some embodiments, improving capping efficiency can increase a translation efficiency and/or translation rate of an RNA, and/or increase expression of an encoded polypeptide.

In some embodiments, an RNA described herein comprises a 5'-cap or a 5' cap analog, e.g., a Cap0, a Cap1 or a Cap2. In some embodiments, a provided RNA does not have uncapped 5'-triphosphates. In some embodiments, an RNA may be capped with a 5'-cap analog. In some embodiments, an RNA described herein comprises a Cap0. In some embodiments, an RNA described herein comprises a Cap1, e.g., as described herein. In some embodiments, an RNA described herein comprises a Cap2.

In some embodiments, a Cap0 structure comprises a guanosine nucleoside methylated at the 7-position of guanine (m7G). In some embodiments, a Cap0 structure is connected to an RNA via a 5'- to 5'-triphosphate linkage and is also referred to herein as m7Gppp or m7G(5')ppp(5').

In some embodiments, a Cap1 structure comprises a guanosine nucleoside methylated at the 7-position of guanine (m7G) and a 2'O methylated first nucleotide in an RNA (2'OMe$N_1$). In some embodiments, a Cap1 structure is connected to an RNA via a 5'- to 5'-triphosphate linkage and is also referred to herein as m7Gppp(2'OMe$N_1$) or m7G(5')ppp(5')(2'OMe$N_1$). In some embodiments, $N_1$ is chosen from A, C, G, or U. In some embodiments, $N_1$ is A. In some embodiments, $N_1$ is C. In some embodiments, $N_1$ is G. In some embodiments, $N_1$ is U.

In some embodiments, a m7G(5')ppp(5')(2'OMe$N_1$) Cap1 structure comprises a second nucleotide, $N_2$ which is a cap proximal nucleotide at position 2 and is chosen from A, G, C, or U (m7G(5')ppp(5')(2'OMe$N_1$)$N_2$). In some embodiments, $N_2$ is A. In some embodiments, $N_2$ is C. In some embodiments, $N_2$ is G. In some embodiments, $N_2$ is U.

In some embodiments, a cap1 structure is or comprises m7G(5')ppp(5')(2'OMe$A_1$)p$G_2$ wherein A is a cap proximal nucleotide at position +1 and G is a cap proximal nucleotide at position +2, and has the following structure:

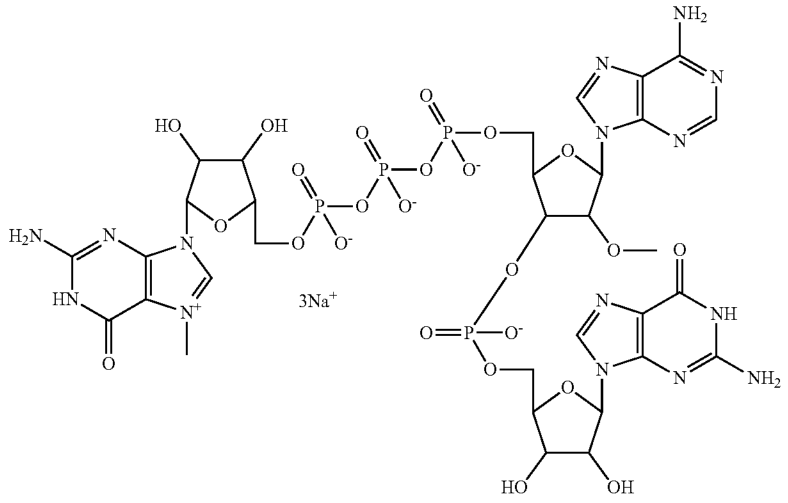 [SMILES: COC1C(OP(=O)([O-])OCC2OC(n3cnc4c(=O)[nH]c(N)nc43)C(O)C2O)C(COP(=O)([O-])OP(=O)([O-])OP(=O)([O-])OCC2OC(n3c[n+](C)c4c(=O)[nH]c(N)nc43)C(O)C2O)OC1n1cnc2c(N)ncnc21]
In some embodiments, a cap1 structure is or comprises m7G(5')ppp(5')(2'OMeA$_1$)pU$_2$ wherein A is a cap proximal nucleotide at position 1 and U is a cap proximal nucleotide at position 2, and has the following structure:
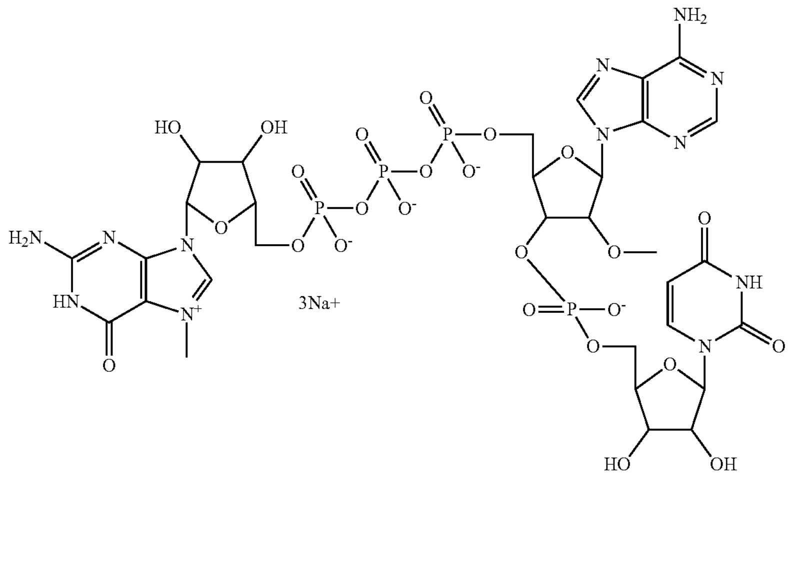 [SMILES: COC1C(OP(=O)([O-])OCC2OC(n3ccc(=O)[nH]c3=O)C(O)C2O)C(COP(=O)([O-])OP(=O)([O-])OP(=O)([O-])OCC2OC(n3c[n+](C)c4c(=O)[nH]c(N)nc43)C(O)C2O)OC1n1cnc2c(N)ncnc21]

In some embodiments, a cap1 structure is or comprises m7G(5')ppp(5')(2'OMeG$_1$)pG$_2$ wherein G is a cap proximal nucleotide at position 1 and G is a cap proximal nucleotide at position 2, and has the following structure:

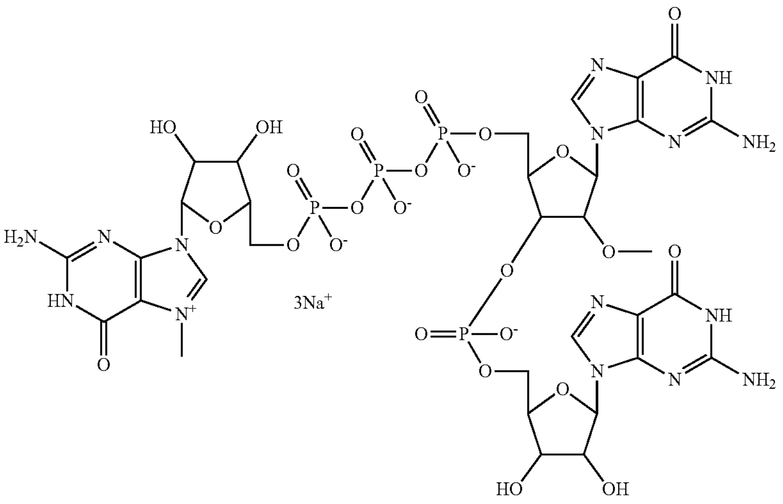 [SMILES: COC1C(OP(=O)([O-])OCC2OC(n3cnc4c(=O)[nH]c(N)nc43)C(O)C2O)C(COP(=O)([O-])OP(=O)([O-])OP(=O)([O-])OCC2OC(n3c[n+](C)c4c(=O)[nH]c(N)nc43)C(O)C2O)OC1n1cnc2c(=O)[nH]c(N)nc21]

In some embodiments, a Cap1 structure comprises a guanosine nucleoside methylated at the 7-position of guanine (m7G) and one or more additional modifications, e.g., methylation on a ribose, and a 2'O methylated first nucleotide in an RNA. In some embodiments, a Cap1 structure comprises a guanosine nucleoside methylated at the 7-position of guanine and a 3'O methylation at a ribose (m7 (3'OMeG)); and a 2'O methylated first nucleotide in an RNA (2'OMeN$_1$). In some embodiments, a Cap1 structure is connected to an RNA via a 5'- to 5'-triphosphate linkage and is also referred to herein as m7(3'OMeG)ppp(2'OMeN$_1$) or m7(3'OMeG)(5')ppp(5')(2'OMeN$_1$). In some embodiments, N$_1$ is chosen from A, C, G, or U. In some embodiments, N$_1$ is A. In some embodiments, N$_1$ is C. In some embodiments, N$_1$ is G. In some embodiments, N$_1$ is U.

In some embodiments, a m7(3'oMeG)(5')ppp(5') (2'OMeN$_1$) Cap1 structure comprises a second nucleotide, N$_2$ which is a cap proximal nucleotide at position 2 and is chosen from A, G, C, or U (m7(3'OMeG)(5')ppp(5') (2'OMeN$_1$)N$_2$). In some embodiments, N$_2$ is A. In some embodiments, N$_2$ is C. In some embodiments, N$_2$ is G. In some embodiments, N$_2$ is U.

In some embodiments, a cap1 structure is or comprises m7(3'OMeG)(5')ppp(5')(2'OMeA$_1$)pG$_2$ wherein A is a cap proximal nucleotide at position 1 and G is a cap proximal nucleotide at position 2 and has the following structure:

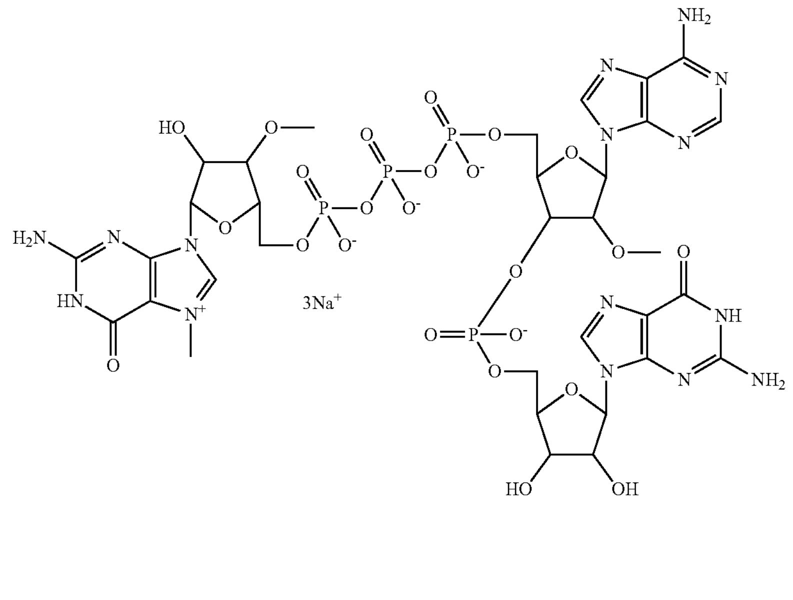 [SMILES: COC1C(COP(=O)([O-])OP(=O)([O-])OP(=O)([O-])OCC2OC(n3cnc4c(N)ncnc43)C(OC)C2OP(=O)([O-])OCC2OC(n3cnc4c(=O)[nH]c(N)nc43)C(O)C2O)OC(n2c[n+](C)c3c(=O)[nH]c(N)nc32)C1O]

In some embodiments, a cap1 structure is or comprises m7(3'OMeG)(5')ppp(5')(2'OMe$G_1$)p$G_2$ wherein G is a cap proximal nucleotide at position 1 and G is a cap proximal nucleotide at position 2, and has the following structure:

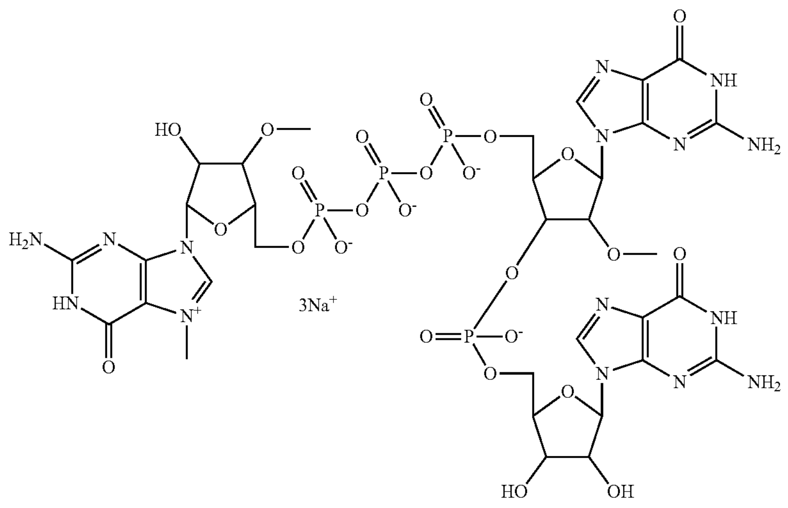 [SMILES: COC1C(COP(=O)([O-])OP(=O)([O-])OP(=O)([O-])OCC2OC(n3cnc4c(=O)[nH]c(N)nc43)C(OC)C2OP(=O)([O-])OCC2OC(n3cnc4c(=O)[nH]c(N)nc43)C(O)C2O)OC(n2c[n+](C)c3c(=O)[nH]c(N)nc32)C1O]

In some embodiments, a second nucleotide in a Cap1 structure can comprise one or more modifications, e.g., methylation. In some embodiments, a Cap1 structure comprising a second nucleotide comprising a 2'O methylation is a Cap2 structure.

In some embodiments, an RNA polynucleotide comprising a Cap1 structure has increased translation efficiency, increased translation rate and/or increased expression of an encoded payload relative to an appropriate reference comparator. In some embodiments, an RNA polynucleotide comprising a cap1 structure having m7(3'OMeG)(5')ppp(5')(2'OMe$A_1$)p$G_2$ wherein A is a cap proximal nucleotide at position 1 and G is a cap proximal nucleotide at position 2, has increased translation efficiency relative to an RNA polynucleotide comprising a cap1 structure having m7(3'OMeG)(5')ppp(5')(2'OMe$G_1$)p$G_2$ wherein $G_1$ is a cap proximal nucleotide at position 1 and $G_2$ is a cap proximal nucleotide at position 2. In some embodiments, increased translation efficiency is assessed upon administration of an RNA polynucleotide to a cell or an organism.

In some embodiments, a cap analog used in an RNA polynucleotide is $m_2^{7,3'\text{-}O}$Gppp($m_1^{2'\text{-}O}$)ApG (also sometimes referred to as $m_2^{7,3'O}$G(5')ppp(5')$m^{2'\text{-}O}$ApG or m7(3'OMeG)(5')ppp(5')(2'OMeA)pG), which has the following structure:

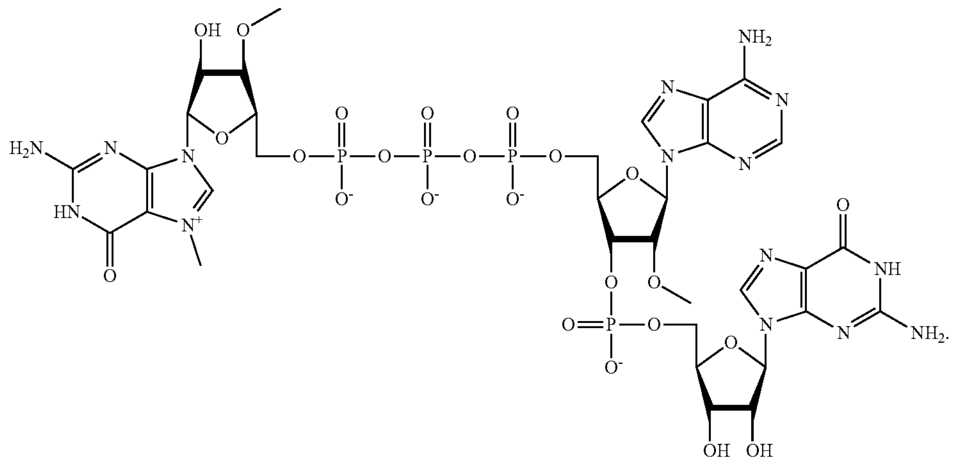

Below is an exemplary Cap1 RNA, which comprises RNA and $m_2^{7,3'-O}G(5')ppp(5')m^{2'-O}ApG$:

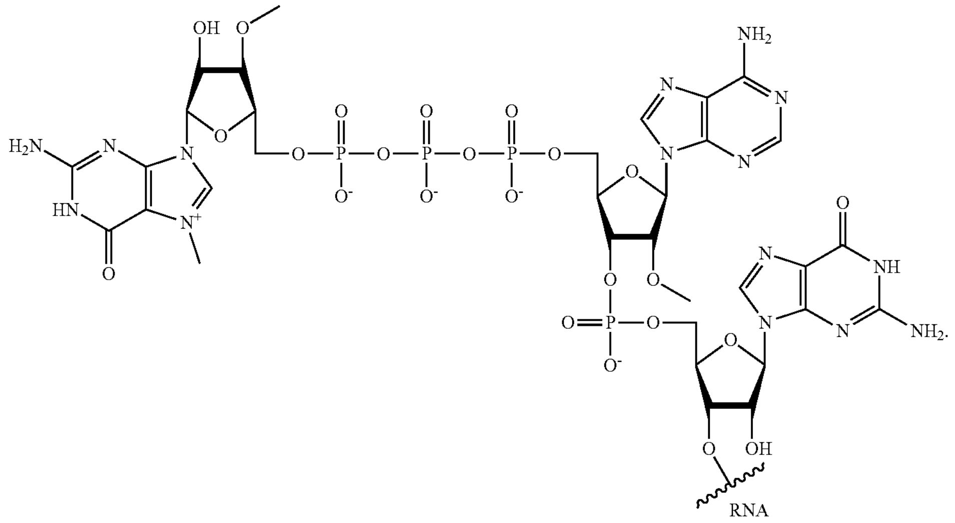

Below is another exemplary Cap1 RNA:

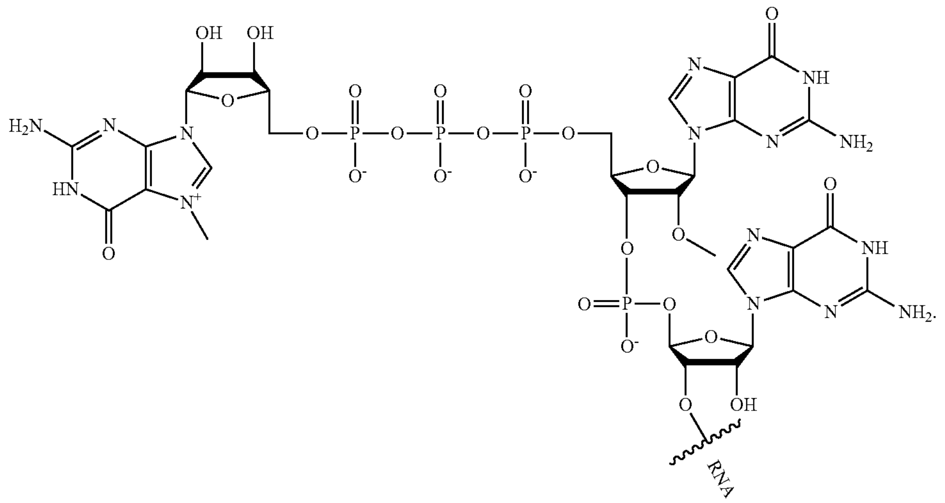

In some embodiments, an RNA polynucleotide disclosed herein comprises a Cap shown in any one of FIGS. 3A-3I. In some embodiments, an RNA polynucleotide disclosed herein comprises a Cap shown in FIG. 3A. In some embodiments, an RNA polynucleotide disclosed herein comprises a Cap shown in FIG. 3B. In some embodiments, an RNA polynucleotide disclosed herein comprises a Cap shown in FIG. 3C. In some embodiments, an RNA polynucleotide disclosed herein comprises a Cap shown in FIG. 3D. In some embodiments, an RNA polynucleotide disclosed herein comprises a Cap shown in FIG. 3E. In some embodiments, an RNA polynucleotide disclosed herein comprises a Cap shown in FIG. 3F. In some embodiments, an RNA polynucleotide disclosed herein comprises a Cap shown in FIG. 3G. In some embodiments, an RNA polynucleotide disclosed herein comprises a Cap shown in FIG. 3H. In some embodiments, an RNA polynucleotide disclosed herein comprises a Cap shown in FIG. 3I.

5' UTR and Cap Proximal Sequences

In some embodiments, an RNA disclosed herein comprises a 5'-UTR. The term “untranslated region” or “UTR” relates to a region in a DNA molecule which is transcribed but is not translated into an amino acid sequence, or to the corresponding region in an RNA polynucleotide, such as an mRNA molecule. An untranslated region (UTR) can be present 5' (upstream) of an open reading frame (5'-UTR) and/or 3' (downstream) of an open reading frame (3'-UTR). A 5'-UTR, if present, is located at the 5' end, upstream of the start codon of a protein-encoding region. A 5'-UTR is downstream of the 5'-cap (if present), e.g. directly adjacent to the 5'-cap.

In some embodiments, a 5' UTR disclosed herein comprises a cap proximal sequence, e.g., as disclosed herein. In some embodiments, a cap proximal sequence comprises a sequence adjacent to a 5' cap. In some embodiments, a cap proximal sequence comprises nucleotides in positions +1, +2, +3, +4, and/or +5 of an RNA polynucleotide.

In some embodiments, a Cap structure comprises one or more polynucleotides of a cap proximal sequence. In some embodiments, a Cap structure comprises an m7 Guanosine cap and nucleotide +1 ($N_1$) of an RNA polynucleotide. In some embodiments, a Cap structure comprises an m7 Guanosine cap and nucleotide +2 ($N_2$) of an RNA polynucleotide. In some embodiments, a Cap structure comprises an m7 Guanosine cap and nucleotides +1 and +2 ($N_1$ and $N_2$) of an RNA polynucleotide.

Those skilled in the art, reading the present disclosure, will appreciate that, in some embodiments, one or more residues of a cap proximal sequence (e.g., one or more of residues +1, +2, +3, +4, and/or +5) may be included in an RNA by virtue of having been included in a cap entity that (e.g., a Cap1 structure, etc); alternatively, in some embodiments, at least some of the residues in a cap proximal sequence may be enzymatically added (e.g., by a polymerase such as a T7 polymerase). For example, in certain exemplified embodiments where a $m_2^{7,3'-O}Gppp(m_1^{2'-O})ApG$ cap is utilized, +1 and +2 are the $(m_1^{2'-O})$A and G residues of the cap, and +3, +4, and +5 are added by polymerase (e.g., T7 polymerase).

In some embodiments, a cap proximal sequence comprises $N_1$ and $N_2$ of a Cap structure, wherein $N_1$ and $N_2$ are any nucleotide, e.g., A, C, G or U. In some embodiments, $N_1$ is A. In some embodiments, $N_1$ is C. In some embodiments, $N_1$ is G. In some embodiments, $N_1$ is U. In some embodiments, $N_2$ is A. In some embodiments, $N_2$ is C. In some embodiments, $N_2$ is G. In some embodiments, $N_2$ is U.

In some embodiments, $N_1$ is A and $N_2$ is A. In some embodiments, $N_1$ is A and $N_2$ is C. In some embodiments, $N_1$ is A and $N_2$ is G. In some embodiments, $N_1$ is A and $N_2$ is U.

In some embodiments, $N_1$ is C and $N_2$ is A. In some embodiments, $N_1$ is C and $N_2$ is C. In some embodiments, $N_1$ is C and $N_2$ is G. In some embodiments, $N_1$ is C and $N_2$ is U.

In some embodiments, $N_1$ is G and $N_2$ is A. In some embodiments, $N_1$ is G and $N_2$ is C. In some embodiments, $N_1$ is G and $N_2$ is G. In some embodiments, $N_1$ is G and $N_2$ is U.

In some embodiments, $N_1$ is U and $N_2$ is A. In some embodiments, $N_1$ is U and $N_2$ is C. In some embodiments, $N_1$ is U and $N_2$ is G. In some embodiments, $N_1$ is U and $N_2$ is U.

In some embodiments, a cap proximal sequence comprises $N_1$ and $N_2$ of a Cap structure and $N_3$, $N_4$ and $N_5$, wherein $N_1$ to $N_5$ correspond to positions +1, +2, +3, +4, and/or +5 of an RNA polynucleotide.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is A. In some embodiments, $N_4$ is A. In some embodiments, $N_5$ is A.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is A. In some embodiments, $N_4$ is C. In some embodiments, $N_5$ is A.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is A. In some embodiments, $N_4$ is G. In some embodiments, $N_5$ is A.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is A. In some embodiments, $N_4$ is U. In some embodiments, $N_5$ is A.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is A. In some embodiments, $N_4$ is A. In some embodiments, $N_5$ is G.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is A. In some embodiments, $N_4$ is G. In some embodiments, $N_5$ is G.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is A. In some embodiments, $N_4$ is C. In some embodiments, $N_5$ is G.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is A. In some embodiments, $N_4$ is U. In some embodiments, $N_5$ is G.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is A. In some embodiments, $N_4$ is A. In some embodiments, $N_5$ is C.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is A. In some embodiments, $N_4$ is C. In some embodiments, $N_5$ is C.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is A. In some embodiments, $N_4$ is G. In some embodiments, $N_5$ is C.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is A. In some embodiments, $N_4$ is U. In some embodiments, $N_5$ is C.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is A. In some embodiments, $N_4$ is A. In some embodiments, $N_5$ is U.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is A. In some embodiments, $N_4$ is C. In some embodiments, $N_5$ is U.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is A. In some embodiments, $N_4$ is G. In some embodiments, $N_5$ is U.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is A. In some embodiments, $N_4$ is U. In some embodiments, $N_5$ is U.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is C. In some embodiments, $N_4$ is A. In some embodiments, $N_5$ is A.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is C. In some embodiments, $N_4$ is C. In some embodiments, $N_5$ is A.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is C. In some embodiments, $N_4$ is G. In some embodiments, $N_5$ is A.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is C. In some embodiments, $N_4$ is U. In some embodiments, $N_5$ is A.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is C. In some embodiments, $N_4$ is A. In some embodiments, $N_5$ is G.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is C. In some embodiments, $N_4$ is G. In some embodiments, $N_5$ is G.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is C. In some embodiments, $N_4$ is C. In some embodiments, $N_5$ is G.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is C. In some embodiments, $N_4$ is U. In some embodiments, $N_5$ is G.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is C. In some embodiments, $N_4$ is A. In some embodiments, $N_5$ is C.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is C. In some embodiments, $N_4$ is C. In some embodiments, $N_5$ is C.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is C. In some embodiments, $N_4$ is G. In some embodiments, $N_5$ is C.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is C. In some embodiments, $N_4$ is U. In some embodiments, $N_5$ is C.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is C. In some embodiments, $N_4$ is A. In some embodiments, $N_5$ is U.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is C. In some embodiments, $N_4$ is C. In some embodiments, $N_5$ is U.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is C. In some embodiments, $N_4$ is G. In some embodiments, $N_5$ is U.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is C. In some embodiments, $N_4$ is U. In some embodiments, $N_5$ is U.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is G. In some embodiments, $N_4$ is A. In some embodiments, $N_5$ is A.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is G. In some embodiments, $N_4$ is C. In some embodiments, $N_5$ is A.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is G. In some embodiments, $N_4$ is G. In some embodiments, $N_5$ is A.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is G. In some embodiments, $N_4$ is U. In some embodiments, $N_5$ is A.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is G. In some embodiments, $N_4$ is A. In some embodiments, $N_5$ is G.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is G. In some embodiments, $N_4$ is G. In some embodiments, $N_5$ is G.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is G. In some embodiments, $N_4$ is C. In some embodiments, $N_5$ is G.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is G. In some embodiments, $N_4$ is U. In some embodiments, $N_5$ is G.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is G. In some embodiments, $N_4$ is A. In some embodiments, $N_5$ is C.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is G. In some embodiments, $N_4$ is C. In some embodiments, $N_5$ is C.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is G. In some embodiments, $N_4$ is G. In some embodiments, $N_5$ is C.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is G. In some embodiments, $N_4$ is U. In some embodiments, $N_5$ is C.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is G. In some embodiments, $N_4$ is A. In some embodiments, $N_5$ is U.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is G. In some embodiments, $N_4$ is C. In some embodiments, $N_5$ is U.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is G. In some embodiments, $N_4$ is G. In some embodiments, $N_5$ is U.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is G. In some embodiments, $N_4$ is U. In some embodiments, $N_5$ is U.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is U. In some embodiments, $N_4$ is A. In some embodiments, $N_5$ is A.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is U. In some embodiments, $N_4$ is C. In some embodiments, $N_5$ is A.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is U. In some embodiments, $N_4$ is G. In some embodiments, $N_5$ is A.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is U. In some embodiments, $N_4$ is U. In some embodiments, $N_5$ is A.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is U. In some embodiments, $N_4$ is A. In some embodiments, $N_5$ is G.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is U. In some embodiments, $N_4$ is G. In some embodiments, $N_5$ is G.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is U. In some embodiments, $N_4$ is C. In some embodiments, $N_5$ is G.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is U. In some embodiments, $N_4$ is U. In some embodiments, $N_5$ is G.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is U. In some embodiments, $N_4$ is A. In some embodiments, $N_5$ is C.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is U. In some embodiments, $N_4$ is C. In some embodiments, $N_5$ is C.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is U. In some embodiments, $N_4$ is G. In some embodiments, $N_5$ is C.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is U. In some embodiments, $N_4$ is U. In some embodiments, $N_5$ is C.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is U. In some embodiments, $N_4$ is A. In some embodiments, $N_5$ is U.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is U. In some embodiments, $N_4$ is C. In some embodiments, $N_5$ is U.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is U. In some embodiments, $N_4$ is G. In some embodiments, $N_5$ is U.

In some embodiments, $N_1$, $N_2$, $N_3$, $N_4$, or $N_5$ are any nucleotide, e.g., A, C, G or U. In some embodiments, $N_1$ is A and $N_2$ is G. In some embodiments, $N_3$ is U. In some embodiments, $N_4$ is U. In some embodiments, $N_5$ is U.

In some embodiments, a 5' UTR disclosed herein comprises a cap proximal sequence, e.g., as disclosed herein. In some embodiments, a cap proximal sequence comprises a sequence adjacent to a 5' cap. In some embodiments, a cap proximal sequence comprises nucleotides in positions +1, +2, +3, +4, and/or +5 of an RNA polynucleotide.

In some embodiments, a Cap structure comprises one or more polynucleotides of a cap proximal sequence. In some embodiments, a Cap structure comprises an m7 Guanosine cap and nucleotide +1 ($N_1$) of an RNA polynucleotide. In some embodiments, a Cap structure comprises an m7 Guanosine cap and nucleotide +2 ($N_2$) of an RNA polynucleotide. In some embodiments, a Cap structure comprises an m7 Guanosine cap and nucleotides +1 and +2 ($N_1$ and $N_2$) of an RNA polynucleotide.

In some embodiments, $N_1$ and $N_2$ are each independently chosen from: A, C, G, or U. In some embodiments, $N_1$ is A. In some embodiments, $N_1$ is C. In some embodiments, $N_1$ is G. In some embodiments, $N_1$ is U. In some embodiments, $N_2$ is A. In some embodiments, $N_2$ is C. In some embodiments, $N_2$ is G. In some embodiments, $N_2$ is U.

In some embodiments, $N_1$ and $N_2$ are each independently chosen from: A, C, G, or U. In some embodiments, $N_1$ is A. In some embodiments, $N_1$ is C. In some embodiments, $N_1$ is G. In some embodiments, $N_1$ is U. In some embodiments, $N_2$ is A. In some embodiments, $N_2$ is C. In some embodiments, $N_2$ is G. In some embodiments, $N_2$ is U.

In some embodiments, $N_1$ is A and $N_2$ is A. In some embodiments, $N_1$ is A and $N_2$ is C. In some embodiments, $N_1$ is A and $N_2$ is G. In some embodiments, $N_1$ is A and $N_2$ is U.

In some embodiments, $N_1$ is C and $N_2$ is A. In some embodiments, $N_1$ is C and $N_2$ is C. In some embodiments, $N_1$ is C and $N_2$ is G. In some embodiments, $N_1$ is C and $N_2$ is U.

In some embodiments, $N_1$ is G and $N_2$ is A. In some embodiments, $N_1$ is G and $N_2$ is C. In some embodiments, $N_1$ is G and $N_2$ is G. In some embodiments, $N_1$ is G and $N_2$ is U.

In some embodiments, $N_1$ is U and $N_2$ is A. In some embodiments, $N_1$ is U and $N_2$ is C. In some embodiments, $N_1$ is U and $N_2$ is G. In some embodiments, $N_1$ is U and $N_2$ is U.

In some embodiments, a cap proximal sequence comprises $N_1$ and $N_2$ of a Cap structure, and a sequence comprising: $A_3A_4X_5$ (SEQ ID NO: 1). In some embodiments, $N_1$ and $N_2$ are each independently chosen from: A, C, G, or U. In some embodiments, $N_1$ is A and $N_2$ is G. In some embodiments, $X_5$ is chosen from A, C, G or U. In some embodiments, $X_5$ is A. In some embodiments, $X_5$ is C. In some embodiments, $X_5$ is G. In some embodiments, $X_5$ is U.

In some embodiments, a cap proximal sequence comprises $N_1$ and $N_2$ of a Cap structure, and a sequence comprising: $C_3A_4X_5$ (SEQ ID NO: 2). In some embodiments, $N_1$ and $N_2$ are each independently chosen from: A, C, G, or U. In some embodiments, $N_1$ is A and $N_2$ is G. In some embodiments, $X_5$ is chosen from A, C, G or U. In some embodiments, $X_5$ is A. In some embodiments, $X_5$ is C. In some embodiments, $X_5$ is G. In some embodiments, $X_5$ is U.

In some embodiments, a cap proximal sequence comprises $N_1$ and $N_2$ of a Cap structure, and a sequence comprising $X_3Y_4X_5$ (SEQ ID NO: 7). In some embodiments, $N_1$ and $N_2$ are each independently chosen from: A, C, G, or U. In some embodiments, $N_1$ is A and $N_2$ is G. In some embodiments, $X_3$ and $X_5$ is each independently chosen from A, C, G or U. In some embodiments, $X_3$ and/or $X_5$ is A. In some embodiments, $X_3$ and/or $X_5$ is C. In some embodiments, $X_3$ and/or $X_5$ is G. In some embodiments, $X_3$ and/or $X_5$ is U. In some embodiments, $Y_4$ is not C. In some embodiments, $Y_4$ is A. In some embodiments, $Y_4$ is G. In some embodiments, $Y_4$ is U.

In some embodiments, a cap proximal sequence comprises $N_1$ and $N_2$ of a Cap structure, and a sequence comprising $X_3Y_4X_5$ (SEQ ID NO: 7). In some embodiments, $N_1$ and $N_2$ are each independently chosen from: A, C, G, or U. In some embodiments, $N_1$ is A and $N_2$ is G. In some embodiments, $X_3$ and $X_5$ is each independently chosen from A, C, G or U. In some embodiments, $X_3$ and/or $X_5$ is A. In some embodiments, $X_3$ and/or $X_5$ is C. In some embodiments, $X_3$ and/or $X_5$ is G. In some embodiments, $X_3$ and/or $X_5$ is U. In some embodiments, $Y_4$ is not G. In some embodiments, $Y_4$ is A. In some embodiments, $Y_4$ is C. In some embodiments, $Y_4$ is U.

In some embodiments, a cap proximal sequence comprises $N_1$ and $N_2$ of a Cap structure, and a sequence comprising $A_3C_4A_5$ (SEQ ID NO: 3). In some embodiments, $N_1$ and $N_2$ are each independently chosen from: A, C, G, or U. In some embodiments, $N_1$ is A and $N_2$ is G.

In some embodiments, a cap proximal sequence comprises $N_1$ and $N_2$ of a Cap structure, and a sequence comprising $A_3U_4G_5$ (SEQ ID NO: 4). In some embodiments, $N_1$ and $N_2$ are each independently chosen from: A, C, G, or U. In some embodiments, $N_1$ is A and $N_2$ is G.

In some embodiments, a Cap structure comprises one or more polynucleotides of a cap proximal sequence. In some embodiments, a Cap structure comprises an m7 Guanosine cap and nucleotide +1 ($N_1$) of an RNA polynucleotide. In some embodiments, a Cap structure comprises an m7 Guanosine cap and nucleotide +2 ($N_2$) of an RNA polynucleotide. In some embodiments, a Cap structure comprises an m7 Guanosine cap and nucleotides +1 and +2 ($N_1$ and $N_2$) of an RNA polynucleotide.

In some embodiments, $N_1$ and $N_2$ are any nucleotide, e.g., A, C, G, or U. In some embodiments, $N_1$ is A. In some embodiments, $N_1$ is C. In some embodiments, $N_1$ is G. In some embodiments, $N_1$ is U. In some embodiments, $N_2$ is A. In some embodiments, $N_2$ is C. In some embodiments, $N_2$ is G. In some embodiments, $N_2$ is U.

In some embodiments, $N_1$ and $N_2$ are any nucleotide, e.g., A, C, G, or U. In some embodiments, $N_1$ is A. In some embodiments, $N_1$ is C. In some embodiments, $N_1$ is G. In some embodiments, $N_1$ is U. In some embodiments, $N_2$ is A. In some embodiments, $N_2$ is C. In some embodiments, $N_2$ is G. In some embodiments, $N_2$ is U.

In some embodiments, $N_1$ is A and $N_2$ is A. In some embodiments, $N_1$ is A and $N_2$ is C. In some embodiments, $N_1$ is A and $N_2$ is G. In some embodiments, $N_1$ is A and $N_2$ is U.

In some embodiments, $N_1$ is C and $N_2$ is A. In some embodiments, $N_1$ is C and $N_2$ is C. In some embodiments, $N_1$ is C and $N_2$ is G. In some embodiments, $N_1$ is C and $N_2$ is U.

In some embodiments, $N_1$ is G and $N_2$ is A. In some embodiments, $N_1$ is G and $N_2$ is C. In some embodiments, $N_1$ is G and $N_2$ is G. In some embodiments, $N_1$ is G and $N_2$ is U.

In some embodiments, $N_1$ is U and $N_2$ is A. In some embodiments, $N_1$ is U and $N_2$ is C. In some embodiments, $N_1$ is U and $N_2$ is G. In some embodiments, $N_1$ is U and $N_2$ is U.

In some embodiments, a cap proximal sequence comprises $N_1$ and $N_2$ of a Cap structure, and a sequence comprising: $A_3A_4X_5$ (SEQ ID NO: 1). In some embodiments, $N_1$ and $N_2$ are any nucleotide, e.g., A, C, G, or U. In some embodiments, $N_1$ is A and $N_2$ is G. In some embodiments, $X_5$ is chosen from A, C, G or U. In some embodiments, $X_5$ is A. In some embodiments, $X_5$ is C. In some embodiments, $X_5$ is G. In some embodiments, $X_5$ is U.

In some embodiments, a cap proximal sequence comprises $N_1$ and $N_2$ of a Cap structure, and a sequence comprising: $C_3A_4$X5 (SEQ ID NO: 2). In some embodiments, $N_1$ and $N_2$ are any nucleotide, e.g., A, C, G, or U. In some embodiments, $N_1$ is A and $N_2$ is G. In some embodiments, $X_5$ is any nucleotide, e.g., A, C, G or U. In some embodiments, $X_5$ is A. In some embodiments, $X_5$ is C. In some embodiments, $X_5$ is G. In some embodiments, $X_5$ is U.

In some embodiments, a cap proximal sequence comprises $N_1$ and $N_2$ of a Cap structure, and a sequence comprising $X_3Y_4X_5$ (SEQ ID NO: 7). In some embodiments, $N_1$ and $N_2$ are any nucleotide, e.g., A, C, G, or U. In some embodiments, $N_1$ is A and $N_2$ is G. In some embodiments, $X_3$ and $X_5$ is any nucleotide, e.g., A, C, G or U. In some embodiments, $X_3$ and/or $X_5$ is A. In some embodiments, $X_3$ and/or $X_5$ is C. In some embodiments, $X_3$ and/or $X_5$ is G. In some embodiments, $X_3$ and/or $X_5$ is U. In some embodiments, $Y_4$ is not C. In some embodiments, $Y_4$ is A. In some embodiments, $Y_4$ is G. In some embodiments, $Y_4$ is U.

In some embodiments, a cap proximal sequence comprises $N_1$ and $N_2$ of a Cap structure, and a sequence comprising $X_3Y_4X_5$ (SEQ ID NO: 7). In some embodiments, $N_1$ and $N_2$ are any nucleotide, e.g., A, C, G, or U. In some embodiments, $N_1$ is A and $N_2$ is G. In some embodiments, $X_3$ and $X_5$ is any nucleotide, e.g., A, C, G or U. In some embodiments, $X_3$ and/or $X_5$ is A. In some embodiments, $X_3$ and/or $X_5$ is C. In some embodiments, $X_3$ and/or $X_5$ is G. In some embodiments, $X_3$ and/or $X_5$ is U. In some embodiments, $Y_4$ is not G. In some embodiments, $Y_4$ is A. In some embodiments, $Y_4$ is C. In some embodiments, $Y_4$ is U.

In some embodiments, a cap proximal sequence comprises $N_1$ and $N_2$ of a Cap structure, and a sequence comprising $A_3C_4A_5$ (SEQ ID NO: 3). In some embodiments, $N_1$ and $N_2$ are any nucleotide, e.g., A, C, G, or U. In some embodiments, $N_1$ is A and $N_2$ is G.

In some embodiments, a cap proximal sequence comprises $N_1$ and $N_2$ of a Cap structure, and a sequence comprising $A_3U_4G_5$ (SEQ ID NO: 4). In some embodiments, $N_1$ and $N_2$ are any nucleotide, e.g., A, C, G, or U. In some embodiments, $N_1$ is A and $N_2$ is G.

Exemplary 5' UTRs include a human alpha globin (hAg) 5'UTR or a fragment thereof, a TEV 5' UTR or a fragment thereof, a HSP70 5' UTR or a fragment thereof, or a c-Jun 5' UTR or a fragment thereof.

In some embodiments, an RNA disclosed herein comprises a hAg 5' UTR or a fragment thereof. In some embodiments, an RNA disclosed herein comprises a hAg 5' UTR having 99%, 98%, 97%, 96%, 95%, 90%, 85%, or 80% identity to a human alpha globin 5' UTR provided in SEQ ID NO: 11. In some embodiments, an RNA disclosed herein comprises a hAg 5' UTR provided in SEQ ID NO: 11. In some embodiments, an RNA disclosed herein comprises a hAg 5' UTR having 99%, 98%, 97%, 96%, 95%, 90%, 85%, or 80% identity to a human alpha globin 5' UTR provided in SEQ ID NO: 12. In some embodiments, an RNA disclosed herein comprises a hAg 5' UTR provided in SEQ ID NO: 12.

3' UTR

In some embodiments, an RNA disclosed herein comprises a 3'-UTR. A 3'-UTR, if present, is located at the 3' end, downstream of the termination codon of a protein-encoding region, but the term "3'-UTR" does preferably not include the poly(A) sequence. Thus, the 3'-UTR is upstream of the poly(A) sequence (if present), e.g. directly adjacent to the poly(A) sequence.

In some embodiments, an RNA disclosed herein comprises a 3' UTR comprising an F element and/or an I element. In some embodiments, a 3' UTR or a proximal sequence thereto comprises a restriction site. In some embodiments, a restriction site is a BamHI site. In some embodiments, a restriction site is a XhoI site.

In some embodiments, an RNA disclosed herein comprises a 3' UTR having 99%, 98%, 97%, 96%, 95%, 90%, 85%, or 80% identity to a 3' UTR provided in SEQ ID NO: 13. In some embodiments, an RNA disclosed herein comprises a 3' UTR provided in SEQ ID NO: 13.

PolyA

In some embodiments, an RNA disclosed herein comprises a polyadenylate (PolyA) sequence, e.g., as described herein. In some embodiments, a PolyA sequence is situated downstream of a 3'-UTR, e.g., adjacent to a 3'-UTR.

As used herein, the term "poly(A) sequence" or "poly-A tail" refers to an uninterrupted or interrupted sequence of adenylate residues which is typically located at the 3'-end of an RNA polynucleotide. Poly(A) sequences are known to those of skill in the art and may follow the 3'-UTR in the RNAs described herein. An uninterrupted poly(A) sequence is characterized by consecutive adenylate residues. In nature, an uninterrupted poly(A) sequence is typical. RNAs disclosed herein can have a poly(A) sequence attached to the free 3'-end of the RNA by a template-independent RNA polymerase after transcription or a poly(A) sequence encoded by DNA and transcribed by a template-dependent RNA polymerase.

It has been demonstrated that a poly(A) sequence of about 120 A nucleotides has a beneficial influence on the levels of RNA in transfected eukaryotic cells, as well as on the levels of protein that is translated from an open reading frame that is present upstream (5') of the poly(A) sequence (Holtkamp et al., 2006, Blood, vol. 108, pp. 4009-4017).

The poly(A) sequence may be of any length. In some embodiments, a poly(A) sequence comprises, essentially consists of, or consists of at least 20, at least 30, at least 40, at least 80, or at least 100 and up to 500, up to 400, up to 300, up to 200, or up to 150 A nucleotides, and, in particular, about 120 A nucleotides. In this context, "essentially consists of" means that most nucleotides in the poly(A) sequence, typically at least 75%, at least 80%, at least 85%, at least 90%, at least 95%, at least 96%, at least 97%, at least 98%, or at least 99% by number of nucleotides in the poly(A) sequence are A nucleotides, but permits that remaining nucleotides are nucleotides other than A nucleotides, such as U nucleotides (uridylate), G nucleotides (guanylate), or C nucleotides (cytidylate). In this context, "consists of" means that all nucleotides in the poly(A) sequence, i.e., 100% by number of nucleotides in the poly(A) sequence, are A nucleotides. The term "A nucleotide" or "A" refers to adenylate.

In some embodiments, a poly(A) sequence is attached during RNA transcription, e.g., during preparation of in vitro transcribed RNA, based on a DNA template comprising repeated dT nucleotides (deoxythymidylate) in the strand complementary to the coding strand. The DNA sequence encoding a poly(A) sequence (coding strand) is referred to as poly(A) cassette.

In some embodiments, the poly(A) cassette present in the coding strand of DNA essentially consists of dA nucleotides, but is interrupted by a random sequence of the four nucleotides (dA, dC, dG, and dT). Such random sequence may be 5 to 50, 10 to 30, or 10 to 20 nucleotides in length. Such a cassette is disclosed in WO 2016/005324 A1, hereby incorporated by reference. Any poly(A) cassette disclosed in WO 2016/005324 A1 may be used in the present invention. A poly(A) cassette that essentially consists of dA nucleotides, but is interrupted by a random sequence having an equal distribution of the four nucleotides (dA, dC, dG, dT) and having a length of e.g., 5 to 50 nucleotides shows, on DNA level, constant propagation of plasmid DNA in *E. coli* and is still associated, on RNA level, with the beneficial properties with respect to supporting RNA stability and translational efficiency is encompassed. In some embodiments, the poly (A) sequence contained in an RNA polynucleotide described herein essentially consists of A nucleotides, but is interrupted by a random sequence of the four nucleotides (A, C, G, U). Such random sequence may be 5 to 50, 10 to 30, or 10 to 20 nucleotides in length.

In some embodiments, no nucleotides other than A nucleotides flank a poly(A) sequence at its 3'-end, i.e., the poly(A) sequence is not masked or followed at its 3'-end by a nucleotide other than A.

In some embodiments, the poly(A) sequence may comprise at least 20, at least 30, at least 40, at least 80, or at least 100 and up to 500, up to 400, up to 300, up to 200, or up to 150 nucleotides. In some embodiments, the poly(A) sequence may essentially consist of at least 20, at least 30, at least 40, at least 80, or at least 100 and up to 500, up to 400, up to 300, up to 200, or up to 150 nucleotides. In some embodiments, the poly(A) sequence may consist of at least 20, at least 30, at least 40, at least 80, or at least 100 and up to 500, up to 400, up to 300, up to 200, or up to 150 nucleotides. In some embodiments, the poly(A) sequence comprises at least 100 nucleotides. In some embodiments, the poly(A) sequence comprises about 150 nucleotides. In some embodiments, the poly(A) sequence comprises about 120 nucleotides.

In some embodiments, an RNA disclosed herein comprises a poly(A) sequence comprising the nucleotide sequence of SEQ ID NO: 14, or a nucleotide sequence having at least 99%, 98%, 97%, 96%, 95%, 90%, 85%, or 80% identity to the nucleotide sequence of SEQ ID NO: 14. In some embodiments, an RNA disclosed herein comprises a poly(A) sequence of SEQ ID NO: 14.

Payloads

In some embodiments, an RNA polynucleotide disclosed herein comprises a sequence encoding a payload, e.g., as described herein. In some embodiments, a sequence encoding a payload comprises a promoter sequence. In some embodiments, a sequence encoding a payload comprises a sequence encoding a secretory signal peptide.

In some embodiments, a payload is chosen from: a protein replacement polypeptide; an antibody agent; a cytokine; an antigenic polypeptide; a gene editing component; a regenerative medicine component or combinations thereof.

In some embodiments, a payload is or comprises a protein replacement polypeptide. In some embodiments, a protein replacement polypeptide comprises a polypeptide with aberrant expression in a disease or disorder. In some embodiments, a protein replacement polypeptide comprises an intracellular protein, an extracellular protein, or a transmembrane protein. In some embodiments, a protein replacement polypeptide comprises an enzyme.

In some embodiments, a disease or disorder with aberrant expression of a polypeptide includes but is not limited to: a rare disease, a metabolic disorder, a muscular dystrophy, a cardiovascular disease, or a monogenic disease.

In some embodiments, a payload is or comprises an antibody agent. In some embodiments, an antibody agent binds to a polypeptide expressed on a cell. In some embodiments, an antibody agent comprises a CD3 antibody, a Claudin 6 antibody, or a combination thereof.

In some embodiments, a payload is or comprises a cytokine or a fragment or a variant thereof. In some embodiments, a cytokine comprises: IL-12 or a fragment or variant or a fusion thereof, IL-15 or a fragment or a variant or a fusion thereof, GMCSF or a fragment or a variant thereof; or IFN-alpha or a fragment or a variant thereof.

In some embodiments, a payload is or comprises an antigenic polypeptide or an immunogenic variant or an immunogenic fragment thereof. In some embodiments, an antigenic polypeptide comprises one epitope from an antigen. In some embodiments, an antigenic polypeptide comprises a plurality of distinct epitopes from an antigen. In some embodiments, an antigenic polypeptide comprising a plurality of distinct epitopes from an antigen is polyepitopic.

In some embodiments, an antigenic polypeptide comprises: an antigenic polypeptide from an allergen, a viral antigenic polypeptide, a bacterial antigenic polypeptide, a fungal antigenic polypeptide, a parasitic antigenic polypeptide, an antigenic polypeptide from an infectious agent, an antigenic polypeptide from a pathogen, a tumor antigenic polypeptide, or a self-antigenic polypeptide.

In some embodiments, a viral antigenic polypeptide comprises an HIV antigenic polypeptide, an influenza antigenic polypeptide, a Coronavirus antigenic polypeptide, a Rabies antigenic polypeptide, or a Zika virus antigenic polypeptide.

In some embodiments, a viral antigenic polypeptide is or comprises a Coronavirus antigenic polypeptide. In some embodiments, a Coronavirus antigen is or comprises a SARS-CoV-2 protein. In some embodiments, a SARS-CoV-2 protein comprises a SARS-CoV-2 Spike (S) protein, or an immunogenic variant or an immunogenic fragment thereof. In some embodiments, a SARS-CoV-2 protein, or immunogenic variant or immunogenic fragment thereof, comprises proline residues at positions 986 and 987.

In some embodiments, a SARS-CoV-2 S polypeptide has at least 99%, 98%, 97%, 96%, 95%, 90%, 85%, or 80% identity to a SARS-CoV-2 S polypeptide disclosed herein. In some embodiments, a SARS-CoV-2 S polypeptide has at least 99%, 98%, 97%, 96%, 95%, 90%, 85%, or 80% identity to SEQ ID NO: 9.

In some embodiments, a SARS-CoV-2 S polypeptide is encoded by an RNA having at least 99%, 98%, 97%, 96%, 95%, 90%, 85%, or 80% identity to a SARS-CoV-2 S polynucleotide disclosed herein. In some embodiments, a SARS-CoV-2 S polypeptide is encoded by an RNA having at least 99%, 98%, 97%, 96%, 95%, 90%, 85%, or 80% identity to SEQ ID NO: 10.

In some embodiments, a payload is or comprises a tumor antigenic polypeptide or an immunogenic variant or an immunogenic fragment thereof. In some embodiments, a tumor antigenic polypeptide comprises a tumor specific antigen, a tumor associated antigen, a tumor neoantigen, or a combination thereof. In some embodiments, a tumor antigenic polypeptide comprises p53, ART-4, BAGE, ss-catenin/m, Bcr-abL CAMEL, CAP-1, CASP-8, CDC27/m, CDK4/m, CEA, CLAUDIN-12, c-MYC, CT, Cyp-B, DAM, ELF2M, ETV6-AML1, G250, GAGE, GnT-V, Gap100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12, MAGE-B, MAGE-C, MART-1/Melan-A, MC1R, Myosin/m, MUC1, MUM-1, -2, -3, NA88-A, NF1, NY-ESO-1, NY-BR-1, p190 minor BCR-abL, Plac-1, Pm1/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE, WT, WT-1, or a combination thereof.

In some embodiments, a tumor antigenic polypeptide comprises a tumor antigen from a carcinoma, a sarcoma, a melanoma, a lymphoma, a leukemia, or a combination thereof.

In some embodiments, a tumor antigenic polypeptide comprises a melanoma tumor antigen.

In some embodiments, a tumor antigenic polypeptide comprises a prostate cancer antigen.

In some embodiments, a tumor antigenic polypeptide comprises a HPV16 positive head and neck cancer antigen.

In some embodiments, a tumor antigenic polypeptide comprises a breast cancer antigen.

In some embodiments, a tumor antigenic polypeptide comprises an ovarian cancer antigen.

In some embodiments, a tumor antigenic polypeptide comprises a lung cancer antigen.

In some embodiments, a tumor antigenic polypeptide comprises an NSCLC antigen.

In some embodiments, a payload is or comprises a self-antigenic polypeptide or an immunogenic variant or an immunogenic fragment thereof. In some embodiments, a self-antigenic polypeptide comprises an antigen that is typically expressed on cells and is recognized as a self-antigen by an immune system. In some embodiments, a self-antigenic polypeptide comprises: a multiple sclerosis antigenic polypeptide, a Rheumatoid arthritis antigenic polypeptide, a lupus antigenic polypeptide, a celiac disease antigenic polypeptide, a Sjogren's syndrome antigenic polypeptide, or an ankylosing spondylitis antigenic polypeptide, or a combination thereof.

Exemplary Polynucleotides

In some embodiments, an RNA polynucleotide described herein or a composition or medical preparation comprising the same comprises a nucleotide sequence disclosed herein. In some embodiments, an RNA polynucleotide comprises a sequence having at least 80% identity to a nucleotide sequence disclosed herein. In some embodiments, an RNA polynucleotide comprises a sequence encoding a polypeptide having at least 80% identity to a polypeptide sequence disclosed herein. Exemplary nucleotide and polypeptide sequences are provided e.g., in Table 1 or in this section titled "Exemplary polynucleotides" or in Example 2.

In some embodiments, an RNA polynucleotide described herein or a composition or medical preparation comprising the same is transcribed by a DNA template. In some embodiments, a DNA template used to transcribe an RNA polynucleotide described herein comprises a sequence complementary to an RNA polynucleotide.

In some embodiments, a payload described herein is encoded by an RNA polynucleotide described herein comprising a nucleotide sequence disclosed herein, e.g., in Table 1 or in this section titled "Exemplary polynucleotides" or in Example 2. In some embodiments, an RNA polynucleotide encodes a polypeptide payload having at least 80% identity to a polypeptide payload sequence disclosed herein. In some embodiments, a payload described herein is encoded by an RNA polynucleotide transcribed by a DNA template comprising a sequence complementary to an RNA polynucleotide.

TABLE 1

Exemplary sequences of RNA constructs disclosed herein

| SEQ ID NO | Sequence information | Sequence |
|---|---|---|
| 1 | Cap proximal consensus sequence (nucleotides 1-5 of a 5' UTR) | $A_3A_4X_5$<br>wherein $X_5$ is A, G, C, or U |
| 2 | Cap proximal consensus sequence (nucleotides +3 to +5 of a 5' UTR) | $C_3A_4X_5$<br>wherein $X_5$ is A, G, C, or U |

TABLE 1-continued

Exemplary sequences of RNA constructs disclosed herein

| SEQ ID NO | Sequence information | Sequence |
|---|---|---|
| 3 | Cap proximal sequence (nucleotides +3 to +5 of a 5' UTR) | $A_3C_4A_5$ |
| 4 | Cap proximal sequence (nucleotides +3 to +5 of a 5' UTR) | $A_3U_4G_5$ |
| 5 | Cap proximal sequence (nucleotides +3 to +5 of a 5' UTR) | $A_3A_4U_5$ |
| 6 | Cap proximal sequence (nucleotides +3 to +5 of a 5' UTR) | $C_3A_4C_5$ |
| 7 | Cap proximal sequence (nucleotides +3 to +5 of a 5' UTR) | $X_3Y_4X_5$<br>wherein $X_3$ or $X_5$ are each independently chosen from A, G, C, or U; and $Y_4$ is not C. |
| 8 | Ligation 3 sequence | GAGUCGCUAGCCGCGUCGCU |
| 9 | S protein PP (amino acid) (V08N09) | MFVFLVLLPLVSSQCVNLTTRTQLPPAYTNSFTRGVYYPDKVFRS<br>SVLHSTQDLFLPFFSNVTWFHAIHVSGTNGTKRFDNPVLPFNDGV<br>YFASTEKSNIIRGWIFGTTLDSKTQSLLIVNNATNVVIKVCEFQFC<br>NDPFLGVYYHKNNKSWMESEFRVYSSANNCTFEYVSQPFLMDL<br>EGKQGNFKNLREFVFKNIDGYFKIYSKHTPINLVRDLPQGFSALE<br>PLVDLPIGINITRFQTLLALHRSYLTPGDSSSGWTAGAAAYYVGY<br>LQPRTFLLKYNENGTITDAVDCALDPLSETKCTLKSFTVEKGIYQ<br>TSNFRVQPTESIVRFPNITNLCPFGEVFNATRFASVYAWNRKRISN<br>CVADYSVLYNSASFSTFKCYGVSPTKLNDLCFTNVYADSFVIRG<br>DEVRQIAPGQTGKIADYNYKLPDDFTGCVIAWNSNNLDSKVGG<br>NYNYLYRLFRKSNLKPFERDISTEIYQAGSTPCNGVEGFNCYFPL<br>QSYGFQPTNGVGYQPYRVVVLSFELLHAPATVCGPKKSTNLVK<br>NKCVNFNFNGLTGTGVLTESNKKFLPFQQFGRDIADTTDAVRDP<br>QTLEILDITPCSFGGVSVITPGTNTSNQVAVLYQDVNCTEVPVAIH<br>ADQLTPTWRVYSTGSNVFQTRAGCLIGAEHVNNSYECDIPIGAGI<br>CASYQTQTNSPRRARSVASQSIIAYTMSLGAENSVAYSNNSIAIPT<br>NFTISVTTEILPVSMTKTSVDCTMYICGDSTECSNLLLQYGSFCTQ<br>LNRALTGIAVEQDKNTQEVFAQVKQIYKTPPIKDFGGFNFSQILP<br>DPSKPSKRSFIEDLLFNKVTLADAGFIKQYGDCLGDIAARDLICA<br>QKFNGLTVLPPLLTDEMIAQYTSALLAGTITSGWTFGAGAALQIP<br>FAMQMAYRFNGIGVTQNVLYENQKLIANQFNSAIGKIQDSLSST<br>ASALGKLQDVVNQNAQALNTLVKQLSSNFGAISSVLNDILSRLD<br>PPEAEVQIDRLITGRLQSLQTYVTQQLIRAAEIRASANLAATKMS<br>ECVLGQSKRVDFCGKGYHLMSFPQSAPHGVVFLHVTYVPAQEK<br>NFTTAPAICHDGKAHFPREGVFVSNGTHWFVTQRNFYEPQIITTD<br>NTFVSGNCDVVIGIVNNTVYDPLQPELDSFKEELDKYFKNHTSPD<br>VDLGDISGINASVVNIQKEIDRLNEVAKNLNESLIDLQELGKYEQ<br>YIKWPWYIWLGFIAGLIAIVMVTIMLCCMTSCCSCLKGCCSCGSC<br>CKFDEDDSEPVLKGVKLHYT |
| 10 | RBP020.2 | agaauaaacu aguauucuuc ugguccccac agacucagag agaacccgcc accauguucg<br>uguuccuggu gcugcugccu cuggugucca gccagugugu gaaccugacc<br>accagaacac agcugccucc agccuacacc aacagcuuua ccagaggcgu guacuacccc<br>gacaaggugu ucagauccag cgugcugcac ucuacccagg accuguuccu<br>gccuuucuuc agcaacguga ccugguucca cgccauccac guguccggca<br>ccaauggcac caagagauuc gacaaccccg ugcugcccuu caacgacggg<br>guguacuuug ccagcaccga gaaguccaac aucaucagag gcuggaucuu<br>cggcaccaca cuggacagca agacccagag ccugcugauc gugaacaacg<br>ccaccaacgu ggucaucaaa gugugcgagu uccaguucug caacgacccc<br>uuccugggcg ucuacuacca caagaacaac aagagcugga uggaaagcga<br>guuccgggug uacagcagcg ccaacaacug caccuucgag uacguguccc<br>agccuuuccu gauggaccug gaaggcaagc agggcaacuu caagaaccug<br>cgcgaguucg uguuuaagaa caucgacggc uacuucaaga ucuacagcaa<br>gcacaccccu aucaaccucg ugcgggaucu gccucagggc uucucugcuc<br>uggaaccccu gguggaucug cccaucggca ucaacaucac ccgguuucag<br>acacugcugg cccugcacag aagcuaccug acaccuggcg auagcagcag<br>cggauggaca gcuggugccg ccgcuuacua ugugggcuac cugcagccua |

TABLE 1-continued

Exemplary sequences of RNA constructs disclosed herein

| SEQ ID NO | Sequence information | Sequence |
| --- | --- | --- |
| | | gaaccuuccu gcugaaguac aacgagaacg gcaccaucac cgacgccgug<br>gauugugcuc uggauccucu gagcgagaca aagugcaccc ugaaguccuu<br>caccguggaa aagggcaucu accagaccag caacuuccgg gugcagccca<br>ccgaauccau cgugcgguuc cccaauauca ccaaucugug ccccuucggc<br>gagguguuca augccaccag auucgccucu guguacgccu ggaaccggaa<br>gcggaucagc aauugcgugg ccgacuacuc cgugcuguac aacuccgcca<br>gcuucagcac cuucaagugc uacggcgugu ccccuaccaa gcugaacgac<br>cugugcuuca caaacgugua cgccgacagc uucgugaucc ggggagauga<br>agugcggcag auugccccug gacagacagg caagaucgcc gacuacaacu<br>acaagcugcc cgacgacuuc accggcugug ugauugccug gaacagcaac<br>aaccuggacu ccaaagucgg cggcaacuac aauuaccugu accggcuguu<br>ccggaagucc aaucugaagc ccuucgagcg ggacaucucc accgagaucu<br>aucaggccgg cagcaccccu uguaacggcg uggaaggcuu caacugcuac<br>uucccacugc aguccuacgg cuuucagccc acaaauggcg ugggcuauca<br>gcccuacaga gugguggugc ugagcuucga acugcugcau gccccugcca<br>cagugugcgg cccuaagaaa agcaccaauc ucgugaagaa caaaugcgug aacuucaacu<br>ucaacggccu gaccggcacc ggcgugcuga cagagagcaa caagaaguuc<br>cugccauucc agcaguuugg ccgggauauc gccgauacca cagacgccgu<br>uagagauccc cagacacugg aaauccugga caucaccccu ugcagcuucg<br>gcggaguguc ugugaucacc ccuggcacca acaccagcaa ucagguggca<br>gugcuguacc aggacgugaa cuguaccgaa gugcccgugg ccauucacgc<br>cgaucagcug acaccuacau ggcgggugua cuccaccggc agcaaugugu<br>uucagaccag agccggcugu cugaucggag ccgagcacgu gaacaauagc<br>uacgagugcg acauccccau cggcgcugga aucugcgcca gcuaccagac acagacaaac<br>agcccucgga gagccagaag cguggccagc cagagcauca uugccuacac<br>aaugucucug ggcgccgaga acagcguggc cuacuccaac aacucuaucg cuauccccac<br>caacuucacc aucagcguga ccacagagau ccugccugug uccaugacca agaccagcgu<br>ggacugcacc auguacaucu gcggcgauuc caccgagugc uccaaccugc<br>ugcugcagua cggcagcuuc ugcacccagc ugaauagagc ccugacaggg<br>aucgccgugg aacaggacaa gaacacccaa gagguguucg cccaagugaa gcagaucuac<br>aagaccccuc cuaucaagga cuucggcggc uucaauuuca gccagauucu<br>gcccgauccu agcaagccca gcaagcggag cuucaucgag gaccugcugu<br>ucaacaaagu gacacuggcc gacgccggcu ucaucaagca guauggcgau<br>ugucugggcg acauugccgc cagggaucug auuugcgccc agaaguuuaa<br>cggacugaca gugcugccuc cucugcugac cgaugagaug aucgcccagu<br>acacaucugc ccugcuggcc ggcacaauca caagcggcug gacauuugga<br>gcaggcgccg cucugcagau ccccuuugcu augcagaugg ccuaccgguu<br>caacggcauc ggagugaccc agaaugugcu guacgagaac cagaagcuga<br>ucgccaacca guucaacagc gccaucggca agauccagga cagccugagc agcacagcaa<br>gcgcccuggg aaagcugcag gacgugguca accagaaugc ccaggcacug<br>aacacccugg ucaagcagcu guccuccaac uucggcgcca ucagcucugu<br>gcugaacgau auccugagca gacuggaccc uccugaggcc gaggugcaga<br>ucgacagacu gaucacaggc agacugcaga gccuccagac auacgugacc cagcagcuga<br>ucagagccgc cgagauuaga gccucugcca aucuggccgc caccaagaug<br>ucugagugug ugcugggcca gagcaagaga guggacuuuu gcggcaaggg<br>cuaccaccug augagcuucc cucagucugc cccucacggc gugguguuuc<br>ugcacgugac auaugugccc gcucaagaga agaauuucac caccgcucca gccaucugcc<br>acgacggcaa agcccacuuu ccuagagaag gcguguucgu guccaacggc<br>acccauuggu ucgugacaca gcggaacuuc uacgagcccc agaucaucac caccgacaac<br>accuucgugu cuggcaacug cgacgucgug aucggcauug ugaacaauac<br>cguguacgac ccucugcagc ccgagcugga cagcuucaaa gaggaacugg<br>acaaguacuu uaagaaccac acaagccccg acguggaccu gggcgauauc agcggaauca<br>augccagcgu cgugaacauc cagaaagaga ucgaccggcu gaacgaggug<br>gccaagaauc ugaacgagag ccugaucgac cugcaagaac uggggaagua<br>cgagcaguac aucaaguggc ccugguacau cuggcugggc uuuaucgccg<br>gacugauugc caucgugaug gucacaauca ugcuguguug caugaccagc<br>ugcuguagcu gccugaaggg cuguuguagc uguggcagcu gcugcaaguu<br>cgacgaggac gauucugagc ccgugcugaa gggcgugaaa cugcacuaca<br>caugaugacu cgagcuggua cugcaugcac gcaaugcuag cugccccuuu<br>cccguccugg guaccccgag ucucccccga ccucgggucc cagguaugcu cccaccucca<br>ccugccccac ucaccaccuc ugcuaguucc agacaccucc caagcacgca gcaaugcagc<br>ucaaaacgcu uagccuagcc acacccccac gggaaacagc agugauuaac cuuuagcaau<br>aaacgaaagu uuaacuaagc uauacuaacc ccaggguugg ucaauuucgu<br>gccagccaca cccuggagcu agcaaaaaaa aaaaaaaaaa aaaaaaaaaa aaagcauaug<br>acuaaaaaaa aaaaaaaaaa aaaaaaaaaa aaaaaaaaaa aaaaaaaaaa aaaaaaaaaa<br>aaaaaaaaaa aaa |
| 11 | Human alpha globin 5' UTR with (**AGAAU** first 5 nucleotides) | **AGAAU**AAACUAGUAUUCUUCUGGUCCCCACAGACUCA<br>GAGAGAACCC |

TABLE 1-continued

Exemplary sequences of RNA constructs disclosed herein

| SEQ ID NO | Sequence information | Sequence |
|---|---|---|
| 12 | Human alpha globin 5' UTR (without first 5 nucleotides) | AAACUAGUAUUCUUCUGGUCCCCACAGACUCAGAGAG<br>AACCC |
| 13 | 3' UTR | CUGGUACUGCAUGCACGCAAUGCUAGCUGCCCCUUUCCCGU<br>CCUGGGUACCCCGAGUCUCCCCCGACCUCGGGUCCCAGGUA<br>UGCUCCCACCUCCACCUGCCCCACUCACCACCUCUGCUAGUU<br>CCAGACACCUCCCAAGCACGCAGCAAUGCAGCUCAAAACGC<br>UUAGCCUAGCCACACCCCCACGGGAAACAGCAGUGAUUAAC<br>CUUUAGCAAUAAACGAAAGUUUAACUAAGCUAUACUAACCC<br>CAGGGUUGGUCAAUUUCGUGCCAGCCACACC |
| 14 | A30L70 PolyA | AAAAAAAAAAAAAAAAAAAAAAAAAAAAAAGCAUAUGACU<br>AAAAAAAAAAAAAAAAAAAAAAAAAAAAAAAAAAAAAAAA<br>AAAAAAAAAAAAAAAAAAAAAAAAAAAAAA |
| 15 | Exemplary RNA polynucleotide (vA 3.0.1) without coding sequence of a payload<br>Bold = 5' UTR<br>Bold and underlined = cap proximal sequence<br>Underlined = Kozak sequence<br>Italicized and underlined = 3' UTR<br>Italicized = PolyA | **AGAAUAAACUAGUAUUCUUCUGGUCCCCACAGACUC**<br>**AGAGAGAACCC**GCCACCCUCGAG*CUGGUACUGCAUGCA*<br>*CGCAAUGCUAGCUGCCCCUUUCCCGUCCUGGGUACCCCG*<br>*AGUCUCCCCCGACCUCGGGUCCCAGGUAUGCUCCCACCU*<br>*CCACCUGCCCCACUCACCACCUCUGCUAGUUCCAGACAC*<br>*CUCCCAAGCACGCAGCAAUGCAGCUCAAAACGCUUAGCCU*<br>*AGCCACACCCCCACGGGAAACAGCAGUGAUUAACCUUUAG*<br>*CAAUAAACGAAAGUUUAACUAAGCUAUACUAACCCCAGGG*<br>*UUGGUCAAUUUCGUGCCAGCCACAC*CCUGGAGCUAGC*AA*<br>*AAAAAAAAAAAAAAAAAAAAAAAAAAAAGCAUAUGACUAAAA*<br>*AAAAAAAAAAAAAAAAAAAAAAAAAAAAAAAAAAAAAAAAAAA*<br>*AAAAAAAAAAAAAAAAAAAAAAA* |
| 16 | Exemplary RNA polynucleotide (vA 3.0.1) with a payload sequence<br>Underline = exemplary payload sequence (BNT162b2) | AGAAUAAACUAGUAUUCUUCUGGUCCCCACAGACUCA<br>GAGAGAACCCGCCACCAUGUUCGUGUUCCUGGUGCUGC<br>UGCCUCUGGUGUCCAGCCAGUGUGUGAACCUGACCACC<br>AGAACACAGCUGCCUCCAGCCUACACCAACAGCUUUAC<br>CAGAGGCGUGUACUACCCCGACAAGGUGUUCAGAUCC<br>AGCGUGCUGCACUCUACCCAGGACCUGUUCCUGCCUUU<br>CUUCAGCAACGUGACCUGGUUCCACGCCAUCCACGUGU<br>CCGGCACCAAUGGCACCAAGAGAUUCGACAACCCCGUG<br>CUGCCCUUCAACGACGGGGUGUACUUUGCCAGCACCGA<br>GAAGUCCAACAUCAUCAGAGGCUGGAUCUUCGGCACC<br>ACACUGGACAGCAAGACCCAGAGCCUGCUGAUCGUGA<br>ACAACGCCACCAACGUGGUCAUCAAAGUGUGCGAGUU<br>CCAGUUCUGCAACGACCCCUUCCUGGGCGUCUACUACC<br>ACAAGAACAACAAGAGCUGGAUGGAAAGCGAGUUCCG<br>GGUGUACAGCAGCGCCAACAACUGCACCUUCGAGUACG<br>UGUCCCAGCCUUUCCUGAUGGACCUGGAAGGCAAGCA<br>GGGCAACUUCAAGAACCUGCGCGAGUUCGUGUUUAAG<br>AACAUCGACGGCUACUUCAAGAUCUACAGCAAGCACAC<br>CCCUAUCAACCUCGUGCGGGAUCUGCCUCAGGGCUUCU<br>CUGCUCUGGAACCCCUGGUGGAUCUGCCCAUCGGCAUC<br>AACAUCACCCGGUUUCAGACACUGCUGGCCCUGCACAG<br>AAGCUACCUGACACCUGGCGAUAGCAGCAGCGGAUGG<br>ACAGCUGGUGCCGCCGCUUACUAUGUGGGCUACCUGCA<br>GCCUAGAACCUUCCUGCUGAAGUACAACGAGAACGGC<br>ACCAUCACCGACGCCGUGGAUUGUGCUCUGGAUCCUCU<br>GAGCGAGACAAAGUGCACCCUGAAGUCCUUCACCGUG<br>GAAAAGGGCAUCUACCAGACCAGCAACUUCCGGGUGC<br>AGCCCACCGAAUCCAUCGUGCGGUUCCCCAAUAUCACC<br>AAUCUGUGCCCCUUCGGCGAGGUGUUCAAUGCCACCAG<br>AUUCGCCUCUGUGUACGCCUGGAACCGGAAGCGGAUC<br>AGCAAUUGCGUGGCCGACUACUCCGUGCUGUACAACUC<br>CGCCAGCUUCAGCACCUUCAAGUGCUACGGCGUGUCCC<br>CUACCAAGCUGAACGACCUGUGCUUCACAAACGUGUAC<br>GCCGACAGCUUCGUGAUCCGGGGAGAUGAAGUGCGGC<br>AGAUUGCCCCUGGACAGACAGGCAAGAUCGCCGACUAC<br>AACUACAAGCUGCCCGACGACUUCACCGGCUGUGUGAU<br>UGCCUGGAACAGCAACAACCUGGACUCCAAAGUCGGCG<br>GCAACUACAAUUACCUGUACCGGCUGUUCCGGAAGUCC<br>AAUCUGAAGCCCUUCGAGCGGGACAUCUCCACCGAGAU<br>CUAUCAGGCCGGCAGCACCCCUUGUAACGGCGUGGAAG<br>GCUUCAACUGCUACUUCCCACUGCAGUCCUACGGCUUU |

TABLE 1-continued

| Exemplary sequences of RNA constructs disclosed herein | | |
|---|---|---|
| SEQ ID NO | Sequence information | Sequence |
| | | CAGCCCACAAAUGGCGUGGGCUAUCAGCCCUACAGAGU |
| | | GGUGGUGCUGAGCUUCGAACUGCUGCAUGCCCCUGCCA |
| | | CAGUGUGCGGCCCUAAGAAAAGCACCAAUCUCGUGAA |
| | | GAACAAAUGCGUGAACUUCAACUUCAACGGCCUGACC |
| | | GGCACCGGCGUGCUGACAGAGAGCAACAAGAAGUUCC |
| | | UGCCAUUCCAGCAGUUUGGCCGGGAUAUCGCCGAUACC |
| | | ACAGACGCCGUUAGAGAUCCCCAGACACUGGAAAUCCU |
| | | GGACAUCACCCCUUGCAGCUUCGGCGGAGUGUCUGUG |
| | | AUCACCCCUGGCACCAACACCAGCAAUCAGGUGGCAGU |
| | | GCUGUACCAGGACGUGAACUGUACCGAAGUGCCCGUG |
| | | GCCAUUCACGCCGAUCAGCUGACACCUACAUGGCGGGU |
| | | GUACUCCACCGGCAGCAAUGUGUUUCAGACCAGAGCCG |
| | | GCUGUCUGAUCGGAGCCGAGCACGUGAACAAUAGCUA |
| | | CGAGUGCGACAUCCCCAUCGGCGCUGGAAUCUGCGCCA |
| | | GCUACCAGACACAGACAAACAGCCCUCGGAGAGCCAGA |
| | | AGCGUGGCCAGCCAGAGCAUCAUUGCCUACACAAUGUC |
| | | UCUGGGCGCCGAGAACAGCGUGGCCUACUCCAACAACU |
| | | CUAUCGCUAUCCCCACCAACUUCACCAUCAGCGUGACC |
| | | ACAGAGAUCCUGCCUGUGUCCAUGACCAAGACCAGCGU |
| | | GGACUGCACCAUGUACAUCUGCGGCGAUUCCACCGAGU |
| | | GCUCCAACCUGCUGCUGCAGUACGGCAGCUUCUGCACC |
| | | CAGCUGAAUAGAGCCCUGACAGGGAUCGCCGUGGAAC |
| | | AGGACAAGAACACCCAAGAGGUGUUCGCCCAAGUGAA |
| | | GCAGAUCUACAAGACCCCUCCUAUCAAGGACUUCGGCG |
| | | GCUUCAAUUUCAGCCAGAUUCUGCCCGAUCCUAGCAAG |
| | | CCCAGCAAGCGGAGCUUCAUCGAGGACCUGCUGUUCAA |
| | | CAAAGUGACACUGGCCGACGCCGGCUUCAUCAAGCAGU |
| | | AUGGCGAUUGUCUGGGCGACAUUGCCGCCAGGGAUCU |
| | | GAUUUGCGCCCAGAAGUUUAACGGACUGACAGUGCUG |
| | | CCUCCUCUGCUGACCGAUGAGAUGAUCGCCCAGUACAC |
| | | AUCUGCCCUGCUGGCCGGCACAAUCACAAGCGGCUGGA |
| | | CAUUUGGAGCAGGCGCCGCUCUGCAGAUCCCCUUUGCU |
| | | AUGCAGAUGGCCUACCGGULJCAACGGCAUCGGAGUGA |
| | | CCCAGAAUGUGCUGUACGAGAACCAGAAGCUGAUCGC |
| | | CAACCAGUUCAACAGCGCCAUCGGCAAGAUCCAGGACA |
| | | GCCUGAGCAGCACAGCAAGCGCCCUGGGAAAGCUGCAG |
| | | GACGUGGUCAACCAGAAUGCCCAGGCACUGAACACCCU |
| | | GGUCAAGCAGCUGUCCUCCAACUUCGGCGCCAUCAGCU |
| | | CUGUGCUGAACGAUAUCCUGAGCAGACUGGACCCUCCU |
| | | GAGGCCGAGGUGCAGAUCGACAGACUGAUCACAGGCA |
| | | GACUGCAGAGCCUCCAGACAUACGUGACCCAGCAGCUG |
| | | AUCAGAGCCGCCGAGAUUAGAGCCUCUGCCAAUCUGGC |
| | | CGCCACCAAGAUGUCUGAGUGUGUGCUGGGCCAGAGC |
| | | AAGAGAGUGGACUUUUGCGGCAAGGGCUACCACCUGA |
| | | UGAGCUUCCCUCAGUCUGCCCCUCACGGCGUGGUGUUU |
| | | CUGCACGUGACAUAUGUGCCCGCUCAAGAGAAGAAUU |
| | | UCACCACCGCUCCAGCCAUCUGCCACGACGGCAAAGCC |
| | | CACUUUCCUAGAGAAGGCGUGUUCGUGUCCAACGGCA |
| | | CCCAUUGGUUCGUGACACAGCGGAACUUCUACGAGCCC |
| | | CAGAUCAUCACCACCGACAACACCUUCGUGUCUGGCAA |
| | | CUGCGACGUCGUGAUCGGCAUUGUGAACAAUACCGUG |
| | | UACGACCCUCUGCAGCCCGAGCUGGACAGCUUCAAAGA |
| | | GGAACUGGACAAGUACUUUAAGAACCACACAAGCCCC |
| | | GACGUGGACCUGGGCGAUAUCAGCGGAAUCAAUGCCA |
| | | GCGUCGUGAACAUCCAGAAAGAGAUCGACCGGCUGAA |
| | | CGAGGUGGCCAAGAAUCUGAACGAGAGCCUGAUCGAC |
| | | CUGCAAGAACUGGGGAAGUACGAGCAGUACAUCAAGU |
| | | GGCCCUGGUACAUCUGGCUGGGCUUUAUCGCCGGACU |
| | | GAUUGCCAUCGUGAUGGUCACAAUCAUGCUGUGUUGC |
| | | AUGACCAGCUGCUGUAGCUGCCUGAAGGGCUGUUGUA |
| | | GCUGUGGCAGCUGCUGCAAGUUCGACGAGGACGAUUC |
| | | UGAGCCCGUGCUGAAGGGCGUGAAACUGCACUACACA |
| | | UGAUGACUCGAGCUGGUACUGCAUGCACGCAAUGCUA |
| | | GCUGCCCCUUUCCCGUCCUGGGUACCCCGAGUCUCCCC |
| | | CGACCUCGGGUCCCAGGUAUGCUCCCACCUCCACCUGC |
| | | CCCACUCACCACCUCUGCUAGUUCCAGACACCUCCCAA |
| | | GCACGCAGCAAUGCAGCUCAAAACGCUUAGCCUAGCCA |
| | | CACCCCCACGGGAAACAGCAGUGAUUAACCUUUAGCAA |
| | | UAAACGAAAGUUUAACUAAGCUAUACUAACCCCAGGG |
| | | UUGGUCAAUUUCGUGCCAGCCACACCCUGGAGCUAGCA |
| | | AAAAAAAAAAAAAAAAAAAAAAAAAAAAGCAUAUGA |
| | | CUAAAAAAAAAAAAAAAAAAAAAAAAAAAAAAAAAA |
| | | AAAAAAAAAAAAAAAAAAAAAAAAAAAAAAAAAA |

RBL063.1 (SEQ ID NO: 28 Nucleotide; SEQ ID NO: 9 Amino Acid)

Structure beta-S-ARCA(D1)-hAg-Kozak-S1S2-PP-FI-A30L70

Encoded antigen Viral spike protein (S1S2 protein) of the SARS-CoV-2 (S1S2 full-length protein, sequence variant)

```
                                                         SEQ ID NO: 28
gggcgaacua guauucuucu gguccccaca gacucagaga gaacccgcca ccauguuugu    60

guuucuugug cugcugccuc uugugucuuc ucagugugug aauuugacaa caagaacaca   120

gcugccacca gcuuauacaa auucuuuuac cagaggagug uauuauccug auaaaguguu   180

uagaucuucu gugcugcaca gcacacagga ccuguuucug ccauuuuuua gcaaugugac   240

augguuucau gcaauucaug ugucuggaac aaauggaaca aaaagauuug auaauccugu   300

gcugccuuuu aaugauggag uguauuuugc uucaacagaa aagucaaaua uuauuagagg   360

auggauuuuu ggaacaacac uggauucuaa aacacagucu cugcugauug ugaauaaugc   420

aacaaaugug gugauuaaag ugugugaauu ucaguuuugu aaugauccuu uucugggagu   480

guauuaucac aaaaauaaua aaucuuggau ggaaucugaa uuuagagugu auuccucugc   540

aaauaauugu acauuugaau augugucuca gccuuuucug auggaucugg aaggaaaaca   600

gggcaauuuu aaaaaucuga gagaauuugu guuuaaaaau auugauggau auuuuaaaau   660

uuauucuaaa cacacaccaa uuaauuuagu gagagaucug ccucagggau uuucugcucu   720

ggaaccucug guggaucugc caauuggcau uaauauuaca agauuucaga cacugcuggc   780

ucugcacaga ucuuaucuga caccuggaga uucuucuucu ggauggacag ccggagcugc   840

agcuuauuau gugggcuauc ugcagccaag aacauuucug cugaaauaua augaaaaugg   900

aacaauuaca gaugcugugg auugugcucu ggauccucug ucugaaacaa aauguacauu   960

aaaaucuuuu acaguggaaa aaggcauuua ucagacaucu aauuuuagag ugcagccaac  1020

agaaucuauu gugagauuuc caaauauuac aaaucugugu ccauuuggag aaguguuuaa  1080

ugcaacaaga uuugcaucug uguaugcaug gaauagaaaa agaauuucua auuguguggc  1140

ugauuauucu gugcuguaua auagugcuuc uuuuuccaca uuuaaauguu auggaguguc  1200

uccaacaaaa uuaaaugauu uauguuuuac aaauguguau gcugauucuu uugugaucag  1260

aggugaugaa gugagacaga uugcccccgg acagacagga aaaauugcug auuacaauua  1320

caaacugccu gaugauuuua caggaugugu gauugcuugg aauucuaaua auuuagauuc  1380

uaaaguggga ggaaauuaca auuaucugua cagacuguuu agaaaaucaa aucugaaacc  1440

uuuugaaaga gauauuucaa cagaaauuua ucaggcugga ucaacaccuu guaauggagu  1500

ggaaggauuu aauuguuauu uuccauuaca gagcuaugga uuucagccaa ccaauggugu  1560

gggauaucag ccauauagag ugguggugcu gucuuuugaa cugcugcaug caccugcaac  1620

agugugugga ccuaaaaaau cuacaaauuu agugaaaaau aaauguguga auuuuaauuu  1680

uaauggauua acaggaacag gagugcugac agaaucuaau aaaaaauuuc ugccuuuuca  1740

gcaguuuggc agagauauug cagauaccac agaugcagug agagauccuc agacauuaga  1800

aauucuggau auuacaccuu guucuuuugg ggguguguca gugauuacac cuggaacaaa  1860

uacaucuaau cagguggcug ugcuguauca ggaugugaau uguacagaag ugccaguggc  1920

aauucaugca gaucagcuga caccaacaug gagaguguau ucuacaggau cuaauguguu  1980

ucagacaaga gcaggauguc ugauuggagc agaacaugug aauaauucuu augaauguga  2040

uauuccaauu ggagcaggca uuugugcauc uuaucagaca cagacaaauu ccccaaggag  2100

agcaagaucu guggcaucuc agucuauuau ugcauacacc augucucugg gagcagaaaa  2160
```

-continued

```
uucuguggca uauucuaaua auucuauugc uauuccaaca aauuuuacca uuucugugac  2220

aacagaaauu uuaccugugu cuaugacaaa aacaucugug gauuguacca uguacauuug  2280

uggagauucu acagaauguu cuaaucugcu gcugcaguau ggaucuuuuu guacacagcu  2340

gaauagagcu uuaacaggaa uugcugugga acaggauaaa aauacacagg aaguguuugc  2400

ucaggugaaa cagauuuaca aaacaccacc aauuaaagau uuuggaggau uuaauuuuag  2460

ccagauucug ccugauccuu cuaaaccuuc uaaaagaucu uuuauugaag aucugcuguu  2520

uaauaaagug acacuggcag augcaggauu uauuaaacag uauggagauu gccugggguga  2580

uauugcugca agagaucuga uuugugcuca gaaauuuaau ggacugacag ugcugccucc  2640

ucugcugaca gaugaaauga uugcucagua cacaucugcu uuacuggcug gaacaauuac  2700

aagcggaugg acauuuggag cuggagcugc ucugcagauu ccuuuugcaa ugcagauggc  2760

uuacagauuu aauggaauug gagugacaca gaauguguua uaugaaaauc agaaacugau  2820

ugcaaaucag uuuaauucug caauuggcaa aauucaggau ucucugucuu cuacagcuuc  2880

ugcucuggga aaacugcagg auguggugaa ucagaaugca caggcacuga auacucuggu  2940

gaaacagcug ucuagcaauu uuggggcaau uucuucugug cugaaugaua uucugucuag  3000

acuggauccu ccugaagcug aagugcagau ugauagacug aucacaggaa gacugcaguc  3060

ucugcagacu uaugugacac agcagcugau uagagcugcu gaaauuagag cuucugcuaa  3120

ucuggcugcu acaaaaaugu cugaaugugu gcugggacag ucaaaaagag uggauuuuug  3180

uggaaaagga uaucaucuga ugucuuuucc acagucugcu ccacauggag ugguguuuuu  3240

acaugugaca uaugugccag cacaggaaaa gaauuuuacc acagcaccag caauuuguca  3300

ugauggaaaa gcacauuuuc caagagaagg aguguuugug ucuaauggaa cacauugguu  3360

ugugacacag agaaauuuuu augaaccuca gauuauuaca acagauaaua cauuuguguc  3420

aggaaauugu gauguggug a uuggaauugu gaauaauaca guguaugauc cacugcagcc  3480

agaacuggau ucuuuuaaag aagaacugga uaaauauuuu aaaaaucaca caucuccuga  3540

uguggauuua ggagauauuu cuggaaucaa ugcaucugug gugaauauuc agaaagaaau  3600

ugauagacug aaugaagugg ccaaaaaucu gaaugaaucu cugauugauc ugcaggaacu  3660

uggaaaauau gaacaguaca uuaaauggcc uugguacauu uggcuuggau uuauugcagg  3720

auuaauugca auugugaugg ugacaauuau guuauguugu augacaucau guuguucuug  3780

uuuaaaagga uguuguucuu guggaagcug uuguaaauuu gaugaagaug auucugaacc  3840

uguguuaaaa ggagugaaau ugcauuacac augaugacuc gagcugguac ugcaugcacg  3900

caaugcuagc ugccccuuuc ccguccuggg uaccccgagu cucccccgac cucgggu ccc  3960

agguaugcuc ccaccuccac cugccccacu caccaccucu gcuaguucca gacaccuccc  4020

aagcacgcag caaugcagcu caaaacgcuu agccuagcca cacccccacg ggaaacagca  4080

gugauuaacc uuuagcaaua aacgaaaguu uaacuaagcu auacuaaccc cagggu uggu  4140

caauuucgug ccagccacac ccuggagcua gcaaaaaaaa aaaaaaaaaa aaaaaaaaaa  4200

aagcauauga cuaaaaaaaa aaaaaaaaaa aaaaaaaaaa aaaaaaaaaa aaaaaaaaaa  4260

aaaaaaaaaa aaaaaaaaaa aa                                            4282
```

RBL063.2 (SEQ ID NO: 29 Nucleotide; SEQ ID NO: 9 Amino Acid)

Structure beta-S-ARCA(D1)-hAg-Kozak-S1S2-PP-FI-A30L70

Encoded antigen Viral spike protein (S1S2 protein) of the SARS-CoV-2 (S1S2 full-length protein, sequence variant)

SEQ ID NO: 29

```
gggcgaacua guauucuucu gguccccaca gacucagaga gaacccgcca ccauguucgu    60

guuccuggug cugcugccuc ugguguccag ccagugugug aaccugacca ccagaacaca   120

gcugccucca gccuacacca acagcuuuac cagaggcgug uacuaccccg acaaggugu u  180

cagauccagc gugcugcacu cuacccagga ccuguuccug ccuuucuuca gcaacgugac   240

cugguuccac gccauccacg uguccggcac caauggcacc aagagauucg acaaccccgu   300

gcugcccuuc aacgacgggg uguacuuugc cagcaccgag aaguccaaca ucaucagagg   360

cuggaucuuc ggcaccacac uggacagcaa gacccagagc cugcugaucg ugaacaacgc   420

caccaacgug gucaucaaag ugugcgaguu ccaguucugc aacgaccccu uccugggcgu   480

cuacuaccac aagaacaaca agagcuggau ggaaagcgag uuccgggugu acagcagcgc   540

caacaacugc accuucgagu acgugucca gccuuuccug auggaccugg aaggcaagca   600

gggcaacuuc aagaaccugc gcgaguucgu guuuaagaac aucgacggcu acuucaagau   660

cuacagcaag cacaccccua ucaaccucgu gcgggaucug ccucagggcu ucucugcucu   720

ggaaccccug guggaucugc ccaucggcau caacaucacc cgguuucaga cacugcuggc   780

ccugcacaga agcuaccuga caccuggcga uagcagcagc ggauggacag cuggugccgc   840

cgcuuacuau gugggcuacc ugcagccuag aaccuuccug cugaaguaca acgagaacgg   900

caccaucacc gacgccgugg auugugcucu ggauccucug agcgagacaa agugcacccu   960

gaaguccuuc accguggaaa agggcaucua ccagaccagc aacuuccggg ugcagcccac  1020

cgaauccauc gugcgguucc ccaauaucac caaucugugc cccuucggcg agguguucaa  1080

ugccaccaga uucgccucug uguacgccug gaaccggaag cggaucagca auugcguggc  1140

cgacuacucc gugcuguaca acuccgccag cuucagcacc uucaagugcu acggcguguc  1200

cccuaccaag cugaacgacc ugugcuucac aaacguguac gccgacagcu ucgugauccg  1260

gggagaugaa gugcggcaga uugccccugg acagacaggc aagaucgccg acuacaacua  1320

caagcugccc gacgacuuca ccggcugugu gauugccugg aacagcaaca accuggacuc  1380

caaagucggc ggcaacuaca auuaccugua ccggcuguuc cggaagucca aucugaagcc  1440

cuucgagcgg gacaucucca ccgagaucua ucaggccggc agcaccccuu guaacggcgu  1500

ggaaggcuuc aacugcuacu ucccacugca guccuacggc uuucagccca caaauggcgu  1560

gggcuaucag cccuacagag ugguggugcu gagcuucgaa cugcugcaug ccccugccac  1620

agugugcggc ccuaagaaaa gcaccaaucu cgugaagaac aaaugcguga acuucaacuu  1680

caacggccug accggcaccg gcgugcugac agagagcaac aagaaguucc ugccauucca  1740

gcaguuuggc cgggauaucg ccgauaccac agacgccguu agagaucccc agacacugga  1800

aauccuggac aucaccccuu gcagcuucgg cggagugucu gugaucaccc cuggcaccaa  1860

caccagcaau cagguggcag ugcuguacca ggacgugaac uguaccgaag ugcccguggc  1920

cauucacgcc gaucagcuga caccuacaug gcggguguac uccaccggca gcaauguguu  1980

ucagaccaga gccggcuguc ugaucggagc cgagcacgug aacaauagcu acgagugcga  2040

caucccccauc ggcgcuggaa ucugcgccag cuaccagaca cagacaaaca gcccucggag  2100

agccagaagc guggccagcc agagcaucau ugccuacaca augucucugg gcgccgagaa  2160
```

-continued

```
cagcguggcc uacuccaaca acucuaucgc uaucccccacc aacuucacca ucagcgugac  2220
cacagagauc cugccugugu ccaugaccaa gaccagcgug gacugcacca uguacaucug  2280
cggcgauucc accgagugcu ccaaccugcu gcugcaguac ggcagcuucu gcacccagcu  2340
gaauagagcc cugacaggga ucgccgugga acaggacaag aacacccaag agguguucgc  2400
ccaagugaag cagaucuaca agaccccucc uaucaaggac uucggcggcu ucaauuucag  2460
ccagauucug cccgauccua gcaagcccag caagcggagc uucaucgagg accugcuguu  2520
caacaaagug acacuggccg acgccggcuu caucaagcag uauggcgauu gucugggcga  2580
cauugccgcc agggaucuga uuugcgccca gaaguuuaac ggacugacag ugcugccucc  2640
ucugcugacc gaugagauga ucgcccagua cacaucugcc cugcuggccg gcacaaucac  2700
aagcggcugg acauuuggag caggcgccgc ucugcagauc cccuuugcua ugcagauggc  2760
cuaccgguuc aacggcaucg gagugaccca gaaugugcug uacgagaacc agaagcugau  2820
cgccaaccag uucaacagcg ccaucggcaa gauccaggac agccugagca gcacagcaag  2880
cgcccuggga aagcugcagg acguggucaa ccagaaugcc caggcacuga acacccuggu  2940
caagcagcug uccuccaacu ucggcgccau cagcucugug cugaacgaua uccugagcag  3000
acuggacccu ccugaggccg aggugcagau cgacagacug aucacaggca gacugcagag  3060
ccuccagaca uacgugaccc agcagcugau cagagccgcc gagauuagag ccucugccaa  3120
ucuggccgcc accaagaugu cugagugugu gcugggccag agcaagagag uggacuuuug  3180
cggcaagggc uaccaccuga ugagcuuccc ucagucugcc ccucacggcg ugguguuucu  3240
gcacgugaca uaugugcccg cucaagagaa gaauuucacc accgcuccag ccaucugcca  3300
cgacggcaaa gcccacuuuc cuagagaagg cguguucgug uccaacggca cccauugguu  3360
cgugacacag cggaacuucu acgagcccca gaucaucacc accgacaaca ccuucguguc  3420
uggcaacugc gacgucguga ucggcauugu gaacaauacc guguacgacc cucugcagcc  3480
cgagcuggac agcuucaaag aggaacugga caaguacuuu aagaaccaca caagccccga  3540
cguggaccug ggcgauauca gcggaaucaa ugccagcguc gugaacaucc agaaagagau  3600
cgaccggcug aacgaggugg ccaagaaucu gaacgagagc cugaucgacc ugcaagaacu  3660
ggggaaguac gagcaguaca ucaaguggcc cugguacauc uggcugggcu uuaucgccgg  3720
acugauugcc aucgugaugg ucacaaucau gcuguguugc augaccagcu gcuguagcug  3780
ccugaagggc uguuguagcu guggcagcug cugcaaguuc gacgaggacg auucugagcc  3840
cgugcugaag ggcgugaaac ugcacuacac augaugacuc gagcugguac ugcaugcacg  3900
caaugcuagc ugccccuuuc ccguccuggg uaccccgagu cucccccgac cucgggaccc  3960
agguaugcuc ccaccuccac cugccccacu caccaccucu gcuaguucca gacaccuccc  4020
aagcacgcag caaugcagcu caaaacgcuu agccuagcca cacccccacg ggaaacagca  4080
gugauuaacc uuuagcaaua aacgaaaguu uaacuaagcu auacuaaccc cagggguuggu  4140
caauuucgug ccagccacac ccuggagcua gcaaaaaaaa aaaaaaaaaa aaaaaaaaaa  4200
aagcauauga cuaaaaaaaa aaaaaaaaaa aaaaaaaaaa aaaaaaaaaa aaaaaaaaaa  4260
aaaaaaaaaa aaaaaaaaaa aa                                          4282
```

BNT162a1; RBL063.3 (SEQ ID NO: 30 Nucleotide; SEQ ID NO: 21 Amino Acid)

Structure beta-S-ARCA(D1)-hAg-Kozak-RBD-GS-Fibritin-FI-A30L70

Encoded antigen Viral spike protein (S protein) of the SARS-CoV-2 (partial sequence, Receptor Binding Domain (RBD) of S1S2 protein)

```
                                                         SEQ ID NO: 30
gggcgaacua guauucuucu gguccccaca gacucagaga gaacccgcca ccauguuugu    60

guuucuugug cugcugccuc uugugucuuc ucagugugug gugagauuuc caaauauuac   120

aaaucugugu ccauuuggag aaguguuuaa ugcaacaaga uuugcaucug uguaugcaug   180

gaauagaaaa agaauuucua auugugugge ugauuauucu gugcuguaua auagugcuuc   240

uuuuuccaca uuuaaauguu auggaguguc uccaacaaaa uuaaaugauu uauguuuuac   300

aaauguguau gcugauucuu uugugaucag aggugaugaa gugagacaga uugcccccgg   360

acagacagga aaaauugcug auuacaauua caaacugccu gaugauuuua caggaugugu   420

gauugcuugg aauucuaaua auuuagauuc uaaaguggga ggaaauuaca auuaucugua   480

cagacuguuu agaaaaucaa aucugaaacc uuuugaaaga gauauuucaa cagaaauuua   540

ucaggcugga ucaacaccuu guaauggagu ggaaggauuu aauuguuauu uuccauuaca   600

gagcuaugga uuucagccaa ccaauggugu gggauaucag ccauauagag ugguggugcu   660

gucuuuugaa cugcugcaug caccugcaac agugugugga ccuaaaggcu cccccggcuc   720

cggcuccgga ucugguuaua uuccugaagc uccaagagau gggcaagcuu acguucguaa   780

agauggcgaa uggguauuac uuucuaccuu uuuaggccgg ucccuggagg ugcuguucca   840

gggcccegge ugaugacucg agcugguacu gcaugcacgc aaugcuagcu gccccuuucc   900

cguccugggu accccgaguc ucccccgacc ucggguccca gguaugcucc caccuccacc   960

ugccccacuc accaccucug cuaguuccag acaccuccca agcacgcagc aaugcagcuc  1020

aaaacgcuua gccuagccac acccccacgg gaaacagcag ugauuaaccu uuagcaauaa  1080

acgaaaguuu aacuaagcua uacuaacccc aggguugguc aauuucgugc cagccacacc  1140

cuggagcuag caaaaaaaaa aaaaaaaaaa aaaaaaaaaa agcauaugac uaaaaaaaaa  1200

aaaaaaaaaa aaaaaaaaaa aaaaaaaaaa aaaaaaaaaa aaaaaaaaaa aaaaaaaaaa  1260

a                                                                  1261
```

BNT162b2; RBP020.1 (SEQ ID NO: 31 Nucleotide; SEQ ID NO: 9 Amino Acid)

Structure $m_2^{7,3'-O}Gppp(m_1^{2'-O})ApG)$-hAg-Kozak-S1S2-PP-FI-A30L70

Encoded antigen Viral spike protein (S1S2 protein) of the SARS-CoV-2 (S1S2 full-length protein, sequence variant)

```
                                                         SEQ ID NO: 31
agaauaaacu aguauucuuc ugguccccac agacucagag agaacccgcc accauguuug    60

uguuucuugu gcugcugccu cuugugucuu cucagugugu gaauuugaca acaagaacac   120

agcugccacc agcuuauaca aauucuuuua ccagaggagu guauuauccu gauaaagugu   180

uuagaucuuc ugugcugcac agcacacagg accuguuucu gccauuuuuu agcaauguga   240

caugguuuca ugcaauucau gugucuggaa caaauggaac aaaaagauuu gauaauccug   300

ugcugccuuu uaaugaugga guguauuuug cuucaacaga aaagucaaau auuauuagag   360

gauggauuuu uggaacaaca cuggauucua aaacacaguc ucugcugauu gugaauaaug   420

caacaaaugu ggugauuaaa gugugugaau uucaguuuug uaaugauccu uuucugggag   480
```

-continued

```
uguauuauca caaaaauaau aaaucuugga uggaaucuga auuuagagug uauuccucug  540
caaauaauug uacauuugaa uaugugucuc agccuuuucu gauggaucug gaaggaaaac  600
agggcaauuu uaaaaaucug agagaauuug uguuuaaaaa uauugaugga uauuuuaaaa  660
uuuauucuaa acacacacca auuaauuuag ugagagaucu gccucaggga uuuucugcuc  720
uggaaccucu gguggaucug ccaauuggca uuaauauuac aagauuucag acacugcugg  780
cucugcacag aucuuaucug acaccuggag auucuucuuc uggauggaca gccggagcug  840
cagcuuauua ugugggcuau cugcagccaa gaacauuucu gcugaaauau aaugaaaaug  900
gaacaauuac agaugcugug gauugugcuc uggauccucu gucugaaaca aaauguacau  960
uaaaaucuuu uacaguggaa aaaggcauuu aucagacauc uaauuuuaga gugcagccaa 1020
cagaaucuau ugugagauuu ccaaauauua caaaucugug uccauuugga gaaguguuua 1080
augcaacaag auuugcaucu guguaugcau ggaauagaaa aagaauuucu aauugugugg 1140
cugauuauuc ugugcuguau aauagugcuu cuuuuuccac auuuaaaugu uauggagugu 1200
cuccaacaaa auuaaaugau uuauguuuua caaaugugua ugcugauucu uuugugauca 1260
gaggugauga agugagacag auugcccccg gacagacagg aaaaauugcu gauuacaauu 1320
acaaacugcc ugaugauuuu acaggaugug ugauugcuug gaauucuaau aauuuagauu 1380
cuaaagugg g aggaaauuac aauuaucugu acagacuguu uagaaaauca aaucugaaac 1440
cuuuugaaag agauauuuca acagaaauuu aucaggcugg aucaacaccu uguaauggag 1500
uggaaggauu uaauuguuau uuuccauuac agagcuaugg auuucagcca accaauggug 1560
ugggauauca gccauauaga gugguggugc ugucuuuuga acugcugcau gcaccugcaa 1620
cagugugugg accuaaaaaa ucuacaaauu uagugaaaaa uaaaugugug aauuuuaauu 1680
uuaauggauu aacaggaaca ggagugcuga cagaaucuaa uaaaaaauuu cugccuuuuc 1740
agcaguuugg cagagauauu gcagauacca cagaugcagu gagagauccu cagacauuag 1800
aaauucugga uauuacaccu uguucuuuug gggugugucu gugauuaca ccuggaacaa 1860
auacaucuaa ucagguggcu gugcuguauc aggaugugaa uuguacagaa gugccagugg 1920
caauucaugc agaucagcug acaccaacau ggagagugua uucuacagga ucuaaugugu 1980
uucagacaag agcaggaugu cugauuggag cagaacaugu gaauaauucu uaugaaugug 2040
auauuccaau uggagcaggc auuugugcau cuuaucagac acagacaaau uccccaagga 2100
gagcaagauc uguggcaucu cagucuauua uugcauacac caugucucug ggagcagaaa 2160
auucuguggc auauucuaau aauucuauug cuauuccaac aaauuuuacc auuucugug a 2220
caacagaaau uuuaccugug ucuaugacaa aaacaucugu ggauuguacc auguacauuu 2280
guggagauuc uacagaaugu ucuaaucugc ugcugcagua uggaucuuuu uguacacagc 2340
ugaauagagc uuuaacagga auugcugugg aacaggauaa aaauacacag gaaguguuug 2400
cucaggugaa acagauuuac aaaacaccac caauuaaaga uuuuggagga uuuaauuuua 2460
gccagauucu gccugauccu ucuaaaccuu cuaaaagauc uuuuauugaa gaucugcugu 2520
uuaauaaagu gacacuggca gaugcaggau uuauuaaaca guauggagau ugccugggug 2580
auauugcugc aagagaucug auuugugcuc agaaauuuaa uggacugaca gugcugccuc 2640
cucugcugac agaugaaaug auugcucagu acacaucugc uuuacuggcu ggaacaauua 2700
caagcggaug gacauuugga gcuggagcug cucugcagau uccuuuugca augcagaugg 2760
cuuacagauu uaauggaauu ggagugacac agaauguguu auaugaaaau cagaaacuga 2820
uugcaaauca guuuaauucu gcaauuggca aaauucagga uucucugucu ucuacagcuu 2880
cugcucuggg aaaacugcag gaugugguga aucagaaugc acaggcacug aauacucugg 2940
```

-continued

```
ugaaacagcu gucuagcaau uuuggggcaa uuucuucugu gcugaaugau auucugucua 3000
gacuggaucc uccugaagcu gaagugcaga uugauagacu gaucacagga agacugcagu 3060
cucugcagac uuaugugaca cagcagcuga uuagagcugc ugaaauuaga gcuucugcua 3120
aucuggcugc uacaaaaaug ucugaaugug ugcugggaca gucaaaaaga guggauuuuu 3180
guggaaaagg auaucaucug augucuuuuc cacagucugc uccacaugga guggguuuu 3240
uacaugugac auaugugcca gcacaggaaa agaauuuuac cacagcacca gcaauuuguc 3300
augauggaaa agcacauuuu ccaagagaag gaguguuugu gucuaaugga acacauuggu 3360
uugugacaca gagaaauuuu uaugaaccuc agauuauuac aacagauaau acauuugugu 3420
caggaaauug ugauguggug auuggaauug ugaauaauac aguguaugau ccacugcagc 3480
cagaacugga uucuuuuaaa gaagaacugg auaaauauuu uaaaaaucac acaucuccug 3540
auguggauuu aggagauauu ucuggaauca augcaucugu ggugaauauu cagaaagaaa 3600
uugauagacu gaaugaagug gccaaaaauc ugaaugaauc ucugauugau cugcaggaac 3660
uuggaaaaua ugaacaguac auuaaauggc cuugguacau uuggcuugga uuuauugcag 3720
gauuaauugc aauugugaug gugacaauua uguuauguug uaugacauca uguuguucuu 3780
guuuaaaagg auguuguucu uguggaagcu guuguaaauu ugaugaagau gauucugaac 3840
cuguguuaaa aggagugaaa uugcauuaca caugaugacu cgagcuggua cugcaugcac 3900
gcaaugcuag cugccccuuu cccguccugg guaccccgag ucucccccga ccucgggucc 3960
cagguaugcu cccaccucca ccugccccac ucaccaccuc ugcuaguucc agacaccucc 4020
caagcacgca gcaaugcagc ucaaaacgcu uagccuagcc acacccccac gggaaacagc 4080
agugauuaac cuuuagcaau aaacgaaagu uuaacuaagc uauacuaacc ccaggguugg 4140
ucaauuucgu gccagccaca cccuggagcu agcaaaaaaa aaaaaaaaaa aaaaaaaaaa 4200
aaagcauaug acuaaaaaaa aaaaaaaaaa aaaaaaaaaa aaaaaaaaaa aaaaaaaaaa 4260
aaaaaaaaaa aaaaaaaaaa aaa                                         4283
```

RBP020.2 (SEQ ID NO: 10 Nucleotide; SEQ ID NO: 9 Amino Acid) (See Table 1)

Structure $m_2^{7,3'-O}$Gppp($m_1^{2'-O}$)ApG)-hAg-Kozak-S1S2-PP-FI-A30L70

Encoded antigen Viral spike protein (S1S2 protein) of the SARS-CoV-2 (S1S2 full-length protein, sequence variant)

BNT162b1; RBP020.3 (SEQ ID NO: 32; SEQ ID NO: 21 Amino Acid)

Structure $m_2^{7,3'-O}$Gppp($m_1^{2'-O}$)ApG)-hAg-Kozak-RBD-GS-Fibritin-FI-A30L70

Encoded antigen Viral spike protein (S1S2 protein) of the SARS-CoV-2 (partial sequence, Receptor Binding Domain (RBD) of S1S2 protein fused to fibritin)

SEQ ID NO: 32

```
agaauaaacu aguauucuuc ugguccccac agacucagag agaacccgcc accauguuug   60
uguuucuugu gcugcugccu cuugugucuu cucagugugu ggugagauuu ccaaauauua  120
caaaucugug uccauuugga gaaguguuua augcaacaag auuugcaucu guguaugcau  180
ggaauagaaa aagaauuucu aauugugugg cugauuauuc ugugcuguau aauagugcuu  240
cuuuuuccac auuuaaaugu uauggagugu cuccaacaaa auuaaaugau uuauguuuua  300
caaaugugua ugcugauucu uuugugauca gaggugauga agugagacag auugccccccg  360
gacagacagg aaaaauugcu gauuacaauu acaaacugcc ugaugauuuu acaggaugug  420
ugauugcuug gaauucuaau aauuuagauu cuaaaguggg aggaaauuac aauuaucugu  480
acagacuguu uagaaaauca aaucugaaac cuuuugaaag agauauuuca acagaaauuu  540
aucaggcugg aucaacaccu uguaauggag uggaaggauu uaauuguuau uuuccauuac  600
agagcuaugg auuucagcca accaauggug ugggauauca gccauauaga guggguggugc  660
```

-continued

```
ugucuuuuga acugcugcau gcaccugcaa cagugugugg accuaaaggc ucccccggcu   720

ccggcuccgg aucugguuau auuccugaag cuccaagaga ugggcaagcu uacguucgua   780

aagauggcga augguuaua cuuucuaccu uuuuaggccg gucccuggag gugcuguucc   840

agggccccgg cugaugacuc gagcugguac ugcaugcacg caaugcuagc ugccccuuuc   900

ccguccuggg uaccccgagu cuccccccgac cucgggcccc agguaugcuc ccaccuccac   960

cugccccacu caccaccucu gcuaguucca gacaccuccc aagcacgcag caaugcagcu  1020

caaaacgcuu agccuagcca cacccccacg ggaaacagca gugauuaacc uuuagcaaua  1080

aacgaaaguu uaacuaagcu auacuaaccc caggguuggu caauuucgug ccagccacac  1140

ccuggagcua gcaaaaaaaa aaaaaaaaaa aaaaaaaaaa aagcauauga cuaaaaaaaa  1200

aaaaaaaaaa aaaaaaaaaa aaaaaaaaaa aaaaaaaaaa aaaaaaaaaa aaaaaaaaaa  1260

aa                                                                 1262
```

RBS004.1 (SEQ ID NO: 33; SEQ ID NO: 9 Amino Acid)
Structure beta-S-ARCA(D1)-replicase-S1S2-PP-FI-A30L70
Encoded antigen Viral spike protein (S protein) of the SARS-CoV-2 (S1S2 full-length protein, sequence variant)

```
                                                             SEQ ID NO: 33
gaugggcggc gcaugagaga agcccagacc aauuaccuac ccaaaaugga gaaaguucac    60

guugacaucg aggaagacag cccauuccuc agagcuuugc agcggagcuu cccgcaguuu   120

gagguagaag ccaagcaggu cacugauaau gaccaugcua augccagagc guuuucgcau   180

cuggcuucaa aacugaucga aacggaggug gacccauccg acacgauccu ugacauugga   240

agugcgcccg cccgcagaau guauucuaag cacaaguauc auuguaucug uccgaugaga   300

ugugcggaag auccggacag auuguauaag uaugcaacua agcugaagaa aaacuguaag   360

gaaauaacug auaaggaauu ggacaagaaa augaaggagc ucgccgccgu caugagcgac   420

ccugaccugg aaacugagac uaugugccuc cacgacgacg agucgugucg cuacgaaggg   480

caagucgcug uuuaccagga uguauacgcg guugacggac cgacaagucu cuaucaccaa   540

gccaauaagg gaguuagagu cgccuacugg auaggcuuug acaccacccc uuuuauguuu   600

aagaacuugg cuggagcaua uccaucauac ucuaccaacu gggccgacga aaccguguua   660

acggcucgua acauaggccu augcagcucu gacguuaugg agcggucacg uagagggaug   720

uccauucuua gaaagaagua uuugaaacca uccaacaaug uucuauucuc uguuggcucg   780

accaucuacc acgaaaagag ggacuuacug aggagcuggc accugccguc uguauuucac   840

uuacguggca agcaaaauua cacaugucgg ugugagacua uaguuaguug cgacggguac   900

gucguuaaaa gaauagcuau caguccaggc cuguauggga agccuucagg cuaugcugcu   960

acgaugcacc gcgagggauu cuugugcugc aaagugacag acacauugaa cggggagagg  1020

gucucuuuuc ccgugugcac guaugugcca gcuacauugu gugaccaaau gacuggcaua  1080

cuggcaacag augucagugc ggacgacgcg caaaaacugc ugguugggcu caaccagcgu  1140

auagucguca acggucgcac ccagagaaac accaauacca ugaaaaauua ccuuuugccc  1200

guaguggccc aggcauuugc uaggugggca aaggaauaua aggaagauca agaagaugaa  1260

aggccacuag gacuacgaga uagacaguua gucauggggu guuguugggc uuuuagaagg  1320

cacaagauaa caucuauuua uaagcgcccg gauacccaaa ccaucaucaa agugaacagc  1380

gauuuccacu cauucgugcu gcccaggaua ggcaguaaca cauuggagau cgggcugaga  1440
```

-continued acaagaauca ggaaaauguu agaggagcac aaggagccgu caccucucau uaccgccgag 1500
gacguacaag aagcuaagug cgcagccgau gaggcuaagg aggugcguga agccgaggag 1560
uugcgcgcag cucuaccacc uuuggcagcu gauguugagg agcccacucu ggaagccgau 1620
gucgacuuga uguuacaaga ggcuggggcc ggcucagugg agacaccucg uggcuugaua 1680
aagguuacca gcuacgcugg cgaggacaag aucggcucuu acgcugugcu uucuccgcag 1740
gcuguacuca agagugaaaa auuaucuugc auccacccuc ucgcugaaca agucauagug 1800
auaacacacu cuggccgaaa agggcguuau gccguggaac cauaccaugg uaaaguagug 1860
gugccagagg gacaugcaau acccguccag gacuuucaag cucugaguga aagugccacc 1920
auuguguaca acgaacguga guucguaaac agguaccugc accauauugc cacacaugga 1980
ggagcgcuga acacugauga agaauauuac aaaacuguca agcccagcga gcacgacggc 2040
gaauaccugu acgacaucga caggaaacag ugcgucaaga aagagcuagu cacugggcua 2100
gggcucacag gcgagcuggu cgauccuccc uuccaugaau ucgccuacga gagucugaga 2160
acacgaccag ccgcuccuua ccaaguacca accauagggg uguauggcgu gccaggauca 2220
ggcaagucug gcaucauuaa aagcgcaguc accaaaaaag aucuaguggu gagcgccaag 2280
aaagaaaacu gugcagaaau uauaagggac gucaagaaaa ugaaagggcu ggacgucaau 2340
gccagaacug uggacucagu gcucuugaau ggaugcaaac accccguaga gacccuguau 2400
auugacgagg cuuuugcuug ucaugcaggu acucucagag cgcucauagc cauuauaaga 2460
ccuaaaaagg cagugcucug cggagauccc aaacagugcg guuuuuuuaa caugaugugc 2520
cugaaagugc auuuuaacca cgagauuugc acacaagucu uccacaaaag caucucucgc 2580
cguugcacua aaucugugac uucggucguc ucaaccuugu uuuacgacaa aaaaaugaga 2640
acgacgaauc cgaaagagac uaagauugug auugacacua ccggcaguac caaaccuaag 2700
caggacgauc ucauucucac uuguuucaga gggugggguga agcaguugca aauagauuac 2760
aaaggcaacg aaauaaugac ggcagcugcc ucucaagggc ugacccguaa agguguguau 2820
gccguucggu acaaggugaa ugaaaauccu cuguacgcac ccaccucaga acaugugaac 2880
guccuacuga cccgcacgga ggaccgcauc guguggaaaa cacuagccgg cgacccaugg 2940
auaaaaaacac ugacugccaa guacccuggg aauuucacug ccacgauaga ggaguggcaa 3000
gcagagcaug augccaucau gaggcacauc uuggagagac cggacccuac cgacgucuuc 3060
cagaauaagg caaacgugug uugggccaag gcuuuagugc cggugcugaa gaccgcuggc 3120
auagacauga ccacugaaca auggaacacu guggauuauu uugaaacgga caaagcucac 3180
ucagcagaga uaguauugaa ccaacuaugc gugagguucu uuggacucga ucuggacucc 3240
ggucuauuuu cugcacccac uguuccguua uccauuagga auaaucacug ggauaacucc 3300
ccgucgccua acauguacgg gcugaauaaa gaaguggucc gucagcucuc ucgcagguac 3360
ccacaacugc cucgggcagu ugccacuggu agagucuaug acaugaacac ugguacacug 3420
cgcaauuaug auccgcgcau aaaccuagua ccuguaaaca gaagacugcc ucaugcuuua 3480
guccuccacc auaaugaaca cccacagagu gacuuuucuu cauucgucag caaauugaag 3540
ggcagaacug uccugguggu cggggaaaag uuguccgucc caggcaaaau gguugacugg 3600
uugucagacc ggccugaggc uaccuucaga gcucggcugg auuuaggcau cccaggugau 3660
gugcccaaau augacauaau auuuguuaau gugaggaccc cauauaaaua ccaucacuau 3720
cagcagugug aagaccaugc cauuaagcua agcauguuga ccaagaaagc augucugcau 3780
cugaaucccg gcggaaccug ugucagcaua gguuaugguu acgcugacag ggccagcgaa 3840
agcaucauug gugcuauagc gcggcaguuc aaguuucccc gaguaugcaa accgaaaucc 3900

-continued

```
ucacuugagg agacggaagu ucuguuugua uucauugggu acgaucgcaa ggcccguacg  3960
cacaauccuu acaagcuauc aucaaccuug accaacauuu auacagguuc cagacuccac  4020
gaagccggau gugcacccuc auaucaugug gugcgagggg auauugccac ggccaccgaa  4080
ggagugauua uaaaugcugc uaacagcaaa ggacaaccug gcggaggggu gugcggagcg  4140
cuguauaaga aauucccgga aaguuucgau uuacagccga ucgaaguagg aaaagcgcga  4200
cuggucaaag gugcagcuaa acauaucauu caugccguag gaccaaacuu caacaaaguu  4260
ucggagguug aaggugacaa acaguuggca gaggcuuaug aguccaucgc uaagauuguc  4320
aacgauaaca auuacaaguc aguagcgauu ccacuguugu ccaccggcau cuuuuccggg  4380
aacaaagauc gacuaaccca aucauugaac cauuugcuga cagcuuuaga caccacugau  4440
gcagauguag ccauauacug cagggacaag aaaugggaaa ugacucucaa ggaagcagug  4500
gcuaggagag aagcagugga ggagauaugc auauccgacg auucuucagu gacagaaccu  4560
gaugcagagc uggugagggu gcaucccaag aguucuuugg cuggaaggaa gggcuacagc  4620
acaagcgaug gcaaaacuuu cucauauuug gaagggacca aguuucacca ggcggccaag  4680
gauauagcag aaauuaaugc cauguggccc guugcaacgg aggccaauga gcagguaugc  4740
auguauaucc ucggagaaag caugagcagu auuaggucga aaugccccgu cgaggagucg  4800
gaagccucca caccaccuag cacgcugccu ugcuugugca uccaugccau gacuccagaa  4860
agaguacagc gccuaaaagc cucacgucca gaacaaauua cugugugcuc auccuuucca  4920
uugccgaagu auagaaucac uggugugcag aagauccaau gcucccagcc uauauuguuc  4980
ucaccgaaag ugccugcgua uauucaucca aggaaguauc ucguggaaac accaccggua  5040
gacgagacuc cggagccauc ggcagagaac caauccacag aggggacacc ugaacaacca  5100
ccacuuauaa ccgaggauga gaccaggacu agaacgccug agccgaucau caucgaagaa  5160
gaagaagaag auagcauaag uuugcuguca gauggcccga cccaccaggu gcugcaaguc  5220
gaggcagaca uucacgggcc gcccucugua ucuagcucau ccugguccau uccucaugca  5280
uccgacuuug auguggacag uuuauccaua cuugacaccc uggagggagc uagcgugacc  5340
agcggggcaa cgucagccga gacuaacucu uacuucgcaa agaguaugga guuucuggcg  5400
cgaccggugc cugcgccucg aacaguauuc aggaacccuc cacaucccgc uccgcgcaca  5460
agaacaccgu cacuugcacc cagcagggcc ugcuccagaa ccagccuagu uuccaccccg  5520
ccaggcguga auagggugau cacuagagag gagcucgaag cgcuuacccc gucacgcacu  5580
ccuagcaggu cggucuccag aaccagccug gucuccaacc cgccaggcgu aaauagggug  5640
auuacaagag aggaguuuga ggcguucgua gcacaacaac aaugacgguu ugaugcgggu  5700
gcauacaucu uuuccuccga caccggucaa gggcauuuac aacaaaaauc aguaaggcaa  5760
acggugcuau ccgaaguggu guuggagagg accgaauugg agauuucgua ugccccgcgc  5820
cucgaccaag aaaaagaaga auuacuacgc aagaaauuac aguuaaaucc cacaccugcu  5880
aacagaagca gauaccaguc caggaaggug gagaacauga aagccauaac agcuagacgu  5940
auucugcaag gccuagggca uuauuugaag gcagaaggaa aaguggagug cuaccgaacc  6000
cugcauccug uuccuuugua uucaucuagu gugaaccgug ccuuuucaag ccccaagguc  6060
gcaguggaag ccuguaacgc cauguugaaa gagaacuuuc cgacuguggc uucuuacugu  6120
auuauuccag aguacgaugc cuauuuggac augguugacg gagcuucaug cugcuuagac  6180
acugccaguu uuugcccugc aaagcugcgc agcuuuccaa agaaacacuc cuauuuggaa  6240
cccacaauac gaucggcagu gccuucagcg auccagaaca cgcuccagaa cguccuggca  6300
```

-continued

```
gcugccacaa aaagaaauug caaugucacg caaaugagag aauugcccgu auuggauucg  6360
gcggccuuua auguggaaug cuucaagaaa uaugcgugua auaaugaaua uugggaaacg  6420
uuuaaagaaa accccaucag gcuuacugaa gaaaacgugg uaaauuacau uaccaaauua  6480
aaaggaccaa aagcugcugc ucuuuuugcg aagacacaua auuugaauau guugcaggac  6540
auaccaaugg acagguuugu aauggacuua aagagagacg ugaaagugac uccaggaaca  6600
aaacauacug aagaacggcc caagguacag gugauccagg cugccgaucc gcuagcaaca  6660
gcguaucugu gcggaaucca ccgagagcug guuaggagau uaaaugcggu ccugcuuccg  6720
aacauucaua cacuguuuga uaugucggcu gaagacuuug acgcuauuau agccgagcac  6780
uuccagccug ggauugugu ucuggaaacu gacaucgcgu cguuugauaa aagugaggac  6840
gacgccaugg cucugaccgc guuaaugauu cuggaagacu uaggugugga cgcagagcug  6900
uugacgcuga uugaggcggc uuucggcgaa auuucaucaa uacauuugcc cacuaaaacu  6960
aaauuuaaau ucggagccau gaugaaaucu ggaauguucc ucacacuguu ugugaacaca  7020
gucauuaaca uuguaaucgc aagcagagug uugagagaac ggcuaaccgg aucaccaugu  7080
gcagcauuca uuggagauga caauaucgug aaaggaguca aaucggacaa auuaauggca  7140
gacaggugcg ccaccugguu gaauauggaa gucaagauua uagaugcugu ggugggcgag  7200
aaagcgccuu auuucugugg aggguuuauu uugugugacu ccgugaccgg cacagcgugc  7260
cguguggcag acccccuaaa aaggcuguuu aagcuaggca aaccucuggc agcagacgau  7320
gaacaugaug augacaggag aagggcauug caugaggagu caacacgcug gaaccgagug  7380
gguauucuuu cagagcugug caaggcagua gaaucaaggu augaaaccgu aggaacuucc  7440
aucauaguua uggccaugac uacucuagcu agcaguguua aaucauucag cuaccugaga  7500
ggggccccua uaacucucua cggcuaaccu gaauggacua cgacauaguc uaguccgcca  7560
agacuaguau guuuguguuu cuugugcugc ugccucuugu gucuucucag ugugugaauu  7620
ugacaacaag aacacagcug ccaccagcuu auacaaauuc uuuuaccaga ggaguguauu  7680
auccugauaa aguguuuaga ucuucugugc ugcacagcac acaggaccug uuucugccau  7740
uuuuuagcaa ugugacaugg uuucaugcaa uucauguguc uggaacaaau ggaacaaaaa  7800
gauuugauaa uccugugcug ccuuuuaaug auggagugua uuuugcuuca acagaaaagu  7860
caaauauuau uagaggaugg auuuuuggaa caacacugga uucuaaaaca cagucucugc  7920
ugauugugaa uaaugcaaca aaugugguga uuaaagugug ugaauuucag uuuuguaaug  7980
auccuuuucu gggaguguau uaucacaaaa auaauaaauc uuggauggaa ucugaauuua  8040
gaguguauuc cucugcaaau aauuguacau uugaauaugu gucucagccu uuucugaugg  8100
aucuggaagg aaaacagggc aauuuuaaaa aucugagaga auuuguguuu aaaaauauug  8160
auggauauuu uaaaauuuau ucuaaacaca caccaauuaa uuuagugaga gaucugccuc  8220
agggauuuuc ugcucuggaa ccucuggugg aucugccaau uggcauuaau auuacaagau  8280
uucagacacu gcuggcucug cacagaucuu aucugacacc uggagauucu ucuucuggau  8340
ggacagccgg agcugcagcu uauuaugugg gcuaucugca gccaagaaca uuucugcuga  8400
aauauaauga aaauggaaca auuacagaug cuguggauug ugcucuggau ccucugucug  8460
aaacaaaaug uacauuaaaa ucuuuuacag uggaaaaagg cauuuaucag acaucuaauu  8520
uuagagugca gccaacagaa ucuauuguga gauuuccaaa uauuacaaau cuguguccau  8580
uuggagaagu guuuaaugca acaagauuug caucugugua ugcauggaau agaaaaagaa  8640
uuucuaauug uguggcugau uauucugugc uguauaauag ugcuucuuuu uccacauuua  8700
aauguuaugg agugucucca acaaaauuaa augauuuaug uuuuacaaau guguaugcug  8760
```

-continued auucuuuugu gaucagaggu gaugaaguga gacagauugc ccccggacag acaggaaaaa 8820
uugcugauua caauuacaaa cugccugaug auuuuacagg augugugauu gcuuggaauu 8880
cuaauaauuu agauucuaaa gugggaggaa auuacaauua ucuguacaga cuguuuagaa 8940
aaucaaaucu gaaaccuuuu gaaagagaua uuucaacaga aauuuaucag gcuggaucaa 9000
caccuuguaa uggaguggaa ggauuuaauu guuauuuucc auuacagagc uauggauuuc 9060
agccaaccaa uggugugggga uaucagccau auagaguggu ggugcugucu uuugaacugc 9120
ugcaugcacc ugcaacagug uguggaccua aaaaaucuac aaauuuagug aaaaauaaau 9180
gugugaauuu uaauuuuaau ggauuaacag gaacaggagu gcugacagaa ucuaauaaaa 9240
aauuucugcc uuuucagcag uuuggcagag auauugcaga uaccacagau gcagugagag 9300
auccucagac auuagaaauu cuggauauua caccuuguuc uuuugggggu gugucuguga 9360
uuacaccugg aacaaauaca ucuaaucagg uggcugugcu guaucaggau gugaauugua 9420
cagaagugcc aguggcaauu caugcagauc agcugacacc aacauggaga guguauucua 9480
caggaucuaa uguguuucag acaagagcag gaugucugau uggagcagaa caugugaaua 9540
auucuuauga augugauauu ccaauuggag caggcauuug ugcaucuuau cagacacaga 9600
caaauucccc aaggagagca agaucugugg caucucaguc uauuauugca uacaccaugu 9660
cucugggagc agaaaauucu guggcauauu cuaauaauuc uauugcuauu ccaacaaauu 9720
uuaccauuuc ugugacaaca gaaauuuuac cugugucuau gacaaaaaca ucuguggauu 9780
guaccaugua cauuugugga gauucuacag aauguucuaa ucugcugcug caguauggau 9840
cuuuuuguac acagcugaau agagcuuuaa caggaauugc uguggaacag gauaaaaaua 9900
cacaggaagu guuugcucag gugaaacaga uuuacaaaac accaccaauu aaagauuuug 9960
gaggauuuaa uuuuagccag auucugccug auccuucuaa accuucuaaa agaucuuuua 10020
uugaagaucu gcuguuuaau aaagugacac uggcagaugc aggauuuauu aaacaguaug 10080
gagauugccu gggugauauu gcugcaagag aucugauuug ugcucagaaa uuuaauggac 10140
ugacagugcu gccuccucug cugacagaug aaaugauugc ucaguacaca ucugcuuuac 10200
uggcuggaac aauuacaagc ggauggacau uuggagcugg agcugcucug cagauuccuu 10260
uugcaaugca gauggcuuac agauuuaaug gaauuggagu gacacagaau guguuauaug 10320
aaaaucagaa acugauugca aaucaguuua auucugcaau uggcaaaauu caggauucuc 10380
ugucuucuac agcuucugcu cugggaaaac ugcaggaugu ggugaaucag aaugcacagg 10440
cacugaauac ucuggugaaa cagcugucua gcaauuuugg ggcaauuucu ucugugcuga 10500
augauauucu gucuagacug gauccuccug aagcugaagu gcagauugau agacugauca 10560
caggaagacu gcagucucug cagacuuaug ugacacagca gcugauuaga gcugcugaaa 10620
uuagagcuuc ugcuaaucug gcugcuacaa aaaugucuga augugugcug ggacagucaa 10680
aaagagugga uuuuugugga aaaggauauc aucugauguc uuuuccacag ucugcuccac 10740
auggaguggu guuuuuacau gugacauaug ugccagcaca ggaaaagaau uuuaccacag 10800
caccagcaau uugucaugau ggaaaagcac auuuuccaag agaaggagug uuugugucua 10860
auggaacaca uugguuugug acacagagaa auuuuuauga accucagauu auuacaacag 10920
auaauacauu ugugucagga aauugugaug uggugauugg aauugugaau aauacagugu 10980
augauccacu gcagccagaa cuggauucuu uuaaagaaga acuggauaaa uauuuuaaaa 11040
aucacacauc uccugaugug gauuuaggag auauuucugg aaucaaugca ucugugguga 11100
auauucagaa agaaauugau agacugaaug aaguggccaa aaaucugaau gaaucucuga 11160

-continued

```
uugaucugca ggaacuugga aaauaugaac aguacauuaa auggccuugg uacauuuggc   11220

uuggauuuau ugcaggauua auugcaauug ugauggugac aauuauguua uguuguauga   11280

caucauguug uucuuguuua aaaggauguu guucuugugg aagcuguugu aaauuugaug   11340

aagaugauuc ugaaccugug uuaaaaggag ugaaauugca uuacacauga ugacucgagc   11400

gguacugca ugcacgcaau gcuagcugcc ccuuucccgu ccuggguacc ccgagucucc    11460

cccgaccucg ggucccaggu augcucccac cuccaccugc cccacucacc accucugcua   11520

guuccagaca ccucccaagc acgcagcaau gcagcucaaa acgcuuagcc uagccacacc   11580

cccacgggaa acagcaguga uuaaccuuua gcaauaaacg aaaguuuaac uaagcuauac   11640

uaaccccagg guuggucaau uucgugccag ccacaccgcg gccgcaugaa uacagcagca   11700

auuggcaagc ugcuuacaua gaacucgcgg cgauuggcau gccgccuuaa aauuuuuauu   11760

uuauuuuuuc uuuucuuuuc cgaaucggau uuuguuuuua auauuucaaa aaaaaaaaa    11820

aaaaaaaaaa aaaaaaagca uaugacuaaa aaaaaaaaaa aaaaaaaaaa aaaaaaaaaa   11880

aaaaaaaaaa aaaaaaaaaa aaaaaaaaaa aaaaaaa                            11917
```

RBS004.2 (SEQ ID NO: 34; SEQ ID NO: 9 Amino Acid)
Structure   beta-S-ARCA(D1)-replicase-S1S2-PP-FI-
A30L70
Encoded antigen Viral spike protein (S protein) of the
SARS-CoV-2 (S1S2 full-length protein, sequence variant)

```
                                                   SEQ ID NO: 34
gaugggcggc gcaugagaga agcccagacc aauuaccuac ccaaaaugga gaaaguucac     60

guugacaucg aggaagacag cccauuccuc agagcuuugc agcggagcuu cccgcaguuu    120

gagguagaag ccaagcaggu cacugauaau gaccaugcua augccagagc guuuucgcau    180

cuggcuucaa aacugaucga aacggaggug gacccauccg acacgauccu ugacauugga    240

agugcgcccg cccgcagaau guauucaag cacaaguauc auuguaucug uccgaugaga     300

ugugcggaag auccggacag auuguauaag uaugcaacua agcugaagaa aaacuguaag   360

gaaauaacug auaaggaauu ggacaagaaa augaaggagc ucgccgccgu caugagcgac   420

ccugaccugg aaacugagac uaugugccuc cacgacgacg agucgugucg cuacgaaggg   480

caagucgcug uuuaccagga uguauacgcg guugacggac cgacaagucu cuaucaccaa   540

gccauaagg gaguuagagu cgccuacugg auaggcuuug acaccacccc uuuuauguuu   600

aagaacuugg cuggagcaua uccaucauac ucuaccaacu gggccgacga aaccuguuua   660

acggcucgua acauaggccu augcagcucu gacguuaugg agcggucacg uagagggaug   720

uccauucuua gaaagaagua uuugaaacca uccaacaaug uucuauucuc guuuggcucg   780

accaucuacc acgaaaagag ggacuuacug aggagcuggc accugccguc uguauuucac   840

uuacguggca agcaaaauua cacaugucgg ugugagacua uaguuaguug cgacgggguac   900

gucguuaaaa gaauagcuau caguccaggc cuguauggga agccuucagg cuaugcugcu   960

acgaugcacc gcgagggauu cuugugcugc aaagugacag acacauugaa cggggagagg   1020

gucucuuuuc ccgugugcac guaugugcca gcuacauugu gugaccaaau gacuggcaua   1080

cuggcaacag augucagugc ggacgacgcg caaaaacgc ugguugggcu caaccagcgu   1140

auagucguca acgucgcac ccagagaaac accaauacca ugaaaaauua ccuuuugccc   1200

guaguggccc aggcauuugc uaggugggca aggaauauaa aggaagauca agaagaugaa   1260

aggccacuag gacuacgaga uagacaguua gucauggggu guuguggc uuuuagaagg   1320

cacaagauaa caucuauuua uaagcgcccg gauacccaaa ccaucaucaa agugaacagc   1380
```

-continued gauuuccacu cauucgugcu gcccaggaua ggcaguaaca cauuggagau cgggcugaga 1440
acaagaauca ggaaaauguu agaggagcac aaggagccgu caccucucau uaccgccgag 1500
gacguacaag aagcuaagug cgcagccgau gaggcuaagg aggugcguga agccgaggag 1560
uugcgcgcag cucuaccacc uuuggcagcu gauguugagg agcccacucu ggaagccgau 1620
gucgacuuga uguuacaaga ggcuggggcc ggcucagugg agacaccucg uggcuugaua 1680
aagguuacca gcuacgcugg cgaggacaag aucggcucuu acgcugugcu uucuccgcag 1740
gcuguacuca agagugaaaa auuaucuugc auccacccuc ucgcugaaca agucauagug 1800
auaacacacu cuggccgaaa agggcguuau gccguggaac cauaccaugg uaaaguagug 1860
gugccagagg gacaugcaau acccguccag gacuuucaag cucugaguga aagugccacc 1920
auuguguaca acgaacguga guucguaaac agguaccugc accauauugc cacacaugga 1980
ggagcgcuga acacugauga agaauauuac aaaacuguca agcccagcga gcacgacggc 2040
gaauaccugu acgacaucga caggaaacag ugcgucaaga aagagcuagu cacugggcua 2100
gggcucacag gcgagcuggu cgauccuccc uuccaugaau ucgccuacga gagucugaga 2160
acacgaccag ccgcuccuua ccaaguacca accauagggg uguauggcgu gccaggauca 2220
ggcaagucug gcaucauuaa aagcgcaguc accaaaaaag aucuaguggu gagcgccaag 2280
aaagaaaacu gugcagaaau uauaagggac gucaagaaaa ugaaagggcu ggacgucaau 2340
gccagaacug uggacucagu gcucuugaau ggaugcaaac accccguaga gacccuguau 2400
auugacgagg cuuuugcuug ucaugcaggu acucucagag cgcucauagc cauuauaaga 2460
ccuaaaaagg cagugcucug cggagauccc aaacagugcg guuuuuuuaa caugaugugc 2520
cugaaagugc auuuuaacca cgagauuugc acacaagucu uccacaaaag caucucucgc 2580
cguugcacua aaucugugac uucggucguc ucaaccuugu uuuacgacaa aaaaaugaga 2640
acgacgaauc cgaaagagac uaagauugug auugacacua ccggcaguac caaaccuaag 2700
caggacgauc ucauucucac uuguuucaga ggguggguga agcaguugca aauagauuac 2760
aaaggcaacg aaauaaugac ggcagcugcc ucucaagggc ugacccguaa agguguguau 2820
gccguucggu acaaggugaa ugaaaauccu cuguacgcac ccaccucaga acaugugaac 2880
guccuacuga cccgcacgga ggaccgcauc guguggaaaa cacuagccgg cgacccaugg 2940
auaaaaaacac ugacugccaa guacccuggg aauuucacug ccacgauaga ggaguggcaa 3000
gcagagcaug augccaucau gaggcacauc uuggagagac cggacccuac cgacgucuuc 3060
cagaauaagg caaacgugug uugggccaag gcuuuagugc cggugcugaa gaccgcuggc 3120
auagacauga ccacugaaca auggaacacu guggauuauu uugaaacgga caaagcucac 3180
ucagcagaga uaguauugaa ccaacuaugc gugagguucu uuggacucga ucuggacucc 3240
ggucuauuuu cugcacccac uguuccguua uccauuagga auaaucacug ggauaacucc 3300
ccgucgccua acauguacgg gcugaauaaa gaaguggucc gucagcucuc ucgcagguac 3360
ccacaacugc cucgggcagu ugccacuggu agagucuaug acaugaacac ugguacacug 3420
cgcaauuaug auccgcgcau aaaccuagua ccuguaaaca gaagacugcc ucaugcuuua 3480
guccuccacc auaaugaaca cccacagagu gacuuuucuu cauucgucag caaauugaag 3540
ggcagaacug uccugguggu cggggaaaag uuguccgucc caggcaaaau gguugacugg 3600
uugucagacc ggccugaggc uaccuucaga gcucggcugg auuuaggcau cccaggugau 3660
gugcccaaau augacauaau auuuguuaau gugaggaccc cauauaaaua ccaucacuau 3720
cagcagugug aagaccaugc cauuaagcua agcauguuga ccaagaaagc augucugcau 3780

-continued

```
cugaaucccg gcggaaccug ugucagcaua gguuaugguu acgcugacag ggccagcgaa  3840
agcaucauug gugcuauagc gcggcaguuc aaguuuuccc gaguaugcaa accgaaaucc  3900
ucacuugagg agacggaagu ucuguuugua uucauugggu acgaucgcaa ggcccguacg  3960
cacaauccuu acaagcuauc aucaaccuug accaacauuu auacagguuc cagacuccac  4020
gaagccggau gugcacccuc auaucaugug gugcgagggg auauugccac ggccaccgaa  4080
ggagugauua uaaaugcugc uaacagcaaa ggacaaccug gcggaggggu gugcggagcg  4140
cuguauaaga aauucccgga aaguuucgau uuacagccga ucgaaguagg aaaagcgcga  4200
cuggucaaag gugcagcuaa acauaucauu caugccguag gaccaaacuu caacaaaguu  4260
ucggagguug aaggugacaa acaguuggca gaggcuuaug aguccaucgc uaagauuguc  4320
aacgauaaca auuacaaguc aguagcgauu ccacuguugu ccaccggcau cuuuuccggg  4380
aacaaagauc gacuaaccca aucauugaac cauuugcuga cagcuuuaga caccacugau  4440
gcagauguag ccauauacug cagggacaag aaaugggaaa ugacucucaa ggaagcagug  4500
gcuaggagag aagcagugga ggagauaugc auauccgacg auucuucagu gacagaaccu  4560
gaugcagagc uggugagggu gcaucccaag aguucuuugg cuggaaggaa gggcuacagc  4620
acaagcgaug gcaaaacuuu cucauauuug gaagggacca aguuucacca ggcggccaag  4680
gauauagcag aaauuaaugc cauguggccc guugcaacgg aggccaauga gcagguaugc  4740
auguauaucc ucggagaaag caugagcagu auuaggucga aaugccccgu cgaggagucg  4800
gaagccucca caccaccuag cacgcugccu ugcuugugca uccaugccau gacuccagaa  4860
agaguacagc gccuaaaagc cucacgucca gaacaaauua cugugugcuc auccuuucca  4920
uugccgaagu auagaaucac uggugugcag aagauccaau gcucccagcc uauauuguuc  4980
ucaccgaaag ugccugcgua uauucaucca aggaaguauc ucguggaaac accaccggua  5040
gacgagacuc cggagccauc ggcagagaac caauccacag aggggacacc ugaacaacca  5100
ccacuuauaa ccgaggauga gaccaggacu agaacgccug agccgaucau caucgaagaa  5160
gaagaagaag auagcauaag uuugcuguca gauggcccga cccaccaggu gcugcaaguc  5220
gaggcagaca uucacgggcc gcccucugua ucuagcucau ccugguccau ucccucaugca  5280
uccgacuuug auguggacag uuuauccaua cuugacaccc uggagggagc uagcgugacc  5340
agcggggcaa cgucagccga gacuaacucu uacuucgcaa agaguaugga guuucuggcg  5400
cgaccggugc cugcgccucg aacaguauuc aggaacccuc cacaucccgc uccgcgcaca  5460
agaacaccgu cacuugcacc cagcagggcc ugcuccagaa ccagccuagu uuccaccccg  5520
ccaggcguga auagggugau cacuagagag gagcucgaag cgcuuacccc gucacgcacu  5580
ccuagcaggu cggucuccag aaccagccug gucuccaacc cgccaggcgu aaauagggug  5640
auuacaagag aggaguuuga ggcguucgua gcacaacaac aaugacgguu ugaugcgggu  5700
gcauacaucu uuuccuccga caccggucaa gggcauuuac aacaaaaauc aguaaggcaa  5760
acggugcuau ccgaaguggu guuggagagg accgaauugg agauuucgua ugccccgcgc  5820
cucgaccaag aaaaagaaga auuacuacgc aagaaauuac aguuaaaucc cacaccugcu  5880
aacagaagca gauaccaguc caggaaggug gagaacauga aagccauaac agcuagacgu  5940
auucugcaag gccuagggca uuauuugaag gcagaaggaa aaguggagug cuaccgaacc  6000
cugcauccug uuccuuugua uucaucuagu gugaaccgug ccuuuucaag ccccaagguc  6060
gcaguggaag ccuguaacgc cauguugaaa gagaacuuuc cgacuguggc uucuuacugu  6120
auuauuccag aguacgaugc cuauuuggac augguugacg gagcuucaug cugcuuagac  6180
acugccaguu uuugcccugc aaagcugcgc agcuuuccaa agaaacacuc cuauuuggaa  6240
```

-continued

```
cccacaauac gaucggcagu gccuucagcg auccagaaca cgcuccagaa cguccuggca  6300
gcugccacaa aaagaaauug caaugucacg caaaugagag aauugcccgu auuggauucg  6360
gcggccuuua auguggaaug cuucaagaaa uaugcgugua auaaugaaua uugggaaacg  6420
uuuaaagaaa accccaucag gcuuacugaa gaaaacgugg uaaauuacau uaccaaauua  6480
aaaggaccaa aagcugcugc ucuuuuugcg aagacacaua auuugaauau guugcaggac  6540
auaccaaugg acagguuugu aauggacuua aagagagacg ugaaagugac uccaggaaca  6600
aaacauacug aagaacggcc caagguacag gugauccagg cugccgaucc gcuagcaaca  6660
gcguaucugu gcggaaucca ccgagagcug guuaggagau uaaaugcggu ccugcuuccg  6720
aacauucaua cacuguuuga uaugucggcu gaagacuuug acgcuauuau agccgagcac  6780
uuccagccug ggauuguguu ucuggaaacu gacaucgcgu cguuugauaa aagugaggac  6840
gacgccaugg cucugaccgc guuaaugauu cuggaagacu uaggugugga cgcagagcug  6900
uugacgcuga uugaggcggc uuucggcgaa auuucaucaa uacauuugcc cacuaaaacu  6960
aaauuuaaau ucggagccau gaugaaaucu ggaauguucc ucacacuguu ugugaacaca  7020
gucauuaaca uuguaaucgc aagcagagug uugagagaac ggcuaaccgg aucaccaugu  7080
gcagcauuca uuggagauga caauaucgug aaaggaguca aaucggacaa auuaauggca  7140
gacaggugcg ccaccugguu gaauauggaa gucaagauua uagaugcugu ggugggcgag  7200
aaagcgccuu auuucugugg aggguuuauu uugugugacu ccgugaccgg cacagcgugc  7260
cguguggcag acccccuaaa aaggcuguuu aagcuaggca aaccucuggc agcagacgau  7320
gaacaugaug augacaggag aagggcauug caugaggagu caacacgcug gaaccgagug  7380
gguauucuuu cagagcugug caaggcagua gaaucaaggu augaaaccgu aggaacuucc  7440
aucauaguua uggccaugac uacucuagcu agcaguguua aaucauucag cuaccugaga  7500
ggggccccua uaacucucua cggcuaaccu gaauggacua cgacauaguc uaguccgcca  7560
agacuaguau guucguguuc cuggugcugc ugccucuggu guccagccag ugugugaacc  7620
ugaccaccag aacacagcug ccuccagccu acaccaacag cuuuaccaga ggcguguacu  7680
accccgacaa gguguucaga uccagcgugc ugcacucuac ccaggaccug uuccugccuu  7740
ucuucagcaa cgugaccugg uuccacgcca uccacguguc cggcaccaau ggcaccaaga  7800
gauucgacaa ccccgugcug cccuucaacg acggggugua cuuugccagc accgagaagu  7860
ccaacaucau cagaggcugg aucuucggca ccacacugga cagcaagacc cagagccugc  7920
ugaucgugaa caacgccacc aacgugguca ucaaagugug cgaguuccag uucugcaacg  7980
accccuuccu gggcgucuac uaccacaaga acaacaagag cuggauggaa agcgaguucc  8040
ggguguacag cagcgccaac aacugcaccu ucgaguacgu gucccagccu uuccugaugg  8100
accuggaagg caagcagggc aacuucaaga accugcgcga guucguguuu aagaacaucg  8160
acggcuacuu caagaucuac agcaagcaca ccccuaucaa ccucgugcgg gaucugccuc  8220
agggcuucuc ugcucuggaa ccccuggugg aucugcccau cggcaucaac aucacccggu  8280
uucagacacu gcuggcccug cacagaagcu accugacacc uggcgauagc agcagcggau  8340
ggacagcugg ugccgccgcu uacuaugugg gcuaccugca gccuagaacc uuccugcuga  8400
aguacaacga gaacggcacc aucaccgacg ccguggauug ugcucuggau ccucugagcg  8460
agacaaagug cacccugaag uccuucaccg uggaaaaggg caucuaccag accagcaacu  8520
uccgggugca gcccaccgaa uccaucgugc gguuccccaa uaucaccaau cugugccccu  8580
ucggcgaggu guucaaugcc accagauucg ccucugugua cgccuggaac cggaagcgga  8640
```

-continued

```
ucagcaauug cguggccgac uacuccgugc uguacaacuc cgccagcuuc agcaccuuca  8700
agugcuacgg cguguccccu accaagcuga acgaccugug cuucacaaac guguacgccg  8760
acagcuucgu gauccgggga gaugaagugc ggcagauugc cccuggacag acaggcaaga  8820
ucgccgacua caacuacaag cugcccgacg acuucaccgg cugugugauu gccuggaaca  8880
gcaacaaccu ggacuccaaa gucggcggca acuacaauua ccuguaccgg cuguuccgga  8940
aguccaaucu gaagcccuuc gagcgggaca ucuccaccga gaucuaucag gccggcagca  9000
ccccuuguaa cggcguggaa ggcuucaacu gcuacuuccc acugcagucc uacggcuuuc  9060
agcccacaaa uggcgugggc uaucagcccu acagaguggu ggugcugagc uucgaacugc  9120
ugcaugcccc ugccacagug ugcggcccua agaaaagcac caaucucgug aagaacaaau  9180
gcgugaacuu caacuucaac ggccugaccg gcaccggcgu gcugacagag agcaacaaga  9240
aguuccugcc auuccagcag uuuggccggg auaucgccga uaccacagac gccguuagag  9300
auccccagac acuggaaauc cuggacauca ccccuugcag cuucggcgga gugucuguga  9360
ucaccccugg caccaacacc agcaaucagg uggcagugcu guaccaggac gugaacugua  9420
ccgaagugcc cguggccauu cacgccgauc agcugacacc uacauggcgg guguacucca  9480
ccggcagcaa uguguuucag accagagccg gcugucugau cggagccgag cacgugaaca  9540
auagcuacga gugcgacauc cccaucggcg cuggaaucug cgccagcuac cagacacaga  9600
caaacagccc ucggagagcc agaagcgugg ccagccagag caucauugcc uacacaaugu  9660
cucugggcgc cgagaacagc guggccuacu ccaacaacuc uaucgcuauc cccaccaacu  9720
ucaccaucag cgugaccaca gagauccugc cuguguccau gaccaagacc agcguggacu  9780
gcaccaugua caucugcggc gauuccaccg agugcuccaa ccugcugcug caguacggca  9840
gcuucugcac ccagcugaau agagcccuga cagggaucgc cguggaacag gacaagaaca  9900
cccaagaggu guucgcccaa gugaagcaga ucuacaagac cccuccuauc aaggacuucg  9960
gcggcuucaa uuucagccag auucugcccg auccuagcaa gcccagcaag cggagcuuca 10020
ucgaggaccu gcuguucaac aaagugacac uggccgacgc cggcuucauc aagcaguaug 10080
gcgauugucu gggcgacauu gccgccaggg aucugauuug cgcccagaag uuuaacggac 10140
ugacagugcu gccuccucug cugaccgaug agaugaucgc ccaguacaca ucugcccugc 10200
uggccggcac aaucacaagc ggcuggacau uuggagcagg cgccgcucug cagauccccu 10260
uugcuaugca gauggccuac cgguucaacg gcaucggagu gacccagaau gugcuguacg 10320
agaaccagaa gcugaucgcc aaccaguuca acagcgccau cggcaagauc caggacagcc 10380
ugagcagcac agcaagcgcc cugggaaagc ugcaggacgu ggucaaccag aaugcccagg 10440
cacugaacac ccuggucaag cagcuguccu ccaacuucgg cgccaucagc ucugugcuga 10500
acgauauccu gagcagacug gacccuccug aggccgaggu gcagaucgac agacugauca 10560
caggcagacu gcagagccuc cagacauacg ugacccagca gcugaucaga gccgccgaga 10620
uuagagccuc ugccaaucug gccgccacca agaugucuga gugugugcug ggccagagca 10680
agagagugga cuuuugcggc aagggcuacc accugaugag cuucccucag ucugccccuc 10740
acggcguggu guuucugcac gugacauaug ugcccgcuca agagaagaau uucaccaccg 10800
cuccagccau cugccacgac ggcaaagccc acuuuccuag agaaggcgug uucgugucca 10860
acggcaccca uugguucgug acacagcgga acuucuacga gccccagauc aucaccaccg 10920
acaacaccuu cgugucuggc aacugcgacg ucgugaucgg cauugugaac aauaccgugu 10980
acgacccucu gcagcccgag cuggacagcu ucaaagagga acuggacaag uacuuuaaga 11040
accacacaag ccccgacgug gaccugggcg auaucagcgg aaucaaugcc agcgucguga 11100
```

-continued

```
acauccagaa agagaucgac cggcugaacg agguggccaa gaaucugaac gagagccuga 11160
ucgaccugca agaacugggg aaguacgagc aguacaucaa guggcccugg uacaucuggc 11220
ugggcuuuau cgccggacug auugccaucg ugauggucac aaucaugcug uguugcauga 11280
ccagcugcug uagcugccug aagggcuguu guagcugugg cagcugcugc aaguucgacg 11340
aggacgauuc ugagcccgug cugaagggcg ugaaacugca cuacacauga ugacucgagc 11400
ugguacugca ugcacgcaau gcuagcugcc ccuuucccgu ccuggguacc ccgagucucc 11460
cccgaccucg ggucccaggu augcucccac cuccaccugc cccacucacc accucugcua 11520
guuccagaca ccucccaagc acgcagcaau gcagcucaaa acgcuuagcc uagccacacc 11580
cccacgggaa acagcaguga uuaaccuuua gcaauaaacg aaaguuuaac uaagcuauac 11640
uaaccccagg guuggucaau uucgugccag ccacaccgcg gccgcaugaa uacagcagca 11700
auuggcaagc ugcuuacaua gaacucgcgg cgauuggcau gccgccuuaa aauuuuuauu 11760
uuauuuuuuc uuuucuuuuc cgaaucggau uuuguuuuua auauuucaaa aaaaaaaaaa 11820
aaaaaaaaaa aaaaaaagca uaugacuaaa aaaaaaaaaa aaaaaaaaaa aaaaaaaaaa 11880
aaaaaaaaaa aaaaaaaaaa aaaaaaaaaa aaaaaaa                          11917
```

BNT162c1; RBS004.3 (SEQ ID NO: 35; SEQ ID NO: 21 Amino Acid)

Structure beta-S-ARCA(D1)-replicase-RBD-GS-Fibritin-FI-A30L70

Encoded antigen Viral spike protein (S protein) of the SARS-CoV-2 (partial sequence, Receptor Binding Domain (RBD) of S1S2 protein)

```
                                                      SEQ ID NO: 35
gaugggcggc gcaugagaga agcccagacc aauuaccuac ccaaaaugga gaaaguucac   60
guugacaucg aggaagacag cccauuccuc agagcuuugc agcggagcuu cccgcaguuu  120
gagguagaag ccaagcaggu cacugauaau gaccaugcua augccagagc guuuucgcau  180
cuggcuucaa aacugaucga aacggaggug gacccauccg acacgauccu ugacauugga  240
agugcgcccg cccgcagaau guauucuaag cacaaguauc auuguaucug uccgaugaga  300
ugugcggaag auccggacag auuguauaag uaugcaacua agcugaagaa aaacuguaag  360
gaaauaacug auaaggaauu ggacaagaaa augaaggagc ucgccgccgu caugagcgac  420
ccugaccugg aaacugagac uaugugccuc cacgacgacg agucgugucg cuacgaaggg  480
caagucgcug uuuaccagga uguauacgcg guugacggac cgacaagucu cuaucaccaa  540
gccaauaagg gaguuagagu cgccuacugg auaggcuuug acaccacccc uuuuauguuu  600
aagaacuugg cuggagcaua uccaucauac ucuaccaacu gggccgacga aaccguguua  660
acggcucgua acauaggccu augcagcucu gacguuaugg agcggucacg uagagggaug  720
uccauucuua gaaagaagua uuugaaacca uccaacaaug uucuauucuc uguuggcucg  780
accaucuacc acgaaaagag ggacuuacug aggagcuggc accugccguc uguauuucac  840
uuacguggca agcaaaauua cacaugucgg ugugagacua uaguuaguug cgacggguac  900
gucguuaaaa gaauagcuau caguccaggc cuguauggga agccuucagg cuaugcugcu  960
acgaugcacc gcgagggauu cuugugcugc aaagugacag acacauugaa cggggagagg 1020
gucucuuuuc ccgugugcac guaugugcca gcuacauugu gugaccaaau gacuggcaua 1080
cuggcaacag augucagugc ggacgacgcg caaaaacugc ugguugggcu caaccagcgu 1140
auagucguca acggucgcac ccagagaaac accaauacca ugaaaaauua ccuuuugccc 1200
```

-continued

```
guaguggccc aggcauuugc uaggugggca aaggaauaua aggaagauca agaagaugaa 1260
aggccacuag gacuacgaga uagacaguua gucaugggggu guuguugggc uuuuagaagg 1320
cacaagauaa caucuauuua uaagcgcccg gauacccaaa ccaucaucaa agugaacagc 1380
gauuuccacu cauucgugcu gcccaggaua ggcaguaaca cauuggagau cgggcugaga 1440
acaagaauca ggaaaauguu agaggagcac aaggagccgu caccucucau uaccgccgag 1500
gacguacaag aagcuaagug cgcagccgau gaggcuaagg aggugcguga agccgaggag 1560
uugcgcgcag cucuaccacc uuuggcagcu gauguugagg agcccacucu ggaagccgau 1620
gucgacuuga uguuacaaga ggcuggggcc ggcucagugg agacaccucg uggcuugaua 1680
aagguuacca gcuacgcugg cgaggacaag aucggcucuu acgcugugcu uucuccgcag 1740
gcuguacuca agagugaaaa auuaucuugc auccacccuc ucgcugaaca agucauagug 1800
auaacacacu cuggccgaaa agggcguuau gccguggaac cauaccaugg uaaaguagug 1860
gugccagagg gacaugcaau acccguccag gacuuucaag cucugaguga aagugccacc 1920
auuguguaca acgaacguga guucguaaac agguaccugc accauauugc cacacaugga 1980
ggagcgcuga acacugauga agaauauuac aaaacuguca agcccagcga gcacgacggc 2040
gaauaccugu acgacaucga caggaaacag ugcgucaaga aagagcuagu cacugggcua 2100
gggcucacag gcgagcuggu cgauccuccc uuccaugaau ucgccuacga gagucugaga 2160
acacgaccag ccgcuccuua ccaaguacca accauagggg uguauggcgu gccaggauca 2220
ggcaagucug gcaucauuaa aagcgcaguc accaaaaaag aucuaguggu gagcgccaag 2280
aaagaaaacu gugcagaaau uauaagggac gucaagaaaa ugaaagggcu ggacgucaau 2340
gccagaacug uggacucagu gcucuugaau ggaugcaaac accccguaga gacccuguau 2400
auugacgagg cuuuugcuug ucaugcaggu acucucagag cgcucauagc cauuauaaga 2460
ccuaaaaagg cagugcucug cggagauccc aaacagugcg guuuuuuuaa caugaugugc 2520
cugaaagugc auuuuaacca cgagauuugc acacaagucu uccacaaaag caucucucgc 2580
cguugcacua aaucugugac uucggucguc ucaaccuugu uuuacgacaa aaaaaugaga 2640
acgacgaauc cgaaagagac uaagauugug auugacacua ccggcaguac caaaccuaag 2700
caggacgauc ucauucucac uuguuucaga gggugggguga agcaguugca aauagauuac 2760
aaaggcaacg aaauaaugac ggcagcugcc ucucaagggc ugacccguaa agguguguau 2820
gccguucggu acaaggugaa ugaaaauccu cuguacgcac ccaccucaga acaugugaac 2880
guccuacuga cccgcacgga ggaccgcauc guguggaaaa cacuagccgg cgacccaugg 2940
auaaaaacac ugacugccaa guacccuggg aauuucacug ccacgauaga ggaguggcaa 3000
gcagagcaug augccaucau gaggcacauc uuggagagac cggacccuac cgacgucuuc 3060
cagaauaagg caaacgugug uugggccaag gcuuuagugc cggugcugaa gaccgcuggc 3120
auagacauga ccacugaaca auggaacacu guggauuauu uugaaacgga caaagcucac 3180
ucagcagaga uaguauugaa ccaacuaugc gugagguucu uuggacucga ucuggacucc 3240
ggucuauuuu cugcacccac uguuccguua uccauuagga auaaucacug ggauaacucc 3300
ccgucgccua acauguacgg gcugaauaaa gaaguggucc gucagcucuc ucgcagguac 3360
ccacaacugc cucgggcagu ugccacuggu agagucuaug acaugaacac ugguacacug 3420
cgcaauuaug auccgcgcau aaaccuagua ccuguaaaca gaagacugcc ucaugcuuua 3480
guccuccacc auaaugaaca cccacagagu gacuuuucuu cauucgucag caaauugaag 3540
ggcagaacug uccugguggu cggggaaaag uuguccgucc caggcaaaau gguugacugg 3600
```

-continued uugucagacc ggccugaggc uaccuucaga gcucggcugg auuuaggcau cccaggugau 3660
gugcccaaau augacauaau auuuguuaau gugaggaccc cauauaaaua ccaucacuau 3720
cagcagugug aagaccaugc cauuaagcua agcauguuga ccaagaaagc augucugcau 3780
cugaaucccg gcggaaccug ugucagcaua gguuaugguu acgcugacag ggccagcgaa 3840
agcaucauug gugcuauagc gcggcaguuc aaguuuuccc gaguaugcaa accgaaaucc 3900
ucacuugagg agacggaagu ucuguuugua uucauugggu acgaucgcaa ggcccguacg 3960
cacaauccuu acaagcuauc aucaaccuug accaacauuu auacagguuc cagacuccac 4020
gaagccggau gugcacccuc auaucaugug gugcgagggg auauugccac ggccaccgaa 4080
ggagugauua uaaaugcugc uaacagcaaa ggacaaccug gcggaggggu gugcggagcg 4140
cuguauaaga aauucccgga aaguuucgau uuacagccga ucgaaguagg aaaagcgcga 4200
cuggucaaag gugcagcuaa acauaucauu caugccguag gaccaaacuu caacaaaguu 4260
ucggagguug aaggugacaa acaguuggca gaggcuuaug aguccaucgc uaagauuguc 4320
aacgauaaca auuacaaguc aguagcgauu ccacuguugu ccaccggcau cuuuuccggg 4380
aacaaagauc gacuaaccca aucauugaac cauuugcuga cagcuuuaga caccacugau 4440
gcagauguag ccauauacug cagggacaag aaaugggaaa ugacucucaa ggaagcagug 4500
gcuaggagag aagcagugga ggagauaugc auauccgacg auucuucagu gacagaaccu 4560
gaugcagagc uggugagggu gcaucccaag aguucuuugg cuggaaggaa gggcuacagc 4620
acaagcgaug gcaaaacuuu cucauauuug gaagggacca aguuucacca ggcggccaag 4680
gauauagcag aaauuaaugc cauguggccc guugcaacgg aggccaauga gcagguaugc 4740
auguauaucc ucggagaaag caugagcagu auuaggucga aaugccccgu cgaggagucg 4800
gaagccucca caccaccuag cacgcugccu ugcuugugca uccaugccau gacuccagaa 4860
agaguacagc gccuaaaagc cucacgucca gaacaaauua cugugugcuc auccuuucca 4920
uugccgaagu auagaaucac uggugugcag aagauccaau gcucccagcc uauauuguuc 4980
ucaccgaaag ugccugcgua uauucaucca aggaaguauc ucguggaaac accaccggua 5040
gacgagacuc cggagccauc ggcagagaac caauccacag aggggacacc ugaacaacca 5100
ccacuuauaa ccgaggauga gaccaggacu agaacgccug agccgaucau caucgaagaa 5160
gaagaagaag auagcauaag uuugcuguca gauggcccga cccaccaggu gcugcaaguc 5220
gaggcagaca uucacgggcc gcccucugua ucuagcucau ccugguccau uccucaugca 5280
uccgacuuug auguggacag uuuauccaua cuugacaccc uggagggagc uagcgugacc 5340
agcggggcaa cgucagccga gacuaacucu uacuucgcaa agaguaugga guuucuggcg 5400
cgaccggugc cugcgccucg aacaguauuc aggaacccuc cacaucccgc uccgcgcaca 5460
agaacaccgu cacuugcacc cagcagggcc ugcuccagaa ccagccuagu uuccaccccg 5520
ccaggcguga auagggugau cacuagagag gagcucgaag cgcuuacccc gucacgcacu 5580
ccuagcaggu cggucuccag aaccagccug gucuccaacc cgccaggcgu aaauagggug 5640
auuacaagag aggaguuuga ggcguucgua gcacaacaac aaugacgguu ugaugcgggu 5700
gcauacaucu uuuccuccga caccggucaa gggcauuuac aacaaaaauc aguaaggcaa 5760
acggugcuau ccgaagugga guuggagagg accgaauugg agauuucgua ugccccgcgc 5820
cucgaccaag aaaaagaaga auuacuacgc aagaaauuac aguuaaaucc cacaccugcu 5880
aacagaagca gauaccaguc caggaaggug gagaacauga aagccauaac agcuagacgu 5940
auucugcaag gccuagggca uuauuugaag gcagaaggaa aaguggagug cuaccgaacc 6000
cugcauccug uuccuuugua uucaucuagu gugaaccgug ccuuuucaag ccccaagguc 6060

-continued gcaguggaag ccuguaacgc cauguugaaa gagaacuuuc cgacuguggc uucuuacugu 6120
auuauuccag aguacgaugc cuauuuggac augguugacg gagcuucaug cugcuuagac 6180
acugccaguu uuugcccugc aaagcugcgc agcuuuccaa agaaacacuc cuauuuggaa 6240
cccacaauac gaucggcagu gccuucagcg auccagaaca cgcuccagaa cguccuggca 6300
gcugccacaa aaagaaauug caaugucacg caaaugagag aauugcccgu auuggauucg 6360
gcggccuuua auguggaaug cuucaagaaa uaugcgugua auaaugaaua uugggaaacg 6420
uuuaaagaaa accccaucag gcuuacugaa gaaaacgugg uaaauuacau uaccaaauua 6480
aaaggaccaa aagcugcugc ucuuuuugcg aagacacaua auuugaauau guugcaggac 6540
auaccaaugg acagguuugu aauggacuua aagagagacg ugaaagugac uccaggaaca 6600
aaacauacug aagaacggcc caagguacag gugauccagg cugccgaucc gcuagcaaca 6660
gcguaucugu gcggaaucca ccgagagcug guuaggagau uaaaugcggu ccugcuuccg 6720
aacauucaua cacuguuuga uaugucggcu gaagacuuug acgcuauuau agccgagcac 6780
uuccagccug ggauugugu ucuggaaacu gacaucgcgu cguuugauaa aagugaggac 6840
gacgccaugg cucugaccgc guuaaugauu cuggaagacu uaggugugga cgcagagcug 6900
uugacgcuga uugaggcggc uuucggcgaa auuucaucaa uacauuugcc cacuaaaacu 6960
aaauuuaaau ucggagccau gaugaaaucu ggaauguucc ucacacuguu ugugaacaca 7020
gucauuaaca uuguaaucgc aagcagagug uugagagaac ggcuaaccgg aucaccaugu 7080
gcagcauuca uuggagauga caauaucgug aaaggaguca aaucggacaa auuaauggca 7140
gacaggugcg ccaccugguu gaauauggaa gucaagauua uagaugcugu ggugggcgag 7200
aaagcgccuu auuucugugg aggguuuauu uugugugacu ccgugaccgg cacagcgugc 7260
cguguggcag acccccuaaa aaggcuguuu aagcuaggca aaccucuggc agcagacgau 7320
gaacaugaug augacaggag aagggcauug caugaggagu caacacgcug gaaccgagug 7380
gguauucuuu cagagcugug caaggcagua gaaucaaggu augaaaccgu aggaacuucc 7440
aucauaguua uggccaugac uacucuagcu agcaguguua aaucauucag cuaccugaga 7500
ggggccccua uaacucucua cggcuaaccu gaauggacua cgacauaguc uaguccgcca 7560
agacuaguau guuuguguuu cuugugcugc ugccucuugu gucuucucag ugugugguga 7620
gauuuccaaa uauuacaaau cuguguccau uuggagaagu guuuaaugca acaagauuug 7680
caucugugua ugcauggaau agaaaaagaa uuucuaauug uguggcugau uauucugugc 7740
uguauaauag ugcuucuuuu uccacauuua aauguuaugg agugucucca acaaaauuaa 7800
augauuuaug uuuuacaaau guguaugcug auucuuuugu gaucagaggu gaugaaguga 7860
gacagauugc ccccggacag acaggaaaaa uugcugauua caauuacaaa cugccugaug 7920
auuuuacagg augugugauu gcuuggaauu cuaauaauuu agauucuaaa gugggaggaa 7980
auuacaauua ucuguacaga cuguuuagaa aaucaaaucu gaaaccuuuu gaaagagaua 8040
uuucaacaga aauuuaucag gcuggaucaa caccuuguaa uggaguggaa ggauuuaauu 8100
guuauuuucc auuacagagc uauggauuuc agccaaccaa ugguguggga uaucagccau 8160
auagaguggu ggugcugucu uuugaacugc ugcaugcacc ugcaacagug uguggaccua 8220
aaggcucccc cggcuccggc uccggaucug guuauauucc ugaagcucca agagaugggc 8280
aagcuuacgu ucguaaagau ggcgaauggg uauuacuuuc uaccuuuuua ggccggucccc 8340
uggaggugcu guuccagggc cccggcugau gacucgagcu gguacugcau gcacgcaaug 8400
cuagcugccc cuuucccguc cuggguaccc cgagucuccc ccgaccucgg gucccaggua 8460

-continued

```
ugcucccacc uccaccugcc ccacucacca ccucugcuag uuccagacac cucccaagca 8520

cgcagcaaug cagcucaaaa cgcuuagccu agccacaccc ccacgggaaa cagcagugau 8580

uaaccuuuag caauaaacga aaguuuaacu aagcuauacu aaccccaggg uuggucaauu 8640

ucgugccagc cacaccgcgg ccgcaugaau acagcagcaa uuggcaagcu gcuuacauag 8700

aacucgcggc gauuggcaug ccgccuuaaa auuuuuauuu uauuuuuucu uuucuuuucc 8760

gaaucggauu uuguuuuuaa uauuucaaaa aaaaaaaaaa aaaaaaaaaa aaaaaagcau 8820

augacuaaaa aaaaaaaaaa aaaaaaaaaa aaaaaaaaaa aaaaaaaaaa aaaaaaaaaa 8880

aaaaaaaaaa aaaaaa                                                 8896
```

RBS004.4 (SEQ ID NO: 36; SEQ ID NO: 37)

Structure beta-S-ARCA(D1)-replicase-RBD-GS-Fibritin-TM-FI-A30L70

Encoded antigen Viral spike protein (S protein) of the SARS-CoV-2 (partial sequence, Receptor Binding Domain (RBD) of S1S2 protein)

```
                                                             SEQ ID NO: 36
gaugggcggc gcaugagaga agcccagacc aauuaccuac ccaaaaugga gaaaguucac     60

guugacaucg aggaagacag cccauuccuc agagcuuugc agcggagcuu cccgcaguuu    120

gagguagaag ccaagcaggu cacugauaau gaccaugcua augccagagc guuuucgcau    180

cuggcuucaa aacugaucga aacggaggug gacccauccg acacgauccu ugacauugga    240

agugcgcccg cccgcagaau guauucuaag cacaaguauc auuguaucug uccgaugaga    300

ugugcggaag auccggacag auuguauaag uaugcaacua agcugaagaa aaacuguaag    360

gaaauaacug auaaggaauu ggacaagaaa augaaggagc ucgccgccgu caugagcgac    420

ccugaccugg aaacugagac uaugugccuc cacgacgacg agucgugucg cuacgaaggg    480

caagucgcug uuuaccagga uguauacgcg guugacggac cgacaagucu cuaucaccaa    540

gccaauaagg gaguuagagu cgccuacugg auaggcuuug acaccacccc uuuuauguuu    600

aagaacuugg cuggagcaua uccaucauac ucuaccaacu gggccgacga aaccguguua    660

acggcucgua acauaggccu augcagcucu gacguuaugg agcggucacg uagagggaug    720

uccauucuua gaaagaagua uuugaaacca uccaacaaug uucuauucuc uguuggcucg    780

accaucuacc acgaaaagag ggacuuacug aggagcuggc accugccguc uguauuucac    840

uuacguggca agcaaaauua cacaugucgg ugugagacua uaguuaguug cgacggguac    900

gucguuaaaa gaauagcuau caguccaggc cuguauggga agccuucagg cuaugcugcu    960

acgaugcacc gcgagggauu cuugugcugc aaagugacag acacauugaa cggggagagg   1020

gucucuuuuc ccgugugcac guaugugcca gcuacauugu gugaccaaau gacuggcaua   1080

cuggcaacag augucagugc ggacgacgcg caaaaacugc ugguugggcu caaccagcgu   1140

auagucguca acggucgcac ccagagaaac accaauacca ugaaaaauua ccuuuugccc   1200

guaguggccc aggcauuugc uaggugggca aaggaauaua aggaagauca agaagaugaa   1260

aggccacuag gacuacgaga uagacaguua gucauggggu guuguugggc uuuuagaagg   1320

cacaagauaa caucuauuua uaagcgcccg gauacccaaa ccaucaucaa agugaacagc   1380

gauuuccacu cauucgugcu gcccaggaua ggcaguaaca cauuggagau cgggcugaga   1440

acaagaauca ggaaaauguu agaggagcac aaggagccgu caccucucau uaccgccgag   1500

gacguacaag aagcuaagug cgcagccgau gaggcuaagg aggugcguga agccgaggag   1560

uugcgcgcag cucuaccacc uuuggcagcu gauguugagg agcccacucu ggaagccgau   1620

gucgacuuga uguuacaaga ggcuggggcc ggcucagugg agacaccucg uggcuugaua   1680

aagguuacca gcuacgcugg cgaggacaag aucggcucuu acgcugugcu uucuccgcag   1740
```

-continued

```
gcuguacuca agagugaaaa auuaucuugc auccacccuc ucgcugaaca agucauagug   1800
auaacacacu cuggccgaaa agggcguuau gccguggaac cauaccaugg uaaaguagug   1860
gugccagagg gacaugcaau acccguccag gacuuucaag cucugaguga aagugccacc   1920
auuguguaca acgaacguga guucguaaac agguaccugc accauauugc cacacaugga   1980
ggagcgcuga acacugauga agaauauuac aaaacuguca agcccagcga gcacgacggc   2040
gaauaccugu acgacaucga caggaaacag ugcgucaaga aagagcuagu cacugggcua   2100
gggcucacag gcgagcuggu cgauccuccc uuccaugaau ucgccuacga gagucugaga   2160
acacgaccag ccgcuccuua ccaaguacca accauagggg uguauggcgu gccaggauca   2220
ggcaagucug gcaucauuaa aagcgcaguc accaaaaaag aucuaguggu gagcgccaag   2280
aaagaaaacu gugcagaaau uauaagggac gucaagaaaa ugaaagggcu ggacgucaau   2340
gccagaacug uggacucagu gcucuugaau ggaugcaaac accccguaga gacccuguau   2400
auugacgagg cuuuugcuug ucaugcaggu acucucagag cgcucauagc cauuauaaga   2460
ccuaaaaagg cagugcucug cggagauccc aaacagugcg guuuuuuuaa caugaugugc   2520
cugaaagugc auuuuaacca cgagauuugc acacaagucu uccacaaaag caucucucgc   2580
cguugcacua aaucugugac uucggucguc ucaaccuugu uuuacgacaa aaaaaugaga   2640
acgacgaauc cgaaagagac uaagauugug auugacacua ccggcaguac caaaccuaag   2700
caggacgauc ucauucucac uuguuucaga ggguggguga agcaguugca aauagauuac   2760
aaaggcaacg aaauaaugac ggcagcugcc ucucaagggc ugacccguaa aggugugua u  2820
gccguucggu acaaggugaa ugaaaauccu cuguacgcac ccaccucaga acaugugaac   2880
guccuacuga cccgcacgga ggaccgcauc guguggaaaa cacuagccgg cgacccaugg   2940
auaaaaacac ugacugccaa guacccuggg aauuucacug ccacgauaga ggaguggcaa   3000
gcagagcaug augccaucau gaggcacauc uuggagagac cggacccuac cgacgucuuc   3060
cagaauaagg caaacgugug uugggccaag gcuuuagugc cggugcugaa gaccgcuggc   3120
auagacauga ccacugaaca auggaacacu guggauuauu uugaaacgga caaagcucac   3180
ucagcagaga uaguauugaa ccaacuaugc gugagguucu uuggacucga ucuggacucc   3240
ggucuauuuu cugcacccac uguuccguua uccauuagga auaaucacug ggauaacucc   3300
ccgucgccua acauguacgg gcugaauaaa gaagugguccc gucagcucuc ucgcagguac   3360
ccacaacugc cucgggcagu ugccacuggu agagucuaug acaugaacac ugguacacug   3420
cgcaauuaug auccgcgcau aaaccuagua ccuguaaaca gaagacugcc ucaugcuuua   3480
guccuccacc auaaugaaca cccacagagu gacuuuucuu cauucgucag caaauugaag   3540
ggcagaacug uccugguggu cggggaaaag uuguccgucc caggcaaaau gguugacugg   3600
uugucagacc ggccugaggc uaccuucaga gcucggcugg auuuaggcau cccaggugau   3660
gugcccaaau augacauaau auuuguuaau gugaggaccc cauauaaaua ccaucacuau   3720
cagcagugug aagaccaugc cauuaagcua agcauguuga ccaagaaagc augucugcau   3780
cugaaucccg gcggaaccug ugucagcaua gguuauggu u acgcugacag ggccagcgaa   3840
agcaucauug gugcuauagc gcggcaguuc aaguuucccc gaguaugcaa accgaaaucc   3900
ucacuugagg agacggaagu ucuguuugua uucauugggu acgaucgcaa ggcccguacg   3960
cacaauccuu acaagcuauc aucaaccuug accaacauuu auacagguuc cagacuccac   4020
gaagccggau gugcacccuc auaucaugug gugcgagggg auauugccac ggccaccgaa   4080
ggagugauua uaaaugcugc uaacagcaaa ggacaaccug gcggaggggu gugcggagcg   4140
```

-continued cuguauaaga aauucccgga aaguuucgau uuacagccga ucgaaguagg aaaagcgcga 4200
cuggucaaag gugcagcuaa acauaucauu caugccguag gaccaaacuu caacaaaguu 4260
ucggagguug aaggugacaa acaguuggca gaggcuuaug aguccaucgc uaagauuguc 4320
aacgauaaca auuacaaguc aguagcgauu ccacuguugu ccaccggcau cuuuuccggg 4380
aacaaagauc gacuaaccca aucauugaac cauuugcuga cagcuuuaga caccacugau 4440
gcagauguag ccauauacug cagggacaag aaaugggaaa ugacucucaa ggaagcagug 4500
gcuaggagag aagcagugga ggagauaugc auauccgacg auucuucagu gacagaaccu 4560
gaugcagagc uggugagggu gcaucccaag aguucuuugg cuggaaggaa gggcuacagc 4620
acaagcgaug gcaaaacuuu cucauauuug gaagggacca aguuucacca ggcggccaag 4680
gauauagcag aaauuaaugc cauguggccc guugcaacgg aggccaauga gcagguaugc 4740
auguauaucc ucggagaaag caugagcagu auuaggucga aaugccccgu cgaggagucg 4800
gaagccucca caccaccuag cacgcugccu ugcuugugca uccaugccau gacuccagaa 4860
agaguacagc gccuaaaagc cucacgucca gaacaaauua cugugugcuc auccuuucca 4920
uugccgaagu auagaaucac uggugugcag aagauccaau gcucccagcc uauauuguuc 4980
ucaccgaaag ugccugcgua uauucaucca aggaaguauc ucguggaaac accaccggua 5040
gacgagacuc cggagccauc ggcagagaac caauccacag aggggacacc ugaacaacca 5100
ccacuuauaa ccgaggauga gaccaggacu agaacgccug agccgaucau caucgaagaa 5160
gaagaagaag auagcauaag uuugcuguca gauggcccga cccaccaggu gcugcaaguc 5220
gaggcagaca uucacgggcc gcccucugua ucuagcucau ccugguccau uccucaugca 5280
uccgacuuug auguggacag uuuauccaua cuugacaccc uggagggagc uagcgugacc 5340
agcggggcaa cgucagccga gacuaacucu uacuucgcaa agaguaugga guuucuggcg 5400
cgaccggugc cugcgccucg aacaguauuc aggaacccuc cacaucccgc uccgcgcaca 5460
agaacaccgu cacuugcacc cagcagggcc ugcuccagaa ccagccuagu uuccaccccg 5520
ccaggcguga auagggugau cacuagagag gagcucgaag cgcuuacccc gucacgcacu 5580
ccuagcaggu cggucuccag aaccagccug gucuccaacc cgccaggcgu aaauagggug 5640
auuacaagag aggaguuuga ggcguucgua gcacaacaac aaugacgguu ugaugcgggu 5700
gcauacaucu uuuccuccga caccggucaa gggcauuuac aacaaaaauc aguaaggcaa 5760
acggugcuau ccgaagugga guuggagagg accgaauugg agauuucgua ugccccgcgc 5820
cucgaccaag aaaaagaaga auuacuacgc aagaaauuac aguuaaaucc cacaccugcu 5880
aacagaagca gauaccaguc caggaaggug gagaacauga aagccauaac agcuagacgu 5940
auucugcaag gccuagggca uuauuugaag gcagaaggaa aaguggagug cuaccgaacc 6000
cugcauccug uuccuuugua uucaucuagu gugaaccgug ccuuuucaag ccccaagguc 6060
gcaguggaag ccuguaacgc cauguugaaa gagaacuuuc cgacuguggc uucuuacugu 6120
auuauuccag aguacgaugc cuauuuggac augguugacg gagcuucaug cugcuuagac 6180
acugccaguu uuugcccugc aaagcugcgc agcuuuccaa agaaacacuc cuauuuggaa 6240
cccacaauac gaucggcagu gccuucagcg auccagaaca cgcuccagaa cguccuggca 6300
gcugccacaa aaagaaauug caaugucacg caaaugagag aauugcccgu auuggauucg 6360
gcggccuuua auguggaaug cuucaagaaa uaugcgugua auaaugaaua uugggaaacg 6420
uuuaaagaaa accccaucag gcuuacugaa gaaaacgugg uaaauuacau uaccaaauua 6480
aaaggaccaa aagcugcugc ucuuuuugcg aagacacaua auuugaauau guugcaggac 6540
auaccaaugg acagguuugu aauggacuua aagagagacg ugaaagugac uccaggaaca 6600

-continued

```
aaacauacug aagaacggcc caagguacag gugauccagg cugccgaucc gcuagcaaca   6660
gcguaucugu gcggaaucca ccgagagcug guuaggagau uaaaugcggu ccugcuuccg   6720
aacauucaua cacuguuuga uaugucggcu gaagacuuug acgcuauuau agccgagcac   6780
uuccagccug gggauugugu ucuggaaacu gacaucgcgu cguuugauaa aagugaggac   6840
gacgccaugg cucugaccgc guuaaugauu cuggaagacu uaggugugga cgcagagcug   6900
uugacgcuga uugaggcggc uuucggcgaa auuucaucaa uacauuugcc cacuaaaacu   6960
aaauuuaaau ucggagccau gaugaaaucu ggaauguucc ucacacuguu ugugaacaca   7020
gucauuaaca uuguaaucgc aagcagagug uugagagaac ggcuaaccgg aucaccaugu   7080
gcagcauuca uuggagauga caauaucgug aaaggaguca aaucggacaa auuaauggca   7140
gacaggugcg ccaccugguu gaauauggaa gucaagauua uagaugcugu ggugggcgag   7200
aaagcgccuu auuucugugg aggguuuauu uugugugacu ccgugaccgg cacagcgugc   7260
cguguggcag accccuaaa aaggcuguuu aagcuaggca aaccucuggc agcagacgau   7320
gaacaugaug augacaggag aagggcauug caugaggagu caacacgcug gaaccgagug   7380
gguauucuuu cagagcugug caaggcagua gaaucaaggu augaaaccgu aggaacuucc   7440
aucauaguua uggccaugac uacucuagcu agcaguguua aaucauucag cuaccugaga   7500
ggggccccua uaacucucua cggcuaaccu gaauggacua cgacauaguc uaguccgcca   7560
agacuaguau guuuguguuu cuugugcugc ugccucuugu gucuucucag uguguggguga   7620
gauuuccaaa uauuacaaau cuguguccau uuggagaagu guuuaaugca acaagauuug   7680
caucugugua ugcauggaau agaaaaagaa uuucuaauug uguggcugau uauucugugc   7740
uguauaauag ugcuucuuuu uccacauuua aauguuaugg agugucucca acaaaauuaa   7800
augauuuaug uuuuacaaau guguaugcug auucuuuugu gaucagaggu gaugaaguga   7860
gacagauugc ccccggacag acaggaaaaa uugcugauua caauuacaaa cugccugaug   7920
auuuuacagg augugugauu gcuuggaauu cuaauaauuu agauucuaaa gugggaggaa   7980
auuacaauua ucuguacaga cuguuuagaa aaucaaaucu gaaaccuuuu gaaagagaua   8040
uuucaacaga aauuuaucag gcuggaucaa caccuuguaa uggaguggaa ggauuuaauu   8100
guuauuuucc auuacagagc uauggauuuc agccaaccaa uggugugga uaucagccau    8160
auagaguggu ggugcugucu uuugaacugc ugcaugcacc ugcaacagug uguggaccua   8220
aaggcucccc cggcuccggc uccggaucug guuauauucc ugaagcucca agagaugggc   8280
aagcuuacgu ucguaaagau ggcgaauggg uauuacuuuc uaccuuuuua ggaagcggca   8340
gcggaucuga acaguacauu aaauggccuu gguacauuug gcuuggauuu auugcaggau   8400
uaauugcaau ugugauggug acaauuaugu uauguuguau gacaucaugu uguucuuguu   8460
uaaaaggaug uuguucuugu ggaagcuguu guaaauuuga ugaagaugau ucugaaccug   8520
uguuaaaagg agugaaauug cauuacacau gaugacucga gcugguacug caugcacgca   8580
augcuagcug ccccuuuccc guccugggua ccccgagucu cccccgaccu cggguccag    8640
guaugcuccc accuccaccu gccccacuca ccaccucugc uaguuccaga caccucccaa   8700
gcacgcagca augcagcuca aaacgcuuag ccuagccaca cccccacggg aaacagcagu   8760
gauuaaccuu uagcaauaaa cgaaaguuua acuaagcuau acuaacccca ggguugguca   8820
auuucgugcc agccacaccg cggccgcaug aauacagcag caauuggcaa gcugcuuaca   8880
uagaacucgc ggcgauuggc augccgccuu aaaauuuuua uuuuauuuuu ucuuuucuuu   8940
uccgaaucgg auuuuguuuu uaauauuuca aaaaaaaaaa aaaaaaaaaa aaaaaaaaag   9000
```

-continued

```
cauaugacua aaaaaaaaaa aaaaaaaaaa aaaaaaaaaa aaaaaaaaaa aaaaaaaaaa   9060

aaaaaaaaaa aaaaaaaaa                                                9079
```

SEQ ID NO: 37

```
Met Phe Val Phe Leu Val Leu Leu Pro Leu Val Ser Ser Gln Cys Val
1               5                   10                  15

Val Arg Phe Pro Asn Ile Thr Asn Leu Cys Pro Phe Gly Glu Val Phe
            20                  25                  30

Asn Ala Thr Arg Phe Ala Ser Val Tyr Ala Trp Asn Arg Lys Arg Ile
        35                  40                  45

Ser Asn Cys Val Ala Asp Tyr Ser Val Leu Tyr Asn Ser Ala Ser Phe
    50                  55                  60

Ser Thr Phe Lys Cys Tyr Gly Val Ser Pro Thr Lys Leu Asn Asp Leu
65                  70                  75                  80

Cys Phe Thr Asn Val Tyr Ala Asp Ser Phe Val Ile Arg Gly Asp Glu
                85                  90                  95

Val Arg Gln Ile Ala Pro Gly Gln Thr Gly Lys Ile Ala Asp Tyr Asn
            100                 105                 110

Tyr Lys Leu Pro Asp Asp Phe Thr Gly Cys Val Ile Ala Trp Asn Ser
        115                 120                 125

Asn Asn Leu Asp Ser Lys Val Gly Gly Asn Tyr Asn Tyr Leu Tyr Arg
    130                 135                 140

Leu Phe Arg Lys Ser Asn Leu Lys Pro Phe Glu Arg Asp Ile Ser Thr
145                 150                 155                 160

Glu Ile Tyr Gln Ala Gly Ser Thr Pro Cys Asn Gly Val Glu Gly Phe
                165                 170                 175

Asn Cys Tyr Phe Pro Leu Gln Ser Tyr Gly Phe Gln Pro Thr Asn Gly
            180                 185                 190

Val Gly Tyr Gln Pro Tyr Arg Val Val Val Leu Ser Phe Glu Leu Leu
        195                 200                 205

His Ala Pro Ala Thr Val Cys Gly Pro Lys Gly Ser Pro Gly Ser Gly
    210                 215                 220

Ser Gly Ser Gly Tyr Ile Pro Glu Ala Pro Arg Asp Gly Gln Ala Tyr
225                 230                 235                 240

Val Arg Lys Asp Gly Glu Trp Val Leu Leu Ser Thr Phe Leu Gly Ser
                245                 250                 255

Gly Ser Gly Ser Glu Gln Tyr Ile Lys Trp Pro Trp Tyr Ile Trp Leu
            260                 265                 270

Gly Phe Ile Ala Gly Leu Ile Ala Ile Val Met Val Thr Ile Met Leu
        275                 280                 285

Cys Cys Met Thr Ser Cys Cys Ser Cys Leu Lys Gly Cys Cys Ser Cys
    290                 295                 300

Gly Ser Cys Cys Lys Phe Asp Glu Asp Asp Ser Glu Pro Val Leu Lys
305                 310                 315                 320

Gly Val Lys Leu His Tyr Thr
                325
```

BNT162b3c (SEQ ID NO: 38; SEQ ID NO: 39)

Structure $m_2^{7,3'-O}Gppp(m_1^{2'-O})ApG$-hAg-Kozak-RBD-GS-Fibritin-GS-TM-FI-A30L70

Encoded antigen Viral spike protein (S1S2 protein) of the SARS-CoV-2 (partial sequence, Receptor Binding Domain (RBD) of S1S2 protein fused to Fibritin fused to Transmembrane Domain (TM) of S1S2 protein); intrinsic S1S2 protein secretory signal peptide (aa 1-19) at the N-terminus of the antigen sequence

SEQ ID NO: 38

```
Met Phe Val Phe Leu Val Leu Leu Pro Leu Val Ser Ser Gln Cys Val
1               5                   10                  15
```

-continued

```
Asn Leu Thr Val Arg Phe Pro Asn Ile Thr Asn Leu Cys Pro Phe Gly
            20                  25                  30

Glu Val Phe Asn Ala Thr Arg Phe Ala Ser Val Tyr Ala Trp Asn Arg
        35                  40                  45

Lys Arg Ile Ser Asn Cys Val Ala Asp Tyr Ser Val Leu Tyr Asn Ser
    50                  55                  60

Ala Ser Phe Ser Thr Phe Lys Cys Tyr Gly Val Ser Pro Thr Lys Leu
65                  70                  75                  80

Asn Asp Leu Cys Phe Thr Asn Val Tyr Ala Asp Ser Phe Val Ile Arg
                85                  90                  95

Gly Asp Glu Val Arg Gln Ile Ala Pro Gly Gln Thr Gly Lys Ile Ala
            100                 105                 110

Asp Tyr Asn Tyr Lys Leu Pro Asp Asp Phe Thr Gly Cys Val Ile Ala
        115                 120                 125

Trp Asn Ser Asn Asn Leu Asp Ser Lys Val Gly Gly Asn Tyr Asn Tyr
    130                 135                 140

Leu Tyr Arg Leu Phe Arg Lys Ser Asn Leu Lys Pro Phe Glu Arg Asp
145                 150                 155                 160

Ile Ser Thr Glu Ile Tyr Gln Ala Gly Ser Thr Pro Cys Asn Gly Val
                165                 170                 175

Glu Gly Phe Asn Cys Tyr Phe Pro Leu Gln Ser Tyr Gly Phe Gln Pro
            180                 185                 190

Thr Asn Gly Val Gly Tyr Gln Pro Tyr Arg Val Val Val Leu Ser Phe
        195                 200                 205

Glu Leu Leu His Ala Pro Ala Thr Val Cys Gly Pro Lys Gly Ser Pro
    210                 215                 220

Gly Ser Gly Ser Gly Ser Gly Tyr Ile Pro Glu Ala Pro Arg Asp Gly
225                 230                 235                 240

Gln Ala Tyr Val Arg Lys Asp Gly Glu Trp Val Leu Leu Ser Thr Phe
                245                 250                 255

Leu Gly Ser Gly Ser Gly Ser Glu Gln Tyr Ile Lys Trp Pro Trp Tyr
            260                 265                 270

Ile Trp Leu Gly Phe Ile Ala Gly Leu Ile Ala Ile Val Met Val Thr
        275                 280                 285

Ile Met Leu Cys Cys Met Thr Ser Cys Cys Ser Cys Leu Lys Gly Cys
    290                 295                 300

Cys Ser Cys Gly Ser Cys Cys
305                 310
```

SEQ ID NO: 39

```
agaauaaacu aguauucuuc ugguccccac agacucagag agaacccgcc accauguuug     60

uguuucuugu gcugcugccu cuugugucuu cucagugugu gaauuugaca gugagauuuc    120

caaauauuac aaaucugugu ccauuuggag aaguguuuaa ugcaacaaga uuugcaucug    180

uguaugcaug gaauagaaaa agaauuucua auuguguggc ugauuauucu gugcuguaua    240

auagugcuuc uuuuuccaca uuuaaauguu auggaguguc uccaacaaaa uuaaaugauu    300

uauguuuuac aaauguguau gcugauucuu uugugaucag aggugaugaa gugagacaga    360

uugcccccgg acagacagga aaaauugcug auuacaauua caaacugccu gaugauuuua    420

caggaugugu gauugcuugg aauucuaaua auuuagauuc uaaaguggga ggaaauuaca    480

auuaucugua cagacuguuu agaaaaucaa aucugaaacc uuuugaaaga gauauuucaa    540

cagaaauuua ucaggcugga ucaacaccuu guaauggagu ggaaggauuu aauuguuauu    600

uuccauuaca gagcuaugga uuucagccaa ccaauggugu gggauaucag ccauauagag    660

ugguggugcu gucuuuugaa cugcugcaug caccugcaac agugugugga ccuaaaggcu    720
```

-continued

```
cccccggcuc cggcuccgga ucugguuaua uuccugaagc uccaagagau gggcaagcuu    780
acguucguaa agauggcgaa ugggguauuac uuucuaccuu uuuaggaagc ggcagcggau    840
cugaacagua cauuaaaugg ccuugguaca uuuggcuugg auuuauugca ggauuaauug    900
caauugugau ggugacaauu auguuauguu guaugacauc auguuguucu uguuuaaaag    960
gauguuguuc uuguggaagc uguuguugau gacucgagcu gguacugcau gcacgcaaug   1020
cuagcugccc cuuucccguc cuggguaccc cgagucuccc ccgaccucgg gucccaggua   1080
ugcucccacc uccaccugcc ccacucacca ccucugcuag uuccagacac cucccaagca   1140
cgcagcaaug cagcucaaaa cgcuuagccu agccacaccc ccacgggaaa cagcagugau   1200
uaaccuuuag caauaaacga aaguuuaacu aagcuauacu aaccccaggg uuggucaauu   1260
ucgugccagc cacacccugg agcuagcaaa aaaaaaaaaa aaaaaaaaaa aaaaaaagca   1320
uaugacuaaa aaaaaaaaaa aaaaaaaaaa aaaaaaaaaa aaaaaaaaaa aaaaaaaaaa   1380
aaaaaaaaaa aaaaaaa                                                  1397
```

BNT162b3d (SEQ ID NO: 40; SEQ ID NO: 41)

Structure $m_2^{7,3'-O}Gppp(m_1^{2'-O})ApG$-hAg-Kozak-RBD-GS-Fibritin-GS-TM-FI-A30L70

Encoded antigen Viral spike protein (S1S2 protein) of the SARS-CoV-2 (partial sequence, Receptor Binding Domain (RBD) of S1S2 protein fused to Fibritin fused to Transmembrane Domain (TM) of S1S2 protein); immunoglobulin secretory signal peptide (aa 1-22) at the N-terminus of the antigen sequence

```
                                                        SEQ ID NO: 40
Met Asp Trp Ile Trp Arg Ile Leu Phe Leu Val Gly Ala Ala Thr Gly
1               5                   10                  15

Ala His Ser Gln Met Gln Val Arg Phe Pro Asn Ile Thr Asn Leu Cys
            20                  25                  30

Pro Phe Gly Glu Val Phe Asn Ala Thr Arg Phe Ala Ser Val Tyr Ala
        35                  40                  45

Trp Asn Arg Lys Arg Ile Ser Asn Cys Val Ala Asp Tyr Ser Val Leu
    50                  55                  60

Tyr Asn Ser Ala Ser Phe Ser Thr Phe Lys Cys Tyr Gly Val Ser Pro
65                  70                  75                  80

Thr Lys Leu Asn Asp Leu Cys Phe Thr Asn Val Tyr Ala Asp Ser Phe
                85                  90                  95

Val Ile Arg Gly Asp Glu Val Arg Gln Ile Ala Pro Gly Gln Thr Gly
            100                 105                 110

Lys Ile Ala Asp Tyr Asn Tyr Lys Leu Pro Asp Asp Phe Thr Gly Cys
        115                 120                 125

Val Ile Ala Trp Asn Ser Asn Asn Leu Asp Ser Lys Val Gly Gly Asn
    130                 135                 140

Tyr Asn Tyr Leu Tyr Arg Leu Phe Arg Lys Ser Asn Leu Lys Pro Phe
145                 150                 155                 160

Glu Arg Asp Ile Ser Thr Glu Ile Tyr Gln Ala Gly Ser Thr Pro Cys
                165                 170                 175

Asn Gly Val Glu Gly Phe Asn Cys Tyr Phe Pro Leu Gln Ser Tyr Gly
            180                 185                 190

Phe Gln Pro Thr Asn Gly Val Gly Tyr Gln Pro Tyr Arg Val Val Val
        195                 200                 205

Leu Ser Phe Glu Leu Leu His Ala Pro Ala Thr Val Cys Gly Pro Lys
    210                 215                 220

Gly Ser Pro Gly Ser Gly Ser Gly Ser Gly Tyr Ile Pro Glu Ala Pro
225                 230                 235                 240
```

-continued

```
Arg Asp Gly Gln Ala Tyr Val Arg Lys Asp Gly Glu Trp Val Leu Leu
                245                 250                 255

Ser Thr Phe Leu Gly Ser Gly Ser Gly Ser Glu Gln Tyr Ile Lys Trp
            260                 265                 270

Pro Trp Tyr Ile Trp Leu Gly Phe Ile Ala Gly Leu Ile Ala Ile Val
        275                 280                 285

Met Val Thr Ile Met Leu Cys Cys Met Thr Ser Cys Cys Ser Cys Leu
    290                 295                 300

Lys Gly Cys Cys Ser Cys Gly Ser Cys Cys
305                 310

                                                SEQ ID NO: 41
agaauaaacu aguauucuuc ugguccccac agacucagag agaacccgcc accauggauu     60

ggauuuggag aauccuguuc cucgugggag ccgcuacagg agcccacucc cagaugcagg    120

ugagauuucc aaauauuaca aaucugugc cauuuggaga aguguuuaau gcaacaagau    180

uugcaucugu guaugcaugg aauagaaaaa gaauuucuaa uuguguggcu gauuauucug    240

ugcuguauaa uagugcuucu uuuuccacau uuaaauguua uggagugucu ccaacaaaau    300

uaaaugauuu auguuuuaca aauguguaug cugauucuuu ugugaucaga ggugaugaag    360

ugagacagau ugcccccgga cagacaggaa aaauugcuga uuacaauuac aaacugccug    420

augauuuuac aggaugugug auugcuugga auucuaauaa uuuagauucu aaagugggag    480

gaaauuacaa uuaucuguac agacuguuua gaaaaucaaa ucugaaaccu uuugaaagag    540

auauuucaac agaaauuuau caggcuggau caacaccuug uaauggagug gaaggauuua    600

auuguuauuu uccauuacag agcuauggau uucagccaac caaugguguug ggauaucagc    660

cauauagagu gguggugcug ucuuuugaac ugcugcaugc accugcaaca gugugugac    720

cuaaaggcuc ccccggcucc ggcuccggau cugguuauau uccugaagcu ccaagagaug    780

ggcaagcuua cguucguaaa gauggcgaau ggguauuacu uucuaccuuu uuaggaagcg    840

gcagcggauc ugaacaguac auuaaauggc cuugguacau uuggcuugga uuuauugcag    900

gauuaauugc aauugugaug gugacaauua uguuauguug uaugacauca uguuguucuu    960

guuuaaaagg auguuguucu uguggaagcu guuguugaug acucgagcug guacugcaug   1020

cacgcaaugc uagcugcccc uuucccgucc uggguacccc gagucucccc cgaccucggg   1080

ucccagguau gcucccaccu ccaccugccc cacucaccac cucugcuagu uccagacacc   1140

ucccaagcac gcagcaaugc agcucaaaac gcuuagccua gccacacccc cacgggaaac   1200

agcagugauu aaccuuuagc aauaaacgaa aguuuaacua agcuauacua accccagggu   1260

uggucaauuu cgugccagcc acacccugga gcuagcaaaa aaaaaaaaaa aaaaaaaaaa   1320

aaaaaagcau augacuaaaa aaaaaaaaaa aaaaaaaaaa aaaaaaaaaa aaaaaaaaaa   1380

aaaaaaaaaa aaaaaaaaaa aaaaaa                                         1406
```

Nucleic Acid Containing Particles

Nucleic acids described herein such as RNA encoding a payload may be administered formulated as particles.

In the context of the present disclosure, the term "particle" relates to a structured entity formed by molecules or molecule complexes. In some embodiments, the term "particle" relates to a micro- or nano-sized structure, such as a micro- or nano-sized compact structure dispersed in a medium. In some embodiments, a particle is a nucleic acid containing particle such as a particle comprising DNA, RNA or a mixture thereof.

Electrostatic interactions between positively charged molecules such as polymers and lipids and negatively charged nucleic acid are involved in particle formation. This results in complexation and spontaneous formation of nucleic acid particles. In some embodiments, a nucleic acid particle is a nanoparticle.

As used in the present disclosure, "nanoparticle" refers to a particle having an average diameter suitable for parenteral administration.

A "nucleic acid particle" can be used to deliver nucleic acid to a target site of interest (e.g., cell, tissue, organ, and the like). A nucleic acid particle may be formed from at least one cationic or cationically ionizable lipid or lipid-like material, at least one cationic polymer such as protamine, or a mixture thereof and nucleic acid. Nucleic acid particles include lipid nanoparticle (LNP)-based and lipoplex (LPX)-based formulations.

Without intending to be bound by any theory, it is believed that the cationic or cationically ionizable lipid or lipid-like material and/or the cationic polymer combine together with the nucleic acid to form aggregates, and this aggregation results in colloidally stable particles.

In some embodiments, particles described herein further comprise at least one lipid or lipid-like material other than a cationic or cationically ionizable lipid or lipid-like material, at least one polymer other than a cationic polymer, or a mixture thereof In some embodiments, nucleic acid particles comprise more than one type of nucleic acid molecules, where the molecular parameters of the nucleic acid molecules may be similar or different from each other, like with respect to molar mass or fundamental structural elements such as molecular architecture, capping, coding regions or other features. Nucleic acid particles described herein may have an average diameter that in some embodiments ranges from about 30 nm to about 1000 nm, from about 50 nm to about 800 nm, from about 70 nm to about 600 nm, from about 90 nm to about 400 nm, or from about 100 nm to about 300 nm.

Nucleic acid particles described herein may exhibit a polydispersity index less than about 0.5, less than about 0.4, less than about 0.3, or about 0.2 or less. By way of example, the nucleic acid particles can exhibit a polydispersity index in a range of about 0.1 to about 0.3 or about 0.2 to about 0.3.

With respect to RNA lipid particles, the N/P ratio gives the ratio of the nitrogen groups in the lipid to the number of phosphate groups in the RNA. It is correlated to the charge ratio, as the nitrogen atoms (depending on the pH) are usually positively charged and the phosphate groups are negatively charged. The N/P ratio, where a charge equilibrium exists, depends on the pH. Lipid formulations are frequently formed at N/P ratios larger than four up to twelve, because positively charged nanoparticles are considered favorable for transfection. In that case, RNA is considered to be completely bound to nanoparticles.

Nucleic acid particles described herein can be prepared using a wide range of methods that may involve obtaining a colloid from at least one cationic or cationically ionizable lipid or lipid-like material and/or at least one cationic polymer and mixing the colloid with nucleic acid to obtain nucleic acid particles.

The term "colloid" as used herein relates to a type of homogeneous mixture in which dispersed particles do not settle out. The insoluble particles in the mixture are microscopic, with particle sizes between 1 and 1000 nanometers. The mixture may be termed a colloid or a colloidal suspension. Sometimes the term "colloid" only refers to the particles in the mixture and not the entire suspension.

For the preparation of colloids comprising at least one cationic or cationically ionizable lipid or lipid-like material and/or at least one cationic polymer methods are applicable herein that are conventionally used for preparing liposomal vesicles and are appropriately adapted. The most commonly used methods for preparing liposomal vesicles share the following fundamental stages: (i) lipids dissolution in organic solvents, (ii) drying of the resultant solution, and (iii) hydration of dried lipid (using various aqueous media).

In the film hydration method, lipids are firstly dissolved in a suitable organic solvent, and dried down to yield a thin film at the bottom of the flask. The obtained lipid film is hydrated using an appropriate aqueous medium to produce a liposomal dispersion. Furthermore, an additional downsizing step may be included.

Reverse phase evaporation is an alternative method to the film hydration for preparing liposomal vesicles that involves formation of a water-in-oil emulsion between an aqueous phase and an organic phase containing lipids. A brief sonication of this mixture is required for system homogenization. The removal of the organic phase under reduced pressure yields a milky gel that turns subsequently into a liposomal suspension.

The term "ethanol injection technique" refers to a process, in which an ethanol solution comprising lipids is rapidly injected into an aqueous solution through a needle. This action disperses the lipids throughout the solution and promotes lipid structure formation, for example lipid vesicle formation such as liposome formation. Generally, the RNA lipoplex particles described herein are obtainable by adding RNA to a colloidal liposome dispersion. Using the ethanol injection technique, such colloidal liposome dispersion is, in some embodiments, formed as follows: an ethanol solution comprising lipids, such as cationic lipids and additional lipids, is injected into an aqueous solution under stirring. In some embodiments, the RNA lipoplex particles described herein are obtainable without a step of extrusion.

The term "extruding" or "extrusion" refers to the creation of particles having a fixed, cross-sectional profile. In particular, it refers to the downsizing of a particle, whereby the particle is forced through filters with defined pores.

Other methods having organic solvent free characteristics may also be used according to the present disclosure for preparing a colloid.

LNPs typically comprise four components: ionizable cationic lipids, neutral lipids such as phospholipids, a steroid such as cholesterol, and a polymer conjugated lipid such as polyethylene glycol (PEG)-lipids. Each component is responsible for payload protection, and enables effective intracellular delivery. LNPs may be prepared by mixing lipids dissolved in ethanol rapidly with nucleic acid in an aqueous buffer.

The term "average diameter" refers to the mean hydrodynamic diameter of particles as measured by dynamic laser light scattering (DLS) with data analysis using the so-called cumulant algorithm, which provides as results the so-called Zaverage with the dimension of a length, and the polydispersity index (PI), which is dimensionless (Koppel, D., J. Chem. Phys. 57, 1972, pp 4814-4820, ISO 13321). Here "average diameter", "diameter" or "size" for particles is used synonymously with this value of the Zaverage.

The "polydispersity index" is preferably calculated based on dynamic light scattering measurements by the so-called cumulant analysis as mentioned in the definition of the "average diameter". Under certain prerequisites, it can be taken as a measure of the size distribution of an ensemble of nanoparticles.

Different types of nucleic acid containing particles have been described previously to be suitable for delivery of nucleic acid in particulate form (e.g. Kaczmarek, J. C. et al., 2017, Genome Medicine 9, 60). For non-viral nucleic acid delivery vehicles, nanoparticle encapsulation of nucleic acid physically protects nucleic acid from degradation and, depending on the specific chemistry, can aid in cellular uptake and endosomal escape.

The present disclosure describes particles comprising nucleic acid, at least one cationic or cationically ionizable lipid or lipid-like material, and/or at least one cationic polymer which associate with nucleic acid to form nucleic acid particles and compositions comprising such particles. The nucleic acid particles may comprise nucleic acid which is complexed in different forms by non-covalent interactions to the particle. The particles described herein are not viral particles, in particular infectious viral particles, i.e., they are not able to virally infect cells. Suitable cationic or cationically ionizable lipids or lipid-like materials and cationic polymers are those that form nucleic acid particles and are included by the term "particle forming components" or "particle forming agents". The term "particle forming components" or "particle forming agents" relates to any components which associate with nucleic acid to form nucleic acid particles. Such components include any component which can be part of nucleic acid particles.

Some embodiments described herein relate to compositions, methods and uses involving more than one, e.g., 2, 3, 4, 5, 6 or even more nucleic acid species such as RNA species, e.g., a) a nucleic acid comprising a first nucleotide sequence encoding an amino acid sequence comprising at least a fragment of a parental virus protein, wherein amino acid positions in the at least a fragment of a parental virus protein are modified to comprise amino acids found in the corresponding amino acid positions of one or more virus protein variants; and b) a nucleic acid comprising a second nucleotide sequence encoding an amino acid sequence comprising at least a fragment of a parental virus protein, wherein amino acid positions in the at least a fragment of a parental virus protein are modified to comprise amino acids found in the corresponding amino acid positions of one or more virus protein variants.

In a particulate formulation, it is possible that each nucleic acid species is separately formulated as an individual particulate formulation. In that case, each individual particulate formulation will comprise one nucleic acid species. The individual particulate formulations may be present as separate entities, e.g. in separate containers. Such formulations are obtainable by providing each nucleic acid species separately (typically each in the form of a nucleic acid-containing solution) together with a particle-forming agent, thereby allowing the formation of particles. Respective particles will contain exclusively the specific nucleic acid species that is being provided when the particles are formed (individual particulate formulations).

In some embodiments, a composition such as a pharmaceutical composition comprises more than one individual particle formulation. Respective pharmaceutical compositions are referred to as mixed particulate formulations. Mixed particulate formulations according to the invention are obtainable by forming, separately, individual particulate formulations, as described above, followed by a step of mixing of the individual particulate formulations. By the step of mixing, a formulation comprising a mixed population of nucleic acid-containing particles is obtainable. Individual particulate populations may be together in one container, comprising a mixed population of individual particulate formulations.

Alternatively, it is possible that different nucleic acid species are formulated together as a combined particulate formulation. Such formulations are obtainable by providing a combined formulation (typically combined solution) of different RNA species together with a particle-forming agent, thereby allowing the formation of particles. As opposed to a mixed particulate formulation, a combined particulate formulation will typically comprise particles which comprise more than one RNA species. In a combined particulate composition different RNA species are typically present together in a single particle.

Cationic Polymeric Materials (e.g., Polymers)

Given their high degree of chemical flexibility, polymeric materials are commonly used for nanoparticle-based delivery. Typically, cationic materials are used to electrostatically condense the negatively charged nucleic acid into nanoparticles. These positively charged groups often consist of amines that change their state of protonation in the pH range between 5.5 and 7.5, thought to lead to an ion imbalance that results in endosomal rupture. Polymers such as poly-L-lysine, polyamidoamine, protamine and polyethyleneimine, as well as naturally occurring polymers such as chitosan have all been applied to nucleic acid delivery and are suitable as cationic materials useful in some embodiments herein. In addition, some investigators have synthesized polymeric materials specifically for nucleic acid delivery. Poly(β-amino esters), in particular, have gained widespread use in nucleic acid delivery owing to their ease of synthesis and biodegradability. In some embodiments, such synthetic materials may be suitable for use as cationic materials herein.

A "polymeric material", as used herein, is given its ordinary meaning, i.e., a molecular structure comprising one or more repeat units (monomers), connected by covalent bonds. In some embodiments, such repeat units can all be identical; alternatively, in some cases, there can be more than one type of repeat unit present within the polymeric material. In some cases, a polymeric material is biologically derived, e.g., a biopolymer such as a protein. In some cases, additional moieties can also be present in the polymeric material, for example targeting moieties such as those described herein.

Those skilled in the art are aware that, when more than one type of repeat unit is present within a polymer (or polymeric moiety), then the polymer (or polymeric moiety) is said to be a "copolymer." In some embodiments, a polymer (or polymeric moiety) utilized in accordance with the present disclosure may be a copolymer. Repeat units forming the copolymer can be arranged in any fashion. For example, in some embodiments, repeat units can be arranged in a random order; alternatively or additionally, in some embodiments, repeat units may be arranged in an alternating order, or as a "block" copolymer, i.e., comprising one or more regions each comprising a first repeat unit (e.g., a first block), and one or more regions each comprising a second repeat unit (e.g., a second block), etc. Block copolymers can have two (a diblock copolymer), three (a triblock copolymer), or more numbers of distinct blocks.

In certain embodiments, a polymeric material for use in accordance with the present disclosure is biocompatible. Biocompatible materials are those that typically do not result in significant cell death at moderate concentrations. In certain embodiments, a biocompatible material is biodegradable, i.e., is able to degrade, chemically and/or biologically, within a physiological environment, such as within the body.

In certain embodiments, a polymeric material may be or comprise protamine or polyalkyleneimine, in particular protamine.

As those skilled in the art are aware term "protamine" is often used to refer to any of various strongly basic proteins of relatively low molecular weight that are rich in arginine and are found associated especially with DNA in place of somatic histones in the sperm cells of various animals (as fish). In particular, the term "protamine" is often used to refer to proteins found in fish sperm that are strongly basic, are soluble in water, are not coagulated by heat, and yield chiefly arginine upon hydrolysis. In purified form, they are used in a long-acting formulation of insulin and to neutralize the anticoagulant effects of heparin.

In some embodiments, the term "protamine" as used herein is refers to a protamine amino acid sequence obtained or derived from natural or biological sources, including fragments thereof and/or multimeric forms of said amino acid sequence or fragment thereof, as well as (synthesized) polypeptides which are artificial and specifically designed for specific purposes and cannot be isolated from native or biological sources.

In some embodiments, a polyalkyleneimine comprises polyethylenimine and/or polypropylenimine, preferably polyethyleneimine. In some embodiments, a preferred polyalkyleneimine is polyethyleneimine (PEI). In some embodiments, the average molecular weight of PEI is preferably 0.75·102 to 107 Da, preferably 1000 to 105 Da, more preferably 10000 to 40000 Da, more preferably 15000 to 30000 Da, even more preferably 20000 to 25000 Da.

Preferred according to certain embodiments of the disclosure is linear polyalkyleneimine such as linear polyethyleneimine (PEI).

Cationic materials (e.g., polymeric materials, including polycationic polymers) contemplated for use herein include those which are able to electrostatically bind nucleic acid. In some embodiments, cationic polymeric materials contemplated for use herein include any cationic polymeric materials with which nucleic acid can be associated, e.g. by forming complexes with the nucleic acid or forming vesicles in which the nucleic acid is enclosed or encapsulated.

In some embodiments, particles described herein may comprise polymers other than cationic polymers, e.g., non-cationic polymeric materials and/or anionic polymeric materials. Collectively, anionic and neutral polymeric materials are referred to herein as non-cationic polymeric materials.

Lipid and Lipid-Like Material

The terms "lipid" and "lipid-like material" are used herein to refer to molecules which comprise one or more hydrophobic moieties or groups and optionally also one or more hydrophilic moieties or groups. Molecules comprising hydrophobic moieties and hydrophilic moieties are also frequently denoted as amphiphiles. Lipids are usually poorly soluble in water. In an aqueous environment, the amphiphilic nature allows the molecules to self-assemble into organized structures and different phases. One of those phases consists of lipid bilayers, as they are present in vesicles, multilamellar/unilamellar liposomes, or membranes in an aqueous environment. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). In some embodiments, hydrophilic groups may comprise polar and/or charged groups and include carbohydrates, phosphate, carboxylic, sulfate, amino, sulfhydryl, nitro, hydroxyl, and other like groups.

As used herein, the term "amphiphilic" refers to a molecule having both a polar portion and a non-polar portion. Often, an amphiphilic compound has a polar head attached to a long hydrophobic tail. In some embodiments, the polar portion is soluble in water, while the non-polar portion is insoluble in water. In addition, the polar portion may have either a formal positive charge, or a formal negative charge. Alternatively, the polar portion may have both a formal positive and a negative charge, and be a zwitterion or inner salt. For purposes of the disclosure, the amphiphilic compound can be, but is not limited to, one or a plurality of natural or non-natural lipids and lipid-like compounds.

The term "lipid-like material", "lipid-like compound" or "lipid-like molecule" relates to substances that structurally and/or functionally relate to lipids but may not be considered as lipids in a strict sense. For example, the term includes compounds that are able to form amphiphilic layers as they are present in vesicles, multilamellar/unilamellar liposomes, or membranes in an aqueous environment and includes surfactants, or synthesized compounds with both hydrophilic and hydrophobic moieties. Generally speaking, the term refers to molecules, which comprise hydrophilic and hydrophobic moieties with different structural organization, which may or may not be similar to that of lipids. As used herein, the term "lipid" is to be construed to cover both lipids and lipid-like materials unless otherwise indicated herein or clearly contradicted by context.

Specific examples of amphiphilic compounds that may be included in an amphiphilic layer include, but are not limited to, phospholipids, aminolipids and sphingolipids.

In certain embodiments, the amphiphilic compound is a lipid. The term "lipid" refers to a group of organic compounds that are characterized by being insoluble in water, but soluble in many organic solvents. Generally, lipids may be divided into eight categories: fatty acids, glycerolipids, glycerophospholipids, sphingolipids, saccharolipids, polyketides (derived from condensation of ketoacyl subunits), sterol lipids and prenol lipids (derived from condensation of isoprene subunits). Although the term "lipid" is sometimes used as a synonym for fats, fats are a subgroup of lipids called triglycerides. Lipids also encompass molecules such as fatty acids and their derivatives (including tri-, di-, monoglycerides, and phospholipids), as well as sterol-containing metabolites such as cholesterol.

Fatty acids, or fatty acid residues are a diverse group of molecules made of a hydrocarbon chain that terminates with a carboxylic acid group; this arrangement confers the molecule with a polar, hydrophilic end, and a nonpolar, hydrophobic end that is insoluble in water. The carbon chain, typically between four and 24 carbons long, may be saturated or unsaturated, and may be attached to functional groups containing oxygen, halogens, nitrogen, and sulfur. If a fatty acid contains a double bond, there is the possibility of either a cis or trans geometric isomerism, which significantly affects the molecule's configuration. Cis-double bonds cause the fatty acid chain to bend, an effect that is compounded with more double bonds in the chain. Other major lipid classes in the fatty acid category are the fatty esters and fatty amides.

Glycerolipids are composed of mono-, di-, and tri-substituted glycerols, the best-known being the fatty acid triesters of glycerol, called triglycerides. The word "triacylglycerol" is sometimes used synonymously with "triglyceride". In these compounds, the three hydroxyl groups of glycerol are each esterified, typically by different fatty acids. Additional subclasses of glycerolipids are represented by glycosylglycerols, which are characterized by the presence of one or more sugar residues attached to glycerol via a glycosidic linkage.

The glycerophospholipids are amphipathic molecules (containing both hydrophobic and hydrophilic regions) that contain a glycerol core linked to two fatty acid-derived "tails" by ester linkages and to one "head" group by a phosphate ester linkage. Examples of glycerophospholipids, usually referred to as phospholipids (though sphingomyelins are also classified as phospholipids) are phosphatidylcholine (also known as PC, GPCho or lecithin), phosphatidylethanolamine (PE or GPEtn) and phosphatidylserine (PS or GPSer).

Sphingolipids are a complex family of compounds that share a common structural feature, a sphingoid base backbone. The major sphingoid base in mammals is commonly referred to as sphingosine. Ceramides (N-acyl-sphingoid bases) are a major subclass of sphingoid base derivatives with an amide-linked fatty acid. The fatty acids are typically saturated or mono-unsaturated with chain lengths from 16 to 26 carbon atoms. The major phosphosphingolipids of mammals are sphingomyelins (ceramide phosphocholines), whereas insects contain mainly ceramide phosphoethanolamines and fungi have phytoceramide phosphoinositols and mannose-containing headgroups. The glycosphingolipids are a diverse family of molecules composed of one or more sugar residues linked via a glycosidic bond to the sphingoid base. Examples of these are the simple and complex glycosphingolipids such as cerebrosides and gangliosides. Sterol lipids, such as cholesterol and its derivatives, or tocopherol and its derivatives, are an important component of membrane lipids, along with the glycerophospholipids and sphingomyelins.

Saccharolipids describe compounds in which fatty acids are linked directly to a sugar backbone, forming structures that are compatible with membrane bilayers. In the saccharolipids, a monosaccharide substitutes for the glycerol backbone present in glycerolipids and glycerophospholipids. The most familiar saccharolipids are the acylated glucosamine precursors of the Lipid A component of the lipopolysaccharides in Gram-negative bacteria. Typical lipid A molecules are disaccharides of glucosamine, which are derivatized with as many as seven fatty-acyl chains. The minimal lipopolysaccharide required for growth in *E. coli* is Kdo2-Lipid A, a hexa-acylated disaccharide of glucosamine that is glycosylated with two 3-deoxy-D-manno-octulosonic acid (Kdo) residues.

Polyketides are synthesized by polymerization of acetyl and propionyl subunits by classic enzymes as well as iterative and multimodular enzymes that share mechanistic features with the fatty acid synthases. They comprise a large number of secondary metabolites and natural products from animal, plant, bacterial, fungal and marine sources, and have great structural diversity. Many polyketides are cyclic molecules whose backbones are often further modified by glycosylation, methylation, hydroxylation, oxidation, or other processes.

According to the disclosure, lipids and lipid-like materials may be cationic, anionic or neutral. Neutral lipids or lipid-like materials exist in an uncharged or neutral zwitterionic form at a selected pH.

Cationic or Cationically Ionizable Lipids or Lipid-Like Materials

In some embodiments, nucleic acid particles described and/or utilized in accordance with the present disclosure may comprise at least one cationic or cationically ionizable lipid or lipid-like material as particle forming agent. Cationic or cationically ionizable lipids or lipid-like materials contemplated for use herein include any cationic or cationically ionizable lipids or lipid-like materials which are able to electrostatically bind nucleic acid. In some embodiments, cationic or cationically ionizable lipids or lipid-like materials contemplated for use herein can be associated with nucleic acid, e.g. by forming complexes with the nucleic acid or forming vesicles in which the nucleic acid is enclosed or encapsulated.

As used herein, a "cationic lipid" or "cationic lipid-like material" refers to a lipid or lipid-like material having a net positive charge. Cationic lipids or lipid-like materials bind negatively charged nucleic acid by electrostatic interaction. Generally, cationic lipids possess a lipophilic moiety, such as a sterol, an acyl chain, a diacyl or more acyl chains, and the head group of the lipid typically carries the positive charge.

In certain embodiments, a cationic lipid or lipid-like material has a net positive charge only at certain pH, in particular acidic pH, while it has preferably no net positive charge, preferably has no charge, i.e., it is neutral, at a different, preferably higher pH such as physiological pH. This ionizable behavior is thought to enhance efficacy through helping with endosomal escape and reducing toxicity as compared with particles that remain cationic at physiological pH.

For purposes of the present disclosure, such "cationically ionizable" lipids or lipid-like materials are comprised by the term "cationic lipid or lipid-like material" unless contradicted by the circumstances.

In some embodiments, a cationic or cationically ionizable lipid or lipid-like material comprises a head group which includes at least one nitrogen atom (N) which is positive charged or capable of being protonated.

Examples of cationic lipids include, but are not limited to: ((4-hydroxybutyl)azanediyl)bis(hexane-6,1-diyl)bis(2-hexyldecanoate); 1,2-dioleoyl-3-trimethylammonium propane (DOTAP); N,N-dimethyl-2,3-dioleyloxypropylamine (DODMA), 1,2-di-O-octadecenyl-3-trimethylammonium propane (DOTMA), 3-(N—(N',N'-dimethylaminoethane)-carbamoyl)cholesterol (DC-Chol), dimethyldioctadecylammonium (DDAB); 1,2-dioleoyl-3-dimethylammonium-propane (DODAP); 1,2-diacyloxy-3-dimethylammonium propanes; 1,2-dialkyloxy-3-dimethylammonium propanes; dioctadecyldimethyl ammonium chloride (DODAC), 1,2-distearyloxy-N,N-dimethyl-3-aminopropane (DSDMA), 2,3-di(tetradecoxy)propyl-(2-hydroxyethyl)-dimethylazanium (DMRIE), 1,2-dimyristoyl-sn-glycero-3-ethylphosphocholine (DMEPC), 1,2-dimyristoyl-3-trimethylammonium propane (DMTAP), 1,2-dioleyloxypropyl-3-dimethyl-hydroxyethyl ammonium bromide (DORIE), and 2,3-dioleoyloxy-N-[2(spermine carboxamide)ethyl]-N,N-dimethyl-l-propanamium trifluoroacetate (DOSPA), 1,2-dilinoleyloxy-N,N-dimethylaminopropane (DLinDMA), 1,2-dilinolenyloxy-N,N-dimethylaminopropane (DLenDMA), dioctadecylamidoglycyl spermine (DOGS), 3-dimethylamino-2-(cholest-5-en-3-beta-oxybutan-4-oxy)-1-(cis,cis-9,12-oc-tadecadienoxy)propane (CLinDMA), 2-[5'-(cholest-5-en-3-beta-oxy)-3'-oxapentoxy)-3-dimethyl-1-(cis,cis-9',12'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 2,3-Dilinoleoyloxy-N,N-dimethylpropylamine (DLinDAP), 1,2-N,N'-Dilinoleylcarbamyl-3-dimethylaminopropane (DLincarbDAP), 1,2-Dilinoleoylcarbamyl-3-dimethylaminopropane (DLinCDAP), 2,2-dilinoleyl-4-dimethylaminomethyl-[1,3]-dioxolane (DLin-K-DMA), 2,2-dilinoleyl-4-dimethylaminoethyl-[1,3]-dioxolane (DLin-K-XTC2-DMA), 2,2-dilinoleyl-4-(2-dimethylaminoethyl)-[1,3]-dioxolane (DLin-KC2-DMA), heptatriaconta-6,9,28,31-tetraen-19-yl-4-(dimethylamino)butanoate (DLin-MC3-DMA), N-(2-Hydroxyethyl)-N,N-dimethyl-2,3-bis(tetradecyloxy)-1-propanaminium bromide (DMRIE), (±)-N-(3-aminopropyl)-N,N-dimethyl-2,3-bis(cis-9-tetradecenyloxy)-1-propanaminium bromide (GAP-DMORIE), (±)-N-(3-aminopropyl)-N,N-dimethyl-2,3-bis(dodecyloxy)-1-propanaminium bromide (GAP-DLRIE), (±)-N-(3-aminopropyl)-N,N-dimethyl-2,3-bis(tetradecyloxy)-1-propanaminium bromide (GAP-DMRIE), N-(2-Aminoethyl)-N,N-dimethyl-2,3-bis(tetradecyloxy)-1-propanaminium bromide (PAE-DMRIE), N-(4-carboxybenzyl)-N,N-dimethyl-2,3-bis(oleoyloxy)propan-1-aminium (DOBAQ), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), 1,2-dimyristoyl-3-dimethylammonium-propane (DMDAP), 1,2-dipalmitoyl-3-dimethylammonium-propane (DPDAP), N1-[2-((1S)-1-[(3-aminopropyl)amino]-4-[di(3-amino-propyl)amino]butylcarboxamido)ethyl]-3,4-di[oleyloxy]-benzamide (MVL5), 1,2-dioleoyl-sn-glycero-3-ethylphosphocholine (DOEPC), 2,3-bis(dodecyloxy)-N-(2-hydroxyethyl)-N,N-dimethylpropan-1-ammonium bromide (DLRIE), N-(2-aminoethyl)-N,N-dimethyl-2,3-bis(tetradecyloxy)propan-1-aminium bromide (DMORIE), di((Z)-non-2-en-1-yl) 8,8'-((((2(dimethylamino)ethyl)thio)carbonyl)azanediyl) dioctanoate (ATX), N,N-dimethyl-2,3-bis(dodecyloxy)propan-1-amine (DLDMA), N,N-dimethyl-2,3-bis(tetradecyloxy)propan-1-amine (DMDMA), Di((Z)-non-2-en-1-yl)-9-((4-(dimethylaminobutanoyl)oxy) heptadecanedioate (L319), N-Dodecyl-3-((2-dodecylcarbamoyl-ethyl)-{2-[(2-dodecylcarbamoyl-ethyl)-2-{(2-dodecylcarbamoyl-ethyl)-[2-(2-dodecylcarbamoyl-ethylamino)-ethyl]-amino}-ethylamino)propionamide (lipidoid 98N12-5), 1-[2-[bis(2-hydroxydodecyl)amino]ethyl-[2-[4-[2-[bis(2 hydroxydodecyl)amino]ethyl]piperazin-1-yl]ethyl]amino]dodecan-2-ol (lipidoid C12-200); or heptadecan-9-yl 8-((2-hydroxyethyl) (6-oxo-6-(undecyloxy) hexyl) amino) octanoate (SM-102).

In some embodiments, a cationic lipid is or comprises heptadecan-9-yl 8-((2-hydroxyethyl) (6-oxo-6-(undecyloxy) hexyl) amino) octanoate (SM-102). In some embodiments, a cationic lipid is or comprises a cationic lipid shown in the structure below.

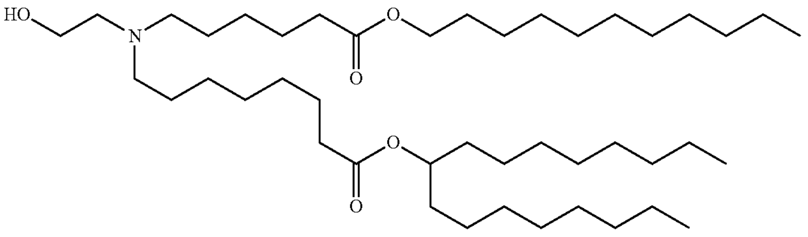 [SMILES: CCCCCCCCCCCOC(=O)CCCCCN(CCO)CCCCCCCC(=O)OC(CCCCCCCC)CCCCCCCC]

In some embodiments, a cationic lipid is or comprises ((4-hydroxybutyl)azanediyl)bis(hexane-6,1-diyl)bis(2-hexyldecanoate) which is also referred to as ALC-0315 herein.

In some embodiments, a cationic lipid may comprise from about 10 mol % to about 100 mol %, about 20 mol % to about 100 mol %, about 30 mol % to about 100 mol %, about 40 mol % to about 100 mol %, or about 50 mol % to about 100 mol % of the total lipid present in the particle.

In some particular embodiments, a particle for use in accordance with the present disclosure includes ALC-0315, for example in a weight percent within a range of about 40-55 mol percent of total lipids.

Additional Lipids or Lipid-Like Materials

In some embodiments, particles described herein comprise (e.g., in addition to a cationic lipid such as ALC315), one or more lipids or lipid-like materials other than cationic or cationically ionizable lipids or lipid-like materials, e.g., non-cationic lipids or lipid-like materials (including non-cationically ionizable lipids or lipid-like materials). Collectively, anionic and neutral lipids or lipid-like materials are referred to herein as non-cationic lipids or lipid-like materials. Optimizing the formulation of nucleic acid particles by addition of other hydrophobic moieties, such as cholesterol and lipids, in addition to an ionizable/cationic lipid or lipid-like material may enhance particle stability and efficacy of nucleic acid delivery.

An additional lipid or lipid-like material may be incorporated which may or may not affect the overall charge of the nucleic acid particles. In certain embodiments, the additional lipid or lipid-like material is a non-cationic lipid or lipid-like material. The non-cationic lipid may comprise, e.g., one or more anionic lipids and/or neutral lipids. As used herein, an "anionic lipid" refers to any lipid that is negatively charged at a selected pH. As used herein, a "neutral lipid" refers to any of a number of lipid species that exist either in an uncharged or neutral zwitterionic form at a selected pH. In preferred embodiments, the additional lipid comprises one of the following neutral lipid components: (1) a phospholipid, (2) cholesterol or a derivative thereof; or (3) a mixture of a phospholipid and cholesterol or a derivative thereof. Examples of cholesterol derivatives include, but are not limited to, cholestanol, cholestanone, cholestenone, coprostanol, cholesteryl-2'-hydroxyethyl ether, cholesteryl-4'-hydroxybutyl ether, tocopherol and derivatives thereof, and mixtures thereof.

Specific phospholipids that can be used include, but are not limited to, phosphatidylcholines, phosphatidylethanolamines, phosphatidylglycerols, phosphatidic acids, phosphatidylserines or sphingomyelin. Such phospholipids include in particular diacylphosphatidylcholines, such as distearoylphosphatidylcholine (DSPC), dioleoylphosphatidylcholine (DOPC), dimyristoylphosphatidylcholine (DMPC), dipentadecanoylphosphatidylcholine, dilauroylphosphatidylcholine, dipalmitoylphosphatidylcholine (DPPC), diarachidoylphosphatidylcholine (DAPC), dibehenoylphosphatidylcholine (DBPC), ditricosanoylphosphatidylcholine (DTPC), dilignoceroylphatidylcholine (DLPC), palmitoyloleoyl-phosphatidylcholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC) and phosphatidylethanolamines, in particular diacylphosphatidylethanolamines, such as dioleoylphosphatidylethanolamine (DOPE), distearoyl-phosphatidylethanolamine (DSPE), dipalmitoyl-phosphatidylethanolamine (DPPE), dimyristoyl-phosphatidylethanolamine (DMPE), dilauroyl-phosphatidylethanolamine (DLPE), diphytanoyl-phosphatidylethanolamine (DPyPE), and further phosphatidylethanolamine lipids with different hydrophobic chains.

In certain preferred embodiments, the additional lipid is DSPC or DSPC and cholesterol. In certain embodiments, the nucleic acid particles include both a cationic lipid and an additional lipid.

In some embodiments, particles described herein include a polymer conjugated lipid such as a pegylated lipid. The term “pegylated lipid” refers to a molecule comprising both a lipid portion and a polyethylene glycol portion. Pegylated lipids are known in the art. In some embodiments, a pegylated lipid is ALC-0159, also referred to herein as (2-[(polyethylene glycol)-2000]-N,N-ditetradecylacetamide).

Without wishing to be bound by theory, the amount of the at least one cationic lipid compared to the amount of the at least one additional lipid may affect important nucleic acid particle characteristics, such as charge, particle size, stability, tissue selectivity, and bioactivity of the nucleic acid. Accordingly, in some embodiments, the molar ratio of the at least one cationic lipid to the at least one additional lipid is from about 10:0 to about 1:9, about 4:1 to about 1:2, or about 3:1 to about 1:1.

In some embodiments, the non-cationic lipid, in particular neutral lipid, (e.g., one or more phospholipids and/or cholesterol) may comprise from about 0 mol % to about 90 mol %, from about 0 mol % to about 80 mol %, from about 0 mol % to about 70 mol %, from about 0 mol % to about 60 mol %, or from about 0 mol % to about 50 mol %, of the total lipid present in the particle.

In some embodiments, particles for use in accordance with the present disclosure may include, for example, ALC-0315, DSPC, CHOL, and ALC-0159, for example, wherein ALC-0315 is at about 40 to 55 mol percent; DSPC is at about 5 to 15 mol percent; CHOL is at about 30 to 50 mol percent; and ALC-0159 is at about 1 to 10 mol percent.

Lipoplex Particles

In certain embodiments of the present disclosure, an RNA may be present in RNA lipoplex particles.

In the context of the present disclosure, the term “RNA lipoplex particle” relates to a particle that contains lipid, in particular cationic lipid, and RNA. Electrostatic interactions between positively charged liposomes and negatively charged RNA results in complexation and spontaneous formation of RNA lipoplex particles. Positively charged liposomes may be generally synthesized using a cationic lipid, such as DOTMA, and additional lipids, such as DOPE. In some embodiments, a RNA lipoplex particle is a nanoparticle.

In certain embodiments, the RNA lipoplex particles include both a cationic lipid and an additional lipid. In an exemplary embodiment, the cationic lipid is DOTMA and the additional lipid is DOPE.

In some embodiments, the molar ratio of the at least one cationic lipid to the at least one additional lipid is from about 10:0 to about 1:9, about 4:1 to about 1:2, or about 3:1 to about 1:1. In specific embodiments, the molar ratio may be about 3:1, about 2.75:1, about 2.5:1, about 2.25:1, about 2:1, about 1.75:1, about 1.5:1, about 1.25:1, or about 1:1. In an exemplary embodiment, the molar ratio of the at least one cationic lipid to the at least one additional lipid is about 2:1.

RNA lipoplex particles described herein have an average diameter that in some embodiments ranges from about 200 nm to about 1000 nm, from about 200 nm to about 800 nm, from about 250 to about 700 nm, from about 400 to about 600 nm, from about 300 nm to about 500 nm, or from about 350 nm to about 400 nm. In specific embodiments, the RNA lipoplex particles have an average diameter of about 200 nm, about 225 nm, about 250 nm, about 275 nm, about 300 nm, about 325 nm, about 350 nm, about 375 nm, about 400 nm, about 425 nm, about 450 nm, about 475 nm, about 500 nm, about 525 nm, about 550 nm, about 575 nm, about 600 nm, about 625 nm, about 650 nm, about 700 nm, about 725 nm, about 750 nm, about 775 nm, about 800 nm, about 825 nm, about 850 nm, about 875 nm, about 900 nm, about 925 nm, about 950 nm, about 975 nm, or about 1000 nm. In an embodiment, the RNA lipoplex particles have an average diameter that ranges from about 250 nm to about 700 nm. In another embodiment, the RNA lipoplex particles have an average diameter that ranges from about 300 nm to about 500 nm. In an exemplary embodiment, the RNA lipoplex particles have an average diameter of about 400 nm.

In some embodiments, RNA lipoplex particles and/or compositions comprising RNA lipoplex particles described herein are useful for delivery of RNA to a target tissue after parenteral administration, in particular after intravenous administration. In some embodiments, RNA lipoplex particles may be prepared using liposomes that may be obtained by injecting a solution of the lipids in ethanol into water or a suitable aqueous phase. In some embodiments, the aqueous phase has an acidic pH. In some embodiments, the aqueous phase comprises acetic acid, e.g., in an amount of about 5 mM. Liposomes may be used for preparing RNA lipoplex particles by mixing the liposomes with RNA. In some embodiments, the liposomes and RNA lipoplex particles comprise at least one cationic lipid and at least one additional lipid. In some embodiments, the at least one cationic lipid comprises 1,2-di-O-octadecenyl-3-trimethylammonium propane (DOTMA) and/or 1,2-dioleoyl-3-trimethylammonium-propane (DOTAP). In some embodiments, the at least one additional lipid comprises 1,2-di-(9Z-octadecenoyl)-sn-glycero-3-phosphoethanolamine (DOPE), cholesterol (Chol) and/or 1,2-dioleoyl-sn-glycero-3-phosphocholine (DOPC). In some embodiments, the at least one cationic lipid comprises 1,2-di-O-octadecenyl-3-trimethylammonium propane (DOTMA) and the at least one additional lipid comprises 1,2-di-(9Z-octadecenoyl)-sn-glycero-3-phosphoethanolamine (DOPE). In some embodiments, the liposomes and RNA lipoplex particles comprise 1,2-di-O-octadecenyl-3-trimethylammonium propane (DOTMA) and 1,2-di-(9Z-octadecenoyl)-sn-glycero-3-phosphoethanolamine (DOPE).

Spleen targeting RNA lipoplex particles are described in WO 2013/143683, herein incorporated by reference. It has been found that RNA lipoplex particles having a net negative charge may be used to preferentially target spleen tissue or spleen cells such as antigen-presenting cells, in particular dendritic cells. Accordingly, following administration of the RNA lipoplex particles, RNA accumulation and/or RNA expression in the spleen occurs. Thus, RNA lipoplex particles of the disclosure may be used for expressing RNA in the spleen. In an embodiment, after administration of the RNA lipoplex particles, no or essentially no RNA accumulation and/or RNA expression in the lung and/or liver occurs. In some embodiments, after administration of the RNA lipoplex particles, RNA accumulation and/or RNA expression in antigen presenting cells, such as professional antigen presenting cells in the spleen occurs. Thus, RNA lipoplex particles of the disclosure may be used for expressing RNA in such antigen presenting cells. In some embodiments, the antigen presenting cells are dendritic cells and/or macrophages.

Lipid Nanoparticles (LNPs)

In some embodiments, nucleic acid such as RNA described herein is administered in the form of lipid nanoparticles (LNPs). The LNP may comprise any lipid capable of forming a particle to which the one or more nucleic acid molecules are attached, or in which the one or more nucleic acid molecules are encapsulated.

In some embodiments, the LNP comprises one or more cationic lipids, and one or more stabilizing lipids. Stabilizing lipids include neutral lipids and pegylated lipids.

In some embodiments, the LNP comprises a cationic lipid, a neutral lipid, a steroid, a polymer conjugated lipid; and the RNA, encapsulated within or associated with the lipid nanoparticle.

In some embodiments, an LNP comprises from 40 to 55 mol percent, from 40 to 50 mol percent, from 41 to 49 mol percent, from 41 to 48 mol percent, from 42 to 48 mol percent, from 43 to 48 mol percent, from 44 to 48 mol percent, from 45 to 48 mol percent, from 46 to 48 mol percent, from 47 to 48 mol percent, or from 47.2 to 47.8 mol percent of the cationic lipid. In some embodiments, the LNP comprises about 47.0, 47.1, 47.2, 47.3, 47.4, 47.5, 47.6, 47.7, 47.8, 47.9 or 48.0 mol percent of the cationic lipid.

In some embodiments, the neutral lipid is present in a concentration ranging from 5 to 15 mol percent, from 7 to 13 mol percent, or from 9 to 11 mol percent. In some embodiments, the neutral lipid is present in a concentration of about 9.5, 10 or 10.5 mol percent.

In some embodiments, the steroid is present in a concentration ranging from 30 to 50 mol percent, from 35 to 45 mol percent or from 38 to 43 mol percent. In some embodiments, the steroid is present in a concentration of about 40, 41, 42, 43, 44, 45 or 46 mol percent.

In some embodiments, the LNP comprises from 1 to 10 mol percent, from 1 to 5 mol percent, or from 1 to 2.5 mol percent of the polymer conjugated lipid.

In some embodiments, the LNP comprises from 40 to 50 mol percent a cationic lipid; from 5 to 15 mol percent of a neutral lipid; from 35 to 45 mol percent of a steroid; from 1 to 10 mol percent of a polymer conjugated lipid; and the RNA, encapsulated within or associated with the lipid nanoparticle.

In some embodiments, the mol percent is determined based on total mol of lipid present in the lipid nanoparticle.

In some embodiments, the neutral lipid is selected from the group consisting of DSPC, DPPC, DMPC, DOPC, POPC, DOPE, DOPG, DPPG, POPE, DPPE, DMPE, DSPE, and SM. In some embodiments, the neutral lipid is selected from the group consisting of DSPC, DPPC, DMPC, DOPC, POPC, DOPE and SM. In some embodiments, the neutral lipid is DSPC.

In some embodiments, the steroid is cholesterol.

In some embodiments, the polymer conjugated lipid is a pegylated lipid. In some embodiments, the pegylated lipid has the following structure:

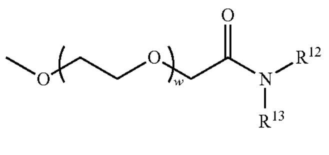

or a pharmaceutically acceptable salt, tautomer or stereoisomer thereof, wherein:

R12 and R13 are each independently a straight or branched, saturated or unsaturated alkyl chain containing from 10 to 30 carbon atoms, wherein the alkyl chain is optionally interrupted by one or more ester bonds; and w has a mean value ranging from 30 to 60. In some embodiments, R12 and R13 are each independently straight, saturated alkyl chains containing from 12 to 16 carbon atoms. In some embodiments, w has a mean value ranging from 40 to 55. In some embodiments, the average w is about 45. In some embodiments, R12 and R13 are each independently a straight, saturated alkyl chain containing about 14 carbon atoms, and w has a mean value of about 45.

In some embodiments, the pegylated lipid is DMG-PEG 2000, e.g., having the following structure:

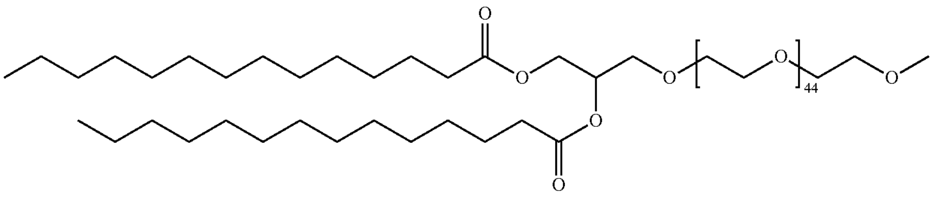

In some embodiments, the cationic lipid component of the LNPs has the structure of Formula (III):

(III)

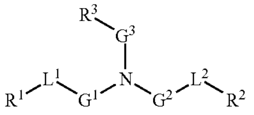

or a pharmaceutically acceptable salt, tautomer, prodrug or stereoisomer thereof, wherein:

one of L1 or L2 is —O(C═O)—, —(C═O)O—, —C(═O)—, —O—, —S(O)x-, —S—S—, —C(═O)S—, SC(═O)—, —NRaC(═O)—, —C(═O)NRa—, NRaC(═O)NRa—, —OC(═O)NRa— or —NRaC(═O)O—, and the other of L1 or L2 is —O(C═O)—, —(C═O)O—, —C(═O)—, —O—, —S(O)x-, —S—S—, —C(═O)S—, SC(═O)—, —NRaC(═O)—, —C(═O)NRa—, NRaC(═O)NRa—, —OC(═O)NRa— or —NRaC(═O)O— or a direct bond;

G1 and G2 are each independently unsubstituted C1-C12 alkylene or C1-C12 alkenylene;

G3 is C1-C24 alkylene, C1-C24 alkenylene, C3-C8 cycloalkylene, C3-C8 cycloalkenylene;

Ra is H or C1-C12 alkyl;

R1 and R2 are each independently C6-C24 alkyl or C6-C24 alkenyl;

R3 is H, OR5, CN, —C(═O)OR4, —OC(═O)R4 or —NR5C(═O)R4;

R4 is C1-C12 alkyl;

R5 is H or C1-C6 alkyl; and x is 0, 1 or 2.

In some of the foregoing embodiments of Formula (III), the lipid has one of the following structures (IIIA) or (IIIB):

(IIIA)

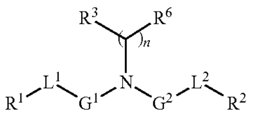

or (IIIB)

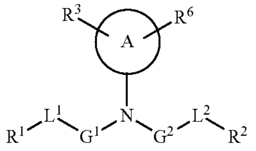

wherein:

A is a 3 to 8-membered cycloalkyl or cycloalkylene ring;

R6 is, at each occurrence, independently H, OH or C1-C24 alkyl;

n is an integer ranging from 1 to 15.

In some of the foregoing embodiments of Formula (III), the lipid has structure (IIIA), and in other embodiments, the lipid has structure (IIIB).

In other embodiments of Formula (III), the lipid has one of the following structures (IIIC) or (IIID):

(IIIC)

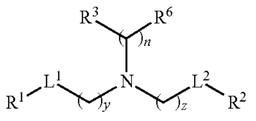

or (IIID)

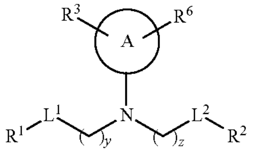

wherein y and z are each independently integers ranging from 1 to 12.

In any of the foregoing embodiments of Formula (III), one of L1 or L2 is —O(C═O)—. For example, in some embodiments each of L1 and L2 are —O(C═O)—. In some different embodiments of any of the foregoing, L1 and L2 are each independently —(C═O)O— or —O(C═O)—. For example, in some embodiments each of L1 and L2 is —(C═O)O—.

In some different embodiments of Formula (III), the lipid has one of the following structures (IIIE) or (IIIF):

(IIIE)

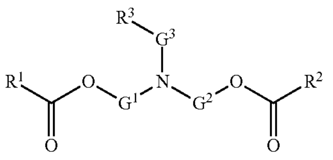

or

-continued (IIIF)

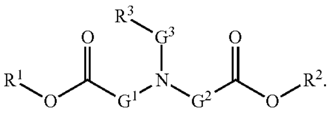

In some of the foregoing embodiments of Formula (III), the lipid has one of the following structures (IIIG), (IIIH), (IIII), or (IIIJ):

(IIIG)

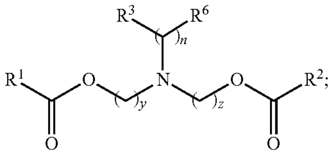

(IIIH)

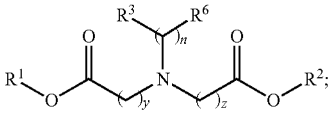

(IIII)

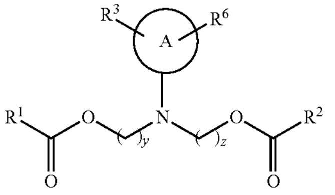

or (IIIJ)

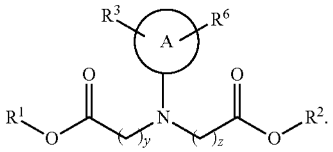

In some of the foregoing embodiments of Formula (III), n is an integer ranging from 2 to 12, for example from 2 to 8 or from 2 to 4. For example, in some embodiments, n is 3, 4, 5 or 6. In some embodiments, n is 3. In some embodiments, n is 4. In some embodiments, n is 5. In some embodiments, n is 6.

In some other of the foregoing embodiments of Formula (III), y and z are each independently an integer ranging from 2 to 10. For example, in some embodiments, y and z are each independently an integer ranging from 4 to 9 or from 4 to 6.

In some of the foregoing embodiments of Formula (III), R6 is H. In other of the foregoing embodiments, R6 is C1-C24 alkyl. In other embodiments, R6 is OH.

In some embodiments of Formula (III), G3 is unsubstituted. In other embodiments, G3 is substituted. In various different embodiments, G3 is linear C1-C24 alkylene or linear C1-C24 alkenylene.

In some other foregoing embodiments of Formula (III), R1 or R2, or both, is C6-C24 alkenyl. For example, in some embodiments, R1 and R2 each, independently have the following structure:

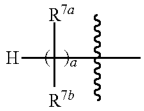, wherein:

R7a and R7b are, at each occurrence, independently H or C1-C12 alkyl; and a is an integer from 2 to 12, wherein R7a, R7b and a are each selected such that R1 and R2 each independently comprise from 6 to 20 carbon atoms. For example, in some embodiments a is an integer ranging from 5 to 9 or from 8 to 12.

In some of the foregoing embodiments of Formula (III), at least one occurrence of R7a is H. For example, in some embodiments, R7a is H at each occurrence. In other different embodiments of the foregoing, at least one occurrence of R7b is C1-C8 alkyl. For example, in some embodiments, C1-C8 alkyl is methyl, ethyl, n-propyl, iso-propyl, n-butyl, iso-butyl, tert-butyl, n-hexyl or n-octyl.

In different embodiments of Formula (III), R1 or R2, or both, has one of the following structures:

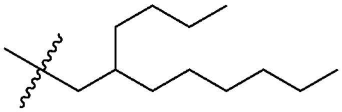;

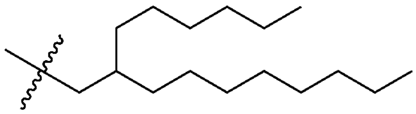;

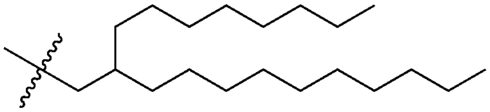;

-continued

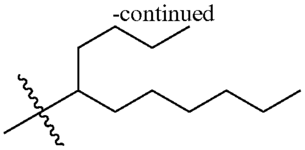;

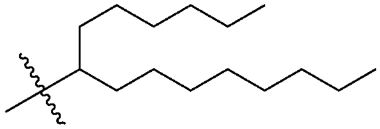;

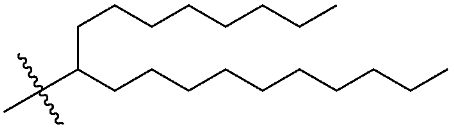;

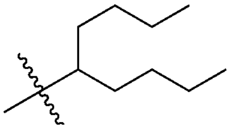;

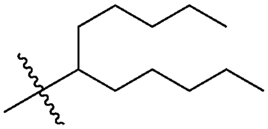;

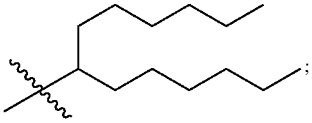;

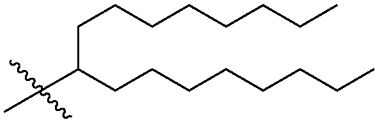.

In some of the foregoing embodiments of Formula (III), R3 is OH,

CN, —C(═O)OR4, —OC(═O)R4 or —NHC(═O)R4. In some embodiments, R4 is methyl or ethyl.

In various different embodiments, the cationic lipid of Formula (III) has one of the structures set forth in the table below.

Representative Compounds of Formula (III).

| No. | Structure |
|---|---|
| III-1 | 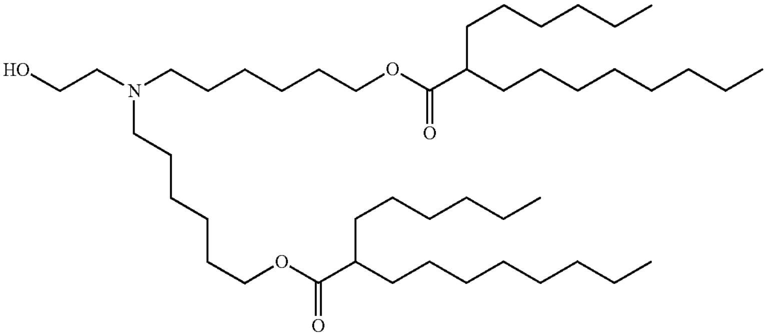 [SMILES: CCCCCCCCC(CCCCCC)C(=O)OCCCCCCN(CCO)CCCCCCOC(=O)C(CCCCCC)CCCCCCCC] |

-continued
| No. | Structure |
|---|---|
| III-2 | 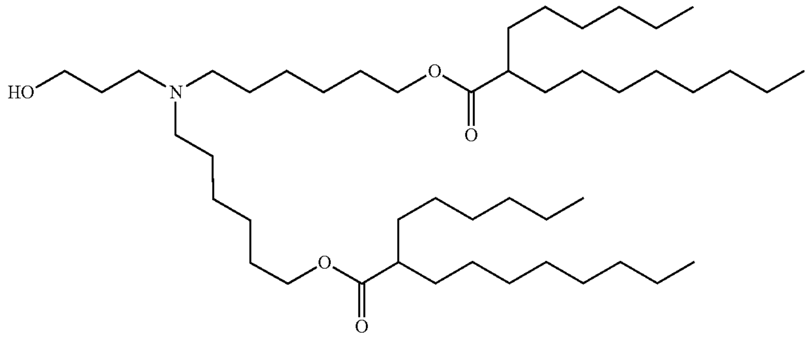 [SMILES: CCCCCCCCC(CCCCCC)C(=O)OCCCCCCN(CCCO)CCCCCCOC(=O)C(CCCCCC)CCCCCCCC] |
| III-3 | 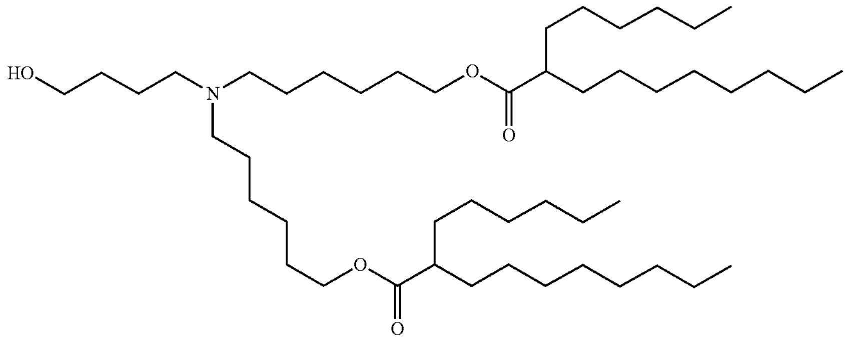 [SMILES: CCCCCCCCC(CCCCCC)C(=O)OCCCCCCN(CCCCO)CCCCCCOC(=O)C(CCCCCC)CCCCCCCC] |
| III-4 | 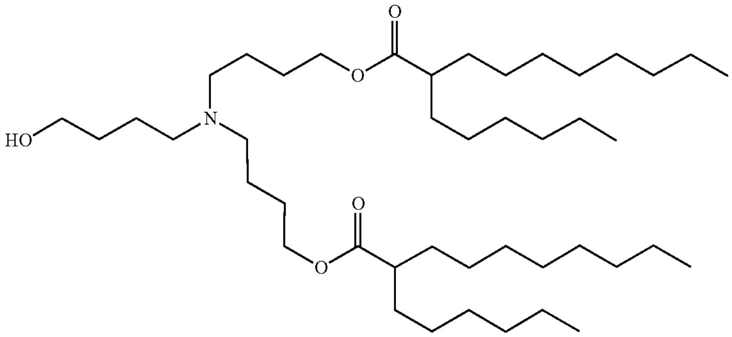 [SMILES: CCCCCCCCC(CCCCCC)C(=O)OCCCCN(CCCCO)CCCCOC(=O)C(CCCCCC)CCCCCCCC] |
| III-5 | 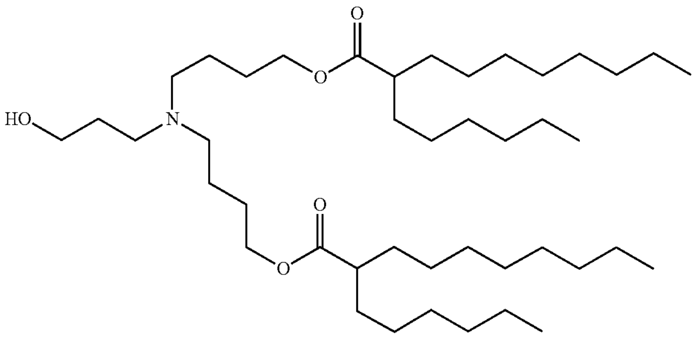 [SMILES: CCCCCCCCC(CCCCCC)C(=O)OCCCCN(CCCO)CCCCOC(=O)C(CCCCCC)CCCCCCCC] |

-continued
| No. | Structure |
|---|---|
| III-6 | 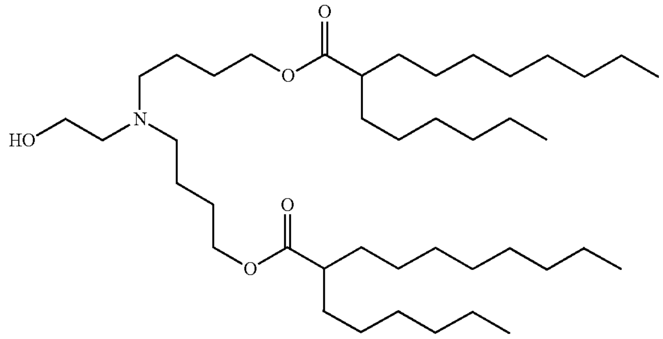 [SMILES: CCCCCCCCC(CCCCCC)C(=O)OCCCCN(CCO)CCCCOC(=O)C(CCCCCC)CCCCCCCC] |
| III-7 | 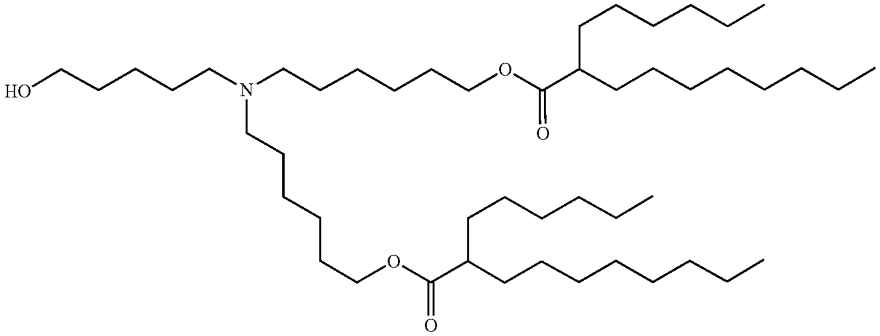 [SMILES: CCCCCCCCC(CCCCCC)C(=O)OCCCCCCN(CCCCCO)CCCCCCOC(=O)C(CCCCCC)CCCCCCCC] |
| III-8 | 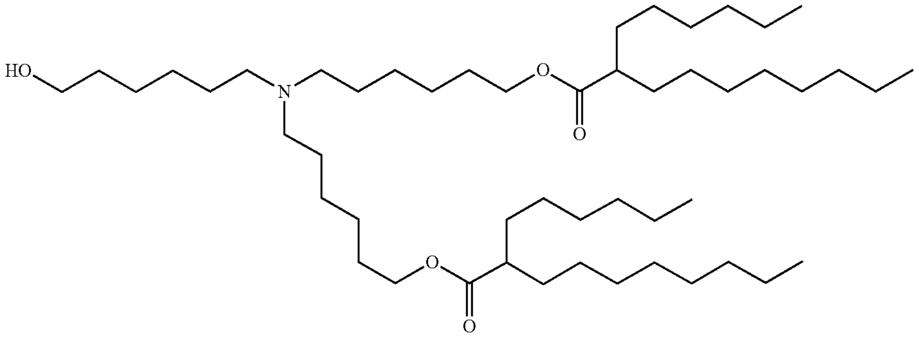 [SMILES: CCCCCCCCC(CCCCCC)C(=O)OCCCCCCN(CCCCCCO)CCCCCCOC(=O)C(CCCCCC)CCCCCCCC] |
| III-9 | 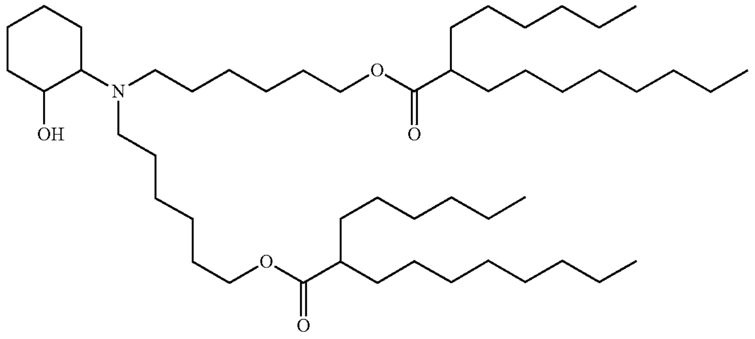 [SMILES: CCCCCCCCC(CCCCCC)C(=O)OCCCCCCN(CCCCCCOC(=O)C(CCCCCC)CCCCCCCC)C1CCCCC1O] |

-continued
| No. | Structure |
| --- | --- |
| III-10 | 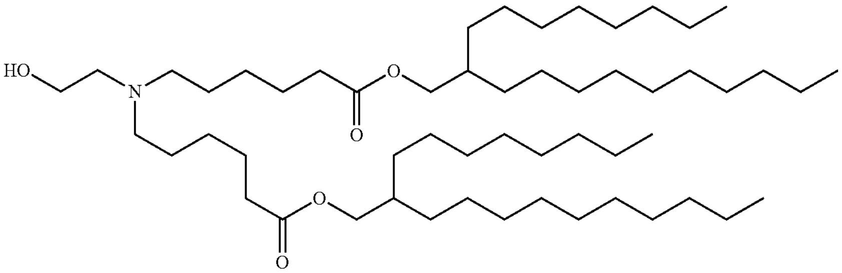 [SMILES: CCCCCCCCCCC(CCCCCCCC)COC(=O)CCCCCN(CCO)CCCCCC(=O)OCC(CCCCCCCC)CCCCCCCCCC] |
| III-11 | 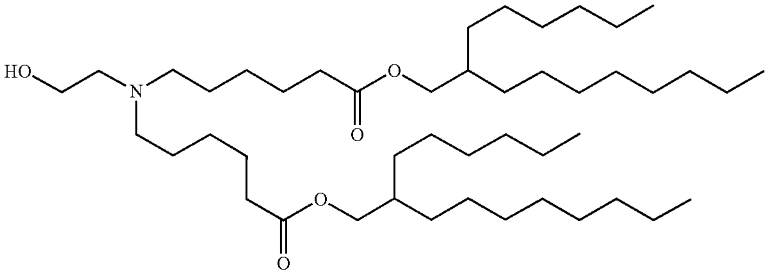 [SMILES: CCCCCCCCC(CCCCCC)COC(=O)CCCCCN(CCO)CCCCCC(=O)OCC(CCCCCC)CCCCCCCC] |
| III-12 | 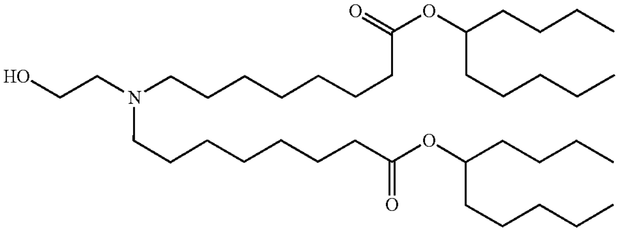 [SMILES: CCCCCC(CCCC)OC(=O)CCCCCCCN(CCO)CCCCCCCC(=O)OC(CCCC)CCCCC] |
| III-13 | 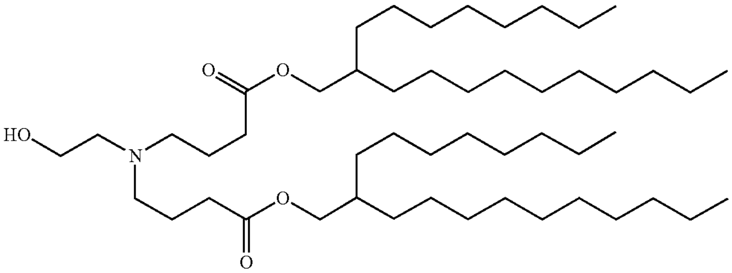 [SMILES: CCCCCCCCCCC(CCCCCCCC)COC(=O)CCCN(CCO)CCCC(=O)OCC(CCCCCCCC)CCCCCCCCCC] |
| III-14 | 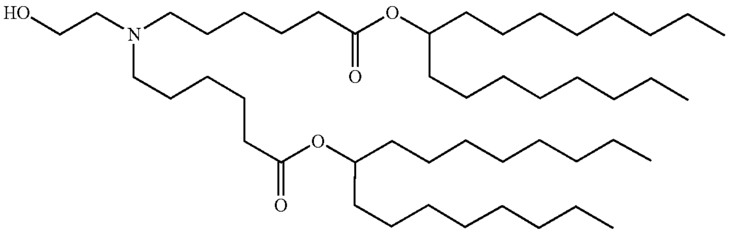 [SMILES: CCCCCCCCC(CCCCCCCC)OC(=O)CCCCCN(CCO)CCCCCC(=O)OC(CCCCCCCC)CCCCCCCC] |
| III-15 | 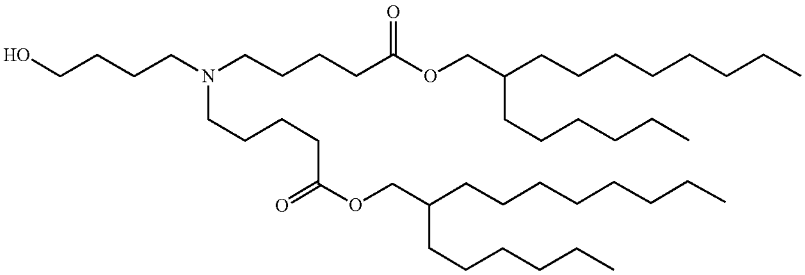 [SMILES: CCCCCCCCC(CCCCCC)COC(=O)CCCCN(CCCCO)CCCCC(=O)OCC(CCCCCC)CCCCCCCC] |

-continued
| No. | Structure |
|---|---|
| III-16 | 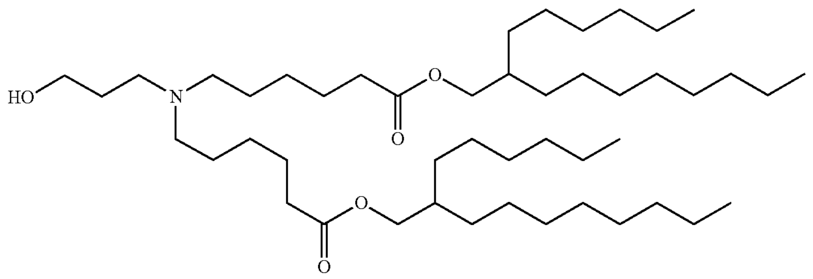 [SMILES: CCCCCCCCC(CCCCCC)COC(=O)CCCCCN(CCCO)CCCCCC(=O)OCC(CCCCCC)CCCCCCCC] |
| III-17 | 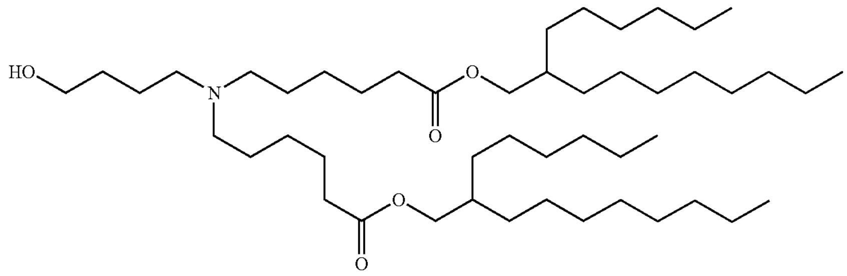 [SMILES: CCCCCCCCC(CCCCCC)COC(=O)CCCCCN(CCCCO)CCCCCC(=O)OCC(CCCCCC)CCCCCCCC] |
| III-18 | 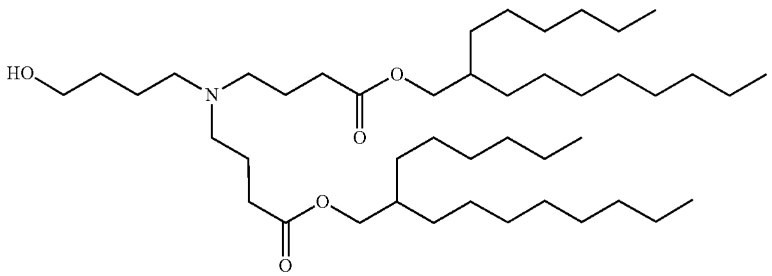 [SMILES: CCCCCCCCC(CCCCCC)COC(=O)CCCN(CCCCO)CCCC(=O)OCC(CCCCCC)CCCCCCCC] |
| III-19 | 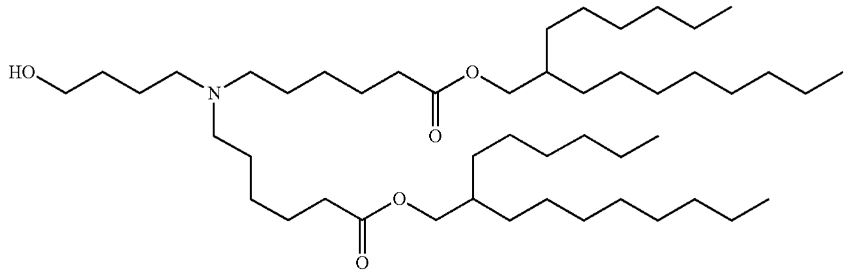 [SMILES: CCCCCCCCC(CCCCCC)COC(=O)CCCCCN(CCCCO)CCCCCC(=O)OCC(CCCCCC)CCCCCCCC] |
| III-20 | 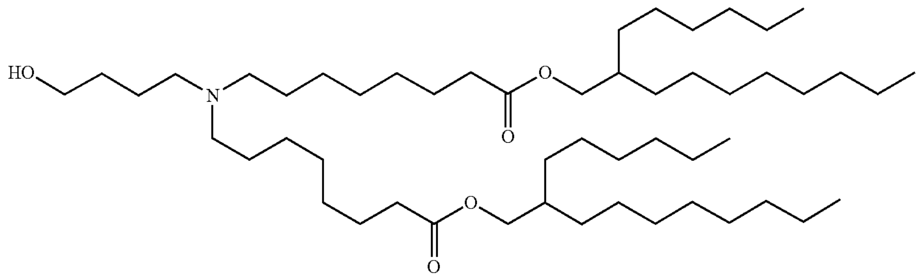 [SMILES: CCCCCCCCC(CCCCCC)COC(=O)CCCCCCCN(CCCCO)CCCCCCCC(=O)OCC(CCCCCC)CCCCCCCC] |

-continued
| No. | Structure |
|---|---|
| III-21 | 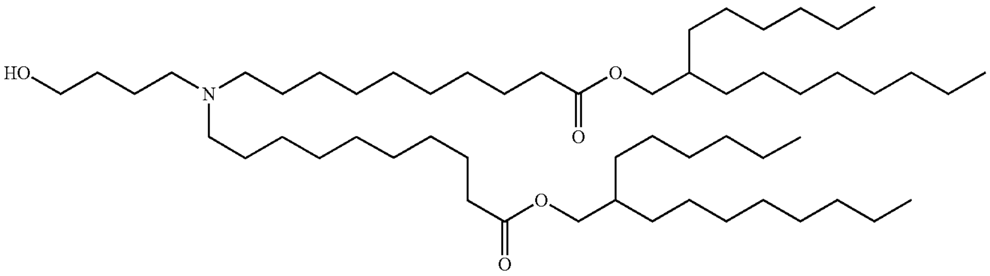 [SMILES: CCCCCCCCC(CCCCCC)COC(=O)CCCCCCCCCN(CCCCO)CCCCCCCCCC(=O)OCC(CCCCCC)CCCCCCCC] |
| III-22 | 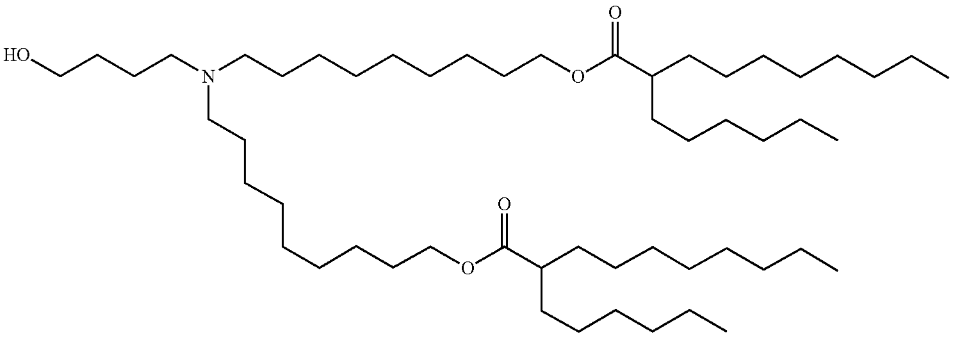 [SMILES: CCCCCCCCC(CCCCCC)C(=O)OCCCCCCCCCN(CCCCO)CCCCCCCCCOC(=O)C(CCCCCC)CCCCCCCC] |
| III-23 | 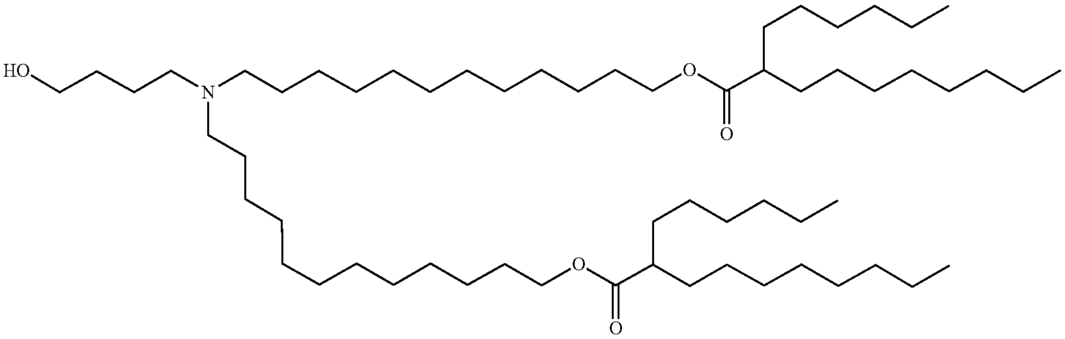 [SMILES: CCCCCCCCC(CCCCCC)C(=O)OCCCCCCCCCCCCN(CCCCO)CCCCCCCCCCCCOC(=O)C(CCCCCC)CCCCCCCC] |
| III-24 | 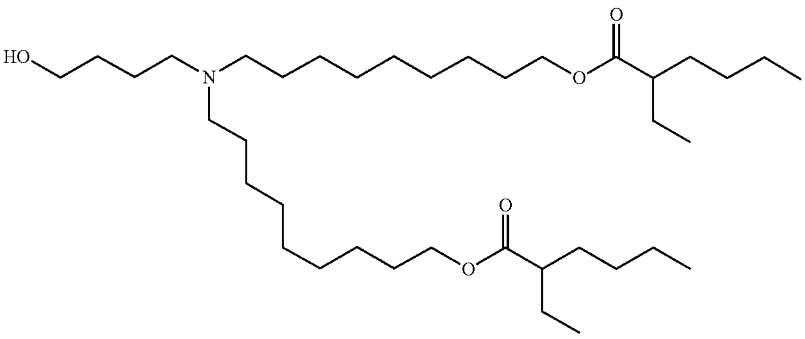 [SMILES: CCCCC(CC)C(=O)OCCCCCCCCCN(CCCCO)CCCCCCCCCOC(=O)C(CC)CCCC] |

-continued
| No. | Structure |
|---|---|
| III-25 | 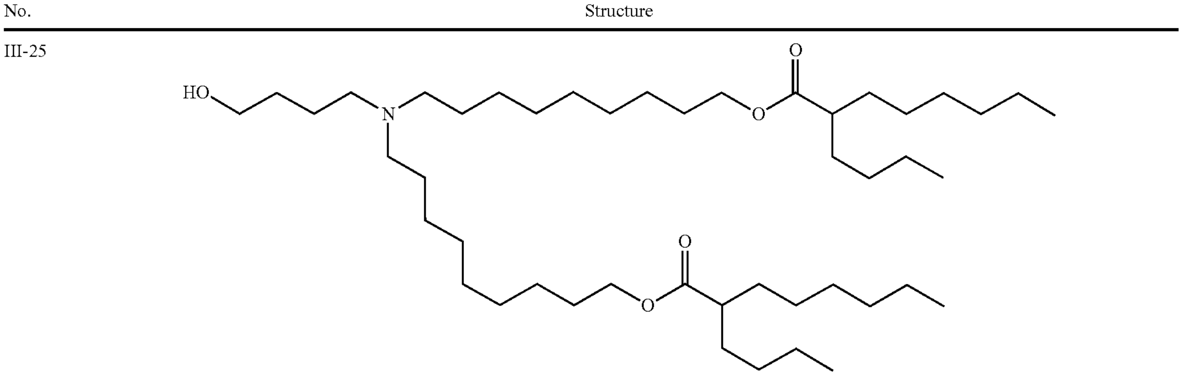 |
| III-26 | 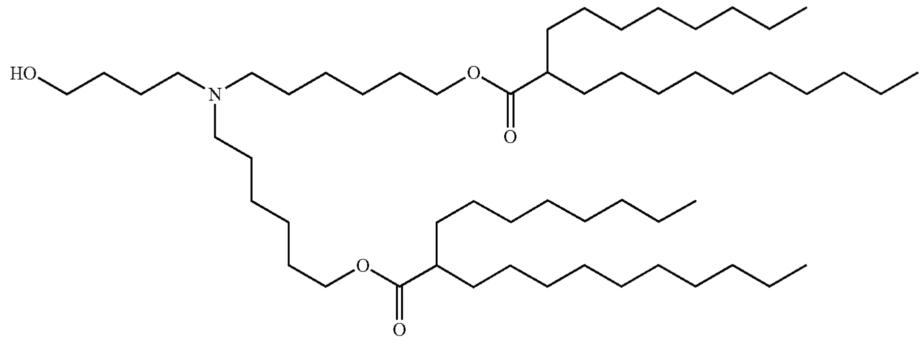 [SMILES: CCCCCCCCCCC(CCCCCCCC)C(=O)OCCCCCCN(CCCCO)CCCCCCOC(=O)C(CCCCCCCC)CCCCCCCCCC] |
| III-27 | 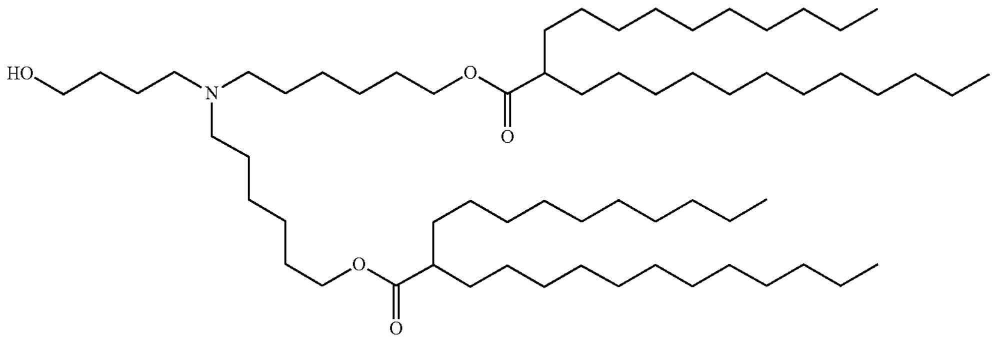 [SMILES: CCCCCCCCCCCCC(CCCCCCCCCC)C(=O)OCCCCCCN(CCCCO)CCCCCCOC(=O)C(CCCCCCCCCC)CCCCCCCCCCCC] |
| III-28 | 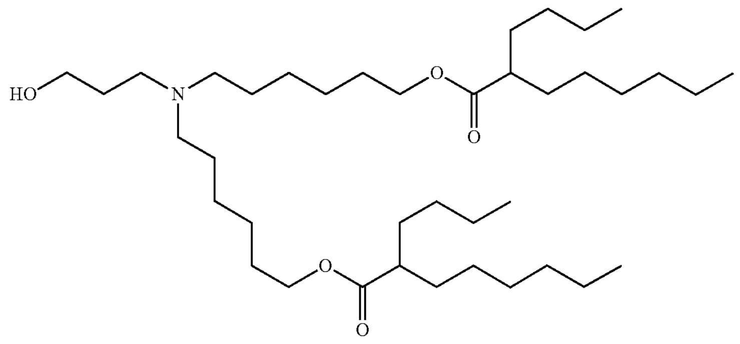 [SMILES: CCCCCCC(CCCC)C(=O)OCCCCCCN(CCCO)CCCCCCOC(=O)C(CCCC)CCCCCC] |

-continued
| No. | Structure |
| --- | --- |
| III-29 | 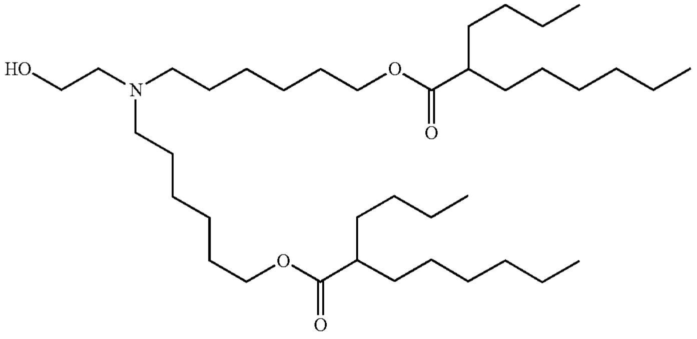 [SMILES: CCCCCCC(CCCC)C(=O)OCCCCCCN(CCO)CCCCCCOC(=O)C(CCCC)CCCCCC] |
| III-30 | 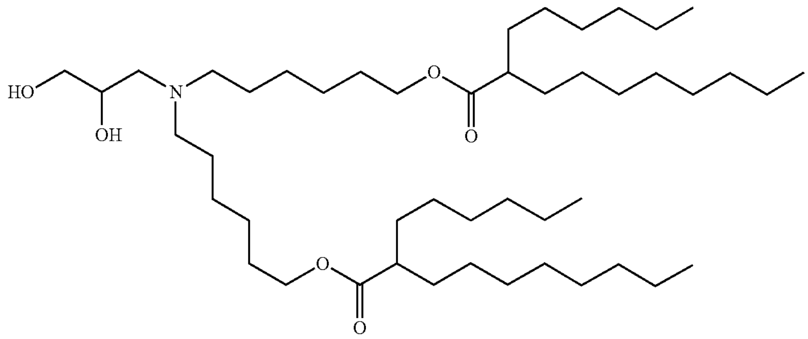 [SMILES: CCCCCCCCC(CCCCCC)C(=O)OCCCCCCN(CCCCCCOC(=O)C(CCCCCC)CCCCCCCC)CC(O)CO] |
| III-31 | 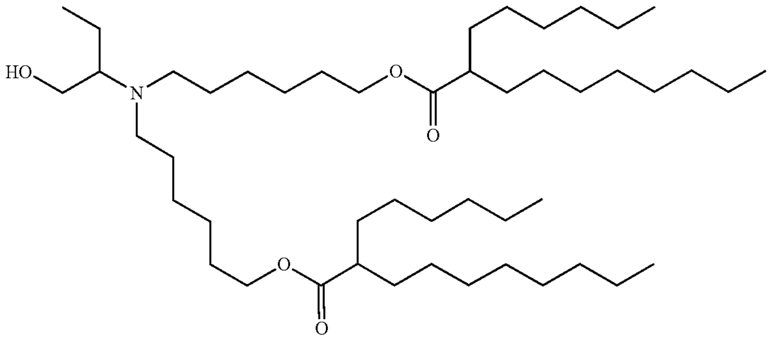 [SMILES: CCCCCCCCC(CCCCCC)C(=O)OCCCCCCN(CCCCCCOC(=O)C(CCCCCC)CCCCCCCC)C(CC)CO] |
| III-32 | 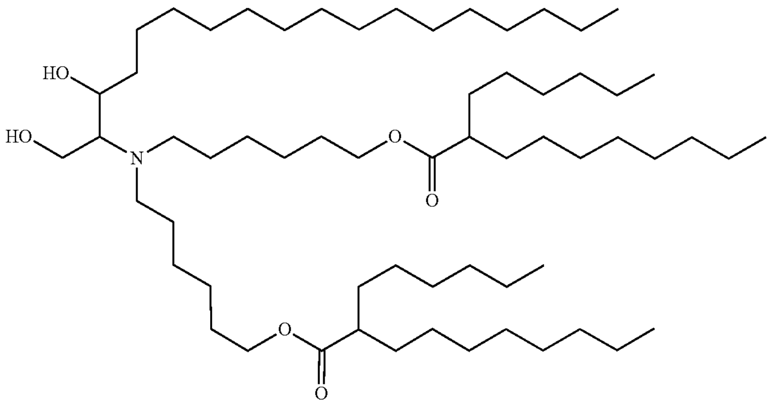 [SMILES: CCCCCCCCCCCCCCCC(O)C(CO)N(CCCCCCOC(=O)C(CCCCCC)CCCCCCCC)CCCCCCOC(=O)C(CCCCCC)CCCCCCCC] |

-continued

| No. | Structure |
| --- | --- |
| III-33 | 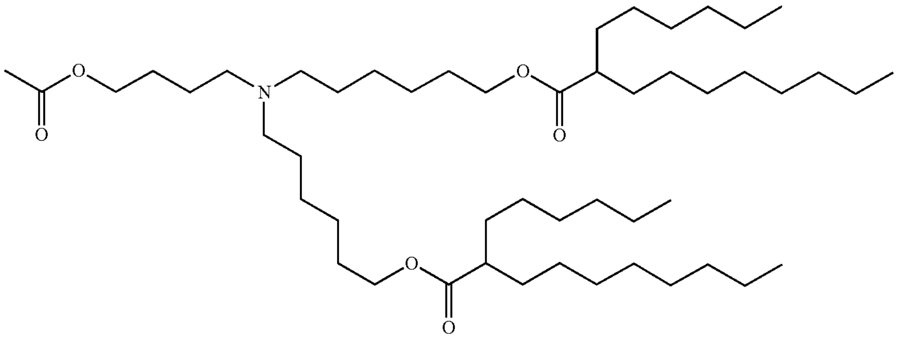 [SMILES: CCCCCCCCC(CCCCCC)C(=O)OCCCCCCN(CCCCCCOC(=O)C(CCCCCC)CCCCCCCC)CCCCOC(C)=O] |
| III-34 | 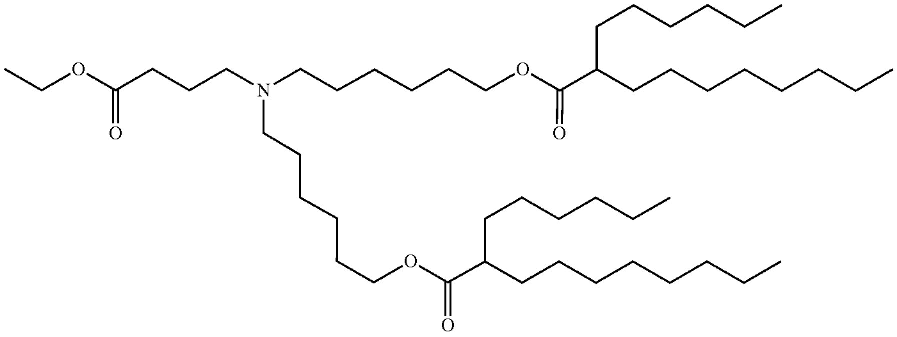 [SMILES: CCCCCCCCC(CCCCCC)C(=O)OCCCCCCN(CCCCCCOC(=O)C(CCCCCC)CCCCCCCC)CCCC(=O)OCC] |
| III-35 | 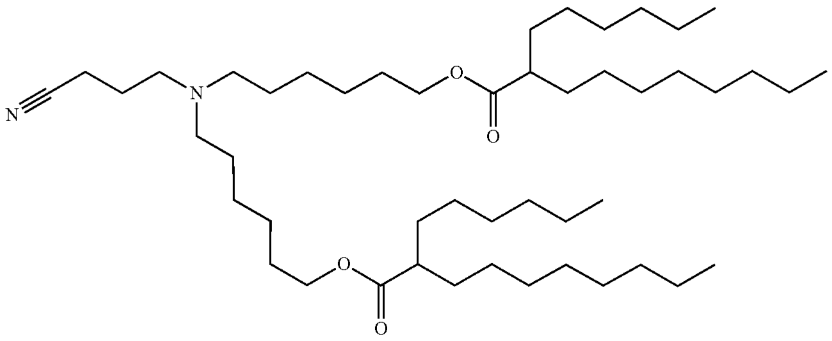 [SMILES: CCCCCCCCC(CCCCCC)C(=O)OCCCCCCN(CCCC#N)CCCCCCOC(=O)C(CCCCCC)CCCCCCCC] |
| III-36 | 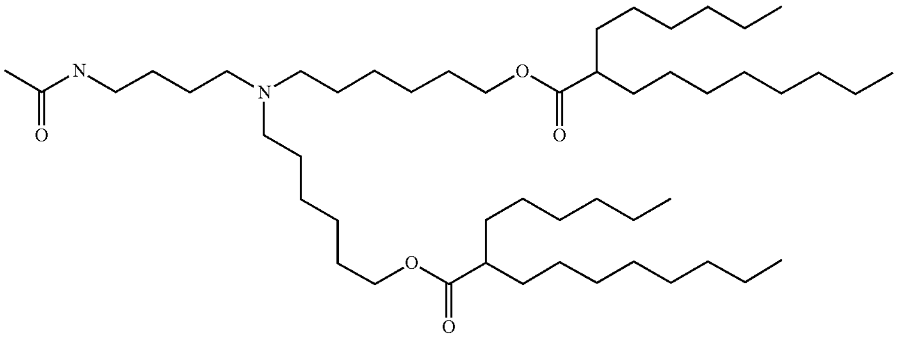 |

In some embodiments, an LNP comprises a lipid of Formula (III), RNA, a neutral lipid, a steroid and a pegylated lipid. In some embodiments, a lipid of Formula (III) is compound III-3. In some embodiments, a neutral lipid is DSPC. In some embodiments, a steroid is cholesterol. In some embodiments, a pegylated lipid is ALC-0159.

In some embodiments, the cationic lipid is present in the LNP in an amount from about 40 to about 50 mole percent. In some embodiments, the neutral lipid is present in the LNP in an amount from about 5 to about 15 mole percent. In some embodiments, the steroid is present in the LNP in an amount from about 35 to about 45 mole percent. In some embodiments, the pegylated lipid is present in the LNP in an amount from about 1 to about 10 mole percent.

In some embodiments, the LNP comprises compound III-3 in an amount from about 40 to about 50 mole percent, DSPC in an amount from about 5 to about 15 mole percent, cholesterol in an amount from about 35 to about 45 mole percent, and ALC-0159 in an amount from about 1 to about 10 mole percent.

In some embodiments, the LNP comprises compound III-3 in an amount of about 47.5 mole percent, DSPC in an amount of about 10 mole percent, cholesterol in an amount of about 40.7 mole percent, and ALC-0159 in an amount of about 1.8 mole percent.

In various different embodiments, the cationic lipid has one of the structures set forth in the table below.

In some embodiments, the LNP comprises a cationic lipid shown in the above table, e.g., a cationic lipid of Formula (B) or Formula (D), in particular a cationic lipid of Formula (D), RNA, a neutral lipid, a steroid and a pegylated lipid. In some embodiments, the neutral lipid is DSPC. In some embodiments, the steroid is cholesterol. In some embodiments, the pegylated lipid is DMG-PEG 2000.

In some embodiments, the LNP comprises a cationic lipid that is an ionizable lipid-like material (lipidoid). In some embodiments, the cationic lipid has the following structure:

| No. | Structure |
|---|---|
| A | 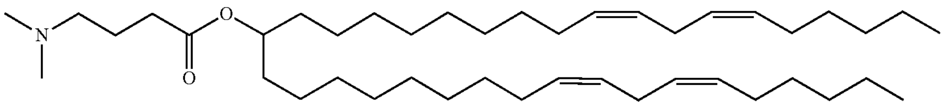 [SMILES: CCCCC/C=C\C/C=C\CCCCCCCCC(CCCCCCCC/C=C\C/C=C\CCCCC)OC(=O)CCCN(C)C] |
| B | 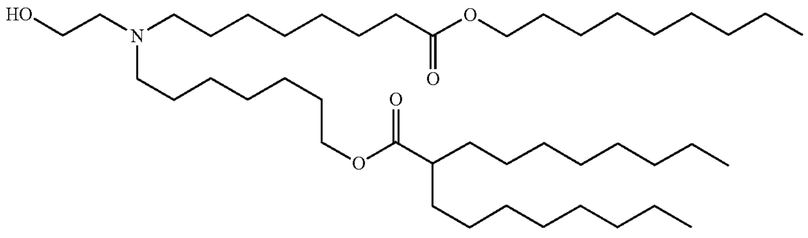 [SMILES: CCCCCCCCCOC(=O)CCCCCCCN(CCO)CCCCCCCOC(=O)C(CCCCCCCC)CCCCCCCC] |
| C | 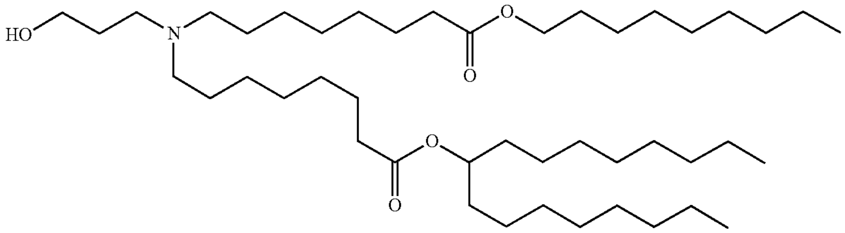 [SMILES: CCCCCCCCCOC(=O)CCCCCCCN(CCCO)CCCCCCCC(=O)OC(CCCCCCCC)CCCCCCCC] |
| D | 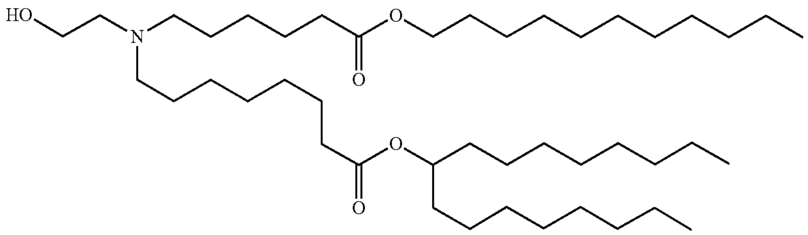 [SMILES: CCCCCCCCCCCOC(=O)CCCCCN(CCO)CCCCCCCC(=O)OC(CCCCCCCC)CCCCCCCC] |
| E | 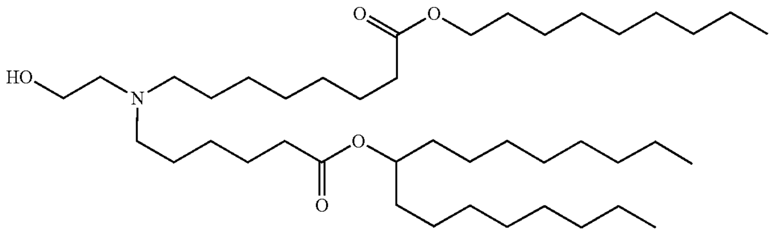 [SMILES: CCCCCCCCCOC(=O)CCCCCCCN(CCO)CCCCCC(=O)OC(CCCCCCCC)CCCCCCCC] |
| F | 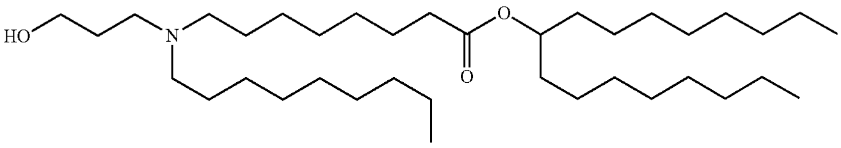 [SMILES: CCCCCCCCCN(CCCO)CCCCCCCC(=O)OC(CCCCCCCC)CCCCCCCC] |

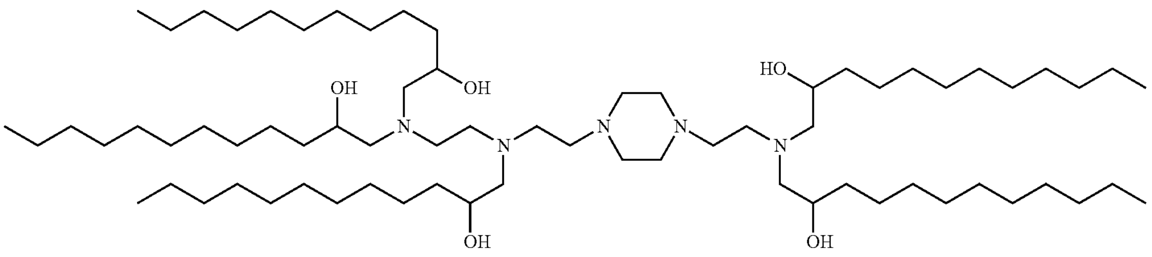 [SMILES: CCCCCCCCCCC(O)CN(CCN1CCN(CCN(CC(O)CCCCCCCCCC)CC(O)CCCCCCCCCC)CC1)CCN(CC(O)CCCCCCCCCC)CC(O)CCCCCCCCCC]

The N/P value is preferably at least about 4. In some embodiments, the N/P value ranges from 4 to 20, 4 to 12, 4 to 10, 4 to 8, or 5 to 7. In some embodiments, the N/P value is about 6.

LNP described herein may have an average diameter that in some embodiments ranges from about 30 nm to about 200 nm, or from about 60 nm to about 120 nm.

Pharmaceutical Compositions

In some embodiments, a pharmaceutical composition comprises an RNA polynucleotide disclosed herein formulated as a particle. In some embodiments, a particle is or comprises a lipid nanoparticle (LNP) or a lipoplex (LPX) particle.

In some embodiments, an RNA polynucleotide disclosed herein may be administered in a pharmaceutical composition or a medicament and may be administered in the form of any suitable pharmaceutical composition.

In some embodiments, a pharmaceutical composition described herein is an immunogenic composition for inducing an immune response. For example, in some embodiments, an immunogenic composition is a vaccine.

In some embodiments, an RNA polynucleotide disclosed herein may be administered in a pharmaceutical composition which may comprise a pharmaceutically acceptable carrier and may optionally comprise one or more adjuvants, stabilizers etc. In some embodiments, a pharmaceutical composition is for therapeutic or prophylactic treatments.

The term "adjuvant" relates to a compound which prolongs, enhances or accelerates an immune response. Adjuvants comprise a heterogeneous group of compounds such as oil emulsions (e.g., Freund's adjuvants), mineral compounds (such as alum), bacterial products (such as *Bordetella pertussis* toxin), or immune-stimulating complexes. Examples of adjuvants include, without limitation, LPS, GP96, CpG oligodeoxynucleotides, growth factors, and cytokines, such as monokines, lymphokines, interleukins, chemokines. The cytokines may be IL1, IL2, IL3, IL4, IL5, IL6, IL7, IL8, IL9, IL10, IL12, IFNα, IFNγ, GM-CSF, LT-a. Further known adjuvants are aluminium hydroxide, Freund's adjuvant or oil such as Montanide® ISA51. Other suitable adjuvants for use in the present disclosure include lipopeptides, such as Pam3Cys.

The pharmaceutical compositions according to the present disclosure are generally applied in a "pharmaceutically effective amount" and in "a pharmaceutically acceptable preparation".

The term "pharmaceutically acceptable" refers to the non-toxicity of a material which does not interact with the action of the active component of the pharmaceutical composition.

The term "pharmaceutically effective amount" or "therapeutically effective amount" refers to the amount which achieves a desired reaction or a desired effect alone or together with further doses. In the case of the treatment of a particular disease, the desired reaction preferably relates to inhibition of the course of the disease. This comprises slowing down the progress of the disease and, in particular, interrupting or reversing the progress of the disease. The desired reaction in a treatment of a disease may also be delay of the onset or a prevention of the onset of said disease or said condition. An effective amount of the compositions described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the compositions described herein may depend on various of such parameters. In the case that a reaction in a patient is insufficient with an initial dose, higher doses (or effectively higher doses achieved by a different, more localized route of administration) may be used.

In some embodiments, a pharmaceutical composition disclosed herein may contain salts, buffers, preservatives, and optionally other therapeutic agents. In some embodiments, a pharmaceutical composition disclosed herein comprises one or more pharmaceutically acceptable carriers, diluents and/or excipients.

Suitable preservatives for use in a pharmaceutical compositions of the present disclosure include, without limitation, benzalkonium chloride, chlorobutanol, paraben and thimerosal.

The term "excipient" as used herein refers to a substance which may be present in a pharmaceutical composition of the present disclosure but is not an active ingredient. Examples of excipients, include without limitation, carriers, binders, diluents, lubricants, thickeners, surface active agents, preservatives, stabilizers, emulsifiers, buffers, flavoring agents, or colorants.

The term "diluent" relates a diluting and/or thinning agent. Moreover, the term "diluent" includes any one or more of fluid, liquid or solid suspension and/or mixing media. Examples of suitable diluents include ethanol, glycerol and water.

The term "carrier" refers to a component which may be natural, synthetic, organic, inorganic in which the active component is combined in order to facilitate, enhance or enable administration of the pharmaceutical composition. A carrier as used herein may be one or more compatible solid or liquid fillers, diluents or encapsulating substances, which are suitable for administration to subject. Suitable carrier include, without limitation, sterile water, Ringer, Ringer lactate, sterile sodium chloride solution, isotonic saline, polyalkylene glycols, hydrogenated naphthalenes and, in particular, biocompatible lactide polymers, lactide/glycolide copolymers or polyoxyethylene/polyoxy-propylene copolymers. In some embodiments, the pharmaceutical composition of the present disclosure includes isotonic saline.

Pharmaceutically acceptable carriers, excipients or diluents for therapeutic use are well known in the pharmaceutical art, and are described, for example, in Remington's Pharmaceutical Sciences, Mack Publishing Co. (A. R Gennaro edit. 1985).

Pharmaceutical carriers, excipients or diluents can be selected with regard to the intended route of administration and standard pharmaceutical practice.

In some embodiments, a pharmaceutical composition described herein may be administered intravenously, intraarterially, subcutaneously, intradermally or intramuscularly. In certain embodiments, the pharmaceutical composition is formulated for local administration or systemic administration. Systemic administration may include enteral administration, which involves absorption through the gastrointestinal tract, or parenteral administration. As used herein, "parenteral administration" refers to the administration in any manner other than through the gastrointestinal tract, such as by intravenous injection. In a preferred embodiment, the pharmaceutical composition is formulated for intramuscular administration. In another embodiment, the pharmaceutical composition is formulated for systemic administration, e.g., for intravenous administration.

Characterization

In some embodiments, an RNA polynucleotide disclosed herein is characterized in that, when assessed in an organism administered a composition or medical preparation comprising an RNA polynucleotide, elevated expression of a payload is observed relative to an appropriate reference comparator.

In some embodiments, an RNA polynucleotide disclosed herein is characterized in that, when assessed in an organism administered a composition or medical preparation comprising an RNA polynucleotide, increased duration of expression (e.g., prolonged expression) of a payload is observed relative to an appropriate reference comparator.

In some embodiments, an RNA polynucleotide disclosed herein is characterized in that, when assessed in an organism administered a composition or medical preparation comprising an RNA polynucleotide, decreased interaction with IFIT1 of an RNA polynucleotide is observed relative to an appropriate reference comparator.

In some embodiments, an RNA polynucleotide disclosed herein is characterized in that, when assessed in an organism administered a composition or medical preparation comprising an RNA polynucleotide, increased translation an RNA polynucleotide is observed relative to an appropriate reference comparator.

In some embodiments, a reference comparator comprises an organism administered an otherwise similar RNA polynucleotide without a m7(3'OMeG)(5')ppp(5')(2'OMe$A_1$)p$G_2$ cap. In some embodiments, a reference comparator comprises an organism administered an otherwise similar RNA polynucleotide without a cap proximal sequence disclosed herein. In some embodiments, a reference comparator comprises an organism administered an otherwise similar RNA polynucleotide with a self-hybridizing sequence.

In some embodiments, an RNA polynucleotide disclosed herein is characterized in that, when assessed in an organism administered a composition or medical preparation comprising an RNA polynucleotide, elevated expression and increased duration of expression (e.g., prolonged expression) of a payload is observed relative to an appropriate reference comparator.

In some embodiments, elevated expression is determined at least 24 hours, at least 48 hours at least 72 hours, at least 96 hours or at least 120 hours after administration of a composition or medical preparation comprising an RNA polynucleotide. In some embodiments, elevated expression is determined at least 24 hours after administration of a composition or medical preparation comprising an RNA polynucleotide. In some embodiments, elevated expression is determined at least 48 hours after administration of a composition or medical preparation comprising an RNA polynucleotide. In some embodiments, elevated expression is determined at least 72 hours after administration of a composition or medical preparation comprising an RNA polynucleotide. In some embodiments, elevated expression is determined at least 96 hours after administration of a composition or medical preparation comprising an RNA polynucleotide. In some embodiments, elevated expression is determined at least 120 hours after administration of a composition or medical preparation comprising an RNA polynucleotide.

In some embodiments, elevated expression is determined at about 24-120 hours after administration of a composition or medical preparation comprising an RNA polynucleotide. In some embodiments, elevated expression is determined at about 24-110 hours, about 24-100 hours, about 24-90 hours, about 24-80 hours, about 24-70 hours, about 24-60 hours, about 24-50 hours, about 24-40 hours, about 24-30 hours, about 30-120 hours, about 40-120 hours, about 50-120 hours, about 60-120 hours, about 70-120 hours, about 80-120 hours, about 90-120 hours, about 100-120 hours, or about 110-120 hours after administration of a composition or medical preparation comprising an RNA polynucleotide.

In some embodiments, elevated expression of a payload is at least 2-fold to at least 10-fold. In some embodiments, elevated expression of a payload is at least 2-fold. In some embodiments, elevated expression of a payload is at least 3-fold. In some embodiments, elevated expression of a payload is at least 4-fold. In some embodiments, elevated expression of a payload is at least 6-fold. In some embodiments, elevated expression of a payload is at least 8-fold. In some embodiments, elevated expression of a payload is at least 10-fold.

In some embodiments, elevated expression of a payload is about 2-fold to about 50-fold. In some embodiments, elevated expression of a payload is about 2-fold to about 45-fold, about 2-fold to about 40-fold, about 2-fold to about 30-fold, about 2-fold to about 25-fold, about 2-fold to about 20-fold, about 2-fold to about 15-fold, about 2-fold to about 10-fold, about 2-fold to about 8-fold, about 2-fold to about 5-fold, about 5-fold to about 50-fold, about 10-fold to about 50-fold, about 15-fold to about 50-fold, about 20-fold to about 50-fold, about 25-fold to about 50-fold, about 30-fold to about 50-fold, about 40-fold to about 50-fold, or about 45-fold to about 50-fold.

In some embodiments, elevated expression (e.g., increased duration of expression) of a payload persists for at least 24 hours, at least 48 hours, at least 72 hours, at least 96 hours, or at least 120 hours after administration of a composition or a medical preparation comprising an RNA polynucleotide. In some embodiments, elevated expression of a payload persists for at least 24 hours after administration. In some embodiments, elevated expression of a payload persists for at least 48 hours after administration. In some embodiments, elevated expression of a payload persists for at least 72 hours after administration. In some embodiments, elevated expression of a payload persists for at least 96 hours after administration. In some embodiments, elevated expression of a payload persists for at least 120 hours after administration of a composition or medical preparation comprising an RNA polynucleotide.

In some embodiments, elevated expression of a payload persists for at about 24-120 hours after administration of a composition or medical preparation comprising an RNA polynucleotide. In some embodiments, elevated expression persists for about 24-110 hours, about 24-100 hours, about 24-90 hours, about 24-80 hours, about 24-70 hours, about 24-60 hours, about 24-50 hours, about 24-40 hours, about 24-30 hours, about 30-120 hours, about 40-120 hours, about 50-120 hours, about 60-120 hours, about 70-120 hours, about 80-120 hours, about 90-120 hours, about 100-120 hours, or about 110-120 hours after administration of a composition or medical preparation comprising an RNA polynucleotide.

Uses

Disclosed herein, among other things, are methods of making and methods of using an RNA polynucleotide comprising a 5'cap; a 5' UTR comprising a cap proximal structure; and a sequence encoding a payload.

In some embodiments, disclosed herein is an in vitro transcription reaction comprising: (i) a template DNA comprising a polynucleotide sequence complementary to an RNA polynucleotide sequence disclosed herein; (ii) a polymerase; and (iii) an RNA polynucleotide. In some embodiments, a polymerase is or comprises a T7 polymerase. In some embodiments, a reaction further comprises a 5' cap or a 5' cap analog. In some embodiments, a 5' cap analog is or comprises a Cap1 structure. In some embodiments, an RNA polynucleotide comprises a cap comprising a Cap1 structure; and a cap proximal sequence comprising positions +1, +2, +3, +4, and +5 of the RNA polynucleotide; and a sequence encoding a payload. In some embodiments, a Cap1 structure comprises m7G(5')ppp(5')(2'OMeN1)pN2, wherein N1 is position +1 of the RNA polynucleotide, and N2 is position +2 of the RNA polynucleotide, and wherein N1 and N2 are each independently chosen from: A, C, G, or U.

In some embodiments, also disclosed herein is a method for producing a capped RNA comprising, transcribing a nucleic acid template in the presence of a cap structure, wherein the cap structure comprises $G^*ppp(m_1^{2'-O})N_1pN_2$, wherein $N_1$ is complementary to position +1 of the nucleic acid template and $N_2$ is complementary to position +2 of the nucleic acid template, and $N_1$ and $N_2$ are independently chosen from A, C, G or U, wherein the RNA comprises: $N_3$ which is complementary to position +3 of the nucleic acid template and is any nucleotide, preferably A or C; $N_4$ which is complementary to position +4 of the nucleic acid template and is a nucleotide selected from the group consisting of A, G and U, preferably T; and $N_5$ which is complementary to position +5 of the nucleic acid template and is any nucleotide, wherein G* comprises the following structure:

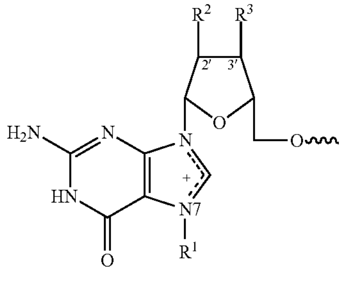

wherein  represents the bond by which G* is bound to the first phosphor atom of the ppp group, $R^1$ is $CH_3$, $R^2$ is OH or O—$CH_3$, and $R^3$ is O—$CH_3$.

In some embodiments, disclosed herein is a method of producing a polypeptide comprising a step of: providing an RNA polynucleotide that comprises a 5' cap, a cap proximal sequence that comprises positions +1, +2, +3, +4, and +5 of an RNA polynucleotide, and a sequence encoding a payload; wherein an RNA polynucleotide is characterized in that when assessed in an organism administered an RNA polynucleotide or a composition comprising the same, elevated expression and/or increased duration of expression of an payload is observed relative to an appropriate reference comparator.

In some embodiments, disclosed herein is a method comprising: administering to a subject, a pharmaceutical composition comprising an RNA polynucleotide formulated in a lipid nanoparticle (LNP) or a lipoplex (LPX) particle disclosed herein.

In some embodiments, disclosed herein is a method of inducing an immune response in a subject, comprising administering to a subject, a pharmaceutical composition comprising an RNA polynucleotide formulated in a lipid nanoparticle (LNP) or a lipoplex (LPX) particle disclosed herein.

In some embodiments, disclosed herein is a method of vaccination of a subject, comprising administering to a subject, a pharmaceutical composition comprising an RNA polynucleotide formulated in a lipid nanoparticle (LNP) or a lipoplex (LPX) particle disclosed herein.

In some embodiments, provided herein is a method of decreasing interaction with IFIT1 of an RNA polynucleotide that comprises a 5' cap and a cap proximal sequence comprising positions +1, +2, +3, +4, and +5 of the RNA polynucleotide, the method comprising a step of: providing a variant of an RNA polynucleotide that differs from a parental RNA polynucleotide by substitution of one or more residues within the cap proximal sequence, and determining that interaction of a variant with IFIT1 is decreased relative to that of a parental RNA polynucleotide. In some embodiments, determining comprises administering the RNA polynucleotide or a composition comprising the same to a cell or an organism.

In some embodiments, disclosed herein is a method of increasing translatability of an RNA polynucleotide that comprises a 5' cap, a cap proximal sequence that comprises positions +1, +2, +3, +4, and +5 of the RNA polynucleotide and a sequence encoding a payload, the method comprising a step of: providing a variant of an RNA polynucleotide that differs from a parental RNA polynucleotide by substitution of one or more residues within a cap proximal sequence; and determining that expression of a variant is increased relative to that of a parental RNA polynucleotide. In some embodiments, determining comprises administering the RNA polynucleotide or a composition comprising the same to a cell or an organism. In some embodiments, increased translatability is assessed by increased expression and/or a persistence of expression of the payload. In some embodiments, increased expression is determined at least 6 hours, at least 24 hours, at least 48 hours at least 72 hours, at least 96 hours or at least 120 hours after administering. In some embodiments, increase in expression is at least 2-fold to 10-fold. In some embodiments, increase in expression is about 2-fold to 50-fold. In some embodiments, elevated expression persists for at least 24 hours, at least 48 hours, at least 72 hours, at least 96 hours, or at least 120 hours after administration.

In some embodiments, provide herein is a therapeutic RNA comprising a 5' cap that includes a Cap1 structure, a cap proximal sequence and a sequence encoding a payload, the improvement that comprises: including one or more of the following residues in a cap proximal sequence: X at position +1 of an RNA polynucleotide, X at position +2 of an RNA polynucleotide, A at position +3 of an RNA polynucleotide, A at position +4 of an RNA polynucleotide, and X at position +5 of an RNA polynucleotide, demonstrated to increase expression of the RNA when administered to a subject in an LNP formulation. In some embodiments, X is chosen from A, C, G or U.

In some embodiments, provide herein is a therapeutic RNA comprising a 5' cap that includes a Cap1 structure, a cap proximal sequence and a sequence encoding a payload, the improvement that comprises: including one or more of the following residues in a cap proximal sequence: A at position +1 of an RNA polynucleotide, G at position +2 of an RNA polynucleotide, A at position +3 of an RNA polynucleotide, A at position +4 of an RNA polynucleotide, and U at position +5 of an RNA polynucleotide, demonstrated to increase expression of the RNA when administered to a subject in an LNP formulation.

In some embodiments, provide herein is a therapeutic RNA comprising a 5' cap that includes a Cap1 structure, a cap proximal sequence and a sequence encoding a payload, the improvement that comprises: including one or more of the following residues in a cap proximal sequence: X at position +1 of an RNA polynucleotide, X at position +2 of an RNA polynucleotide, C at position +3 of an RNA polynucleotide, A at position +4 of an RNA polynucleotide, and X at position +5 of an RNA polynucleotide, demonstrated to increase expression of the RNA when administered to a subject in an LNP formulation. In some embodiments, X is chosen from A, C, G or U.

In some embodiments, provided herein is a method of increasing translation of an RNA polynucleotide comprising a 5' cap that includes a Cap1 structure, a cap proximal sequence and a sequence encoding a payload, the improvement that comprises: including one or more of the following residues in a cap proximal sequence: X at position +1 of an RNA polynucleotide, X at position +2 of an RNA polynucleotide, A at position +3 of an RNA polynucleotide, A at position +4 of an RNA polynucleotide, and X at position +5 of an RNA polynucleotide. In some embodiments, X is chosen from A, C, G or U.

In some embodiments, provided herein is a method of increasing translation of an RNA polynucleotide comprising a 5' cap that includes a Cap1 structure, a cap proximal sequence and a sequence encoding a payload, the improvement that comprises: including one or more of the following residues in a cap proximal sequence: A at position +1 of an RNA polynucleotide, G at position +2 of an RNA polynucleotide, A at position +3 of an RNA polynucleotide, A at position +4 of an RNA polynucleotide, and U at position +5 of an RNA polynucleotide.

In some embodiments, provided herein is a method of increasing translation of an RNA polynucleotide comprising a 5' cap that includes a Cap1 structure, a cap proximal sequence and a sequence encoding a payload, the improvement that comprises: including one or more of the following residues in a cap proximal sequence: X at position +1 of an RNA polynucleotide, X at position +2 of an RNA polynucleotide, C at position +3 of an RNA polynucleotide, A at position +4 of an RNA polynucleotide, and X at position +5 of an RNA polynucleotide. In some embodiments, X is chosen from A, C, G or U.

In some embodiments of any of the methods disclosed herein, an immune response is induced in a subject. In some embodiments of any of the methods disclosed herein, an immune response is a prophylactic immune response or a therapeutic immune response.

In some embodiments of any of the methods disclosed herein, a subject is a mammal.

In some embodiments of any of the methods disclosed herein, a subject is a human.

In some embodiments of any of the methods disclosed herein, a subject has a disease or disorder disclosed herein.

In some embodiments of any of the methods disclosed herein, vaccination generates an immune response to an agent. In some embodiments, an immune response is a prophylactic immune response.

In some embodiments of any of the methods disclosed herein, a subject has a disease or disorder disclosed herein.

In some embodiments of any of the methods disclosed herein, one dose of a pharmaceutical composition is administered.

In some embodiments of any of the methods disclosed herein, a plurality of doses of a pharmaceutical composition is administered.

In some embodiments of any of the methods disclosed herein, the method further comprises administration of one or more therapeutic agents. In some embodiments, one or more therapeutic agents are administered before, after, or concurrently with administration of a pharmaceutical composition comprising an RNA polynucleotide.

Also provided herein in some embodiments, is a method of providing a framework for an RNA polynucleotide that comprises a 5' cap, a cap proximal sequence, and a payload sequence, the method comprising a step of:

assessing at least two variants of an RNA polynucleotide, wherein:

each variant includes a same 5' cap and payload sequence; and the variants differ from one another at one or more specific residues of a cap proximal sequence;

wherein the assessing comprises determining expression levels and/or duration of expression of a payload; and selecting at least one combination of 5' cap and a cap proximal sequence that displays elevated expression relative to at least one other combination.

In some embodiments, assessing comprises administering an RNA construct or a composition comprising the same to a cell or an organism:

In some embodiments, elevated expression of a payload is detected at a time point at least 6 hours, at least 24 hours, at least 48 hours, at least 72 hours, at least 96 hours, or at least 120 hours after administering. In some embodiments, elevated expression is at least 2-fold to 10-fold. In some embodiments, elevated expression is about 2-fold to about 50-fold.

In some embodiments, elevated expression of a payload persists for at least 24 hours, at least 48 hours, at least 72 hours, at least 96 hours, or at least 120 hours after administering.

In some embodiments of any of the methods disclosed herein, an RNA polynucleotide comprises one or more features of an RNA polynucleotide provided herein.

In some embodiments of any of the methods disclosed herein, a composition comprising an RNA polynucleotide comprises a pharmaceutical composition provided herein.

ENUMERATED EMBODIMENTS

1. A composition or medical preparation comprising an RNA polynucleotide comprising:

a 5' cap comprising a Cap1 structure; a cap proximal sequence comprising positions +1, +2, +3, +4, and +5 of the RNA polynucleotide; and a sequence encoding a payload, wherein:

(i) the Cap1 structure comprises m7G(5')ppp(5')(2'OMeN$_1$)pN$_2$, wherein N$_1$ is position +1 of the RNA polynucleotide, and N$_2$ is position +2 of the RNA polynucleotide, and wherein N$_1$ and N$_2$ are each independently chosen from: A, C, G, or U; and (ii) the cap proximal sequence comprises N$_1$ and N$_2$ of the Cap1 structure, and:

(a) a sequence selected from the group consisting of: $A_3A_4X_5$ (SEQ ID NO: 1); $C_3A_4X_5$ (SEQ ID NO: 2); $A_3C_4A_5$ (SEQ ID NO: 3) and $A_3U_4G_5$ (SEQ ID NO: 4); or (b) a sequence comprising: $X_3Y_4X_5$ (SEQ ID NO: 7); wherein $X_3$ (nucleotide X at position +3 in SEQ ID NO: 7) or $X_5$ (nucleotide X at position +5 in SEQ ID NO: 1 or SEQ ID NO: 2) is each independently chosen from A, G, C, or U; and wherein $Y_4$ (nucleotide Y at position +4 in SEQ ID NO: 7) is not C.

2. The composition or medical preparation of embodiment 1, wherein:

(i) the N$_1$ position is A and the N$_2$ position is G, and the Cap1 structure comprises m7G(5')ppp(5')(2'OMeA$_1$)pG$_2$;

(ii) the N$_1$ position is A and the N$_2$ position is U, and the Cap1 structure comprises m7G(5')ppp(5')(2'OMeA$_1$)pU$_2$; or (iii) the N$_1$ position is G and the N$_2$ position is G, and the Cap1 structure comprises m7G(5')ppp(5')(2'OMeG$_1$)pG$_2$.

3. The composition or medical preparation of embodiment 1 or 2, wherein a methylated Guanosine (m7G) in the Cap1 structure further comprises one or more modifications, e.g., wherein the m7G in the Cap1 structure comprises a methylated ribose.

4. The composition or medical preparation of embodiment 3, wherein the m7G in the Cap1 comprises a 3'O methylation (m7(3'OMeG)).

5. A composition or medical preparation comprising an RNA polynucleotide comprising: a 5' cap; a cap proximal sequence comprising positions +1, +2, +3, +4, and +5 of an RNA polynucleotide; and a sequence encoding a payload, wherein:

(i) the 5' cap comprises a Cap1 structure comprising G*ppp($m_1^{2'-O}$)N$_1$pN$_2$, wherein: N1 is position +1 of the RNA polynucleotide, and N$_2$ is position +2 of the RNA polynucleotide, and wherein N$_1$ and N$_2$ are each independently chosen from: A, C, G, or U; and G* comprises the following structure:

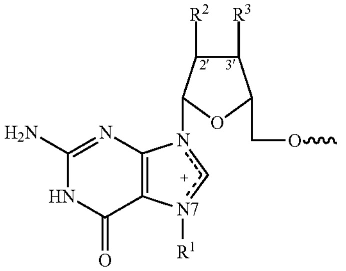

wherein ~~~ represents the bond by which G* is bound to the first phosphor atom of the ppp group, $R^1$ is $CH_3$, $R^2$ is OH or O—$CH_3$, and $R^3$ is O—$CH_3$; and (ii) a cap proximal sequence comprises N$_1$ and N$_2$ of the Cap1 structure, and:

(a) a sequence chosen from the group consisting of: $A_3A_4X_5$ (SEQ ID NO: 1); $C_3A_4X_5$ (SEQ ID NO: 2); $A_3C_4A_5$ (SEQ ID NO: 3) or $A_3U_4G_5$ (SEQ ID NO: 4); or (b) a sequence comprising $X_3Y_4X_5$ (SEQ ID NO: 7); wherein $X_3$ (nucleotide X at position +3 in SEQ ID NO: 7) or $X_5$ (nucleotide X at position +5 in SEQ ID NO: 1 or SEQ ID NO: 2) is each independently chosen from A, G, C, or U; and wherein $Y_4$ (nucleotide Y at position +4 in SEQ ID NO: 7) is not C.

6. The composition or medical preparation of embodiment 5, wherein:

(i) the N$_1$ position is A and the N$_2$ position is G, and the Cap1 structure comprises m7G(5')ppp(5')(2'OMeA$_1$)pG$_2$;

(ii) the N$_1$ position is A and the N$_2$ position is U, and the Cap1 structure comprises m7G(5')ppp(5')(2'OMeA$_1$)pU$_2$; or (iii) the N$_1$ position is G and the N$_2$ position is G, and the Cap1 structure comprises m7G(5')ppp(5')(2'OMeG$_1$)pG2.

7. The composition or medical preparation of any one of the preceding embodiments, wherein the cap proximal sequence comprises N$_1$ and N$_2$ of the Cap1 structure, and a sequence comprising: $A_3A_4X_5$ (SEQ ID NO: 1), optionally wherein $X_5$ is any nucleotide, e.g., A, C, G or U, preferably U.

8. The composition or medical preparation of any one of embodiments 1-6, wherein the cap proximal sequence comprises N$_1$ and N$_2$ of the Cap1 structure, and a sequence comprising $C_3A_4X_5$ (SEQ ID NO: 2), optionally wherein $X_5$ is any nucleotide, e.g., A, C, G or U.

9. The composition or medical preparation of any one of embodiments 1-6, wherein the cap proximal sequence comprises N$_1$ and N$_2$ of the Cap1 structure, and a sequence comprising); $X_3Y_4X_5$ (SEQ ID NO: 7), wherein $X_3$ or $X_5$ are any nucleotide, e.g., A, G, C, or U, and $Y_4$ is not C.

10. The composition or medical preparation of any one of embodiments 1-6, wherein the cap proximal sequence comprises N$_1$ and N$_2$ of the Cap1 structure, and a sequence comprising $A_3C_4A_5$ (SEQ ID NO: 3).

11. The composition or medical preparation of any one of embodiments 1-6, wherein the cap proximal sequence comprises N$_1$ and N$_2$ of the Cap1 structure, and a sequence comprising $A_3U_4G_5$ (SEQ ID NO: 4).

12. A composition or medical preparation comprising an RNA polynucleotide comprising:

a 5' cap comprising a Cap1 structure; a cap proximal sequence comprising positions +1, +2, +3, +4, and +5 of the RNA polynucleotide; and a sequence encoding a payload, wherein:

(i) the Cap1 structure comprises m7(3'OMeG)(5')ppp(5')(2'OMeA$_1$)pG$_2$, wherein A$_1$ is position +1 of the RNA polynucleotide, and G2 is position +2 of the RNA polynucleotide; and (ii) the cap proximal sequence comprises A$_1$ and G$_2$ of the Cap1 structure, and a sequence comprising: $A_3A_4U_5$ (SEQ ID NO: 5) at positions +3, +4 and +5 respectively of the RNA polynucleotide.

13. The composition or medical preparation of any one of the preceding embodiments, wherein the RNA polynucleotide comprises a 5' UTR and the cap proximal sequence is situated in a 5' UTR.

14. A composition or medical preparation comprising a capped RNA polynucleotide encoding a gene product, which RNA polynucleotide comprises the formula:

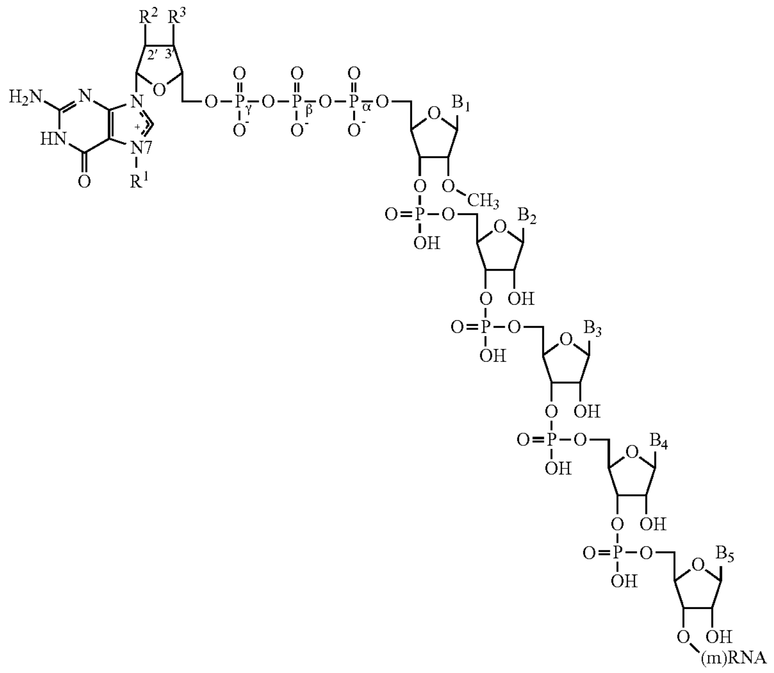

wherein $R^1$ is $CH_3$, $R^2$ is OH or O—$CH_3$, and $R^3$ is O—$CH_3$, wherein $B_1$ is any nucleobase, preferably A; $B_2$ is any nucleobase, preferably G; $B_3$ is any nucleobase, preferably A or C; $B_4$ is any nucleobase; and $B_5$ is any nucleobase, and wherein, when the RNA polynucleotide is administered to a subject, the levels of expression of the encoded gene product at about 6 hours after administration and at about 48 hours after administration do not differ by more than 5-fold.

15. The composition or medical preparation of embodiment 14, wherein, when the RNA polynucleotide is administered to a subject, the expression of the gene product is detectable at least 72 hours after administration.

16. The composition or medical preparation of embodiment 14 or 15, wherein:

the RNA polynucleotide comprises a 5' UTR; and/or the RNA polynucleotide further comprises a 3' UTR sequence; and/or a polyA sequence.

17. The composition or medical preparation of any one of the preceding embodiments, wherein the RNA polynucleotide does not comprise a self-hybridizing sequence, optionally wherein a self-hybridizing sequence is a sequence that can hybridize to a sequence in a 5' UTR or 3' UTR of the RNA polynucleotide, e.g., wherein the self-hybridizing sequence is or comprises SEQ ID NO: 8.

18. The composition or medical preparation of any one of the preceding embodiments, wherein a 5' UTR comprises a human alpha globin (hAg) 5'UTR or a fragment thereof, a TEV 5' UTR or a fragment thereof, a HSP70 5' UTR or a fragment thereof, or a c-Jun 5' UTR or a fragment thereof.

19. The composition or medical preparation of any one of the preceding embodiments, wherein the 5' UTR comprises a human alpha globin 5' UTR provided in SEQ ID NO: 11, or a sequence having at least 99%, 98%, 97%, 96%, 95%, 90%, 85%, or 80% identity thereto.

20. The composition or medical preparation of any one of embodiments 1 to 18, wherein the 5' UTR comprises a human alpha globin 5' UTR provided in SEQ ID NO: 12, or a sequence having at least 99%, 98%, 97%, 96%, 95%, 90%, 85%, or 80% identity thereto.

21. The composition or medical preparation of any one of the preceding embodiments, wherein the 5' UTR further comprises a T7 RNA polymerase promoter sequence.

22. The composition or medical preparation of any one of the preceding embodiments, wherein the 5' cap structure is added co-transcriptionally or is not added enzymatically.

23. The composition or medical preparation of any one of the preceding embodiments, wherein the RNA polynucleotide comprises a 3' UTR or a fragment thereof, optionally wherein the 3' UTR sequence comprises SEQ ID NO: 13, or a sequence having at least 99%, 98%, 97%, 96%, 95%, 90%, 85%, or 80% identity thereto.

24. The composition or medical preparation of any one of embodiments 16-23, wherein the 3' UTR or a proximal sequence thereto comprises a restriction site, optionally wherein the restriction site is a BamHI site or a XhoI site.

25. The composition or medical preparation of any one of the preceding embodiments, wherein a PolyA sequence comprises at least 100 nucleotides, optionally wherein:

(i) a polyA sequence is an interrupted sequence of adenine nucleotides; and/or (ii) a polyA sequence comprises 30 adenine nucleotides followed by 70 adenine nucleotides, wherein the 30 adenine nucleotides and 70 adenine nucleotides are separated by a linker sequence.

26. The composition or medical preparation of embodiment 25, wherein a polyA sequence comprises the sequence of SEQ ID NO: 14.

27. The composition or medical preparation of any one of embodiments 16-26, wherein the 5' cap, the 5' UTR, the sequence encoding the payload, the 3' UTR and the polyA sequence are situated disposed in a 5' to 3' orientation.

28. The composition or medical preparation of any one of the preceding embodiments, wherein the RNA polynucleotide comprises a Kozak sequence upstream of the sequence encoding a payload.

29. The composition or medical preparation of any one of the preceding embodiments, wherein the sequence encoding a payload comprises a promoter sequence and/or wherein the sequence encoding a payload comprises a sequence encoding a secretory signal peptide.

30. The composition or medical preparation of any one of the preceding embodiments, wherein an RNA polynucleotide comprises a sequence encoding a payload chosen from: a protein replacement polypeptide; an antibody agent; a cytokine; an antigenic polypeptide; a gene editing component; a regenerative medicine component or combinations thereof.

31. The composition or medical preparation of any one of the preceding embodiments, characterized in that, when assessed in an organism administered the composition or medical preparation comprising the RNA polynucleotide, elevated expression and/or increased duration of expression of the payload is observed relative to an appropriate reference comparator.

32. The composition or medical preparation of embodiment 30, wherein a payload is or comprises a protein replacement polypeptide, optionally wherein:
a protein replacement polypeptide comprises a polypeptide with aberrant expression in a disease or disorder;
a protein replacement polypeptide comprises an intracellular protein, an extracellular protein, or a transmembrane protein; and/or
a protein replacement polypeptide comprises an enzyme.

33. The composition or medical preparation of embodiment 32, wherein a disease or disorder with aberrant expression of a polypeptide includes but is not limited to: a rare disease, a metabolic disorder, a muscular dystrophy, a cardiovascular disease, or a monogenic disease.

34. The composition or medical preparation of embodiment 30, wherein a payload is or comprises an antibody agent, optionally wherein an antibody agent binds to a polypeptide expressed on a cell.

35. The composition or medical preparation of embodiment 34, wherein an antibody agent comprises a CD3 antibody, a Claudin 6 antibody, or a combination thereof.

36. The composition or medical preparation of embodiment 30, wherein a payload is or comprises a cytokine or a fragment or a variant thereof, optionally wherein a cytokine comprises: IL-12 or a fragment or variant or a fusion thereof, IL-15 or a fragment or a variant or a fusion thereof, GMCSF or a fragment or a variant thereof, or IFN-alpha or a fragment or a variant thereof.

37. The composition or medical preparation of embodiment 30, wherein a payload is or comprises an antigenic polypeptide or an immunogenic variant or an immunogenic fragment thereof, optionally wherein an antigenic polypeptide comprises one epitope from an antigen or a plurality of distinct epitopes from an antigen.

38. The composition or medical preparation of embodiment 37, wherein an antigenic polypeptide comprising a plurality of distinct epitopes from an antigen is polyepitopic.

39. The composition or medical preparation of embodiment 37 or 38, wherein an antigenic polypeptide comprises: an antigenic polypeptide from an allergen, a viral antigenic polypeptide, a bacterial antigenic polypeptide, a fungal antigenic polypeptide, a parasitic antigenic polypeptide, an antigenic polypeptide from an infectious agent, an antigenic polypeptide from a pathogen, a tumor antigenic polypeptide, or a self-antigenic polypeptide.

40. The composition or medical preparation of embodiment 39, wherein a viral antigenic polypeptide comprises an HIV antigenic polypeptide, an influenza antigenic polypeptide, a Coronavirus antigenic polypeptide, a Rabies antigenic polypeptide, or a Zika virus antigenic polypeptide, optionally wherein a viral antigenic polypeptide is or comprises a Coronavirus antigenic polypeptide.

41. The composition or medical preparation of embodiment 40, wherein a Coronavirus antigen is or comprises a SARS-CoV-2 protein, optionally wherein a SARS-CoV-2 protein comprises a SARS-CoV-2 Spike (S) protein, or an immunogenic variant or an immunogenic fragment thereof.

42. The composition or medical preparation of embodiment 41, wherein the SARS-CoV-2 protein, or immunogenic variant or immunogenic fragment thereof, comprises proline residues at positions 986 and 987.

43. The composition or medical preparation of embodiment 41 or 42, wherein a SARS-CoV-2 S polypeptide:
(i) has at least 99%, 98%, 97%, 96%, 95%, 90%, 85%, or 80% identity to SEQ ID NO: 9; or
(ii) is encoded by an RNA having at least 99%, 98%, 97%, 96%, 95%, 90%, 85%, or 80% identity to SEQ ID NO: 10.

44. The composition or medical preparation of embodiment 30, wherein a payload is or comprises a tumor antigenic polypeptide or an immunogenic variant or an immunogenic fragment thereof, optionally wherein a tumor antigenic polypeptide comprises a tumor specific antigen, a tumor associated antigen, a tumor neoantigen, or a combination thereof.

45. The composition or medical preparation of embodiment 43 or 44, wherein a tumor antigenic polypeptide comprises p53, ART-4, BAGE, ss-catenin/m, Bcr-abL CAMEL, CAP-1, CASP-8, CDC27/m, CDK4/m, CEA, CLAUDIN-12, c-MYC, CT, Cyp-B, DAM, ELF2M, ETV6-AML1, G250, GAGE, GnT-V, Gap100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12, MAGE-B, MAGE-C, MART-1/Melan-A, MC1R, Myosin/m, MUC1, MUM-1, -2, -3, NA88-A, NF1, NY-ESO-1, NY-BR-1, p190 minor BCR-abL, Plac-1, Pm1/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE, WT, WT-1, or a combination thereof.

46. The composition or medical preparation of any one of embodiments 44-45, wherein a tumor antigenic polypeptide comprises a tumor antigen from a carcinoma, a sarcoma, a melanoma, a lymphoma, a leukemia, or a combination thereof.

47. The composition or medical preparation of embodiment 46, wherein a tumor antigenic polypeptide comprises: a melanoma tumor antigen; a prostate cancer antigen; a HPV16 positive head and neck cancer antigen; a breast cancer antigen; an ovarian cancer antigen; a lung cancer antigen, e.g., an NSCLC antigen.

48. The composition or medical preparation of embodiment 39, wherein a payload is or comprises a self-antigenic polypeptide or an immunogenic variant or an immunogenic fragment thereof, optionally wherein a self-antigenic polypeptide comprises an antigen that is typically expressed on cells and is recognized as a self-antigen by an immune system.

49. The composition or medical preparation of embodiment 48, wherein a self-antigenic polypeptide comprises: a multiple sclerosis antigenic polypeptide, a Rheumatoid arthritis antigenic polypeptide, a lupus antigenic polypeptide, a celiac disease antigenic polypeptide, a Sjogren's syndrome antigenic polypeptide, or an ankylosing spondylitis antigenic polypeptide, or a combination thereof.

50. The composition or medical preparation of any one of the preceding embodiments, wherein an RNA polynucleotide comprises a modified nucleoside in place of uridine, optionally wherein a modified nucleoside is selected from pseudouridine (ψ), N1-methyl-pseudouridine (m1ψ), and 5-methyl-uridine (m5U).

51. The composition or medical preparation of any one of the preceding embodiments, wherein an RNA polynucleotide further comprises one or more additional sequences, e.g., one or more additional payloads, and/or one or more regulatory elements.

52. The composition or medical preparation of any one of the preceding embodiments, wherein an RNA polynucleotide is characterized in that upon administration to an organism it increases translation efficiency of a payload, compared to administration of an otherwise similar RNA polynucleotide without a m7(3'OMeG)(5')ppp(5')(2'OMeA1)p$G_2$ Cap.

53. The composition or medical preparation of any one of the preceding embodiments, wherein an RNA polynucleotide is characterized in that upon administration to an organism it increases the expression level and/or duration of expression of an encoded payload, compared to administration of an otherwise similar RNA polynucleotide without a m7(3'OMeG)(5')ppp(5')(2'OMe$A_1$)p$G_2$ cap, without a cap proximal sequence disclosed herein, and/or with a self-hybridizing sequence, optionally wherein:

(i) increased expression is determined at least 6 hours, at least 24 hours, at least 48 hours at least 72 hours, at least 96 hours or at least 120 hours after the administering, optionally wherein the increase in expression is at least 2-fold to 10-fold; or (ii) elevated expression persists for at least 24 hours, at least 48 hours, at least 72 hours, at least 96 hours, or at least 120 hours.

54. The composition or medical preparation of any one of the preceding embodiments, wherein the RNA is formulated or is to be formulated as a liquid, a solid, or a combination thereof; wherein the RNA is formulated or is to be formulated for injection; or wherein the RNA is formulated or is to be formulated for intramuscular administration.

55. A pharmaceutical composition comprising an RNA polynucleotide of any one of the preceding embodiments, formulated as a particle, optionally wherein a particle is or comprises a lipid nanoparticle (LNP) or a lipoplex (LPX) particle.

56. The pharmaceutical composition of embodiment 55, wherein a lipid nanoparticle comprises each of: a cationic lipid; a sterol; a neutral lipid; and a lipid conjugate.

57. The pharmaceutical composition of embodiment 56, wherein the cationic lipid is or comprises ((4-hydroxybutyl)azanediyl)bis(hexane-6,1-diyl)bis(2-hexyldecanoate), the sterol is a cholesterol, the neutral lipid is or comprises a phospholipid, and the lipid conjugate is or comprises a polyethylene glycol (PEG)-lipid.

58. The pharmaceutical composition of embodiment 57, wherein the phospholipid is or comprises distearoylphosphatidylcholine (DSPC).

59. The pharmaceutical composition of embodiment 57, wherein the (PEG)-lipid is or comprises 2-[(polyethylene glycol)-2000]-N,N-ditetradecylacetamide.

60. The pharmaceutical composition of any one of embodiments 56-58, wherein the lipid nanoparticle comprises each of: a. ((4-hydroxybutyl)azanediyl)bis(hexane-6,1-diyl)bis(2-hexyldecanoate); b. a cholesterol; c. distearoylphosphatidylcholine (DSPC); and d. 2-[(polyethylene glycol)-2000]-N,N-ditetradecylacetamide.

61. The pharmaceutical composition of any one of embodiments 56-60, wherein:

a neutral lipid is present in a concentration ranging from 5 to 15 mol percent of total lipids;

a cationically ionizable lipid is present in a concentration ranging from 40 to 55 mol percent of total lipids;

a steroid is present in a concentration ranging from 30 to 50 mol percent of total lipids; and/or a pegylated lipid is present in a concentration ranging from 1 to 10 mol percent of total lipids.

62. The pharmaceutical composition of any one of embodiments 56-61, wherein a lipid nanoparticle comprise from 40 to 55 mol percent of a cationically ionizable lipid; from 5 to 15 mol percent of a neutral lipid; from 30 to 50 mol percent of a steroid; and from 1 to 10 mol percent of a pegylated lipid.

62. The pharmaceutical composition of embodiment 55, wherein an RNA lipoplex particle is obtainable by mixing an RNA polynucleotide with liposomes.

63. The composition or medical preparation of any one of embodiments 1-54, or a pharmaceutical composition of any one of embodiments 55-62, wherein the RNA is mRNA or saRNA.

64. The pharmaceutical composition of any one of embodiments 55-63, wherein a pharmaceutical composition further comprises one or more pharmaceutically acceptable carriers, diluents and/or excipients.

65. The pharmaceutical composition of any one of embodiments 55-64, which is packaged as a kit, optionally wherein the kit further comprises instructions for use of said pharmaceutical composition for inducing an immune response in a subject.

66. A method of manufacturing a pharmaceutical composition of any one of embodiments 55-64, by combining an RNA polynucleotide with lipids to form lipid nanoparticles that encapsulate said RNA.

67. A nucleic acid template suitable to produce a cap1-capped RNA, in which the first five nucleotides transcribed from the template strand of the nucleic acid template comprise the sequence Nip$N_2$p$N_3$p$N_4$p$N_5$, wherein $N_1$ is any nucleotide, preferably T; $N_2$ is any nucleotide, preferably C; $N_3$ is any nucleotide, preferably T or G; $N_4$ is any nucleotide; and $N_5$ is any nucleotide.

68. The nucleic acid template of embodiment 67, wherein the DNA template comprises: a 5' UTR, a sequence encoding a payload, a 3' UTR and a polyA sequence.

69. An in vitro transcription reaction comprising:

(i) a template DNA comprising a polynucleotide sequence complementary to an RNA polynucleotide sequence provided in any one of embodiments 1-54;

(ii) a polymerase (e.g., a T7 polymerase); and (iii) an RNA polynucleotide.

70. The in vitro transcription reaction of embodiment 69, further comprising a 5' cap or a 5' cap analog, optionally wherein a 5' cap or a 5' cap analog is or comprises a Cap1 structure.

71. The in vitro transcription reaction of embodiment 69, wherein the RNA polynucleotide comprises a cap comprising a Cap1 structure; and a cap proximal sequence comprising positions +1, +2, +3, +4, and +5 of the RNA polynucleotide; and a sequence encoding a payload, optionally wherein the Cap1 structure comprises m7G(5')ppp(5')(2'OMeN$_1$)pN$_2$, wherein N$_1$ is position +1 of the RNA polynucleotide, and N$_2$ is position +2 of the RNA polynucleotide, and wherein N$_1$ and N$_2$ are each independently chosen from: A, C, G, or U.

72. An RNA polynucleotide isolated from an in vitro transcription reaction provided in any one of embodiments 69-71.

73. A method for producing a capped RNA comprising, transcribing a nucleic acid template in the presence of a cap structure, wherein the cap structure comprises G*ppp(m$_1^{2'}$-$_O$)N$_1$pN$_2$, wherein N$_1$ is complementary to position +1 of the nucleic acid template and N$_2$ is complementary to position +2 of the nucleic acid template, and N$_1$ and N$_2$ are independently chosen from A, C, G or U, wherein position +3 of the nucleic acid template is any nucleotide, preferably T or G; position +4 of the nucleic acid template is any nucleotide; and position +5 of the nucleic acid template is any nucleotide, wherein G* comprises the following structure:

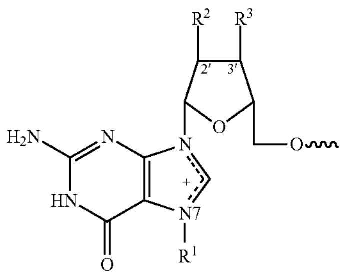

wherein ∿∿∿ represents the bond by which G* is bound to the first phosphor atom of the ppp group, R$^1$ is CH$_3$, R$^2$ is OH or O—CH$_3$, and R$^3$ is O—CH$_3$.

74. A composition comprising a DNA polynucleotide comprising a sequence complementary to an RNA polynucleotide sequence provided in any one of embodiments 1-54.

75. The DNA polynucleotide composition of embodiment 74, which can be used to transcribe an RNA polynucleotide and/or, which is disposed in a vector.

76. A method comprising:
administering to a subject, a pharmaceutical composition comprising an RNA polynucleotide formulated in a lipid nanoparticle (LNP) or a lipoplex (LPX) particle of any one of embodiments 55-64.

77. A method of inducing an immune response in a subject, comprising administering to a subject, a pharmaceutical composition comprising an RNA polynucleotide formulated in a lipid nanoparticle (LNP) or a lipoplex (LPX) particle of any one of embodiments 55-64.

78. The method of embodiment 77, wherein an immune response is induced in a subject, optionally wherein an immune response is a prophylactic immune response or a therapeutic immune response.

79. A method of vaccination of a subject by administering a pharmaceutical composition comprising an RNA polynucleotide formulated in a lipid nanoparticle (LNP) or a lipoplex (LPX) particle of any one of embodiments 55-64.

80. The method of embodiment 79, vaccination generates an immune response, optionally wherein an immune response is a prophylactic immune response.

81. A method of decreasing interaction with IFIT1 of an RNA polynucleotide that comprises a 5' cap and a cap proximal sequence comprising positions +1, +2, +3, +4, and +5 of the RNA polynucleotide, the method comprising a step of:
providing a variant of the RNA polynucleotide that differs from the parental RNA polynucleotide by substitution of one or more residues within the cap proximal sequence, and
determining that interaction of the variant with IFIT1 is decreased relative to that of the parental RNA polynucleotide, optionally wherein the determining comprises administering the RNA polynucleotide or a composition comprising the same to a cell or an organism.

82. A method of producing a polypeptide comprising a step of:
providing an RNA polynucleotide that comprises a 5' cap, a cap proximal sequence that comprises positions +1, +2, +3, +4, and +5 of the RNA polynucleotide, and a sequence encoding a payload;
wherein the RNA polynucleotide is characterized in that when assessed in an organism administered the RNA polynucleotide or a composition comprising the same, elevated expression and/or increased duration of expression of the payload is observed relative to an appropriate reference comparator.

83. A method of increasing translatability of an RNA polynucleotide that comprises a 5' cap, a cap proximal sequence that comprises positions +1, +2, +3, +4, and +5 of the RNA polynucleotide and a sequence encoding a payload, the method comprising a step of:
providing a variant of the RNA polynucleotide that differs from a parental RNA polynucleotide by substitution of one or more residues within the cap proximal sequence; and
determining that expression of the variant is increased relative to that of the parental RNA polynucleotide, optionally wherein the determining comprises administering the RNA polynucleotide or a composition comprising the same to a cell or an organism.

84. The method of embodiment 83, wherein the increased translatability is assessed by increased expression and/or a persistence of expression of the payload.

85. The method of embodiment 84, wherein:
(i) increased expression is determined at least 6 hours, at least 24 hours, at least 48 hours at least 72 hours, at least 96 hours or at least 120 hours after the administering, optionally wherein the increase in expression is at least 2-fold to 10-fold; or
(ii) elevated expression persists for at least 24 hours, at least 48 hours, at least 72 hours, at least 96 hours, or at least 120 hours.

86. In a therapeutic RNA comprising a 5' cap that includes a Cap1 structure, a cap proximal sequence and a sequence encoding a payload, the improvement that comprises:
including one or more of the following residues in a cap proximal sequence: A at position +1 of the RNA polynucleotide, G at position +2 of the RNA polynucleotide, A at position +3 of the RNA polynucleotide, A at position +4 of the RNA polynucleotide, and U at position +5 of the RNA polynucleotide,
demonstrated to increase expression of the RNA when administered to a subject in an LNP formulation.

87. A method of increasing translation of an RNA polynucleotide comprising a 5' cap that includes a Cap1 structure, a cap proximal sequence and a sequence encoding a payload, the improvement that comprises:
including one or more of the following residues in a cap proximal sequence: A at position +1 of the RNA polynucleotide, G at position +2 of the RNA polynucleotide, A at position +3 of the RNA polynucleotide, A at position +4 of the RNA polynucleotide, and U at position +5 of the RNA polynucleotide.

88. The method of any one of embodiments 76-87, wherein one dose or a plurality of doses of a pharmaceutical composition is administered.

89. The method of any one of embodiments 76-88, wherein the method further comprises administration of one or more therapeutic agents.

90. The method of embodiment 89, wherein one or more therapeutic agents are administered before, after, or concurrently with administration of a pharmaceutical composition comprising an RNA polynucleotide.

91. The method of any one of embodiments 76-90, wherein the subject or organism is a mammal.

92. The method of embodiment 91, wherein the subject or organism is a human.

93. The method of any one of embodiments 76-93, wherein the subject has a disease or disorder disclosed herein.

94. A method of providing a framework for an RNA polynucleotide that comprises a 5' cap, a cap proximal sequence, and a payload sequence, the method comprising a step of:

assessing at least two variants of the RNA polynucleotide, wherein:

each variant includes the same 5' cap and payload sequence; and the variants differ from one another at one or more specific residues of the cap proximal sequence;

wherein the assessing comprises determining expression levels and/or duration of expression of the payload sequence; and selecting at least one combination of 5' cap and a cap proximal sequence that displays elevated expression relative to at least one other combination.

95. The method of embodiment 94, wherein the assessing comprises administering the RNA construct or a composition comprising the same to a cell or an organism:

96. The method of embodiment 94 or 95, wherein:

the elevated expression is detected at a time point at least 6 hours, at least 24 hours, at least 48 hours, at least 72 hours, at least 96 hours, or at least 120 hours after the administering, optionally wherein the elevated expression is at least 2-fold to 10-fold; and/or the elevated expression persists for at least 24 hours, at least 48 hours, at least 72 hours, at least 96 hours, or at least 120 hours.

97. The method of any one of embodiments 76-96, wherein the RNA polynucleotide comprises one or more features of an RNA polynucleotide provided in any one of embodiments 1-54.

98. The method of any one of embodiments 76-97, wherein the composition comprises a pharmaceutical composition of any one of embodiments 55-64.

EXEMPLIFICATION

Example 1—Generation of an RNA Cassette that Provides Improved and Sustained Expression of the Encoded Protein The present Example describes the generation of RNA cassettes with improved expression level of an encoded payload, and/or increased duration of expression of an encoded payload in vivo. The methods used in this Example are described below.

Methods:

mRNA Production

For templates, purified plasmids encoding codon-optimized murine erythropoietin (mEPO) were used. The plasmids corresponding to 5' untranslated region sequences of tobacco etch virus 5' leader RNA (TEV) or human α-globin (hAg) mRNA were linearized with BspQI (New England Biolabs, Cat #R0712L) to generate templates. The MEGAscript T7 RNA polymerase kit (Thermo Fisher Scientific, Cat #AMB1334-5) was used for transcription, and UTP was replaced with N1-methylpseudouridine (m1Ψ) 5'-triphosphate (TriLink, Cat #N-1081). Capping of the mRNAs was performed co-transcriptionally using anti-reverse Cap1 analogue CleanCap413 (TriLink, Cat #N-7413) at a final concentration of 3 mM. To obtain the desired transcripts generated with cap analogues, the initial GTP concentration in a transcription reaction was reduced from 7.5 mM to 1.5 mM and was incubated at 37° C. for 30 min in a hybridization chamber. The initial concentration of additional nucleotides including ATP, CTP and m1ΨTP corresponded to the final 7.5 mM concentration. Adding of extra 1.5 mM GTP to the mixture was required after 30, 60, 90 and 120 minutes of incubation and incubated further at 37° C. for 30 minutes. The mRNAs were transcribed to contain 100 nt-long 3' poly(A) tail (SEQ ID NO: 42). To remove the template 1/10 volume of DNA Turbo DNase (Thermo Fisher Scientific, Cat #AM1907) was added to the reaction mix and incubated the mixture at 37° C. for 15 minutes. The synthesized mRNA was isolated from the reaction mix by precipitation with half reaction volume of 8 M LiCl solution (Sigma-Aldrich, Cat #L7026). After chilling at −20° C. for at least 1 hour, the RNA pellet was collected by centrifuging at 17.000×g at 4° C. for 5 minutes. After washing the RNA pellet twice with at least 200 μl ice-cold 75% Ethanol solution, it was dissolved in nuclease free water. The concentration and quality of in vitro transcribed mRNA were measured on a NanoDrop2000C spectrophotometer (Thermo Fisher Scientific, Cat #ND-2000c). Aliquots of denatured IVT mRNAs were analyzed by electrophoresis in agarose gels containing 0.005% (v/v) GelRed™ nucleic acid gel stain (Masek T et al., (2005) Anal Biochem 336: 46-50). Small aliquots of mRNA samples were stored in siliconized tubes at −20° C. All mRNAs were cellulose-purified as described (Baiersdorfer M. et al. (2019) Mol Ther Nucleic Acids 15(15):26-35).

Mouse EPO-Specific Enzyme-Linked Immunosorbent Assay (ELISA)

For quantification of mouse EPO levels, plasma samples were collected from mice injected with IVT mRNA encoding for murine erythropoietin complexed with TransIT mRNA (Mirusbio, Cat #MIR2255) at the indicated time points and analyzed by mouse Erythropoietin DuoSet ELISA kit (R&D Systems, Cat #DY959). Flat-bottom 96-well plates were pre-coated with 2 μg/ml rat anti-mouse EPO capture antibody (100 μl/well) and incubated at room temperature (RT) overnight. The plates were washed three times with PBS containing 0.05% Tween-20 and incubated with 1% BSA (bovine serum albumin) (Sigma-Aldrich, Cat #2153) solution at RT for 2 hours to prevent non-specific binding of the antibody and washed again. A seven point standard curve using 2-fold serial dilutions and a high standard of 4000 μg/ml was applied. At a final volume of 50 μl plasma samples and standard diluted in 1% BSA solution were added to the appropriate wells and incubated at RT for 2 hours. After washing the plates, 100 μl of 1 μg/ml of rat biotinylated anti-mouse EPO detection antibody in 1% BSA solution was distributed to each well and incubated RT for 2 hours. The plates were washed and then incubated with 100 μl Streptavidin conjugated to horseradish peroxidase diluted (1:200) in 1% BSA solution at room temperature for 20 min. After washing, TMB 2-Component Microwell Peroxidase substrate solution (Medac Gmbh, Cat #50-76-11) was added to each well (100 l/well). Samples were incubated at room temperature for 5 min, and 2 M sulfuric acid (R&D Systems, Cat #DY994) was added (50 l/well) to stop the reaction and absorbance was measured at 450 nm and 570 nm using an Infinite 200 Pro plate reader (Tecan).

Animal Protocol

All experiments were performed in accordance with federal policies on animal research using BALB/c female mice from Charles River Laboratories (Sandhofer, Germany) at an age of 6-12 weeks. For determining the translation of mRNA in vivo, 1-3 μg backbone- and nucleoside-modified cap1-TEV-mEPO mRNA or cap1-hAg-mEPO mRNA encoding for murine erythropoietin complexed with TransIT was injected intravenously into mice (3 mice/group). Blood was collected at 6, 24, 48, and 72 h after mRNA injection as described (Kariko K et al., (2012) Mol. Ther. 20:948-953; Mahin A J et al., (2016) Methods Mol Biol 1428:297-306) to avoid an impact of the sampling on the hematological parameters of the animals. In brief, blood (18 μL) was collected by puncture of the tail vein, mixed with 2 μL 0.2 M EDTA, and centrifuged in 20 μL Drummond microcaps glass microcapillary tubes (Sigma-Aldrich). After snapping the microcapillary tubes, the plasma was recovered for the measurement of plasma mEPO levels using the mEPO DuoSet ELISA Development kit (R&D Systems, Minneapolis, Minn., USA) and the Infinite 200 Pro plate reader (Tecan, Mannedorf, Switzerland). For details see EPO-ELISA description.

Results

This Example assesses the effect of sequence elements in an RNA on the expression level and/or duration of expression of a payload encoded by the RNA. The first evaluation focused on assessing the impact of self-hybridization sequences in 3' UTR sequence of an RNA polynucleotide. RNA constructs with or without a self-hybridization sequence termed “Lig3” were generated and injected intravenously into mice. At 6, 24, 48, and 72 h after mRNA injection, blood was collected from the animals and assessed for expression of EPO—the polypeptide encoded by the RNA constructs.

Figure 2A:
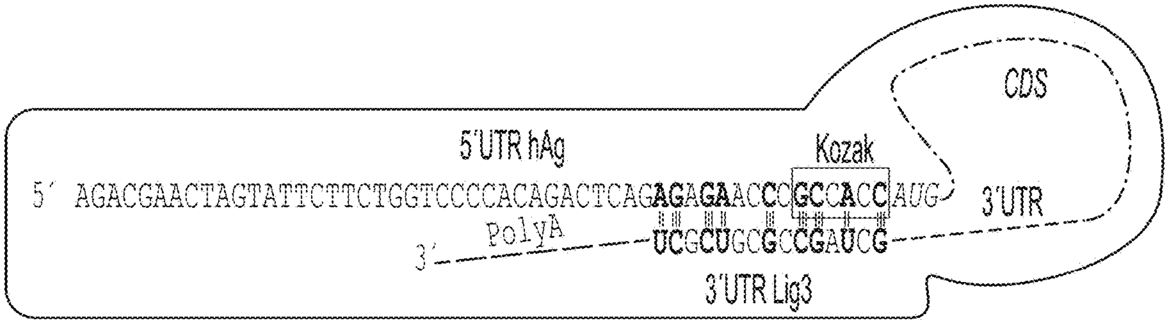
FIGS. 2A-2C are schematics of a Lig3 sequence self-hybridizing to a 5' UTR (FIG. 2A-2B) or a 3' UTR (FIG. 2C).
Figure 2B:
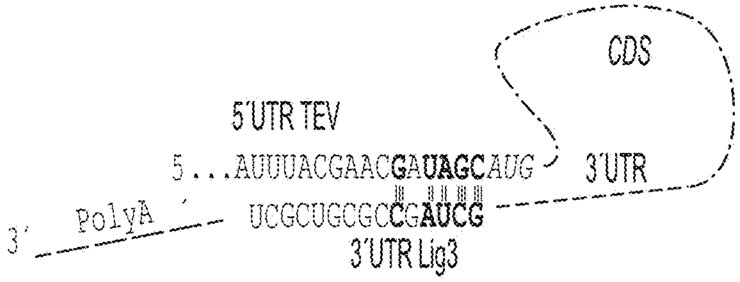
Figure 2C:
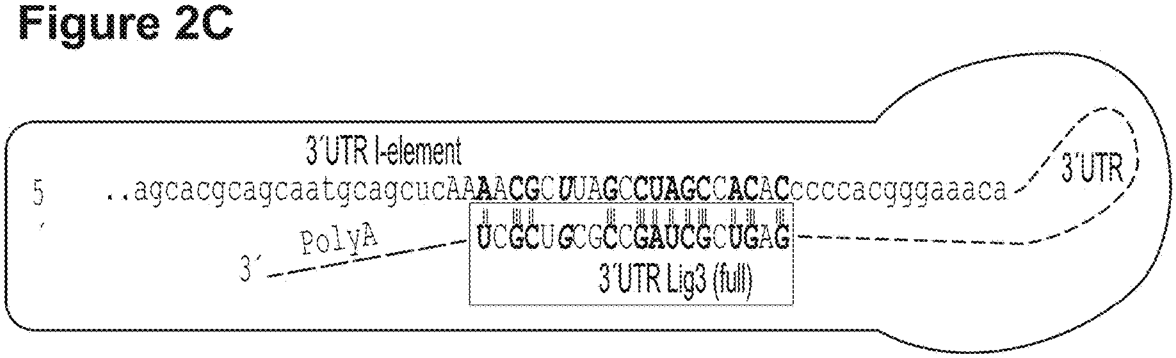
Figure 3A:
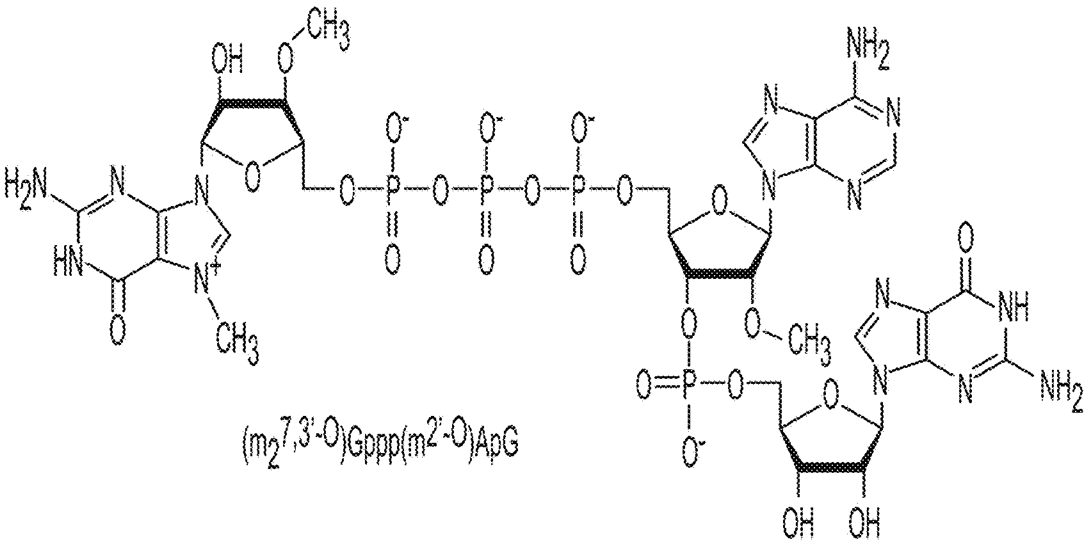
FIGS. 3A-3I are structures of 5' caps that can be incorporated into mRNAs.
Figure 3B:
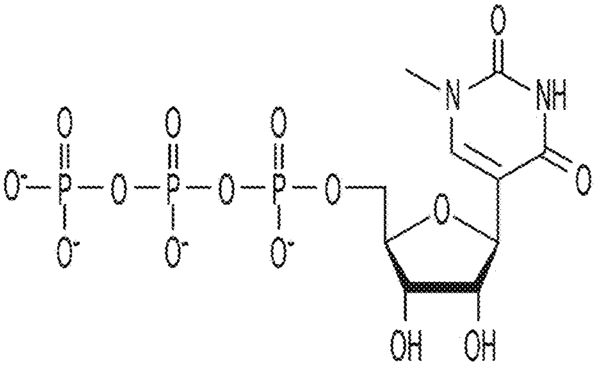
Figure 3C:
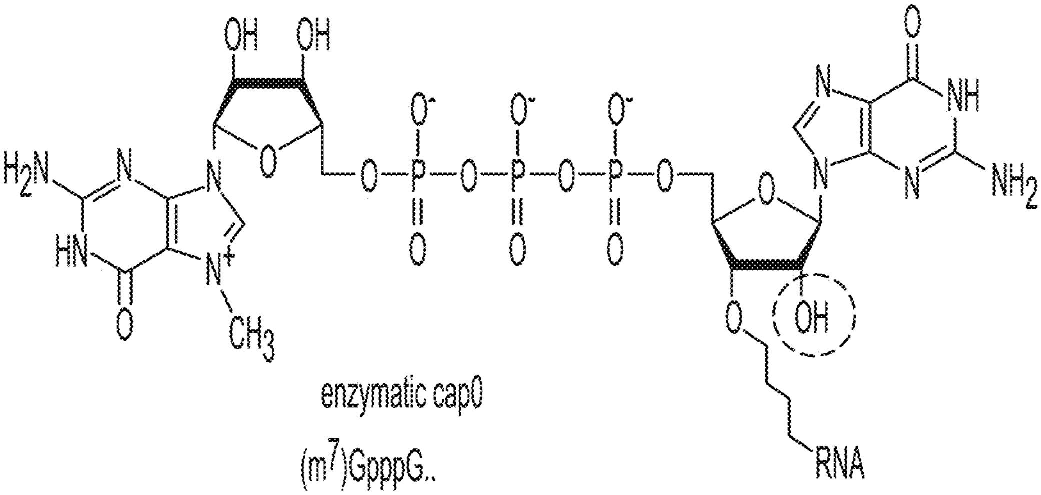
Figure 3D:
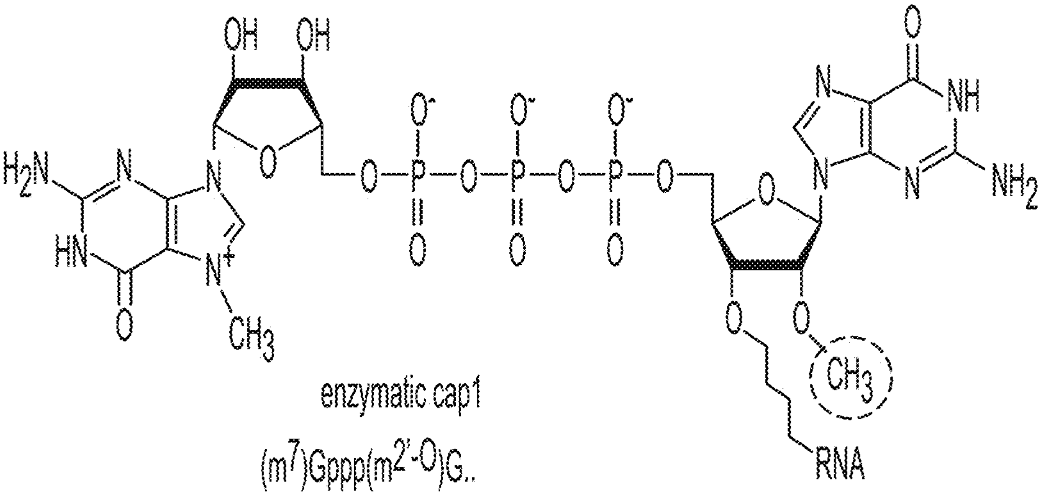
Figure 3E:
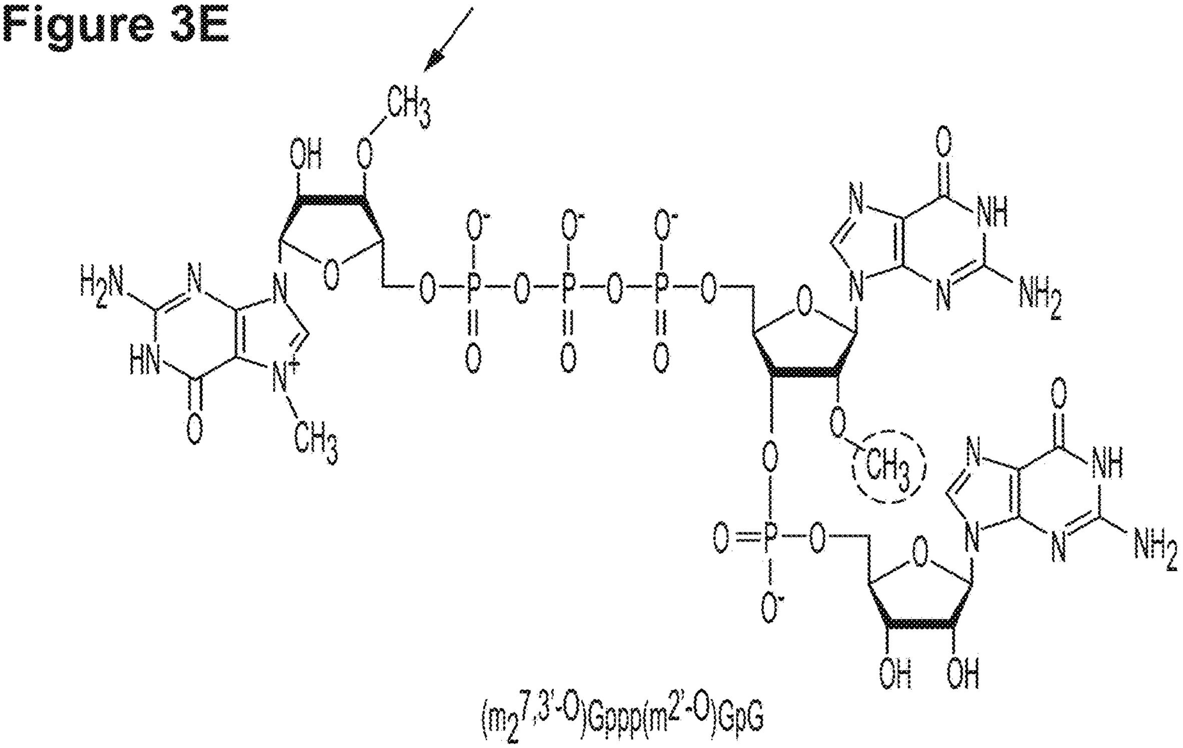
Figure 3F:
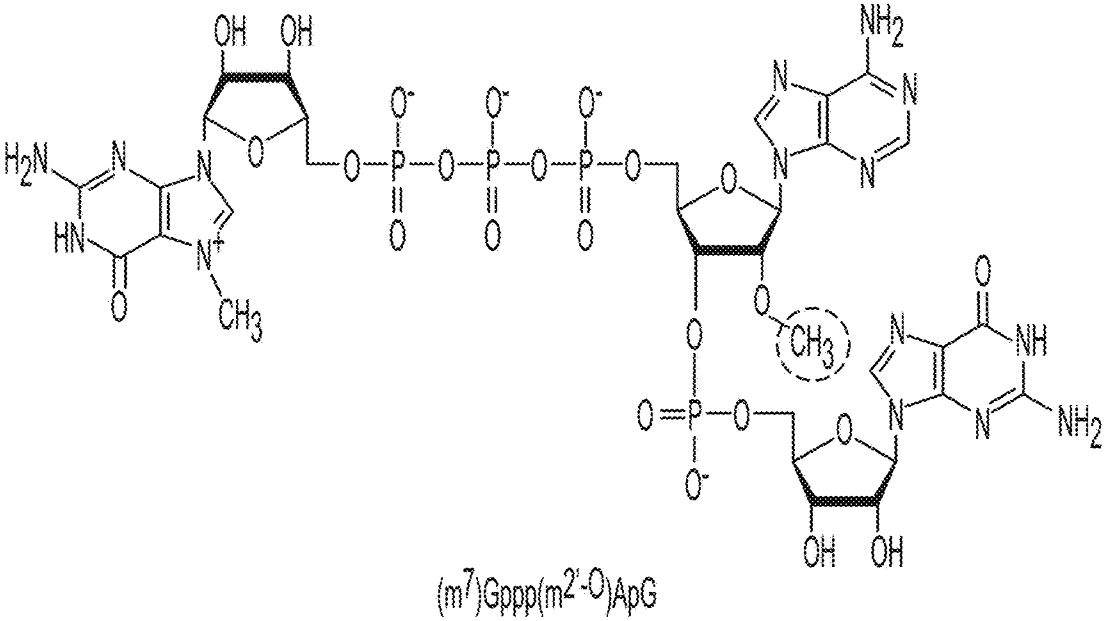
Figure 3G:
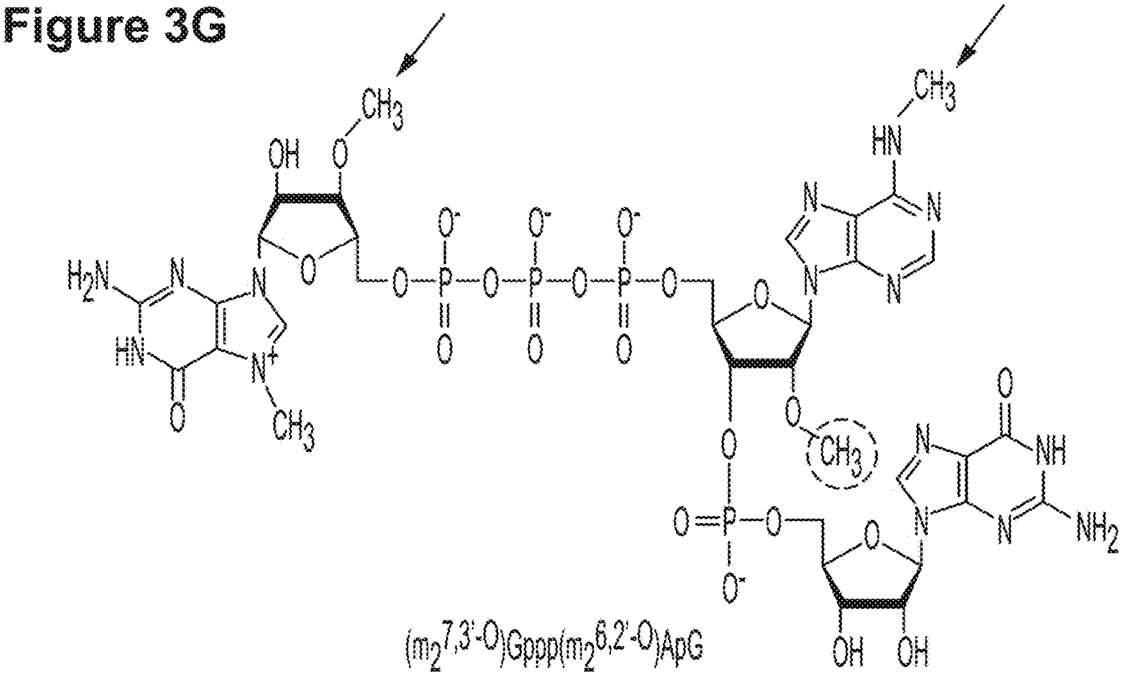
Figure 3H:
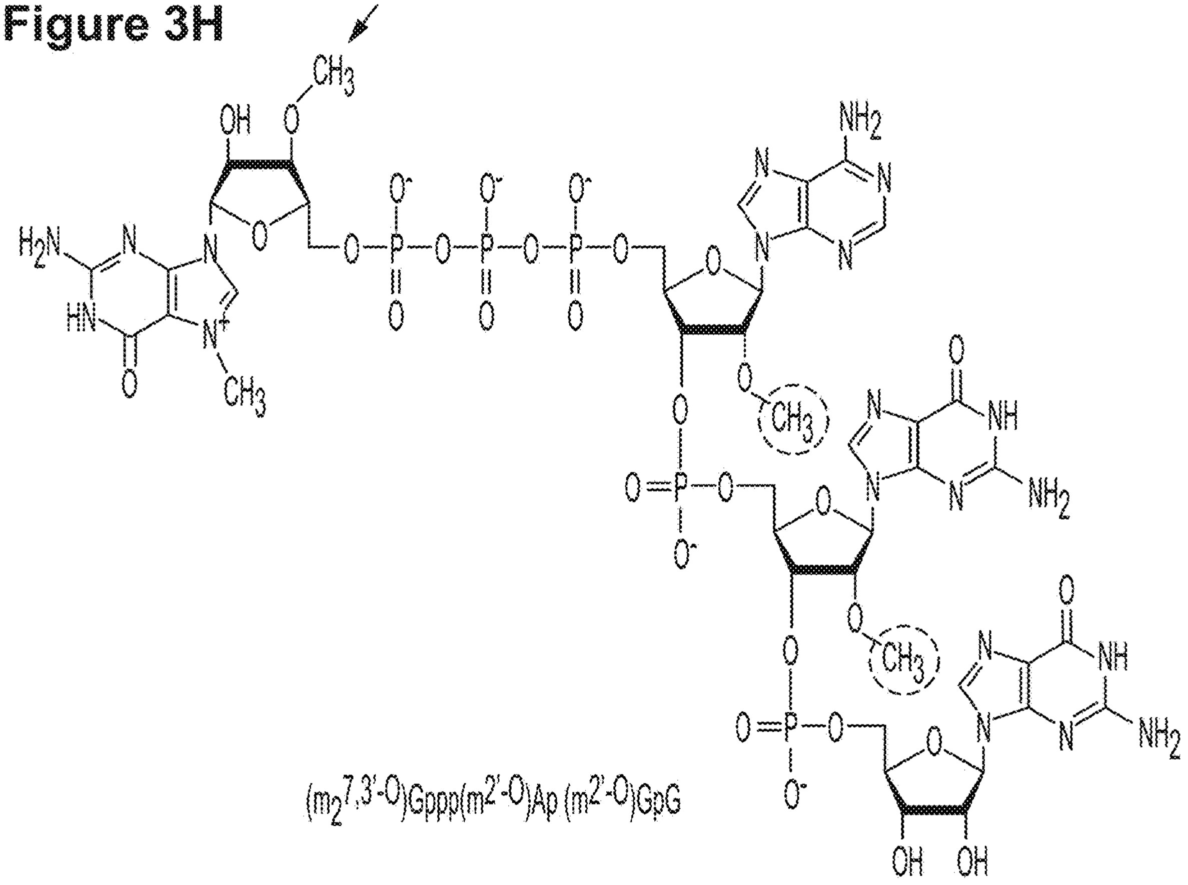
Figure 3I:
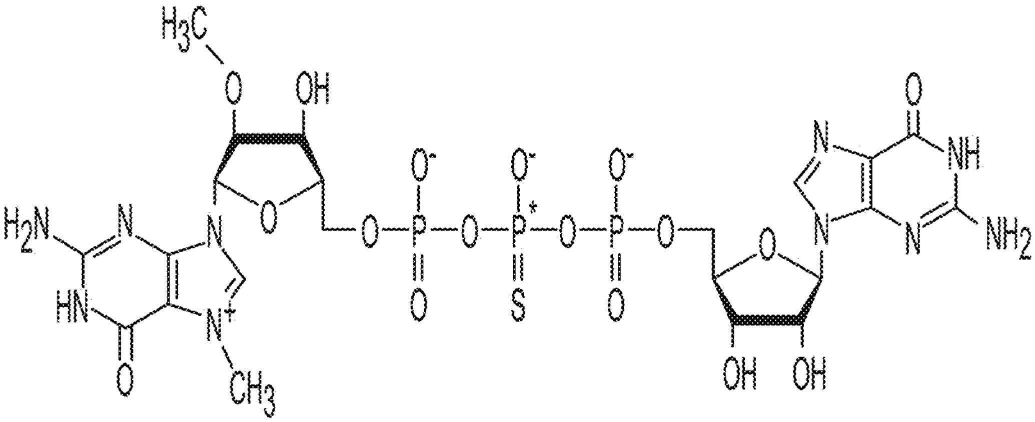

As shown in FIG. 1, expression of EPO from constructs that did not have the Lig3 sequence was more robust. The expression level of EPO in these animals was higher than the control (RNA with Lig3) at 24 hours and 48 hours post-administration, and the duration of expression of EPO was also longer, with significant amounts of EPO detected up to 72 hours after administration. This data demonstrates that absence of self-hybridizing sequence in a 3' UTR which can hybridize to other elements of the RNA, e.g., the 5' UTR or the 3' UTR itself as shown in FIG. 2, are beneficial for improving expression of an RNA encoded payload.

Next, additional sequence elements that could impact the expression of an RNA encoded payload were evaluated. One of the structural elements of an RNA which is required for translation and/or stability is a 5' cap. The different 5' Cap structures that can be used with an RNA are shown in FIGS. 3A-3H. It was previously shown that the IFIT1 (interferon-induced tetratricopeptide1) protein can bind to the 5'-end of the mRNA with very high affinity when the mRNA has a cap0 structure (PLoS pathogens (2013) 9, e1003663). The affinity of IFIT1's interaction with an mRNA reduces when it has a cap1 structure and this allows for preferential binding by translation factors such as the elongation factor eIF4E. Subsequently, it was also reported that the first 4 transcribed nucleotides at the 5'-end of the mRNA are located in a grove of the IFIT1 (PNAS (2017) 114(11): E2106-E2115). Based on these observations, it was hypothesized that the presence of a Cap1 structure on an RNA and the identity of the RNA sequence proximal to the 5' Cap (also referred herein as “cap proximal sequence”) could impact the expression of a payload encoded by the RNA.

Figure 4:
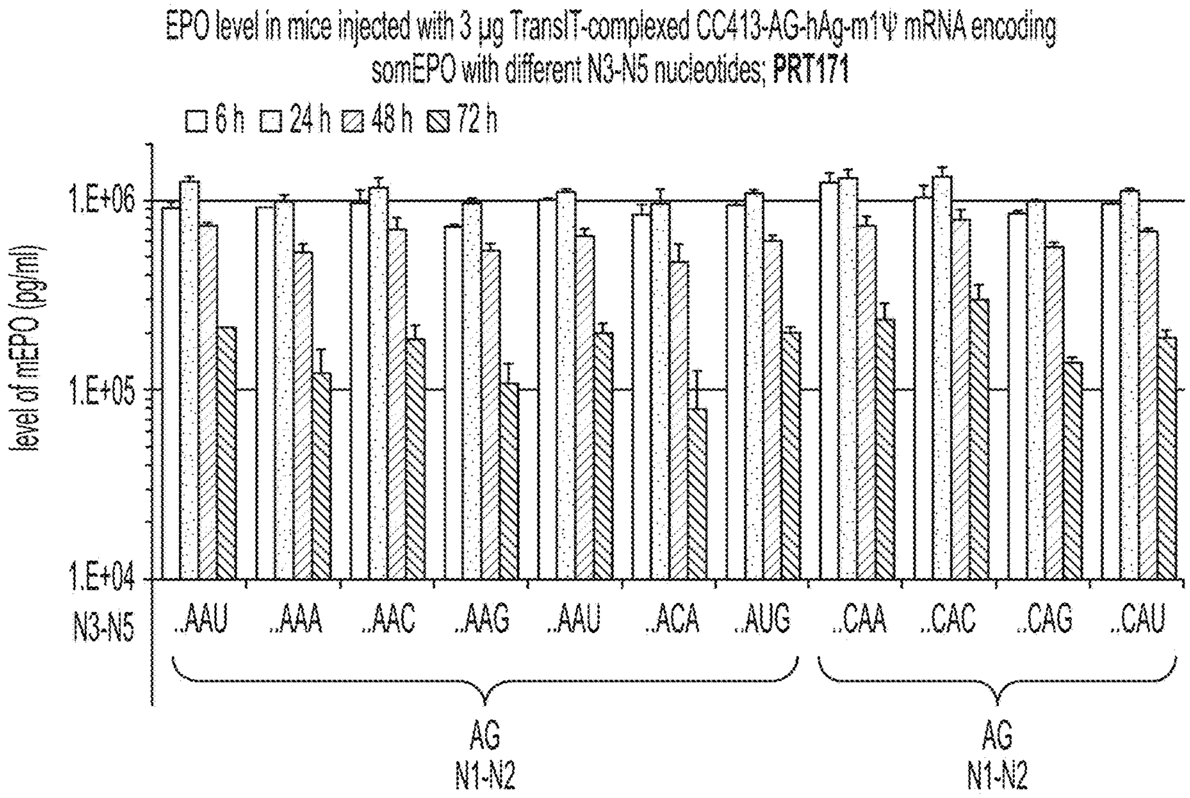
FIG. 4 demonstrates plasma levels of mEPO at 6, 24, 48 and 72 hours after intravenous administration of mice with mEPO mRNA constructs having different nucleotides at the +3, +4 or +5 positions. Blood was collected 6, 24, 48 and 72 hours after administration and samples were analyzed for mEPO levels via ELISA.

To test this hypothesis, RNAs having different residues in positions +3, +4 and +5 of the RNA sequence were generated and tested. Positions +1 and +2 of the RNA sequences tested were A and G respectively. Animals were injected intravenously with the various RNA constructs shown in FIG. 4. At 6, 24, 48, and 72 h after injection, blood was collected from the animals and assessed for expression of EPO—the polypeptide encoded by the RNA constructs.

EPO expression level at 6 hours and 24 hours after administration of RNA was comparable in all animals administered the various constructs. At 48 hours post-administration, some constructs resulted in better in vivo expression of EPO compared to others (compare AGAAU with AGACA at 48 hours). At 72 hours, the difference in in vivo EPO expression between animals dosed with the different constructs was even more significant with the AGACA construct showing more than a 10-fold reduced expression of EPO compared to several constructs including the AGAAU, AGAAC, AGCAA, AGCAC constructs.

This data demonstrates that the identity of the RNA sequences proximal to the 5' cap has a significant impact on the in vivo expression level and/or duration of expression of an RNA encoded payload. In some embodiments, this data suggests that an RNA construct having an optimized cap proximal RNA sequence with increased payload expression and/or duration of expression in vivo, allows for administration of a lower dose of said RNA or a composition comprising the same to an organism relative to a comparator, e.g., an RNA sequence without an optimized cap proximal sequence.

Example 2: Exemplary Coronavirus Vaccine Constructs

The present Example describes certain coronavirus vaccine RNAs. Exemplified constructs include sequences encoding at least one epitope of a coronavirus spike protein, and various other structural elements and/or features. Among other things, documents that exemplified RNAs including, for example, a cap1 structure and proximal cap sequences as described herein are well expressed and strongly immunogenic.

TABLE 2

Exemplary sequences used in this example.
TABLE 2: Exemplary sequences

| SEQ ID NO: | Description | SEQUENCE |
|---|---|---|
| | | Antigenic S protein sequences |
| 17 | S protein (amino acid) | MFVFLVLLPLVSSQCVNLTTRTQLPPAYTNSFTRGVYYPDKVFRSSVLHSTQDLFLPFFSNVTWFHAIHVSGTN<br>GTKRFDNPVLPFNDGVYFASTEKSNIIRGWIFGTTLDSKTQSLLIVNNATNVVIKVCEFQFCNDPFLGVYYHKN<br>NKSWMESEFRVYSSANNCTFEYVSQPFLMDLEGKQGNFKNLREFVFKNIDGYFKIYSKHTPINLVRDLPQGFSA<br>LEPLVDLPIGINITRFQTLLALHRSYLTPGDSSSGWTAGAAAYYVGYLQPRTFLLKYNENGTITDAVDCALDPL<br>SETKCTLKSFTVEKGIYQTSNFRVQPTESIVRFPNITNLCPFGEVFNATRFASVYAWNRKRISNCVADYSVLYN<br>SASFSTFKCYGVSPTKLNDLCFTNVYADSFVIRGDEVRQIAPGQTGKIADYNYKLPDDFTGCVIAWNSNNLDSK<br>VGGNYNYLYRLFRKSNLKPFERDISTEIYQAGSTPCNGVEGFNCYFPLQSYGFQPTNGVGYQPYRVVVLSFELL<br>HAPATVCGPKKSTNLVKNKCVNFNFNGLTGTGVLTESNKKFLPFQQFGRDIADTTDAVRDPQTLEILDITPCSF<br>GGVSVITPGTNTSNQVAVLYQDVNCTEVPVAIHADQLTPTWRVYSTGSNVFQTRAGCLIGAEHVNNSYECDIPI<br>GAGICASYQTQTNSPRRARSVASQSIIAYTMSLGAENSVAYSNNSIAIPTNFTISVTTEILPVSMTKTSVDCTM<br>YICGDSTECSNLLLQYGSFCTQLNRALTGIAVEQDKNTQEVFAQVKQIYKTPPIKDFGGFNFSQILPDPSKPSK<br>RSFIEDLLFNKVTLADAGFIKQYGDCLGDIAARDLICAQKFNGLTVLPPLLTDEMIAQYTSALLAGTITSGWTF<br>GAGAALQIPFAMQMAYRFNGIGVTQNVLYENQKLIANQFNSAIGKIQDSLSSTASALGKLQDVVNQNAQALNTL<br>VKQLSSNFGAISSVLNDILSRLDKVEAEVQIDRLITGRLQSLQTYVTQQLIRAAEIRASANLAATKMSECVLGQ<br>SKRVDFCGKGYHLMSFPQSAPHGVVFLHVTYVPAQEKNFTTAPAICHDGKAHFPREGVFVSNGTHWFVTQRNFY<br>EPQIITTDNTFVSGNCDVVIGIVNNTVYDPLQPELDSFKEELDKYFKNHTSPDVDLGDISGINASVVNIQKEID<br>RLNEVAKNLNESLIDLQELGKYEQYIKWPWYIWLGFIAGLIAIVMVTIMLCCMTSCCSCLKGCCSCGSCCKFDE<br>DDSEPVLKGVKLHYT |
| 18 | S protein (CDS) | auguuuguguuucuugugcugcugccucuugugucuucucagugugugaauuugacaacaagaacacagcugcc<br>accagcuuauacaaauucuuuuaccagaggaguguauuauccugauaaaguguuuagaucuucugugcugcaca<br>gcacacaggaccuguuucugccauuuuuuagcaaugugacaugguuucaugcaauucaugugucuggaacaaau<br>ggaacaaaaagauuugauaauccugugcugccuuuuaaugauggaguguauuuugcuucaacagaaaagucaaa<br>uauuauuagaggauggauuuuuggaacaacacuggauucuaaaacacagucucugcugauugugaauaaugcaa<br>caaauguggugauuaaagugugugaauuucaguuuuguaaugauccuuuucugggaguguauuaucacaaaaau<br>aauaaaucuuggauggaaucugaauuuagaguguauuccucugcaaauaauuguacauuugaauaugugucuca<br>gccuuuucugauggaucuggaaggaaaacagggcaauuuuaaaaaucugagagaauuuguguuuaaaaauauug<br>auggauauuuuaaaauuuauucuaaacacacaccaauuaauuuagugagagaucugccucagggauuuucugcu<br>cuggaaccucugguggaucugccaauuggcauuaauauuacaagauuucagacacugcuggcucugcacagauc<br>uuaucugacaccuggagauucuucuucuggauggacagccggagcugcagcuuauuaugugggcuaucugcagc<br>caagaacauuucugcugaaauauaaugaaaauggaacaauuacagaugcuguggauugugcucuggauccucug<br>ucugaaacaaaauguacauuaaaaucuuuuacaguggaaaaaggcauuuaucagacaucuaauuuuagagugca<br>gccaacagaaucuauugugagauuuccaaauauuacaaaucuguguccauuuggagaaguguuuaaugcaacaa<br>gauuugcaucuguguaugcauggaauagaaaaagaauuucuaauuguguggcugauuauucugugcuguauaau<br>agugcuucuuuuuccacauuuaaauguuauggagugucuccaacaaaauuaaaugauuuauguuuuacaaaugu<br>guaugcugauucuuuugugaucagaggugaugaagugagacagauugccccggacagacaggaaaaauugcug<br>auuacaauuacaaacugccugaugauuuuacaggaugugugauugcuuggaauucuaauaauuuagauucuaaa<br>gugggaggaaauuacaauuaucuguacagacuguuuagaaaaucaaaucugaaaccuuuugaaagagauauuuc<br>aacagaaauuuaucaggcuggaucaacaccuuguaauggaguggaaggauuuaauuguuauuuuccauuacaga<br>gcuauggauuucagccaaccaaugguguggauaucagccauauagagugguggcugucuuuugaacugcug<br>caugcaccugcaacagugugugg accuaaaaaaucuacaaauuuagugaaaaauaaaugugugaauuuuaauuu<br>uaauggauuaacaggaacaggagugcugacagaaucuaauaaaaaauuucugccuuuucagcaguuuggcagag<br>auauugcagauaccacagaugcagugagagauccucagacauuagaaauucuggauauuacaccuuguucuuuu<br>gggggugugucugugauuacaccuggaacaaauacaucuaaucagguggcugugcuguaucaggaugugaauug<br>uacagaagugccaguggcaauucaugcagaucagcugacaccaacauggagaguguauucuacaggaucuaaug<br>uguuucagacaagagcaggaugucugauuggagcagaacaugugaauaauucuuaugaaugugauauuccaauu<br>ggagcaggcauuugugcaucuuaucagacacagacaaauuccccaaggagagcaagaucuguggcaucucaguc<br>uauuauugcauacaccaugucucugggagcagaaaauucuguggcauauucuaauaauucuauugcuauuccaa<br>caaauuuuaccauuucugugacaacagaaauuuuaccugugucuaugacaaaaacaucuguggauuguaccaug<br>uacauuuguggagauucuacagaauguucuaaucugcugcugcaguauggaucuuuuuguacacagcugaauag<br>agcuuuaacaggaauugcuguggaacaggauaaaaauacacaggaaguguuugcucaggugaaacagauuuaca<br>aaacaccaccaauuaaagauuuuggaggauuuaauuuuagccagauucugccugauccuucuaaaccuucuaaa<br>agaucuuuuauugaagaucugcuguuuaauaaagugacacuggcagaugcaggauuuauuaaacaguauggaga<br>uugccugggugauauugcugcaagagaucugauuugugcucagaaauuuaauggacugacagugcugccuccuc<br>ugcugacagaugaaaugauugcucaguacacaucugcuuuacuggcuggaacaauuacaagcggauggacauuu<br>ggagcuggagcugcucugcagauuccuuuugcaaugcagauggcuuacagauuuaauggaauuggagugacaca<br>gaauguguuauaugaaaaucagaaacugauugcaaaucaguuuaauucugcaauuggcaaaauucaggauucuc<br>ugucuucuacagcuucugcucugggaaaacugcaggauguggugaaucagaaugcacaggcacugaauacucug<br>gugaaacagcugucuagcaauuuuggggcaauuucuucugugcugaaugauauucugucuagacuggauaaagu<br>ggaagcugaagugcagauugauagacugaucacaggaagacugcagucucugcagacuuaugugacacagcagc<br>ugauuagagcugcugaaauuagagcuucugcuaaucuggcugcuacaaaaaugucugaaugugugcugggacag<br>ucaaaaagaguggauuuuuguggaaaaggauaucaucugaugucuuuuccacagucugcuccacauggaguggu<br>guuuuuacaugugacauaugugccagcacaggaaaagaauuuuaccacagcaccagcaauuugucaugauggaa<br>aagcacauuuuccaagagaaggaguguuugugucuaauggaacacauugguuugugacacagagaaauuuuuau<br>gaaccucagauuauuacaacagauaauacauuugugucaggaaauugugauguggugauuggaauugugaauaa<br>uacaguguaugauccacugcagccagaacuggauucuuuuaaagaagaacuggauaaauauuuuaaaaaucaca<br>caucuccugauguggauuuaggagauauuucuggaaucaaugcaucugguggugaauauucagaaagaaauugau<br>agacugaaugaaguggccaaaaaucugaaugaaucucugauugaucugcaggaacuuggaaaauaugaacagua<br>cauuaaauggccuugguacauuuggcuuggauuuauugcaggauuaauugcaauugugauggugacaauuaugu<br>uauguuguaugacaucauguuguucuuguuuaaaaggauguuguucuuguggaagcuguuguaaauuugaugaa<br>gaugauucugaaccuguguuaaaaggagugaaauugcauuacaca |

TABLE 2-continued

Exemplary sequences used in this example.
TABLE 2: Exemplary sequences

| SEQ ID NO: | Description | SEQUENCE |
| --- | --- | --- |
| 19 | S protein RBD (amino acid)(V05) | MFVFLVLLPLVSSQCVVRFPNITNLCPFGEVFNATRFASVYAWNRKRISNCVADYSVLYNSASFSTFKCYGVSP<br>TKLNDLCFTNVYADSFVIRGDEVRQIAPGQTGKIADYNYKLPDDFTGCVIAWNSNNLDSKVGGNYNYLYRLFRK<br>SNLKPFERDISTEIYQAGSTPCNGVEGFNCYFPLQSYGFQPTNGVGYQPYRVVVLSFELLHAPATVCGPK |
| 20 | S protein RBD (CDS)(V05) | auguuuguguuucuugugcugcugccucuugugucuucucagugugugguggagauuuccaaauauuacaaaucu<br>guguccauuuggagaaguguuuaaugcaacaagauuugcaucuguguaugcauggaauagaaaaagaauuucua<br>auuguguggcugauuauucugugcuguauaauagugcuucuuuuuccacauuuaaauguuauggagugucucca<br>acaaaauuaaaugauuuauguuuuacaaauguguaugcugauucuuuugugaucagaggugaugaagugagaca<br>gauugcccccggacagacaggaaaaauugcugauuacaauuacaaacugccugaugauuuuacaggauguguga<br>uugcuuggaauucuaauaauuuagauucuaaagugggaggaaauuacaauuaucuguacagacuguuuagaaaa<br>ucaaaucugaaaccuuuugaaagagauauuucaacagaaauuuaucaggcuggaucaacaccuuguaauggagu<br>ggaaggauuuaauuguuauuuuccauuacagagcuauggauuucagccaaccaauggugugggauaucagccau<br>auagagugguggugcugucuuuugaacugcugcaugcaccugcaacagugugugg accuaaa |
| 21 | S protein RBD/ Fibritin (amino acid) (V05) | MFVFLVLLPLVSSQCVVRFPNITNLCPFGEVFNATRFASVYAWNRKRISNCVADYSVLYNSASFSTFKCYGVSP<br>TKLNDLCFTNVYADSFVIRGDEVRQIAPGQTGKIADYNYKLPDDFTGCVIAWNSNNLDSKVGGNYNYLYRLFRK<br>SNLKPFERDISTEIYQAGSTPCNGVEGFNCYFPLQSYGFQPTNGVGYQPYRVVVLSFELLHAPATVCGPKGSPG<br>SGSGSGYIPEAPRDGQAYVRKDGEWVLLSTFLGRSLEVLFQGPG |
| 22 | S protein RBD/ Fibritin (CDS)(V05) | auguuuguguuucuugugcugcugccucuugugucuucucagugugugguggagauuuccaaauauuacaaaucu<br>guguccauuuggagaaguguuuaaugcaacaagauuugcaucuguguaugcauggaauagaaaaagaauuucua<br>auuguguggcugauuauucugugcuguauaauagugcuucuuuuuccacauuuaaauguuauggagugucucca<br>acaaaauuaaaugauuuauguuuuacaaauguguaugcugauucuuuugugaucagaggugaugaagugagaca<br>gauugcccccggacagacaggaaaaauugcugauuacaauuacaaacugccugaugauuuuacaggauguguga<br>uugcuuggaauucuaauaauuuagauucuaaagugggaggaaauuacaauuaucuguacagacuguuuagaaaa<br>ucaaaucugaaaccuuuugaaagagauauuucaacagaaauuuaucaggcuggaucaacaccuuguaauggagu<br>ggaaggauuuaauuguuauuuuccauuacagagcuauggauuucagccaaccaauggugugggauaucagccau<br>auagagugguggugcugucuuuugaacugcugcaugcaccugcaacagugugugg accuaaaggcucccccggc<br>uccggcuccggaucugguuauauuccugaagcuccaagagaugggcaagcuuacguucguaaagauggcgaaug<br>gguauuacuuucuaccuuuuuaggccggucccuggaggugcuguuccagggccccggc |
| 9 | S protein PP (amino acid) (V08/V09) | MFVFLVLLPLVSSQCVNLTTRTQLPPAYTNSFTRGVYYPDKVFRSSVLHSTQDLFLPFFSNVTWFHAIHVSGTN<br>GTKRFDNPVLPFNDGVYFASTEKSNIIRGWIFGTTLDSKTQSLLIVNNATNVVIKVCEFQFCNDPFLGVYYHKN<br>NKSWMESEFRVYSSANNCTFEYVSQPFLMDLEGKQGNFKNLREFVFKNIDGYFKIYSKHTPINLVRDLPQGFSA<br>LEPLVDLPIGINITRFQTLLALHRSYLTPGDSSSGWTAGAAAYYVGYLQPRTFLLKYNENGTITDAVDCALDPL<br>SETKCTLKSFTVEKGIYQTSNFRVQPTESIVRFPNITNLCPFGEVFNATRFASVYAWNRKRISNCVADYSVLYN<br>SASFSTFKCYGVSPTKLNDLCFTNVYADSFVIRGDEVRQIAPGQTGKIADYNYKLPDDFTGCVIAWNSNNLDSK<br>VGGNYNYLYRLFRKSNLKPFERDISTEIYQAGSTPCNGVEGFNCYFPLQSYGFQPTNGVGYQPYRVVVLSFELL<br>HAPATVCGPKKSTNLVKNKCVNFNFNGLTGTGVLTESNKKFLPFQQFGRDIADTTDAVRDPQTLEILDITPCSF<br>GGVSVITPGTNTSNQVAVLYQDVNCTEVPVAIHADQLTPTWRVYSTGSNVFQTRAGCLIGAEHVNNSYECDIPI<br>GAGICASYQTQTNSPRRARSVASQSIIAYTMSLGAENSVAYSNNSIAIPTNFTISVTTEILPVSMTKTSVDCTM<br>YICGDSTECSNLLLQYGSFCTQLNRALTGIAVEQDKNTQEVFAQVKQIYKTPPIKDFGGFNFSQILPDPSKPSK<br>RSFIEDLLFNKVTLADAGFIKQYGDCLGDIAARDLICAQKFNGLTVLPPLLTDEMIAQYTSALLAGTITSGWTF<br>GAGAALQIPFAMQMAYRFNGIGVTQNVLYENQKLIANQFNSAIGKIQDSLSSTASALGKLQDVVNQNAQALNTL<br>VKQLSSNFGAISSVLNDILSRLDPPEAEVQIDRLITGRLQSLQTYVTQQLIRAAEIRASANLAATKMSECVLGQ<br>SKRVDFCGKGYHLMSFPQSAPHGVVFLHVTYVPAQEKNFTTAPAICHDGKAHFPREGVFVSNGTHWFVTQRNFY<br>EPQIITTDNTFVSGNCDVVIGIVNNTVYDPLQPELDSFKEELDKYFKNHTSPDVDLGDISGINASVVNIQKEID<br>RLNEVAKNLNESLIDLQELGKYEQYIKWPWYIWLGFIAGLIAIVMVTIMLCCMTSCCSCLKGCCSCGSCCKFDE<br>DDSEPVLKGVKLHYT |
| 23 | S protein PP (CDS)(V08) | auguuuguguuucuugugcugcugccucuugugucuucucagugugugaauuugacaacaagaacacagcugcc<br>accagcuuauacaaauucuuuuaccagaggaguguauuauccugauaaaguguuuagaucuucugugcugcaca<br>gcacacaggaccuguuucugccauuuuuuagcaaugugacaugguuucaugcaauucaugugucuggaacaaau<br>ggaacaaaaagauuugauaauccugugcugccuuuuaaugauggaguguauuuugcuucaacagaaaagucaaa<br>uauuauuagaggauggauuuuuggaacaacacuggauucuaaaacacagucucugcugauugugaauaaugcaa<br>caaauguggugauuaaagugugugaauuucaguuuuguaaugauccuuuucugggaguguauuaucacaaaaau<br>aauaaaucuuggauggaaucugaauuuagaguguauuccucugcaaauaauuguacauuugaauaugugucuca<br>gccuuuucugauggaucuggaaggaaaacagggcaauuuuaaaaaucugagagaauuuguguuuaaaaauauug<br>auggauauuuuaaaauuuauucuaaacacacaccaauuaauuuagugagagaucugccucagggauuuucugcu<br>cuggaaccucugguggaucugccaauuggcauuaauauuacaagauuucagacacugcuggcucugcacagauc<br>uuaucugacaccuggagauucuucuucuggauggacagccggagcugcagcuuauuauguggg cuaucugcagc<br>caagaacauuucugcugaaauauaaugaaaauggaacaauuacagaugcuguggauugugcucuggauccucug<br>ucugaaacaaaauguacauuaaaaucuuuuacaguggaaaaaggcauuuaucagacaucuaauuuuagagugca<br>gccaacagaaucuauugugagauuuccaaauauuacaaaucuguguccauuuggagaaguguuuaaugcaacaa<br>gauuugcaucuguguaugcauggaauagaaaaagaauuucuaauuguguggcugauuauucugugcuguauaau<br>agugcuucuuuuuccacauuuaaauguuauggagugucuccaacaaaauuaaaugauuuauguuuuacaaaugu<br>guaugcugauucuuuugugaucagaggugaugaagugagacagauugcccccggacagacaggaaaaauugcug<br>auuacaauuacaaacugccugaugauuuuacaggaugugugauugcuuggaauucuaauaauuuagauucuaaa<br>gugggaggaaauuacaauuaucuguacagacuguuuagaaaaucaaaucugaaaccuuuugaaagagauauuuc<br>aacagaaauuuaucaggcuggaucaacaccuuguaauggaguggaaggauuuaauuguuauuuuccauuacaga<br>gcuauggauuucagccaaccaauggugugggauaucagccauauagagugguggugcugucuuuugaacugcug<br>caugcaccugcaacagugugugg accuaaaaaaucuacaaauuuagugaaaaauaaaugugugaauuuuaauuu |

TABLE 2-continued

Exemplary sequences used in this example.
TABLE 2: Exemplary sequences

| SEQ ID NO: Description | SEQUENCE |
|---|---|
| | uaauggauuaacaggaacaggagugcugacagaaucuaauaaaaaauuucugccuuuucagcaguuuggcagag<br>auauugcagauaccacagaugcagugagagauccucagacauuagaaauucuggauauuacaccuuguucuuuu<br>gggggugugucugugauuacaccuggaacaaauacaucuaaucagguggcugugcuguaucaggaugugaauug<br>uacagaagugccaguggcaauucaugcagaucagcugacaccaacauggagaguguauucuacaggaucuaaug<br>uguuucagacaagagcaggaugucugauuggagcagaacaugugaauaauucuuaugaaugugauauuccaauu<br>ggagcaggcauuugugcaucuuaucagacacagacaaauuccccaaggagagcaagaucuguggcaucucaguc<br>uauuauugcauacaccaugucucugggagcagaaaauucuguggcauauucuaauaauucuauugcuauuccaa<br>caaauuuuaccauuucugugacaacagaaauuuuaccugugucuaugacaaaaacaucuguggauuguaccaug<br>uacauuuguggagauucuacagaauguucuaaucugcugcugcaguauggaucuuuuuguacacagcugaauag<br>agcuuuaacaggaauugcuguggaacaggauaaaaauacacaggaaguguuugcucaggugaaacagauuuaca<br>aaacaccaccaauuaaagauuuuggaggauuuaauuuuagccagauucugccugauccuucuaaaccuucuaaa<br>agaucuuuuauugaagaucugcuguuuaauaaagugacacuggcagaugcaggauuuauuaaacaguauggaga<br>uugccugggugauauugcugcaagagaucugauuugugcucagaaauuuaauggacugacagugcugccuccuc<br>ugcugacagaugaaaugauugcucaguacacaucugcuuuacuggcuggaacaauuacaagcggauggacauuu<br>ggagcuggagcugcucugcagauuccuuuugcaaugcagauggcuuacagauuuaauggaauuggagugacaca<br>gaauguguuauaugaaaaucagaaacugauugcaaaucaguuuaauucugcaauuggcaaaauucaggauucuc<br>ugucuucuacagcuucugcucugggaaaacugcaggaugugggugaaucagaaugcacaggcacugaauacucug<br>gugaaacagcugucuagcaauuuuggggcaauuucuucugugcugaaugauauucugucuagacuggauccucc<br>ugaagcugaagugcagauugauagacugaucacaggaagacugcagucucugcagacuuaugugacacagcagc<br>ugauuagagcugcugaaauuagagcuucugcuaaucuggcugcuacaaaaaugucugaaugugugcugggacag<br>ucaaaaagaguggauuuuuguggaaaaggauaucaucugaugucuuuuccacagucugcuccacauggaguggu<br>guuuuuacaugugacauaugugccagcacaggaaaagaauuuuaccacagcaccagcaauuugucaugauggaa<br>aagcacauuuuccaagagaaggaguguuugugucuaauggaacacauugguuugugacacagagaaauuuuuau<br>gaaccucagauuauuacaacagauaauacauuugugucaggaaauugugaugugggugauuggaauugugaauaa<br>uacaguguaugauccacugcagccagaacuggauucuuuuaaagaagaacuggauaaauauuuuaaaaaucaca<br>caucuccugauguggauuuaggagauauuucuggaaucaaugcaucuguggugaauauucagaaagaaauugau<br>agacugaaugaaguggccaaaaaucugaaugaaucucugauugaucugcaggaacuuggaaaauaugaacagua<br>cauuaaauggccuugguacauuuggcuuggauuuauugcaggauuaauugcaauugugauggugacaauuaugu<br>uauguuguaugacaucauguuguucuuguuuaaaaggauguuguucuuguggaagcuguuguaaauuugaugaa<br>gaugauucugaaccuguguuaaaaggagugaaauugcauuacaca |
| 24 S protein PP (CDS)(V09) | auguucguguuccuggugcugcugccucugguguccagccagugugugaaccugaccaccagaacacagcugcc<br>uccagccuacaccaacagcuuuaccagaggcguguacuaccccgacaagguguucagauccagcgugcugcacu<br>cuacccaggaccuguuccugccuuucuucagcaacgugaccugguuccacgccauccacguguccggcaccaau<br>ggcaccaagagauucgacaaccccgugcugcccuucaacgacgggguguacuuugccagcaccgagaaguccaa<br>caucaucagaggcuggaucuucggcaccacacuggacagcaagacccagagccugcugaucgugaacaacgcca<br>ccaacguggucaucaaagugugcgaguuccaguucugcaacgaccccuuccugggcgucuacuaccacaagaac<br>aacaagagcuggauggaaagcgaguuccggguguacagcagcgccaacaacugcaccuucgaguacgugucca<br>gccuuuccugauggaccuggaaggcaagcagggcaacuucaagaaccugcgcgaguucguguuuaagaacaucg<br>acggcuacuucaagaucuacagcaagcacaccccuaucaaccucgugcgggaucugccucagggcuucucugcu<br>cuggaaccccugguggaucugcccaucggcaucaacaucacccgguuucagacacugcuggcccugcacagaag<br>cuaccugacaccuggcgauagcagcagcggauggacagcuggugccgccgcuuacuaugugggcuaccugcagc<br>cuagaaccuuccugcugaaguacaacgagaacggcaccaucaccgacgccguggauugugcucuggauccucug<br>agcgagacaaagugcacccugaaguccuucaccguggaaagggcaucuaccagaccagcaacuuccgggugca<br>gcccaccgaauccaucgugcgguuccccaauaucaccaaucugugccccuucggcgagguguucaaugccacca<br>gauucgccucuguguacgccuggaaccggaagcggaucagcaauugcguggccgacuacuccgugcuguacaac<br>uccgccagcuucagcaccuucaagugcuacggcguguccccuaccaagcugaacgaccugugcuucacaaacgu<br>guacgccgacagcuucgugauccggggagaugaagugcggcagauugccccuggacagacaggcaagaucgccg<br>acuacaacuacaagcugcccgacgacuucaccggcugugugauugccuggaacagcaacaaccuggacuccaaa<br>gucggcggcaacuacaauuaccuguaccggcuguuccggaaguccaaucugaagcccuucgagcgggacaucuc<br>caccgagaucuaucaggccggcagcaccccuuguaacmcguggaaggcuucaacugcuacuucccacugcaguc<br>cuacggcuuucagcccacaaauggcgugggcuaucagcccuacagagugguggugcugagcuucgaacugcugc<br>augccccugccacagugugcggcccuaagaaaagcaccaaucucgugaagaacaaaugcgugaacuucaacuuc<br>aacggccugaccggcaccggcgugcugacagagagcaacaagaaguuccugccauuccagcaguuuggccggga<br>uaucgccgauaccacagacgccguuagagauccccagacacuggaaauccuggacaucaccccuugcagcuucg<br>gcggagugucugugaucaccccuggcaccaacaccagcaaucagguggcagugcuguaccaggacgugaacugu<br>accgaagugcccguggccauucacgccgaucagcugacaccuacauggcggguguacuccaccggcagcaaugu<br>guuucagaccagagccggcugucugaucggagccgagcacgugaacaauagcuacgagugcgacauccccaucg<br>gcgcuggaaucugcgccagcuaccagacacagacaaacagcccucggagagccagaagcguggccagccagagc<br>aucauugccuacacaaugucucugggcgccgagaacagcguggccuacuccaacaacucuaucgcuauccccac<br>caacuucaccaucagcgugaccacagagauccugccuguguccaugaccaagaccagcguggacugcaccaugu<br>acaucugcggcgauuccaccgagugcuccaaccugcugcugcaguacggcagcuucugcacccagcugaauaga<br>gcccugacagggaucgccguggaacaggacaagaacacccaagagguguucgcccaagugaagcagaucuacaa<br>gaccccuccuaucaaggacuucggcggcuucaauuucagccagauucugcccgauccuagcaagcccagcaagc<br>ggagcuucaucgaggaccugcuguucaacaaagugacacuggccgacgccggcuucaucaagcaguauggcgau<br>ugucugggcgacauugccgccagggaucugauuugcgcccagaaguuuaacggacugacagugcugccuccucu<br>gcugaccgaugagaugaucgcccaguacacaucugcccugcuggccggcacaaucacaagcggcuggacauuug<br>gagcaggcgccgcucugcagauccccuuugcuaugcagauggccuaccgguucaacggcaucggagugacccag<br>aaugugcuguacgagaaccagaagcugaucgccaaccaguucaacagcgccaucggcaagauccaggacagccu<br>gagcagcacagcaagcgcccugggaaagcugcaggacguggucaaccagaaugcccaggcacugaacacccugg<br>ucaagcagcuguccuccaacuucggcgccaucagcucugugcugaacgauauccugagcagacuggacccuccu<br>gaggccgaggugcagaucgacagacugaucacaggcagacugcagagccuccagacauacgugacccagcagcu<br>gaucagagccgccgagauuagagccucugccaaucuggccgccaccaagaugucugagugugugcugggccaga |

TABLE 2-continued

| SEQ ID NO: Description | SEQUENCE |
|---|---|
| | Exemplary sequences used in this example. TABLE 2: Exemplary sequences |
| | gcaagagaguggacuuuugcggcaagggcuaccaccugaugagcuucccucagucugccccucacggcguggug uuucugcacgugacauaugugcccgcucaagagaagaauuucaccaccgcuccagccaucugccacgacggcaa agcccacuuuccuagagaaggcguguucguguccaacggcacccauugguucgugacacagcggaacuucuacg agccccagaucaucaccaccgacaacaccuucgugucuggcaacugcgacgucgugaucggcauugugaacaau accguguacgacccucugcagcccgagcuggacagcuucaaagaggaacuggacaaguacuuuaagaaccacac aagccccgacguggaccugggcgauaucagcggaaucaaugccagcgucgugaacauccagaaagagaucgacc ggcugaacgagguggccaagaaucugaacgagagccugaucgaccugcaagaacuggggaaguacgagcaguac aucaaguggcccugguacaucuggcugggcuuuaucgccggacugauugccaucgugauggucacaaucaugcu guguugcaugaccagcugcuguagcugccugaagggcuguuguagcuguggcagcugcugcaaguucgacgagg acgauucugagcccgugcugaagggcgugaaacugcacuacaca |
| | Foldon |
| 25 Foldon (amino acid) | GSGYIPEAPRDGQAYVRKDGEWVLLSTFLGRSLEVLFQGPG |
| 26 Foldon (CDS) | ggaucugguuauauuccugaagcuccaagagaugggcaagcuuacguucguaaagauggcgaaugguauuacu uucuaccuuuuuaggccggucccuggaggugcuguuccagggccccggc |
| | 5'-UTR (hAg-Kozak) |
| 27 5'-UTR | AACUAGUAUUCUUCUGGUCCCCACAGACUCAGAGAGAACCCGCCACC |
| | 3'-UTR (FI element) |
| 13 3'-UTR | CUGGUACUGCAUGCACGCAAUGCUAGCUGCCCCUUUCCCGUCCUGGGUACCCCGAGUCUCCCCCGACCUCGGGU CCCAGGUAUGCUCCCACCUCCACCUGCCCCACUCACCACCUCUGCUAGUUCCAGACACCUCCCAAGCACGCAGC AAUGCAGCUCAAAACGCUUAGCCUAGCCACACCCCCACGGGAAACAGCAGUGAUUAACCUUUAGCAAUAAACGA AAGUUUAACUAAGCUAUACUAACCCCAGGGUUGGUCAAUUUCGUGCCAGCCACACC |
| | A30L70 |
| 14 A30L70 | AAAAAAAAAAAAAAAAAAAAAAAAAAAAAAGCAUAUGACUAAAAAAAAAAAAAAAAAAAAAAAAAAAAAA AAAAAAAAAAAAAAAAAAAAAAAAAAAAAAAAAA |

Primary pharmacodynamics studies were performed in BALB/c mice to test the immunogenicity of the vaccine candidates shown in the following table.

TABLE 3

| Vaccine candidates | | |
|---|---|---|
| Vaccine | mRNA type | Vaccine encoded antigen |
| BNT162a1 | uRNA | RBD (Receptor Binding Domain) of SARS-CoV-2 Spike protein (S protein) |
| BNT162b1 | modRNA | RBD (Receptor Binding Domain) of SARS-CoV-2 Spike protein (S protein) |
| BNT162b2 | modRNA | Modified version of SARS-CoV-2 Spike protein (S protein) |
| BNT162c1 | saRNA | RBD (Receptor Binding Domain) of SARS-CoV-2 Spike protein (S protein) |

In the study, four groups of each eight female BALB/c mice were immunized once with the animal trial material at three different doses, or with buffer (control group; see Table 4). While the clinical trial material will be diluted in saline, the animal trial material was diluted in PBS including 300 mM sucrose. As this is the storage buffer of the material itself, the test items are representative for the vaccine that will be used in the planned clinical trials. Immunizations were given IM using a dose volume of 20 μL.

TABLE 4

| Study design | | | | | | |
|---|---|---|---|---|---|---|
| Group No | No of animals | Vaccine dose | Immunization on Day | Dose volume [μL]/route | Blood collection Day | End of in-life phase |
| 1 | 8 | buffer | 0 | 20/IM | 7, 14, 21 | 28 |
| 2 | 8 | Low | 0 | 20/IM | 7, 14, 21 | 28 |
| 3 | 8 | Medium | 0 | 20/IM | 7, 14, 21 | 28 |
| 4 | 8 | High | 0 | 20/IM | 7, 14, 21 | 28 |

Blood of immunized animals was collected on days 7, 14, 21 and 28, and analyzed for the antibody immune response by ELISA and pseudovirus-based neutralization assay (pVNT).

SARS-CoV-2-S specific antibody responses directed against the recombinant S1 subunit or the RBD were detected by ELISA. In brief, high protein-binding 96-well plates (MaxiSorp ELISA plates, VWR International GmbH, Cat. No. 7341284) were coated with 100 ng recombinant S1 subunit (Sino Biological Inc., Cat. No. 40591-V08H) or RBD (Sino Biological Inc., Cat. No. 40592-V02H) per well in 100 μL coating buffer (50 mM sodium carbonate-bicarbonate buffer, pH9.6) overnight at 4° C. Plates were washed three times with 300 μL/well 1× phosphate-buffered saline (PBS, VWR International GmbH, Cat. No. 0780-10L) supplemented with 0.01% Tween 20 (Carl Roth GmbH & Co. KG, Cat. No. 9127.1) and blocked with 250 μL/well 1× Casein Blocking Buffer (Sigma-Aldrich GmbH, Cat No.

B6429-500 ml) for 1 hour at 37° C. on a microplate shaker. Plates were again washed three times with 300 μL/well 1×PBS supplemented with 0.01% Tween 20 and incubated with mouse serum samples diluted in 1× Casein Blocking Buffer for 1 hour at 37° C. on a microplate shaker. Plates were washed three times with 300 μL/well 1×PBS supplemented with 0.01% Tween 20 and subsequently incubated with Peroxidase-conjugated goat anti-mouse secondary antibody (Jackson ImmunoResearch Ltd., Cat. No. 115-036-071; diluted 1:7500 in 1× Casein Blocking Buffer) for 45 minutes at 37° C. on a microplate shaker. Plates were washed three times with 300 μL/well 1×PBS supplemented with 0.01% Tween 20 and 100 μL/well TMB substrate (Biotrend Chemiekalien GmbH, Cat. No. 4380A) was added. Plates were incubated for 8 min at room temperature and the reaction stopped by addition of 100 μL 25% sulphuric acid (VWR International GmbH, Cat. No. 1007161000). Plates were read on a microplate reader and the recorded absorbance at 450 nm corrected by subtracting the reference absorbance at 620 nM.

Functional antibody responses to the vaccine candidates were detected by pVNT. The pVNT uses a replication-deficient vesicular stomatitis virus (VSV) that lacks the genetic information for the VSV envelope glycoprotein G but contains an open-reading frame (ORF) for green fluorescent protein (GFP). VSV/SARS-CoV-2 pseudovirus was generated according to a published protocol (Hoffmann et al., Cell, 2020; PMID 32142651). The pseudotype virus bears the SARS-CoV-2 S protein, which mediates cell entry. Therefore, the pseudovirus can be inactivated by neutralizing antibodies that bind SARS-CoV-2 S. This inactivation can be analyzed via in vitro methods.

In brief, $4\times10^4$ Vero 76 cells (ATCC® CRL-1587™) per well were seeded in a 96-well plate (Greiner Bio-One GmbH, Cat. No. 655160) in 150 μL/well DMEM (Thermo Fisher Scientific, Cat. No. 61965059) supplemented with 10% fetal bovine serum (FBS, Sigma-Aldrich GmbH, Cat. No. F7524). Cells were incubated for 4 to 6 hours at 37° C. and 7.5% $CO_2$. Meanwhile, mouse serum samples were diluted 1:6 up to 1:768 in DMEM/10% FBS in two-fold dilution steps. Diluted serum samples were combined with an equal volume of titrated and pre-diluted VSV/SARS CoV-2 pseudovirus supernatant, resulting in a serum dilution ranging from 1:12 up to 1:1536. The pseudovirus/serum dilution mix was incubated for 5 min at RT on a microplate shaker at 750 rpm with an additional 5 min incubation at RT without agitation. 50 μL/well pseudovirus/serum dilution mix was added to the seeded Vero-76 cells with the applied pseudovirus volume per well corresponding to 200 infectious units (IU). Each dilution of serum samples was tested in duplicate wells. Cells were incubated for 16 to 24 hours at 37° C. and 7.5% $CO_2$. Vero 76 cells incubated with pseudovirus in the absence of mouse sera were used as positive controls. Vero 76 cells incubated without pseudovirus were used as negative controls. After the incubation, the cell culture plates were removed from the incubator, placed in an IncuCyte Live Cell Analysis system (Essen Bioscience) and incubated for 30 min prior to the analysis. Whole well scanning for brightfield and GFP fluorescence was performed using a 4× objective. To calculate the neutralizing titer, infected GFP-positive cell number per well was compared with the pseudovirus positive control. Mean values of the pseudovirus positive control multiplied by 0.5 represent the pseudovirus neutralization 50% (pVN50). Serum samples with mean values below this cut-off exhibit >50% virus neutralization activity, respectively.

Immunogenicity Study of BNT162a1 (RBL063.3)

To dissect the potency of the LNP-formulated uRNA vaccine coding for BNT162a1, BALB/c mice were immunized IM once as outlined in Table 3. The immunogenicity of the RNA vaccine will be investigated by focusing on the antibody immune response.

Figure 5:
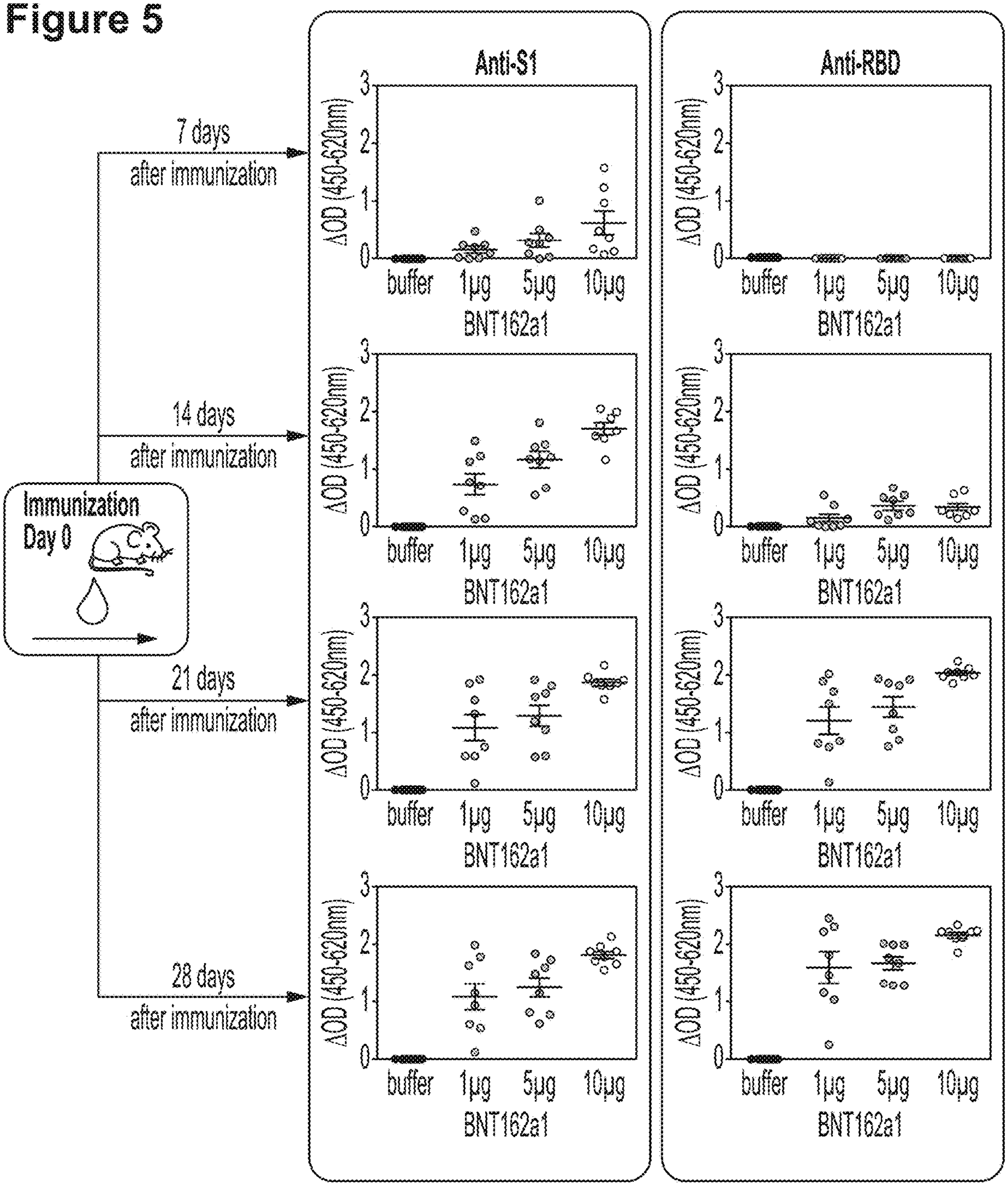
FIG. 5 demonstrates an anti-S protein IgG response 7, 14, 21 and 28 d after immunization with BNT162a1. BALB/c mice were immunized IM once with 1, 5 or 10 μg of LNP-formulated RBL063.3. On day 7, 14, 21 and 28 after immunization, animals were bled and the serum samples were analyzed for total amount of anti-S1 (left) and anti-RBD (right) antigen-specific immunoglobulin G (IgG) measured via ELISA. For day 7, day 14, day 21 and day 28, values for a serum dilution of 1:100 were included in the graph. One point in the graph stands for one mouse, every mouse sample was measured in duplicates (group size n=8; mean+SEM is included for the groups).

ELISA data 7, 14, 21 and 28 d after the first immunization show an early, dose-dependent immune activation against the S1 protein and the receptor binding domain (FIG. 5).

Immunogenicity Study of BNT162b1 (RBP020.3)

To dissect the potency of the LNP-formulated modRNA vaccine coding for BNT162b1, BALB/c mice were immunized IM once as outlined in Table 3. The immunogenicity of the RNA vaccine will be investigated by focusing on the antibody immune response.

Figure 6:
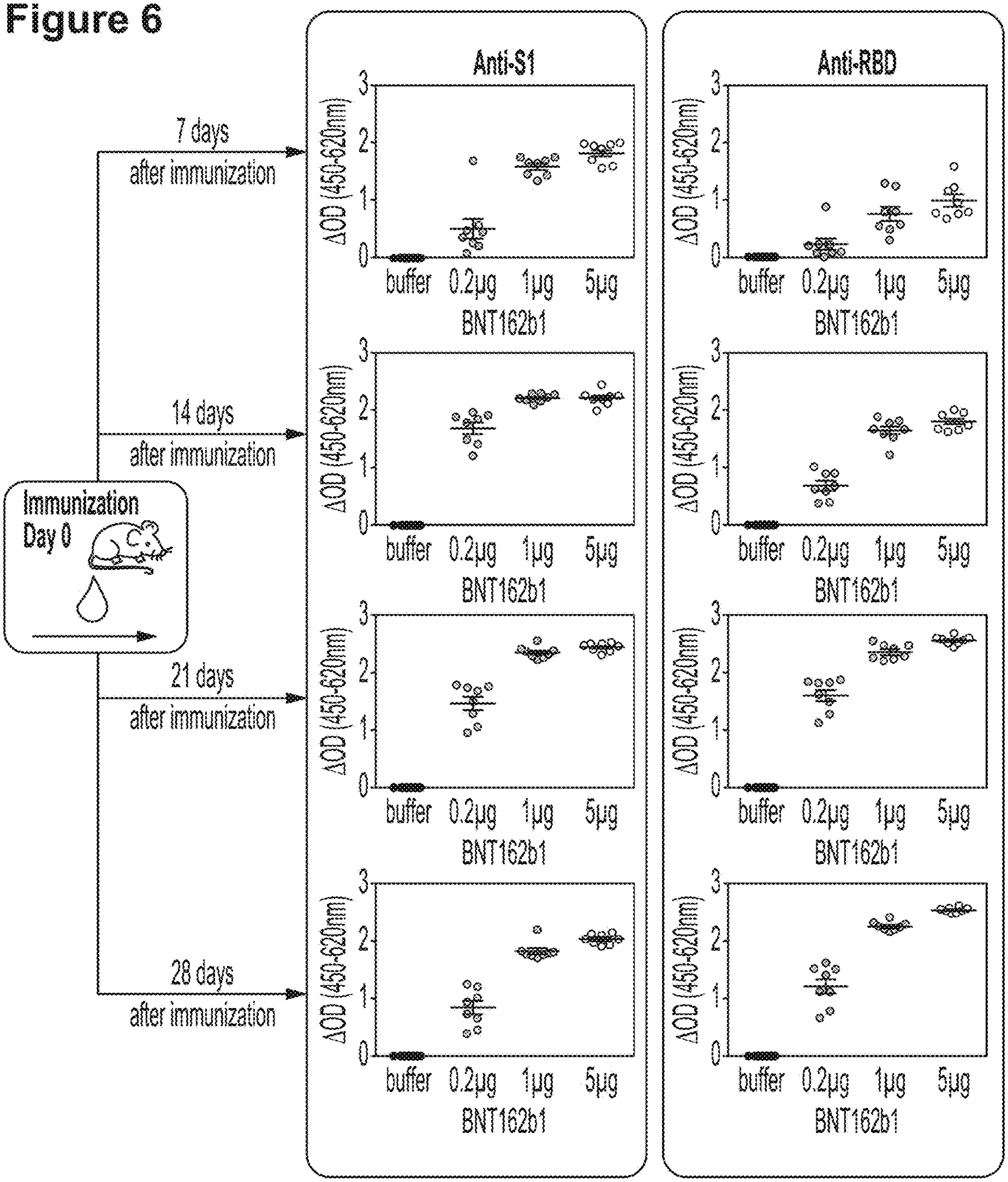
FIG. 6 demonstrates Anti-S protein IgG response 7, 14, 21 and 28 d after immunization with BNT162b1. BALB/c mice were immunized IM once with 0.2, 1 or 5 μg of LNP-formulated RBP020.3. On day 7, 14, 21 and 28 after immunization, animals were bled and the serum samples were analyzed for total amount of anti-S1 (left) and anti-RBD (right) antigen-specific immunoglobulin G (IgG) measured via ELISA. For day 7 (1:100), day 14 (1:300), day 21 (1:900), and day 28 (1:2700) different serum dilutions were included in the graph. One point in the graph stands for one mouse, every mouse sample was measured in duplicates (group size n=8; mean+SEM is included for the groups).
Figure 7:
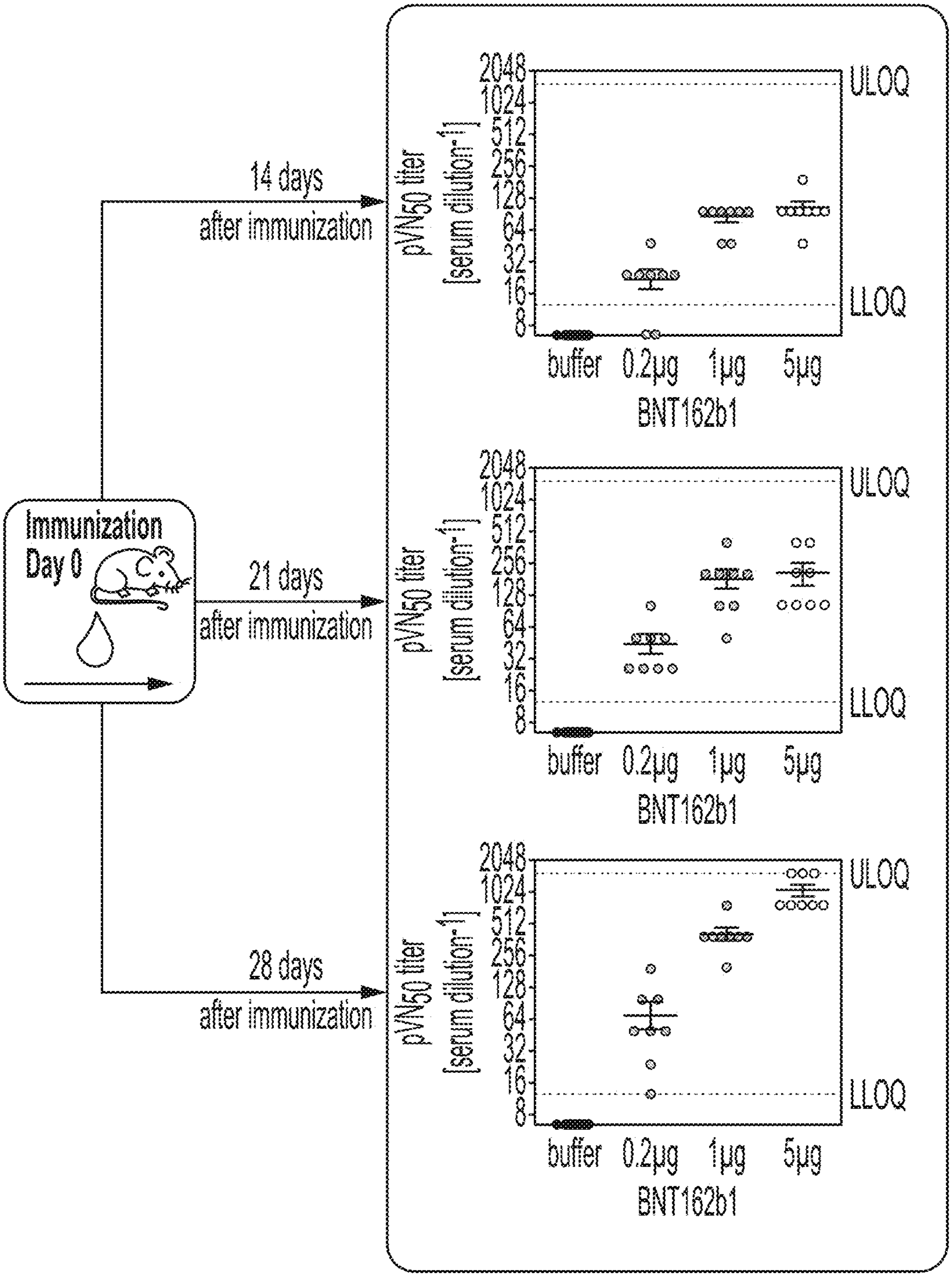
FIG. 7 demonstrates neutralization of SARS-CoV-2 pseudovirus 14, 21 and 28 d after immunization with BNT162b1. BALB/c mice were immunized IM once with 0.2, 1 or 5 μg of LNP-formulated RBP020.3. On 14, 21 and 28 d after immunization, animals were bled, and the sera were tested for SARS-CoV-2 pseudovirus neutralization. Graphs depict pVN50 serum dilutions (50% reduction of infectious events, compared to positive controls without serum). One point in the graphs stands for one mouse. Every mouse sample was measured in duplicate. Group size n=8. Mean+SEM is shown by horizontal bars with whiskers for each group. LLOQ, lower limit of quantification. ULOQ, upper limit of quantification.

ELISA data 7, 14, 21 and 28 d after the first immunization show an early, dose-dependent immune activation against the S1 protein and the receptor binding domain (FIG. 6). Sera obtained 14, 21, and 28 d after immunization show high SARS-CoV-2 pseudovirus neutralization, especially sera from mice immunized with 1 or 5 μg BNT162b1 and correlating with the strong increase of IgG antibody titers (FIG. 7).

Immunogenicity Study of BNT162c1 (RBS004.3)

To dissect the potency of the LNP-formulated saRNA vaccine coding for BNT162c1, BALB/c mice were immunized IM once as outlined in Table 3. The immunogenicity of the RNA vaccine will be investigated by focusing on the antibody immune response.

Figure 8:
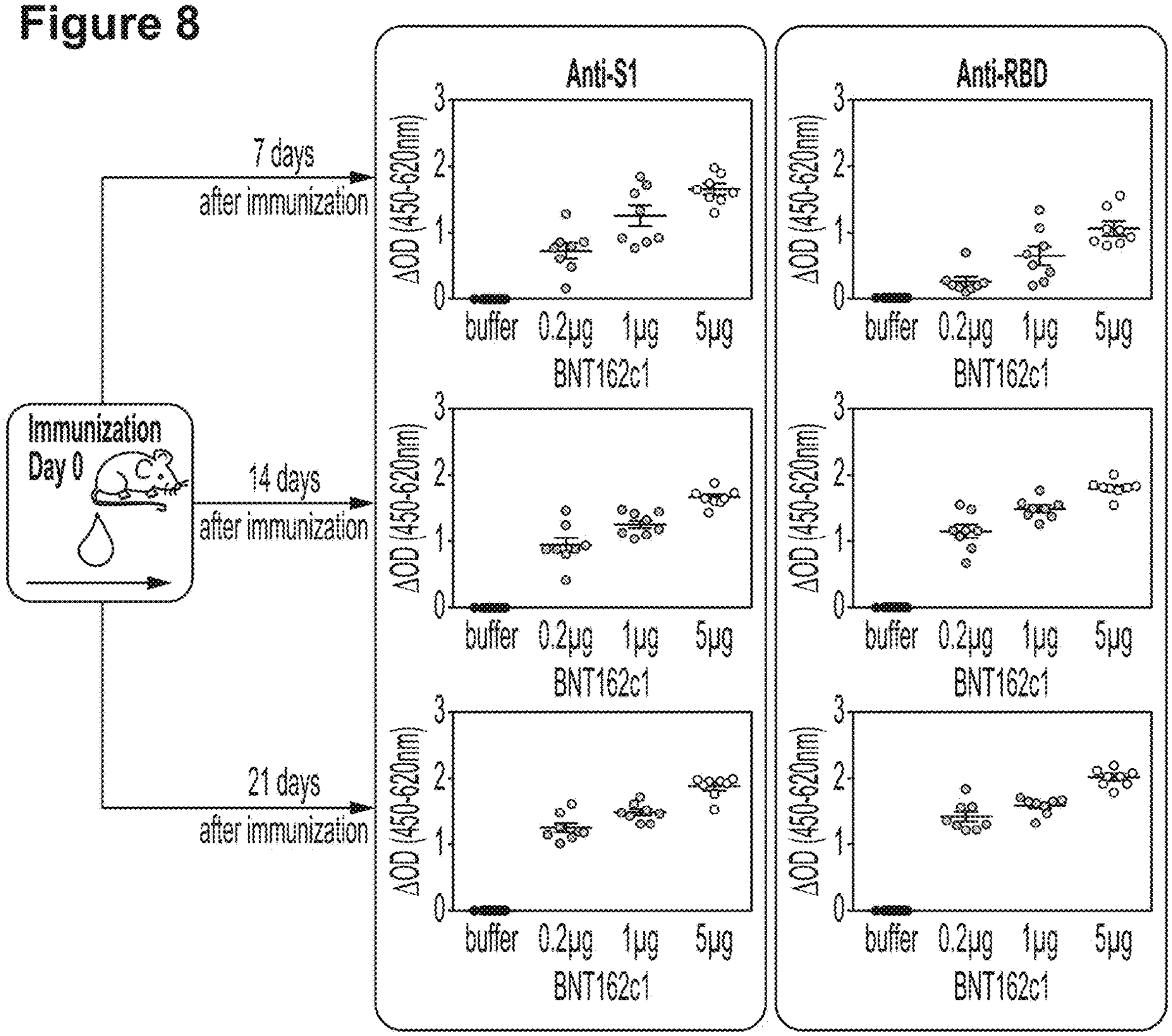
FIG. 8 demonstrates Anti-S protein IgG response 7, 14 and 21 d after immunization with BNT162c1. BALB/c mice were immunized IM once with 0.2, 1 or 5 μg of LNP-formulated RBS004.3. On day 7, 14 and 21 after immunization, animals were bled and the serum samples were analyzed for total amount of anti-S1 (left) and anti-RBD (right) antigen-specific immunoglobulin G (IgG) measured via ELISA. For day 7 (1:100), day 14 (1:300), and day 21 (1:900) different serum dilution were included in the graph. One point in the graph stands for one mouse, every mouse sample was measured in duplicates (group size n=8; mean+SEM is included for the groups).
Figure 9:
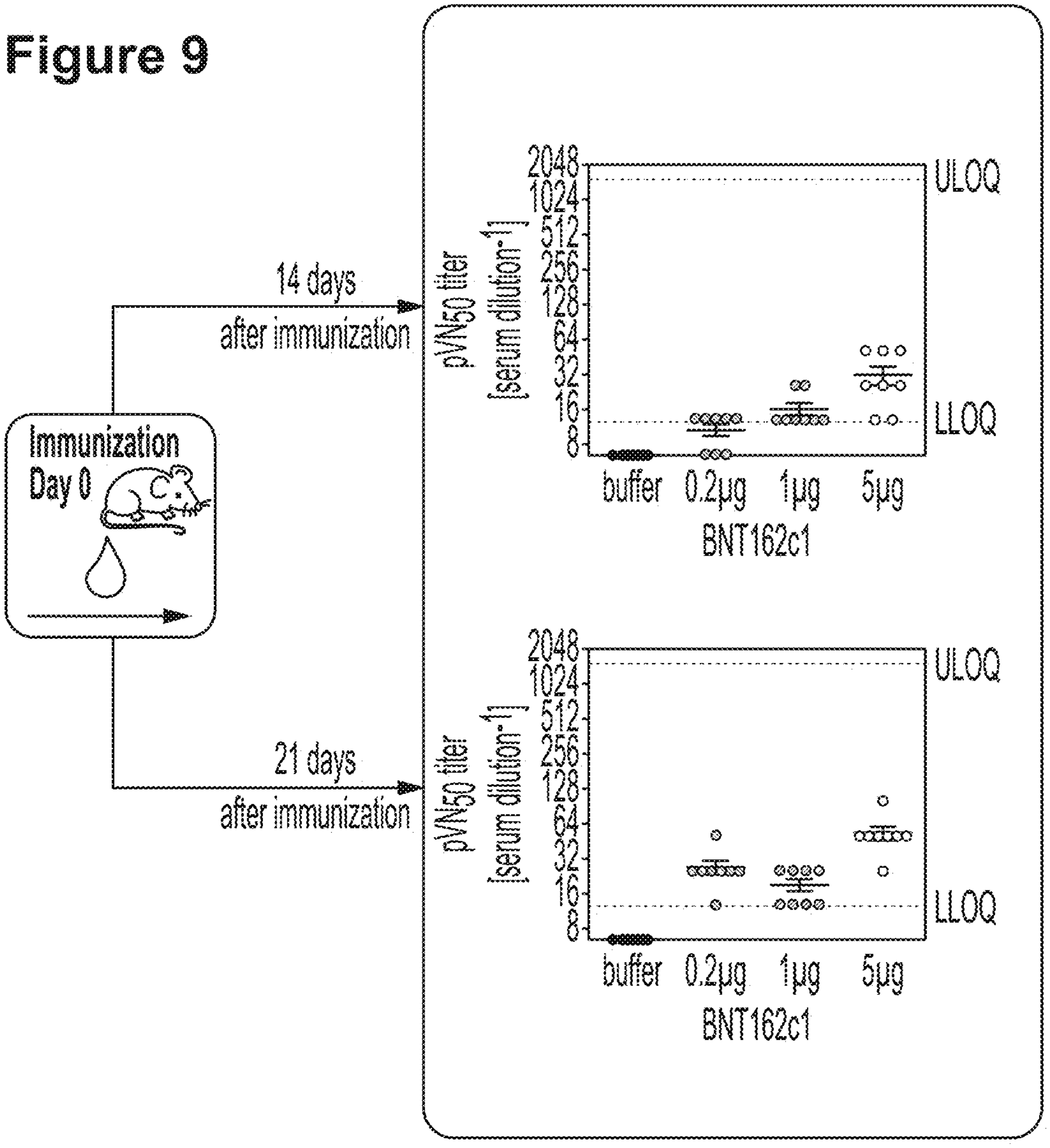
FIG. 9 demonstrates neutralization of SARS-CoV-2 pseudovirus 14 and 21 d after immunization with BNT162c1. BALB/c mice were immunized IM once with 0.2, 1 or 5 μg of LNP-formulated RBS004.3. On 14 and 21 d after immunization, animals were bled and the sera were tested for SARS-CoV-2 pseudovirus neutralization. Graphs depict pVN50 serum dilutions (50% reduction of infectious events, compared to positive controls without serum). One point in the graphs stands for one mouse. Every mouse sample was measured in duplicate. Group size n=8. Mean+SEM is shown by horizontal bars with whiskers for each group. LLOQ, lower limit of quantification. ULOQ, upper limit of quantification.

ELISA data 7, 14 and 21 d after the first immunization show an early, dose-dependent immune activation against the S1 protein and the receptor binding domain (FIG. 8). Sera obtained 14, and 21 d after immunization show dose-dependent SARS-CoV-2 pseudovirus neutralization activity (FIG. 9).

Immunogenicity Study of LNP-Formulated uRNA Encoding the Viral S Protein-V8 (SEQ ID NO: 7, 8) (RBL063.1)

To dissect the potency of the LNP-formulated uRNA vaccine coding for the viral S protein-V8 (RBL063.1), BALB/c mice were immunized IM once as outlined in Table 3. The immunogenicity of the RNA vaccine will be investigated by focusing on the antibody immune response.

Figure 10:
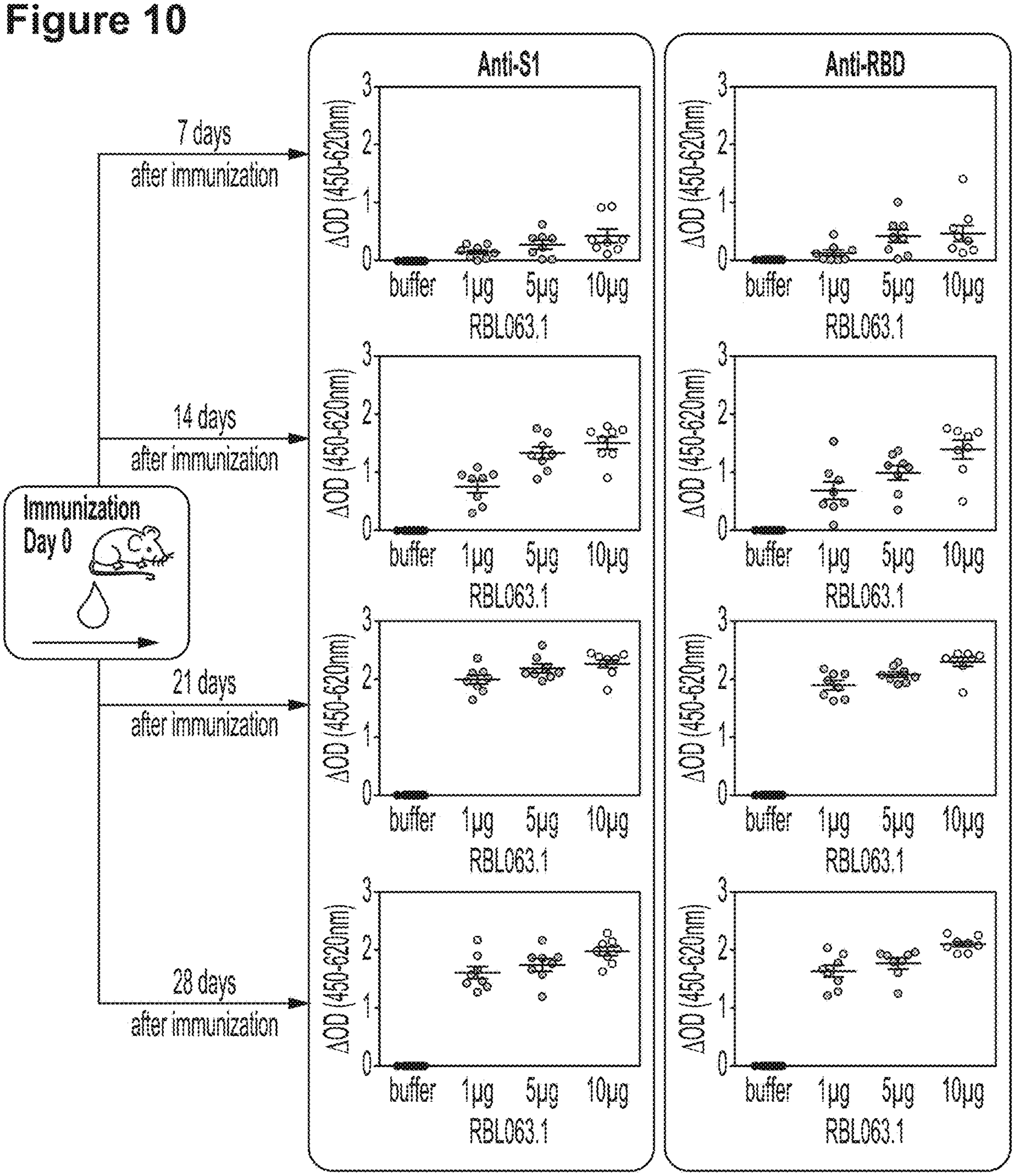
FIG. 10 demonstrates anti-S protein IgG response 7, 14, 21 and 28 d after immunization with LNP-formulated RBL063.1. BALB/c mice were immunized IM once with 1, 5 or 10 μg of LNP-formulated RBL063.1. On day 7, 14, 21 and 28 after immunization, animals were bled and the serum samples were analyzed for total amount of anti-S1 (left) and anti-RBD (right) antigen-specific immunoglobulin G (IgG) measured via ELISA. For day 7 (1:100), day 14 (1:100), day 21 (1:300) and day 28 (1:900) different serum dilution were included in the graph. One point in the graph stands for one mouse, every mouse sample was measured in duplicates (group size n=8; mean+SEM is included for the groups).
Figure 11:
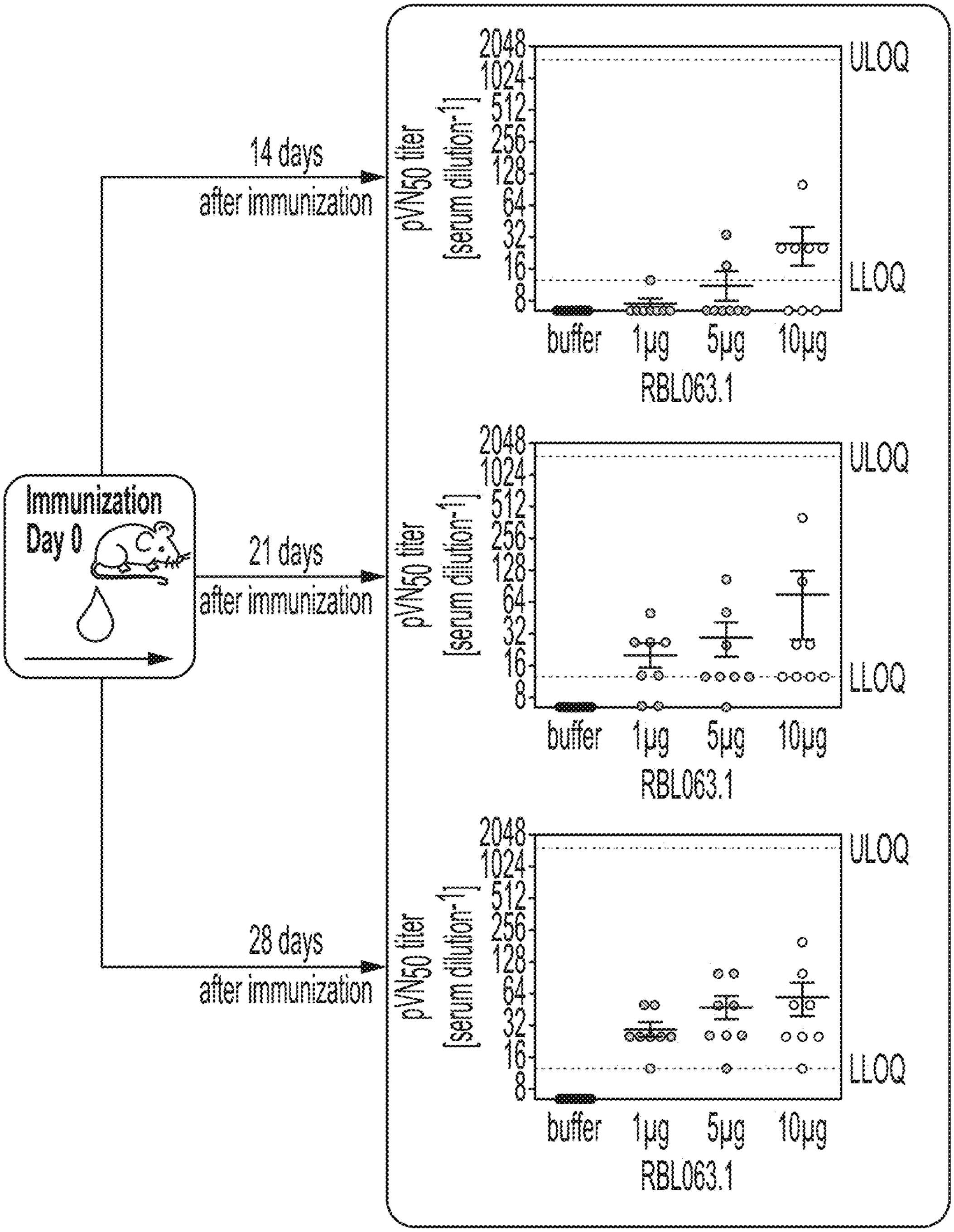
FIG. 11 shows neutralization of SARS-CoV-2 pseudovirus 14, 21 and 28 d after immunization with LNP-formulated RBL063.1. BALB/c mice were immunized IM once with 1, 5 or 10 μg of LNP-formulated RBL063.1. On 14, 21, and 28 d after immunization, animals were bled and the sera were tested for SARS-CoV-2 pseudovirus neutralization. Graphs depict pVN50 serum dilutions (50% reduction of infectious events, compared to positive controls without serum). One point in the graphs stands for one mouse. Every mouse sample was measured in duplicate. Group size n=8. Mean+SEM is shown by horizontal bars with whiskers for each group. LLOQ, lower limit of quantification. ULOQ, upper limit of quantification.

ELISA data 7, 14, 21 and 28 d after the first immunization are available that show an early, dose-dependent immune activation against the S1 protein and the receptor binding domain (FIG. 10). Sera obtained 14, 21 and 28 d after immunization show dose-dependent SARS-CoV-2 pseudovirus neutralization activity (FIG. 11).

Immunogenicity Study of BNT162b2 (RBP020.1)

To dissect the potency of the vaccine BNT162b2 (RBP020.1), the immunogenicity of the construct was investigated. For this purpose, a dose titration study in BALB/c mice was initiated where the immune response will be analyzed focusing on the antibody immune response.

Figure 12:
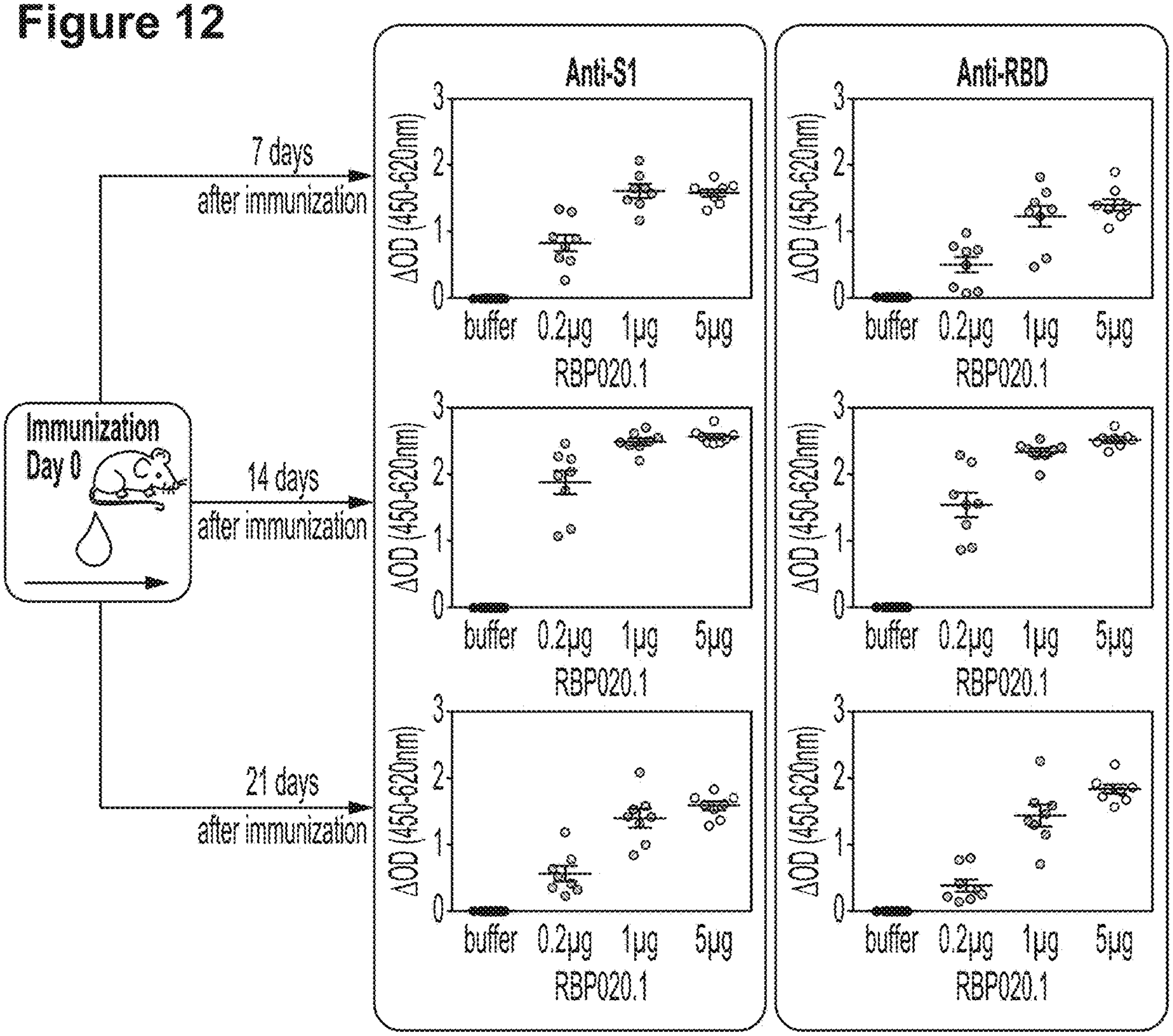
FIG. 12 shows Anti-S protein IgG response 7, 14 and 21 d after immunization with BNT162b2 (LNP-formulated RBP020.1). BALB/c mice were immunized IM once with 0.2, 1 or 5 μg of LNP-formulated RBP020.1. On day 7, 14, and 21 after immunization, animals were bled and the serum samples were analyzed for total amount of anti-S1 (left) and anti-RBD (right) antigen-specific immunoglobulin G (IgG) measured via ELISA. For day 7 (1:100), day 14 (1:300), and day 21 (1:1100) different serum dilution were included in the graph. One point in the graph stands for one mouse, every mouse sample was measured in duplicates (group size n=8; mean+SEM is included for the groups).
Figure 13:
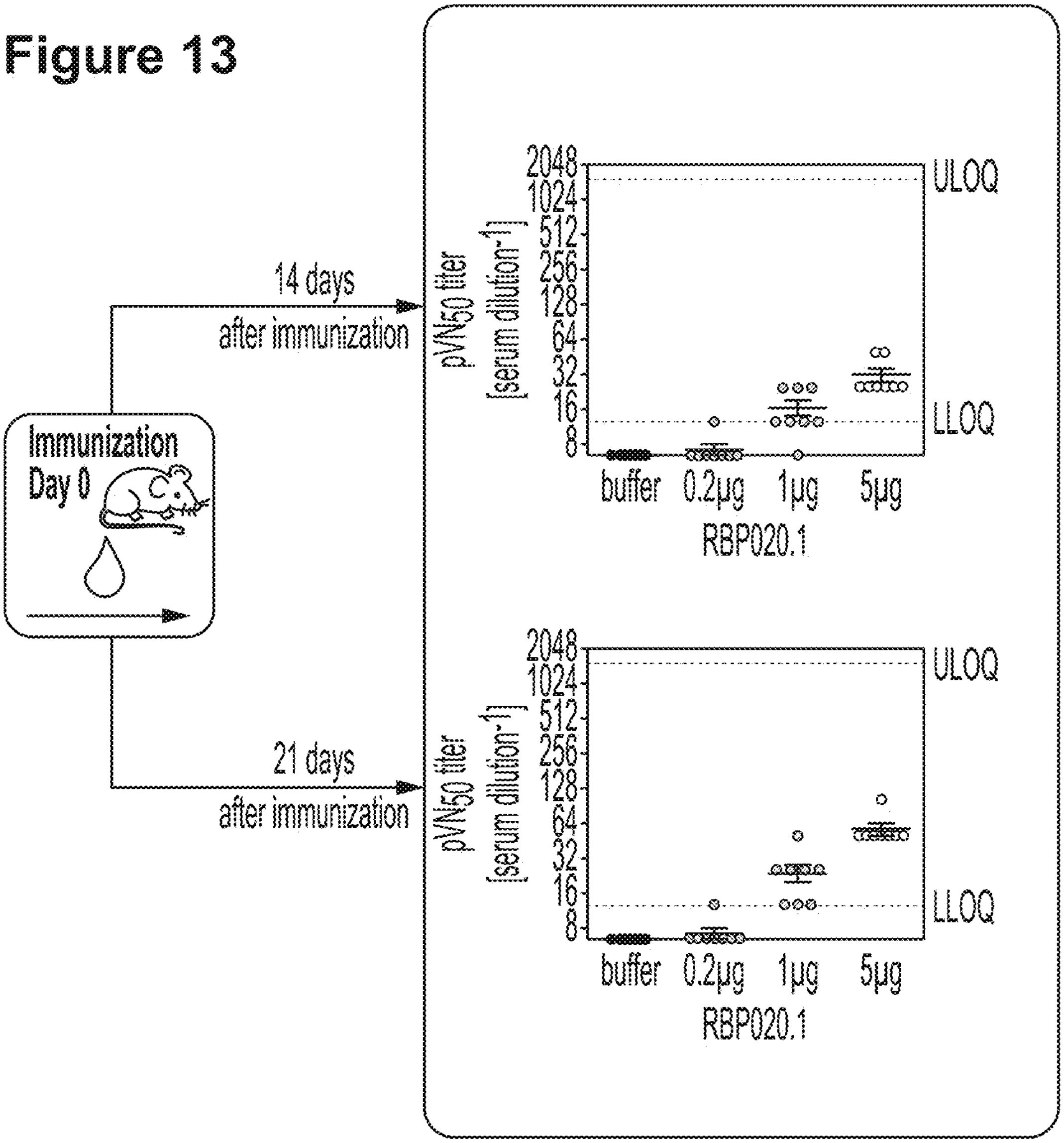
FIG. 13 demonstrates neutralization of SARS-CoV-2 pseudovirus 14 and 21 after immunization with BNT162b2 (LNP-formulated RBP020.1). BALB/c mice were immunized IM once with 0.2, 1 or 5 μg of LNP-formulated RBP020.1. On day 14 and 21 after immunization, animals were bled and the sera were tested for SARS-CoV-2 pseudovirus neutralization. Graphs depict pVN50 serum dilutions (50% reduction of infectious events, compared to positive controls without serum). One point in the graphs stands for one mouse. Every mouse sample was measured in duplicate. Group size n=8. Mean+SEM is shown by horizontal bars with whiskers for each group. LLOQ, lower limit of quantification. ULOQ, upper limit of quantification.

ELISA data 7, 14, and 21 d after the first immunization are available that show an early, dose-dependent immune activation against the S1 protein and the receptor binding domain (FIG. 12). Sera obtained 14, and 21 d after immunization show dose-dependent SARS-CoV-2 pseudovirus neutralization activity (FIG. 13).

Immunogenicity Study of the LNP-Formulated saRNA Encoding the Viral S Protein-V9 (SEQ ID NO: 7, 9) (RBS004.2)

To dissect the potency of the LNP-formulated saRNA vaccine coding for V9, BALB/c mice were immunized IM once as outlined in Table 3. The immunogenicity of the RNA vaccine will be investigated by focusing on the antibody immune response.

Figure 14:
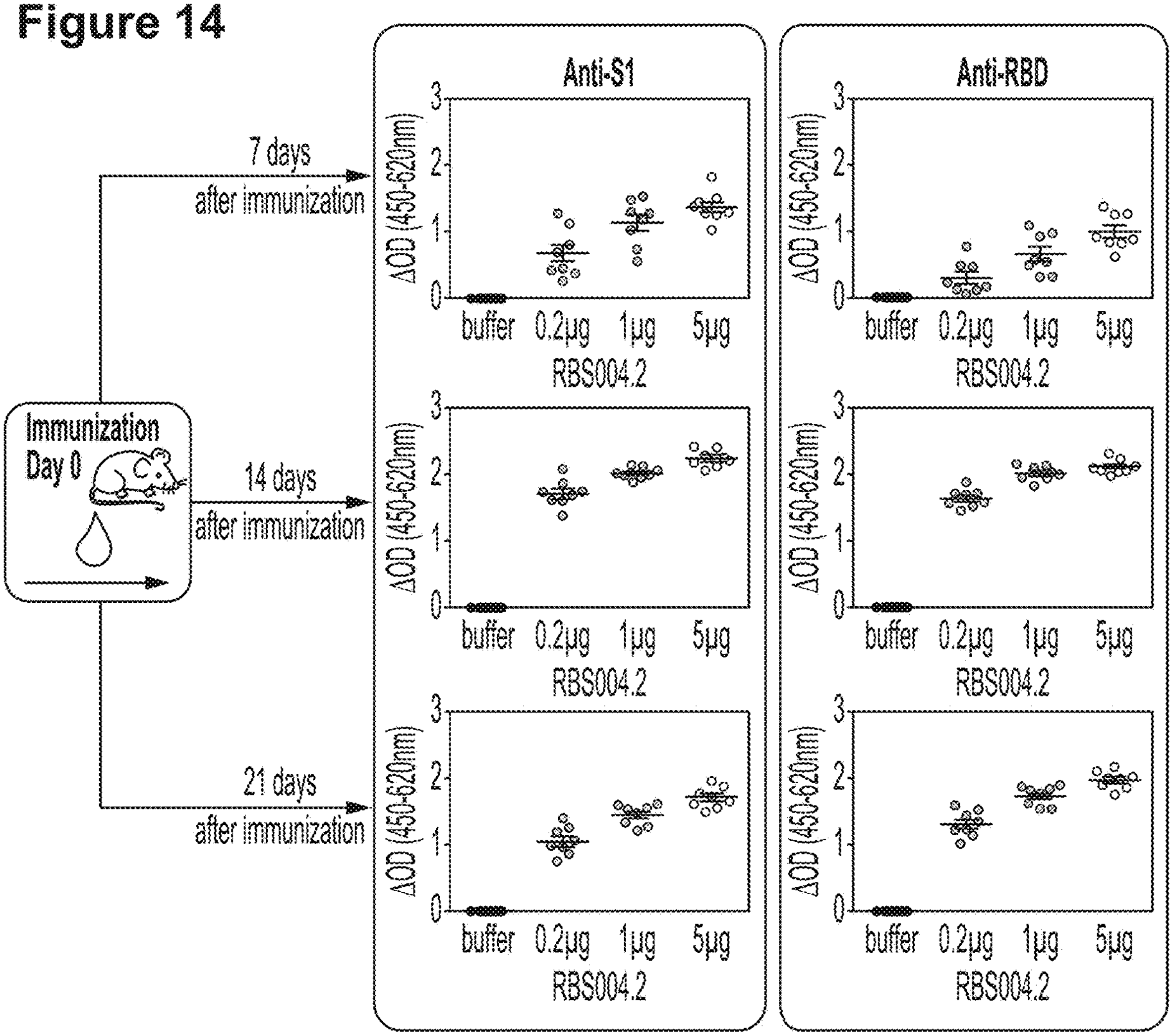
FIG. 14 shows anti-S protein IgG response 7, 14 and 21 d after immunization with LNP-formulated RBS004.2. BALB/c mice were immunized IM once with 0.2, 1 or 5 μg of LNP-formulated RBS004.2. On day 7, 14 and 21 after immunization, animals were bled and the serum samples were analyzed for total amount of anti-S1 (left) and anti-RBD (right) antigen-specific immunoglobulin G (IgG) measured via ELISA. For day 7 (1:100), day 14 (1:300), and day 21 (1:900) different serum dilution were included in the graph. One point in the graph stands for one mouse, every mouse sample was measured in duplicates (group size n=8; mean+SEM is included for the groups).
Figure 15:
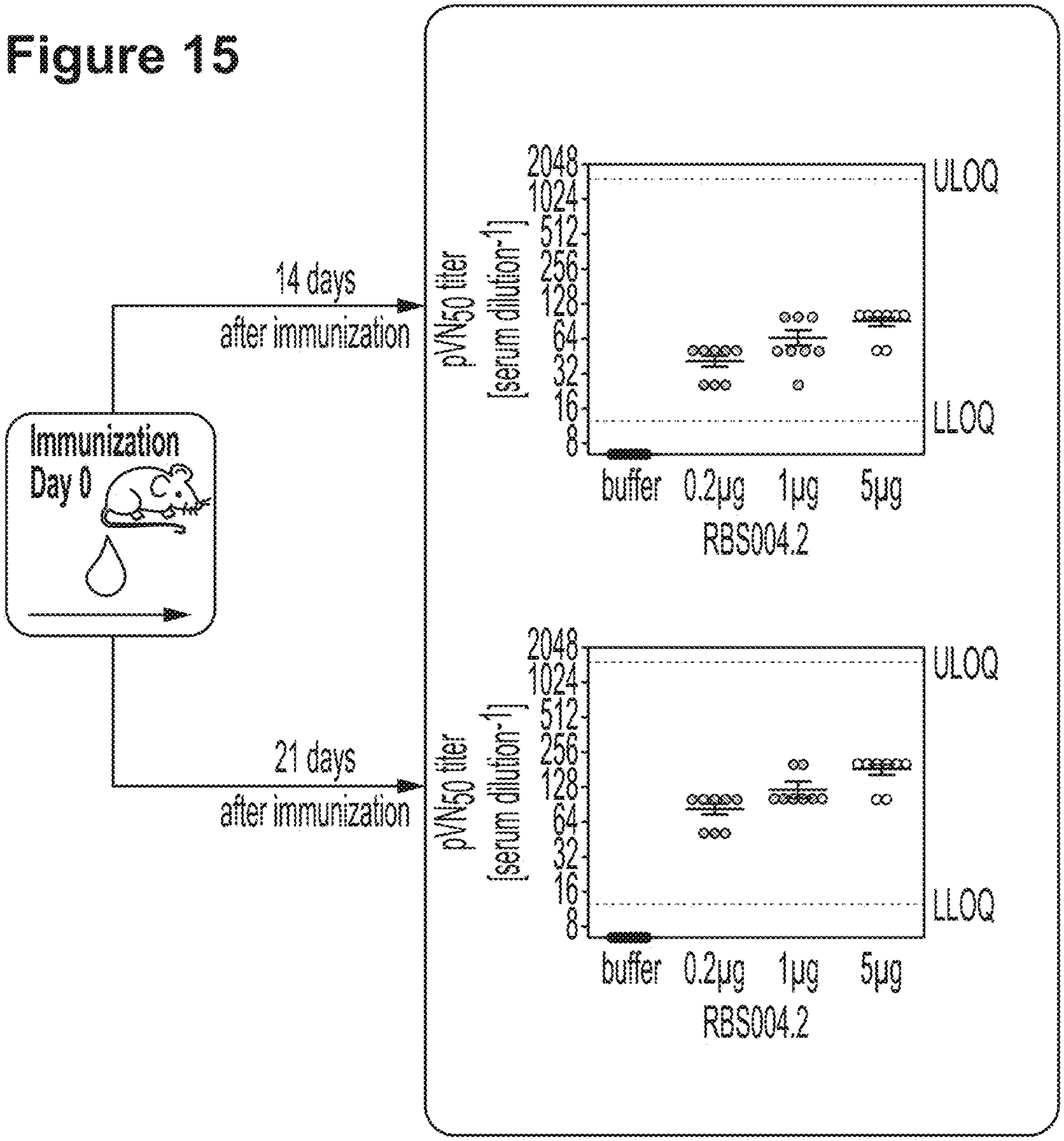
FIG. 15 demonstrates neutralization of SARS-CoV-2 pseudovirus 14 and 21 after immunization with LNP-formulated RBS004.2. BALB/c mice were immunized IM once with 0.2, 1 or 5 μg of LNP-formulated RBS004.2. On 14, and 21 d after immunization, animals were bled, and the sera were tested for SARS-CoV-2 pseudovirus neutralization. Graphs depict pVN50 serum dilutions (50% reduction of infectious events, compared to positive controls without serum). One point in the graphs stands for one mouse. Every mouse sample was measured in duplicate. Group size n=8. Mean+SEM is shown by horizontal bars with whiskers for each group. LLOQ, lower limit of quantification. ULOQ, upper limit of quantification.

ELISA data 7, 14, and 21 d after the first immunization are available that show an early, dose-dependent immune activation against the S1 protein and the receptor binding domain (FIG. 14). Sera obtained 14, and 21 d after immunization show dose-dependent SARS-CoV-2 pseudovirus neutralization activity (FIG. 15).

The above data demonstrate an immune response for both the RBD with a trimerization domain ("V5") and the mutated full-length S protein ("V8"/"V9") in vivo in all tested platforms (including the vaccines BNT162a1, BNT162b1, BNT162b2, and BNT162c1). The antibody immune response was already seen at very early time points by ELISA (i.e., at 7 d post-immunization) Importantly, induced antibodies were able to efficiently neutralize SARS-COV-2 pseudovirus infection in vitro. Also, the induction of an antibody response using a very low immunization dose of 0.2 μg/mouse when using the modRNA platform (BNT162b1, BNT162b2) as well as the saRNA platform (BNT162c1) indicates a high potency of the vaccine candidates.

In mice, BNT162b2 induced a higher antigen-specific titer compared to BNT162b1 encoded with the identical RNA platform. As expected, the immunogenicity in mice against the antigens differs between the RNA platforms. In mice, the most immunogenic platform based on antigen-specific antibody induction is the modRNA followed by saRNA. The uRNA platform induces the lowest antigen-specific antibody titer.

Example 3: LNP Formulation

An exemplary LNP delivery system was developed to effectively and safely deliver therapeutic nucleic acids into the cytosol of various cell types after local administration in vivo. The early formulation work was performed with several promising LNP formulations and surrogate RNA coding for luciferase. The aim of the experiments was to correlate the effect of different ionizable cationic lipids on the efficacy of RNA delivery by LNPs in vivo. Formulations were compared in terms of RNA encapsulation efficiency, apparent pKa, LNP size and polydispersity.

Among the screened cationic lipids, ALC-0315 exhibited suitable physical characteristics regarding particle size, homogeneity, and RNA encapsulation efficiency.

Figure 16:
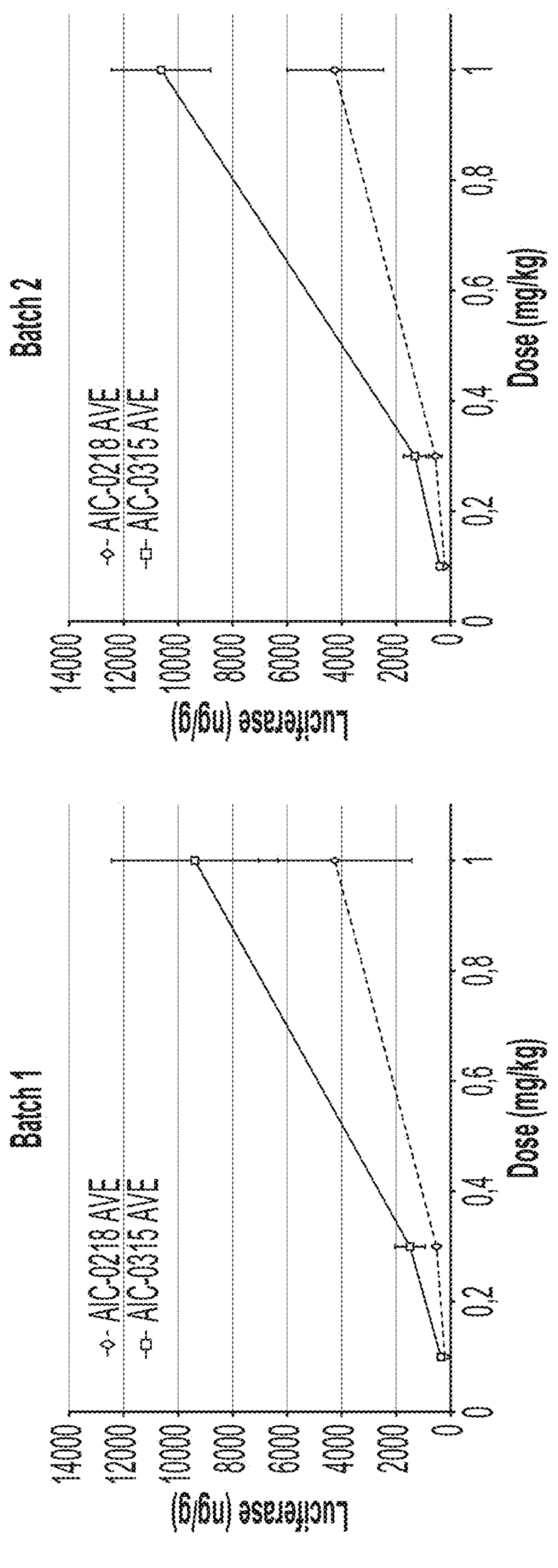
FIG. 16 depicts ALC-0315 activity in the screening process.

Based on this the ALC-0315/DSPC/CHOL/ALC-0159 prototype was submitted for in vivo screening. The results presented in FIG. 16 summarize the in vivo testing of two independent pilot batches using luciferase (Luc) RNA. The results demonstrate improved potency of the ALC-0315 prototype as compared to an internal benchmark (ALC-0218). On the basis of these studies, ALC-0315 was identified as a highly potent cationic lipid and brought forward for further product development studies.

Figure 17A:
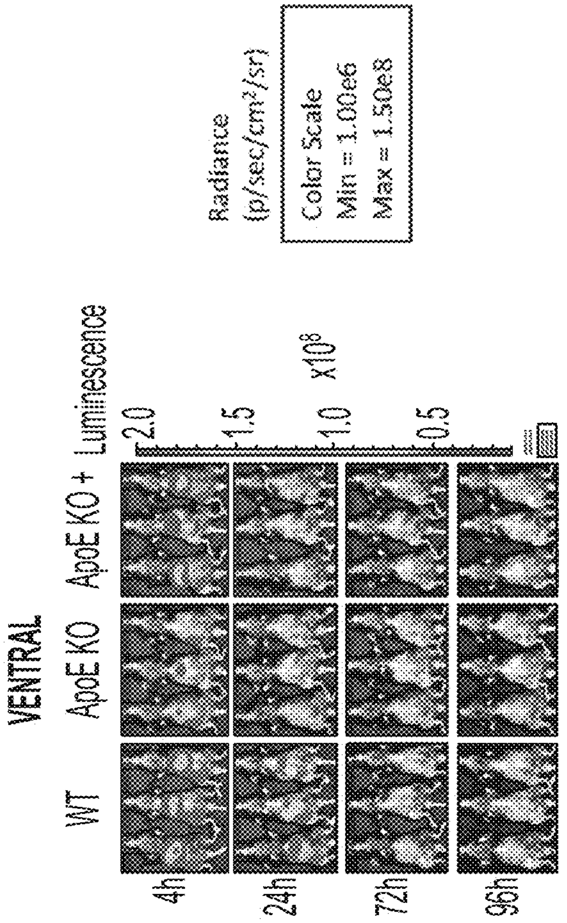
FIGS. 17A-17B demonstrate luciferase expression was monitored on (FIG. 17A) the ventral (drainage to the liver) and (FIG. 17B) the right (site of injection) and dorsal (site of injection) sides of the animal after intramuscular administration in wild-type (WT) or ApoE knockout C57Bl/6 mice in the presence or absence of ApoE3. Luciferase expression was detected using Xenolight D-Luciferin Rediject at 4, 24, 72 and 96 hours post administration.
Figure 17B:
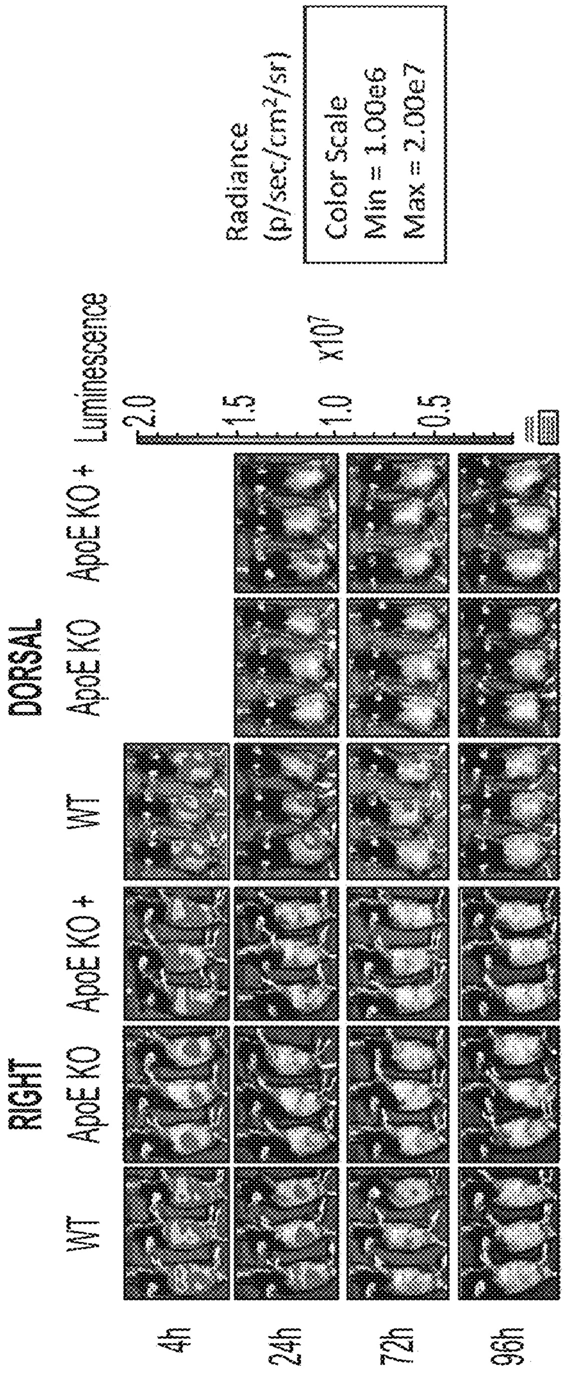

The formulation screening procedure described above involves intravenous administration resulting in delivery primarily to the liver. The mechanism of LNP uptake into hepatocytes is driven by binding of endogenous apolipoproteins to the LNP followed by receptor-mediated endocytosis e.g. through low density lipoprotein receptors. In order to investigate whether the same mechanism is involved for an intramuscular administration, Luc RNA containing LNPs comprising ALC-0315 were injected intravenously (0.3 mg/kg) and intramuscularly (0.2 mg/kg) into ApoE knockout mice in the presence or absence of recombinant human ApoE3. As control, wild-type C57Bl/6 mice were also treated by the different routes of administration. RNA-LNP were pre-incubated with recombinant human ApoE3 (1 mg encapsulated mRNA with 1 mg ApoE3) for 1 hour at room temperature (RT) prior to administration. Luc expression was monitored at 4, 24, 72 and 96 hours post administration (FIG. 17).

Figure 18:
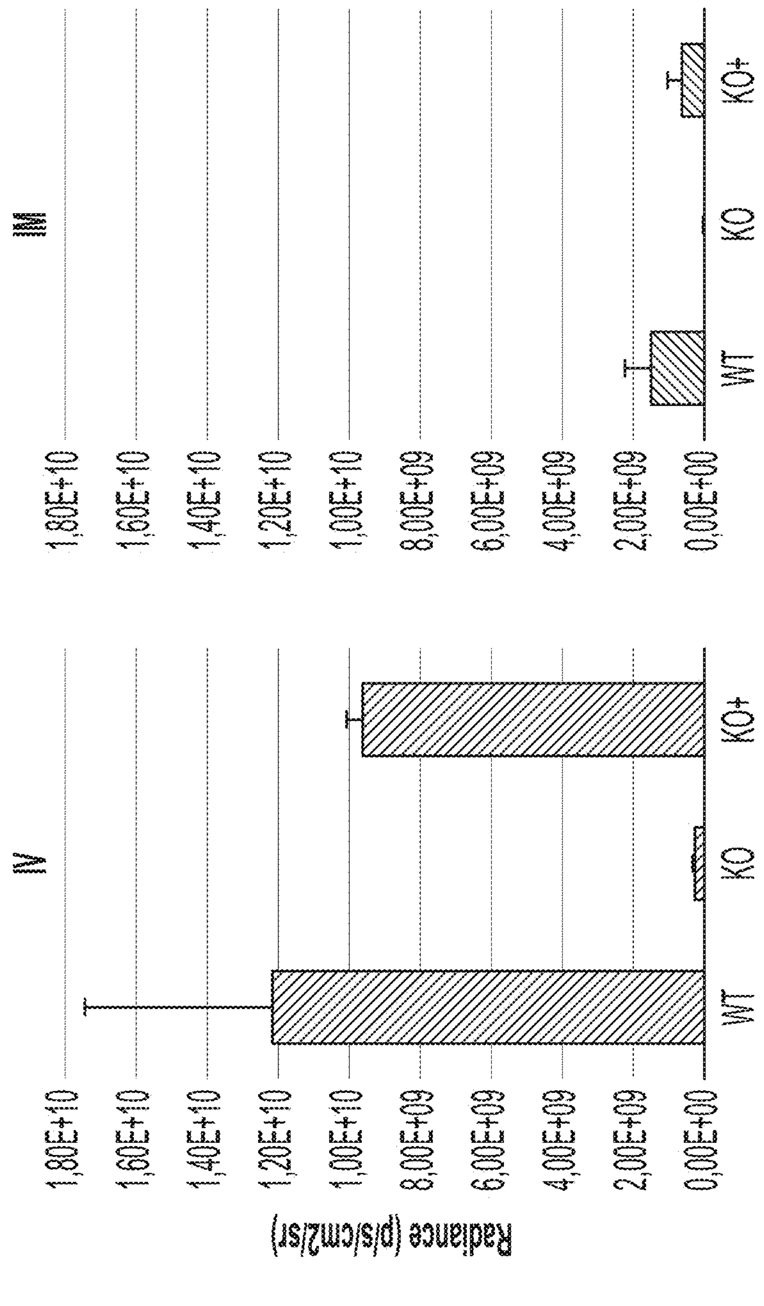
FIG. 18 shows luciferase activity after intravenous (IV) and intramuscular (IM) administration in wild-type (WT) or ApoE knockout C57Bl/6 mice in the presence (KO+) or absence (KO) of ApoE3. Luciferase expression was detected using Xenolight D-Luciferin Rediject at 4 hours post administration.

When mice were administered intravenously, Luc expression was detected in the wild-type C57Bl/6 mice. In the ApoE knockout mice Luc expression was significantly reduced however when preincubated with exogenous ApoE the expression of Luc was recovered to similar expression levels as wild-type mice (FIG. 18).

In vivo Luc expression experiments using mouse models showed, that similar mechanisms are involved in the uptake of RNA-LNP in case of intramuscular administration as for intravenous administration, and this is not only true for hepatocytes but also for the cells local to the administration site.

In vivo experiments after intramuscular administration of the final ALC-0315/DSPC/CHOL/ALC-0159, confirmed minimal drainage with regards to biodistribution, immunogenicity (vaccine activity) and tolerability.

EQUIVALENTS

Those skilled in the art will recognize, or be able to ascertain using no more than routine experimentation, many equivalents to the specific embodiments of the invention described herein. It is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Further, it should also be understood that any embodiment or aspect of the invention can be explicitly excluded from the claims, regardless of whether the specific exclusion is recited in the specification. The scope of the present invention is not intended to be limited to the above Description, but rather is as set forth in the claims that follow.

What is claimed is:

1. A composition or medical preparation comprising an RNA polynucleotide comprising:

(a) a 5' cap comprising a Cap1 structure;

(b) a cap proximal sequence comprising positions +1, +2, +3, +4, and +5 of the RNA polynucleotide;

(c) a 5' UTR sequence comprising the nucleotide sequence of SEQ ID NO: 27;

(d) a sequence encoding a payload;

(e) a 3' UTR sequence comprising the nucleotide sequence of SEQ ID NO: 13; and (f) a polyA sequence comprising the nucleotide sequence of SEQ ID NO: 14;

wherein:

(i) the Cap1 structure comprises m7(3' OMeG)(5')ppp(5)(2'OMeA$_1$)pG$_2$, wherein A$_1$ is position +1 of the RNA polynucleotide, and G2 is position +2 of the RNA polynucleotide;

(ii) the cap proximal sequence comprises A$_1$ and G$_2$ of the Cap1 structure, and a sequence comprising: A$_3$A$_4$U$_5$ (SEQ ID NO: 5) at positions +3, +4 and +5 respectively of the RNA polynucleotide; and (iii) the RNA polynucleotide optionally comprises a modified uridine in place of one or more uridines.

2. The composition or medical preparation of claim 1, wherein the RNA polynucleotide comprises, in a 5' to 3' orientation, the 5' cap, the cap proximal sequence, the 5' UTR, the sequence encoding a payload, the 3' UTR, and the polyA sequence.

3. The composition or medical preparation of claim 1, wherein the RNA polynucleotide comprises a modified uridine in place of one or more uridines.

4. The composition or medical preparation of claim 3, wherein the modified uridine is N1-methyl-pseudouridine (m1Ψ).

5. The composition or medical preparation of claim 1, wherein the sequence encoding a payload comprises a sequence encoding a protein replacement polypeptide; a sequence encoding an antibody agent; a sequence encoding a cytokine; a sequence encoding an antigenic polypeptide; a sequence encoding a gene editing component; a sequence encoding a regenerative medicine component, or combinations thereof

6. The composition or medical preparation of claim 5, wherein the sequence encoding a payload comprises a sequence encoding an antigenic polypeptide.

7. The composition or medical preparation of claim 6, wherein the antigenic polypeptide comprises a plurality of distinct epitopes from one or more antigens.

8. The composition or medical preparation of claim 6, wherein the antigenic polypeptide comprises: a viral antigenic polypeptide, a bacterial antigenic polypeptide, a fungal antigenic polypeptide, a parasitic antigenic polypeptide, an antigenic polypeptide from an infectious agent, or an antigenic polypeptide from a pathogen.

9. The composition or medical preparation of claim 8, wherein the RNA polynucleotide is mRNA.

10. A pharmaceutical composition comprising an RNA polynucleotide formulated in lipid nanoparticles (LNPs) comprising a cationically ionizable lipid, a neutral lipid, a sterol, and a polymer-conjugated lipid, the RNA polynucleotide comprising:

(a) a 5' cap comprising a Cap1 structure;

(b) a cap proximal sequence comprising positions +1, +2, +3, +4, and +5 of the RNA polynucleotide;

(c) a 5' UTR sequence comprising the nucleotide sequence of SEQ ID NO: 27;

(d) a sequence encoding a payload;

(e) a 3' UTR sequence comprising the nucleotide sequence of SEQ ID NO: 13; and (f) a polyA sequence comprising the nucleotide sequence of SEQ ID NO: 14;

wherein:

(i) the Cap1 structure comprises m7(3' OMeG)(5')ppp(5)(2'OMeA$_1$)pG$_2$, wherein A$_1$ is position +1 of the RNA polynucleotide, and G2 is position +2 of the RNA polynucleotide;

(ii) the cap proximal sequence comprises A$_1$ and G$_2$ of the Cap1 structure, and a sequence comprising: A$_3$A$_4$U$_5$ (SEQ ID NO: 5) at positions +3, +4 and +5 respectively of the RNA polynucleotide; and (iii) the RNA polynucleotide optionally comprises a modified uridine in place of one or more uridines.

11. The pharmaceutical composition of claim 10, which is formulated as a liquid.

12. The pharmaceutical composition of claim 10, which is formulated as a solid.

13. The composition or medical preparation of claim 6, wherein the antigenic polypeptide comprises an antigenic polypeptide from an allergen.

14. The composition or medical preparation of claim 6, wherein the antigenic polypeptide comprises a tumor antigenic polypeptide.

15. The composition or medical preparation of claim 6, wherein the antigenic polypeptide comprises a self-antigenic polypeptide.

16. The pharmaceutical composition of claim 10, wherein the RNA polynucleotide comprises, in a 5' to 3' orientation, the 5' cap, the cap proximal sequence, the 5' UTR, the sequence encoding a payload, the 3' UTR, and the polyA sequence.

17. The pharmaceutical composition of claim 10, wherein the RNA polynucleotide comprises a modified uridine in place of one or more uridines.

18. The pharmaceutical composition of claim 17, wherein the modified uridine is N1-methyl-pseudouridine (m1 ).

19. The pharmaceutical composition of claim 10, wherein the RNA polynucleotide comprises a modified uridine in place of every uridine.

20. The pharmaceutical composition of claim 19, wherein the modified uridine is N1-methyl-pseudouridine (m1Ψ).

21. The composition or medical preparation of claim 1, wherein the RNA polynucleotide comprises a modified uridine in place of every uridine.

22. The composition or medical preparation of claim 21, wherein the modified nucleoside uridine is N1-methyl-pseudouridine (m1Ψ).

* * * * *

SEQUENCE LISTING

```
<160> NUMBER OF SEQ ID NOS: 47

<210> SEQ ID NO 1
<211> LENGTH: 3
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

<221> NAME/KEY: modified_base
<222> LOCATION: (3)..(3)
<223> OTHER INFORMATION: a, g, c or u

<400> SEQUENCE: 1 aan 3

<210> SEQ ID NO 2
<211> LENGTH: 3
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (3)..(3)
<223> OTHER INFORMATION: a, g, c or u

<400> SEQUENCE: 2 can 3

<210> SEQ ID NO 3
<211> LENGTH: 3
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 3 aca 3

<210> SEQ ID NO 4
<211> LENGTH: 3
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 4 aug 3

<210> SEQ ID NO 5
<211> LENGTH: 3
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 5 aau 3

<210> SEQ ID NO 6
<211> LENGTH: 3
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 6 cac 3

<210> SEQ ID NO 7

<211> LENGTH: 3
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(1)
<223> OTHER INFORMATION: a, g, c or u
<220> FEATURE:
<221> NAME/KEY: modified_base
<222> LOCATION: (3)..(3)
<223> OTHER INFORMATION: a, g, c or u

<400> SEQUENCE: 7 ndn 3

<210> SEQ ID NO 8
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 8
gagucgcuag ccgcgucgcu 20

<210> SEQ ID NO 9
<211> LENGTH: 1273
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

```
Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605
```

-continued

```
Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990

Ile Asp Arg Leu Ile Thr Gly Arg  Leu Gln Ser Leu Gln  Thr Tyr Val
        995                 1000                 1005

Thr Gln  Gln Leu Ile Arg Ala  Ala Glu Ile Arg Ala  Ser Ala Asn
    1010                 1015                 1020
```

```
Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr
    1265                 1270
```

```
<210> SEQ ID NO 10
<211> LENGTH: 4283
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 10

agaauaaacu aguauucuuc ugguccccac agacucagag agaacccgcc accauguucg      60

uguuccuggu gcugcugccu cuggugucca gccagugugu gaaccugacc accagaacac     120

agcugccucc agccuacacc aacagcuuua ccagaggcgu guacuacccc gacaaggugu     180

ucagauccag cgugcugcac ucuacccagg accuguuccu gccuuucuuc agcaacguga     240

ccugguucca cgccauccac guguccggca ccaauggcac caagagauuc gacaaccccg     300

ugcugcccuu caacgacggg guguacuuug ccagcaccga gaaguccaac aucaucagag     360

gcuggaucuu cggcaccaca cuggacagca agacccagag ccugcugauc gugaacaacg     420

ccaccaacgu ggucaucaaa gugugcgagu uccaguucug caacgacccc uuccugggcg     480

ucuacuacca caagaacaac aagagcugga uggaaagcga guuccgggug uacagcagcg     540
```

-continued ccaacaacug caccuucgag uacgugucc agccuuuccu gauggaccug gaaggcaagc 600
agggcaacuu caagaaccug cgcgaguucg uguuuaagaa caucgacggc uacuucaaga 660
ucuacagcaa gcacaccccu aucaaccucg ugcgggaucu gccucagggc uucucugcuc 720
uggaaccccu gguggaucug cccaucggca ucaacaucac ccgguuucag acacugcugg 780
cccugcacag aagcuaccug acaccuggcg auagcagcag cggauggaca gcugguggccg 840
ccgcuuacua ugugggcuac cugcagccua gaaccuuccu gcugaaguac aacgagaacg 900
gcaccaucac cgacgccgug gauugugcuc uggauccucu gagcgagaca aagugcaccc 960
ugaaguccuu caccguggaa aagggcaucu accagaccag caacuuccgg gugcagccca 1020
ccgaauccau cgugcgguuc cccaauauca ccaaucugug ccccuucggc gagguguuca 1080
augccaccag auucgccucu guguacgccu ggaaccggaa gcggaucagc aauugcgugg 1140
ccgacuacuc cgugcuguac aacuccgcca gcuucagcac cuucaagugc uacggcgugu 1200
ccccuaccaa gcugaacgac cugugcuuca caaacgugua cgccgacagc uucgugaucc 1260
ggggagauga agugcggcag auugccccug gacagacagg caagaucgcc gacuacaacu 1320
acaagcugcc cgacgacuuc accggcugug ugauugccug gaacagcaac aaccuggacu 1380
ccaaagucgg cggcaacuac aauuaccugu accggcuguu ccggaagucc aaucugaagc 1440
ccuucgagcg ggacaucucc accgagaucu aucaggccgg cagcaccccu uguaacggcg 1500
uggaaggcuu caacugcuac uucccacugc aguccuacgg cuuucagccc acaaauggcg 1560
ugggcuauca gcccuacaga gugguggugc ugagcuucga acugcugcau gccccugcca 1620
cagugugcgg cccuaagaaa agcaccaauc ucgugaagaa caaaugcgug aacuucaacu 1680
ucaacggccu gaccggcacc ggcgugcuga cagagagcaa caagaaguuc cugccauucc 1740
agcaguuugg ccgggauauc gccgauacca cagacgccgu uagagauccc cagacacugg 1800
aaauccugga caucaccccu ugcagcuucg gcggagugu c ugugaucacc ccuggcacca 1860
acaccagcaa ucagguggca gugcuguacc aggacgugaa cuguaccgaa gugcccgugg 1920
ccauucacgc cgaucagcug acaccuacau ggcgggugua cuccaccggc agcaaugugu 1980
uucagaccag agccggcugu cugaucggag ccgagcacgu gaacaauagc uacgagugcg 2040
acaucccccau cggcgcugga aucugcgcca gcuaccagac acagacaaac agcccucgga 2100
gagccagaag cguggccagc cagagcauca uugccuacac aaugucucug ggcgccgaga 2160
acagcguggc cuacuccaac aacucuaucg cuaucccac caacuucacc aucagcguga 2220
ccacagagau ccugccugug uccaugacca agaccagcgu ggacugcacc auguacaucu 2280
gcggcgauuc caccgagugc uccaaccugc ugcugcagua cggcagcuuc ugcacccagc 2340
ugaauagagc ccugacaggg aucgccgugg aacaggacaa gaacacccaa gagguguucg 2400
cccaagugaa gcagaucuac aagaccccuc cuaucaagga cuucggcggc uucaauuuca 2460
gccagauucu gcccgauccu agcaagccca gcaagcggag cuucaucgag gaccugcugu 2520
ucaacaaagu gacacuggcc gacgccggcu ucaucaagca guauggcgau ugucugggcg 2580
acauugccgc cagggaucug auuugcgccc agaaguuuaa cggacugaca gugcugccuc 2640
cucugcugac cgaugagaug aucgcccagu acacaucugc ccugcuggcc ggcacaauca 2700
caagcggcug gacauuugga gcaggcgccg cucugcagau ccccuuugcu augcagaugg 2760
ccuaccgguu caacggcauc ggagugaccc agaaugugcu guacgagaac cagaagcuga 2820
ucgccaacca guucaacagc gccaucggca agauccagga cagccugagc agcacagcaa 2880

-continued gcgcccuggg aaagcugcag gacgugguca accagaaugc ccaggcacug aacacccugg 2940
ucaagcagcu guccuccaac uucggcgcca ucagcucugu gcugaacgau auccugagca 3000
gacuggaccc uccugaggcc gaggugcaga ucgacagacu gaucacaggc agacugcaga 3060
gccuccagac auacgugacc cagcagcuga ucagagccgc cgagauuaga gccucugcca 3120
aucuggccgc caccaagaug ucugagugug ugcugggcca gagcaagaga guggacuuuu 3180
gcggcaaggg cuaccaccug augagcuucc cucagucugc cccucacggc gugguguuuc 3240
ugcacgugac auaugugccc gcucaagaga agaauuucac caccgcucca gccaucugcc 3300
acgacggcaa agcccacuuu ccuagagaag gcguguucgu guccaacggc acccauuggu 3360
ucgugacaca gcggaacuuc uacgagcccc agaucaucac caccgacaac accuucgugu 3420
cuggcaacug cgacgucgug aucggcauug ugaacaauac cguguacgac ccucugcagc 3480
ccgagcugga cagcuucaaa gaggaacugg acaaguacuu uaagaaccac acaagccccg 3540
acguggaccu gggcgauauc agcggaauca augccagcgu cgugaacauc cagaaagaga 3600
ucgaccggcu gaacgaggug gccaagaauc ugaacgagag ccugaucgac cugcaagaac 3660
uggggaagua cgagcaguac aucaaguggc ccugguacau cuggcugggc uuuaucgccg 3720
gacugauugc caucgugaug gucacaauca ugcuguguug caugaccagc ugcuguagcu 3780
gccugaaggg cuguuguagc uguggcagcu gcugcaaguu cgacgaggac gauucugagc 3840
ccgugcugaa gggcgugaaa cugcacuaca caugaugacu cgagcuggua cugcaugcac 3900
gcaaugcuag cugccccuuu cccguccugg guaccccgag ucucccccga ccucgggucc 3960
cagguaugcu cccaccucca ccugccccac ucaccaccuc ugcuaguucc agacaccucc 4020
caagcacgca gcaaugcagc ucaaaacgcu uagccuagcc acacccccac gggaaacagc 4080
agugauuaac cuuuagcaau aaacgaaagu uuaacuaagc uauacuaacc ccaggguugg 4140
ucaauuucgu gccagccaca cccuggagcu agcaaaaaaa aaaaaaaaaa aaaaaaaaaa 4200
aaagcauaug acuaaaaaaa aaaaaaaaaa aaaaaaaaaa aaaaaaaaaa aaaaaaaaaa 4260
aaaaaaaaaa aaaaaaaaaa aaa 4283

<210> SEQ ID NO 11
<211> LENGTH: 47
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 11
agaauaaacu aguauucuuc ugguccccac agacucagag agaaccc 47

<210> SEQ ID NO 12
<211> LENGTH: 42
<212> TYPE: RNA
<213> ORGANISM: Homo sapiens

<400> SEQUENCE: 12
aaacuaguau ucuucugguc cccacagacu cagagagaac cc 42

<210> SEQ ID NO 13
<211> LENGTH: 278
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 13
cugguacugc augcacgcaa ugcuagcugc cccuuucccg uccuggguac cccgagucuc 60
ccccgaccuc ggguccaggg uaugcuccca ccuccaccug ccccacucac caccucugcu 120
aguuccagac accucccaag cacgcagcaa ugcagcucaa aacgcuuagc cuagccacac 180
ccccacggga aacagcagug auuaaccuuu agcaauaaac gaaaguuuaa cuaagcuaua 240
cuaaccccag gguuggucaa uuucgugcca gccacacc 278

<210> SEQ ID NO 14
<211> LENGTH: 110
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 14
aaaaaaaaaa aaaaaaaaaa aaaaaaaaaa gcauaugacu aaaaaaaaaa aaaaaaaaaa 60
aaaaaaaaaa aaaaaaaaaa aaaaaaaaaa aaaaaaaaaa aaaaaaaaaa 110

<210> SEQ ID NO 15
<211> LENGTH: 458
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 15
agaauaaacu aguauucuuc ugguccccac agacucagag agaacccgcc acccucgagc 60
ugguacugca ugcacgcaau gcuagcugcc ccuuucccgu ccuggguacc ccgagucucc 120
cccgaccucg ggucccaggu augcucccac cuccaccugc cccacucacc accucugcua 180
guuccagaca ccucccaagc acgcagcaau gcagcucaaa acgcuuagcc uagccacacc 240
cccacgggaa acagcaguga uuaaccuuua gcaauaaacg aaaguuuaac uaagcuauac 300
uaaccccagg guuggucaau uucgugccag ccacacccug gagcuagcaa aaaaaaaaaa 360
aaaaaaaaaa aaaaaaaagc auaugacuaa aaaaaaaaaa aaaaaaaaaa aaaaaaaaaa 420
aaaaaaaaaa aaaaaaaaaa aaaaaaaaaa aaaaaaaa 458

<210> SEQ ID NO 16
<211> LENGTH: 4283
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 16
agaauaaacu aguauucuuc ugguccccac agacucagag agaacccgcc accauguucg 60
uguuccuggu gcugcugccu cuggugucca gccagugugu gaaccugacc accagaacac 120
agcugccucc agccuacacc aacagcuuua ccagaggcgu guacuacccc gacaaggugu 180
ucagauccag cgugcugcac ucuacccagg accuguuccu gccuuucuuc agcaacguga 240
ccugguucca cgccauccac guguccggca ccaauggcac caagagauuc gacaaccccg 300
ugcugcccuu caacgacggg guguacuuug ccagcaccga gaaguccaac aucaucagag 360
gcuggaucuu cggcaccaca cuggacagca agacccagag ccugcugauc gugaacaacg 420

-continued

```
ccaccaacgu ggucaucaaa gugugcgagu uccaguucug caacgacccc uuccugggcg    480
ucuacuacca caagaacaac aagagcugga uggaaagcga guuccgggug uacagcagcg    540
ccaacaacug caccuucgag uacgugucccc agccuuuccu gauggaccug gaaggcaagc    600
agggcaacuu caagaaccug cgcgaguucg uguuuaagaa caucgacggc uacuucaaga    660
ucuacagcaa gcacaccccu aucaaccucg ugcgggaucu gccucagggc uucucugcuc    720
uggaaccccu gguggaucug cccaucggca ucaacaucac ccgguuucag acacugcugg    780
cccugcacag aagcuaccug acaccuggcg auagcagcag cggauggaca gcuggugccg    840
ccgcuuacua ugugggcuac cugcagccua gaaccuuccu gcugaaguac aacgagaacg    900
gcaccaucac cgacgccgug gauugugcuc uggauccucu gagcgagaca aagugcaccc    960
ugaaguccuu caccguggaa aagggcaucu accagaccag caacuuccgg gugcagccca   1020
ccgaauccau cgugcgguuc cccaauauca ccaaucugug ccccuucggc gagguguuca   1080
augccaccag auucgccucu guguacgccu ggaaccggaa gcggaucagc aauugcgugg   1140
ccgacuacuc cgugcuguac aacuccgcca gcuucagcac cuucaagugc uacggcgugu   1200
ccccuaccaa gcugaacgac cugugcuuca caaacgugua cgccgacagc uucgugaucc   1260
ggggagauga agugcggcag auugccccug gacagacagg caagaucgcc gacuacaacu   1320
acaagcugcc cgacgacuuc accggcugug ugauugccug gaacagcaac aaccuggacu   1380
ccaaagucgg cggcaacuac aauuaccugu accggcuguu ccggaagucc aaucugaagc   1440
ccuucgagcg ggacaucucc accgagaucu aucaggccgg cagcaccccu uguaacggcg   1500
uggaaggcuu caacugcuac uucccacugc aguccuacgg cuuucagccc acaaauggcg   1560
ugggcuauca gcccuacaga gugguggugc ugagcuucga acugcugcau gccccugcca   1620
cagugugcgg cccuaagaaa agcaccaauc ucgugaagaa caaaugcgug aacuucaacu   1680
ucaacggccu gaccggcacc ggcgugcuga cagagagcaa caagaaguuc cugccauucc   1740
agcaguuugg ccgggauauc gccgauacca cagacgccgu uagagauccc cagacacugg   1800
aaauccugga caucacccu ugcagcuucg gcggagugucu ugugaucacc ccuggcacca   1860
acaccagcaa ucagguggca gugcuguacc aggacgugaa cuguaccgaa gugcccgugg   1920
ccauucacgc cgaucagcug acaccuacau ggcggguggua cuccaccggc agcaaugugu   1980
uucagaccag agccggcugu cugaucggag ccgagcacgu gaacaauagc uacgagugcg   2040
acaucccccau cggcgcugga aucugcgcca gcuaccagac acagacaaac agcccucgga   2100
gagccagaag cguggccagc cagagcauca uugccuacac aaugucucug ggcgccgaga   2160
acagcguggc cuacuccaac aacucuaucg cuaucccccac caacuucacc aucagcguga   2220
ccacagagau ccugccugug uccaugacca agaccagcgu ggacugcacc auguacaucu   2280
gcggcgauuc caccgagugc uccaaccugc ugcugcagua cggcagcuuc ugcacccagc   2340
ugaauagagc ccugacaggg aucgccgugg aacaggacaa gaacacccaa gaggguguucg   2400
cccaagugaa gcagaucuac aagaccccuc cuaucaagga cuucggcggc uucaauuuca   2460
gccagauucu gcccgauccu agcaagccca gcaagcggag cuucaucgag gaccugcugu   2520
ucaacaaagu gacacuggcc gacgccggcu ucaucaagca guauggcgau ugucugggcg   2580
acauugccgc cagggaucug auuugcgccc agaaguuuaa cggacugaca gugcugccuc   2640
cucugcugac cgaugagaug aucgcccagu acacaucugc ccugcuggcc ggcacaauca   2700
caagcggcug gacauuugga gcaggcgccg cucugcagau ccccuuugcu augcagaugg   2760
```

-continued

```
ccuaccgguu caacggcauc ggagugaccc agaaugugcu guacgagaac cagaagcuga   2820

ucgccaacca guucaacagc gccaucggca agauccagga cagccugagc agcacagcaa   2880

gcgcccuggg aaagcugcag gacgugguca accagaaugc ccaggcacug aacacccugg   2940

ucaagcagcu guccuccaac uucggcgcca ucagcucugu gcugaacgau auccugagca   3000

gacuggaccc uccugaggcc gaggugcaga ucgacagacu gaucacaggc agacugcaga   3060

gccuccagac auacgugacc cagcagcuga ucagagccgc cgagauuaga gccucugcca   3120

aucuggccgc caccaagaug ucugagugug ugcugggcca gagcaagaga guggacuuuu   3180

gcggcaaggg cuaccaccug augagcuucc cucagucugc cccucacggc gugguguuuc   3240

ugcacgugac auaugugccc gcucaagaga agaauuucac caccgcucca gccaucugcc   3300

acgacggcaa agcccacuuu ccuagagaag gcguguucgu guccaacggc acccauuggu   3360

ucgugacaca gcggaacuuc uacgagcccc agaucaucac caccgacaac accuucgugu   3420

cuggcaacug cgacgucgug aucggcauug ugaacaauac cguguacgac ccucugcagc   3480

ccgagcugga cagcuucaaa gaggaacugg acaaguacuu uaagaaccac acaagccccg   3540

acguggaccu gggcgauauc agcggaauca augccagcgu cgugaacauc cagaaagaga   3600

ucgaccggcu gaacgaggug gccaagaauc ugaacgagag ccugaucgac cugcaagaac   3660

uggggaagua cgagcaguac aucaaguggc ccugguacau cuggcugggc uuuaucgccg   3720

gacugauugc caucgugaug gucacaauca ugcuguguug caugaccagc ugcuguagcu   3780

gccugaaggg cuguuguagc uguggcagcu gcugcaaguu cgacgaggac gauucugagc   3840

ccgugcugaa gggcgugaaa cugcacuaca caugaugacu cgagcuggua cugcaugcac   3900

gcaaugcuag cugccccuuu cccguccugg guaccccgag ucucccccga ccucgggucc   3960

cagguaugcu cccaccucca ccugccccac ucaccaccuc ugcuaguucc agacaccucc   4020

caagcacgca gcaaugcagc ucaaaacgcu uagccuagcc acacccccac gggaaacagc   4080

agugauuaac cuuuagcaau aaacgaaagu uuaacuaagc uauacuaacc ccaggguugg   4140

ucaauuucgu gccagccaca cccuggagcu agcaaaaaaa aaaaaaaaaa aaaaaaaaaa   4200

aaagcauaug acuaaaaaaa aaaaaaaaaa aaaaaaaaaa aaaaaaaaaa aaaaaaaaaa   4260

aaaaaaaaaa aaaaaaaaaa aaa                                           4283
```

<210> SEQ ID NO 17
<211> LENGTH: 1273
<212> TYPE: PRT
<213> ORGANISM: Severe acute respiratory syndrome-related coronavirus

<400> SEQUENCE: 17

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95
```

-continued

```
Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510
```

-continued

```
Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925
```

```
Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                 1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr
    1265                 1270
```

<210> SEQ ID NO 18
<211> LENGTH: 3819
<212> TYPE: RNA
<213> ORGANISM: Severe acute respiratory syndrome-related coronavirus

<400> SEQUENCE: 18
auguuugugu uucuugugcu gcugccucuu gugucuucuc agugugugaa uuugacaaca 60
agaacacagc ugccaccagc uuauacaaau ucuuuuacca gaggagugua uuauccugau 120
aaaguguuua gaucuucugu gcugcacagc acacaggacc uguuucugcc auuuuuuagc 180
aaugugacau gguuucaugc aauucaugug ucuggaacaa auggaacaaa aagauuugau 240
aauccugugc ugccuuuuaa ugauggagug uauuuugcuu caacagaaaa gucaaauauu 300
auuagaggau ggauuuuugg aacaacacug gauucuaaaa cacagucucu gcugauugug 360
aauaaaugcaa caaaguggu gauuaaagug ugugaauuuc aguuuuguaa ugauccuuuu 420
cugggagugu auuaucacaa aaauaauaaa ucuuggaugg aaucugaauu uagaguguau 480
uccucugcaa auaauuguac auuugaauau gugucucagc cuuuucugau ggaucuggaa 540
ggaaaacagg gcaauuuuaa aaaucugaga gaauuugugu uuaaaaauau ugauggauau 600
uuuaaaauuu auucuaaaca cacaccaauu aauuuaguga gagaucugcc ucagggauuu 660
ucugcucugg aaccucuggu ggaucugcca auuggcauua auauuacaag auuucagaca 720
cugcuggcuc ugcacagauc uuaucugaca ccuggagauu cuucuucugg auggacagcc 780
ggagcugcag cuuauuaugu gggcuaucug cagccaagaa cauuucugcu gaaauauaau 840
gaaaauggaa caauuacaga ugcuguggau ugugcucugg auccucuguc ugaaacaaaa 900
uguacauuaa aaucuuuuac aguggaaaaa ggcauuuauc agacaucuaa uuuuagagug 960
cagccaacag aaucuauugu gagauuucca aauauuacaa aucugugucc auuuggagaa 1020
guguuuaaug caacaagauu ugcaucugug uaugcaugga auagaaaaag aauuucuaau 1080
ugugugggcug auuauucugu gcuguauaau agugcuucuu uuuccacauu uaaauguuau 1140
ggagugucuc caacaaaauu aaaugauuua uguuuuacaa auguguaugc ugauucuuuu 1200
gugaucagag gugaugaagu gagacagauu gcccccggac agacaggaaa aauugcugau 1260
uacaauuaca aacugccuga ugauuuuaca ggauguguga uugcuuggaa uucuaauaau 1320
uuagauucua aagugggagg aaauuacaau uaucuguaca gacuguuuag aaaaucaaau 1380
cugaaaccuu uugaaagaga uauuucaaca gaaauuuauc aggcuggauc aacaccuugu 1440
aauggagugg aaggauuuaa uuguuauuuu ccauuacaga gcuauggauu ucagccaacc 1500
aaugguguggg gauaucagcc auauagagug guggugcugu cuuuugaacu gcugcaugca 1560
ccugcaacag ugugugggacc uaaaaaaucu acaaauuuag ugaaaaauaa augugugaau 1620
uuuaauuuua auggauuaac aggaacagga gugcugacag aaucuaauaa aaaauuucug 1680
ccuuuucagc aguuuggcag agauauugca gauaccacag augcagugag agauccucag 1740
acauuagaaa uucuggauau uacaccuugu ucuuuugggg gugugucugu gauuacaccu 1800
ggaacaaaua caucuaauca gguggcugug cuguaucagg augugaauug uacagaagug 1860
ccaguggcaa uucaugcaga ucagcugaca ccaacaugga gaguguauuc uacaggaucu 1920
aauguguuuc agacaagagc aggaugucug auuggagcag aacaugugaa uaauucuuau 1980
gaaugugaua uuccaauugg agcaggcauu ugugcaucuu aucagacaca gacaaauucc 2040
ccaaggagag caagaucugu ggcaucucag ucuauuauug cauacaccau gucucuggga 2100
gcagaaaauu cuguggcaua uucuaauaau ucuauugcua uuccaacaaa uuuuaccauu 2160
ucugugacaa cagaaauuuu accugugucu augacaaaaa caucugugga uuguaccaug 2220
uacauuugug gagauucuac agaauguucu aaucugcugc ugcaguaugg aucuuuuugu 2280

-continued

```
acacagcuga auagagcuuu aacaggaauu gcuguggaac aggauaaaaa uacacaggaa   2340

guguuugcuc aggugaaaca gauuuacaaa acaccaccaa uuaaagauuu uggaggauuu   2400

aauuuuagcc agauucugcc ugauccuucu aaaccuucua aaagaucuuu uauugaagau   2460

cugcuguuua auaaagugac acuggcagau gcaggauuua uuaaacagua uggagauugc   2520

cugggugaua uugcugcaag agaucugauu ugugcucaga aauuuaaugg acugacagug   2580

cugccuccuc ugcugacaga ugaaaugauu gcucaguaca caucugcuuu acuggcugga   2640

acaauuacaa gcggauggac auuuggagcu ggagcugcuc ugcagauucc uuuugcaaug   2700

cagauggcuu acagauuuaa uggaauugga gugacacaga auguguuaua ugaaaaucag   2760

aaacugauug caaaucaguu uaauucugca auuggcaaaa uucaggauuc ucugucuucu   2820

acagcuucug cucugggaaa acugcaggau guggugaauc agaaugcaca ggcacugaau   2880

acucugguga aacagcuguc uagcaauuuu ggggcaauuu cuucugugcu gaaugauauu   2940

cugucuagac uggauaaagu ggaagcugaa gugcagauug auagacugau cacaggaaga   3000

cugcagucuc ugcagacuua ugugacacag cagcugauua gagcugcuga aauuagagcu   3060

ucugcuaauc uggcugcuac aaaaaugucu gaaugugugc ugggacaguc aaaaagagug   3120

gauuuuugug gaaaaggaua ucaucugaug ucuuuuccac agucugcucc acauggagug   3180

guguuuuuac augugacaua ugugccagca caggaaaaga auuuuaccac agcaccagca   3240

auuugucaug auggaaaagc acauuuucca agagaaggag uguuuguguc uaauggaaca   3300

cauugguuug ugacacagag aaauuuuuau gaaccucaga uuauuacaac agauaauaca   3360

uuugugucag gaaauuguga uguggugauu ggaauuguga auaauacagu guaugaucca   3420

cugcagccag aacuggauuc uuuuaaagaa gaacuggaua aauauuuuaa aaaucacaca   3480

ucuccugaug uggauuuagg agauauuucu ggaaucaaug caucuguggu gaauauucag   3540

aaagaaauug auagacugaa ugaaguggcc aaaaaucuga augaaucucu gauugaucug   3600

caggaacuug gaaaauauga acaguacauu aaauggccuu gguacauuug gcuuggauuu   3660

auugcaggau uaauugcaau ugugauggug acaauuaugu uauguuguau gacaucaugu   3720

uguucuuguu uaaaaggaug uuguucuugu ggaagcuguu guaaauuuga ugaagaugau   3780

ucugaaccug uguuaaaagg agugaaauug cauuacaca                          3819
```

<210> SEQ ID NO 19
<211> LENGTH: 218
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

```
Met Phe Val Phe Leu Val Leu Leu Pro Leu Val Ser Ser Gln Cys Val
1               5                   10                  15

Val Arg Phe Pro Asn Ile Thr Asn Leu Cys Pro Phe Gly Glu Val Phe
            20                  25                  30

Asn Ala Thr Arg Phe Ala Ser Val Tyr Ala Trp Asn Arg Lys Arg Ile
        35                  40                  45

Ser Asn Cys Val Ala Asp Tyr Ser Val Leu Tyr Asn Ser Ala Ser Phe
    50                  55                  60

Ser Thr Phe Lys Cys Tyr Gly Val Ser Pro Thr Lys Leu Asn Asp Leu
65                  70                  75                  80
```

Cys Phe Thr Asn Val Tyr Ala Asp Ser Phe Val Ile Arg Gly Asp Glu
85 90 95

Val Arg Gln Ile Ala Pro Gly Gln Thr Gly Lys Ile Ala Asp Tyr Asn
100 105 110

Tyr Lys Leu Pro Asp Asp Phe Thr Gly Cys Val Ile Ala Trp Asn Ser
115 120 125

Asn Asn Leu Asp Ser Lys Val Gly Gly Asn Tyr Asn Tyr Leu Tyr Arg
130 135 140

Leu Phe Arg Lys Ser Asn Leu Lys Pro Phe Glu Arg Asp Ile Ser Thr
145 150 155 160

Glu Ile Tyr Gln Ala Gly Ser Thr Pro Cys Asn Gly Val Glu Gly Phe
165 170 175

Asn Cys Tyr Phe Pro Leu Gln Ser Tyr Gly Phe Gln Pro Thr Asn Gly
180 185 190

Val Gly Tyr Gln Pro Tyr Arg Val Val Val Leu Ser Phe Glu Leu Leu
195 200 205

His Ala Pro Ala Thr Val Cys Gly Pro Lys
210 215

<210> SEQ ID NO 20
<211> LENGTH: 654
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 20
auguuugugu uucuugugcu gcugcccucuu gugucuucuc agugugugggu gagauuucca 60 aauauuacaa aucugugucc auuuggagaa guguuuaaug caacaagauu ugcaucugug 120
uaugcaugga auagaaaaag aauuucuaau uguguggcug auuauucugu gcuguauaau 180
agugcuucuu uuuccacauu uaaauguuau ggagugucuc caacaaaauu aaaugauuua 240
uguuuuacaa auguguaugc ugauucuuuu gugaucagag gugaugaagu gagacagauu 300
gcccccggac agacaggaaa aauugcugau uacaauuaca aacugccuga ugauuuuaca 360
ggauguguga uugcuuggaa uucuaauaau uuagauucua aagugggagg aaauuacaau 420
uaucuguaca gacuguuuag aaaaucaaau cugaaaccuu uugaaagaga uauuucaaca 480
gaaauuuauc aggcuggauc aacaccuugu aauggagugg aaggauuuaa uuguuauuuu 540
ccauuacaga gcuauggauu ucagccaacc aauggugugg gauaucagcc auauagagug 600
guggugcugu cuuuugaacu gcugcaugca ccugcaacag ugugugggacc uaaa 654

<210> SEQ ID NO 21
<211> LENGTH: 266
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

Met Phe Val Phe Leu Val Leu Leu Pro Leu Val Ser Ser Gln Cys Val
1 5 10 15

Val Arg Phe Pro Asn Ile Thr Asn Leu Cys Pro Phe Gly Glu Val Phe
20 25 30

-continued

```
Asn Ala Thr Arg Phe Ala Ser Val Tyr Ala Trp Asn Arg Lys Arg Ile
        35                  40                  45

Ser Asn Cys Val Ala Asp Tyr Ser Val Leu Tyr Asn Ser Ala Ser Phe
    50                  55                  60

Ser Thr Phe Lys Cys Tyr Gly Val Ser Pro Thr Lys Leu Asn Asp Leu
65                  70                  75                  80

Cys Phe Thr Asn Val Tyr Ala Asp Ser Phe Val Ile Arg Gly Asp Glu
                85                  90                  95

Val Arg Gln Ile Ala Pro Gly Gln Thr Gly Lys Ile Ala Asp Tyr Asn
            100                 105                 110

Tyr Lys Leu Pro Asp Asp Phe Thr Gly Cys Val Ile Ala Trp Asn Ser
        115                 120                 125

Asn Asn Leu Asp Ser Lys Val Gly Gly Asn Tyr Asn Tyr Leu Tyr Arg
    130                 135                 140

Leu Phe Arg Lys Ser Asn Leu Lys Pro Phe Glu Arg Asp Ile Ser Thr
145                 150                 155                 160

Glu Ile Tyr Gln Ala Gly Ser Thr Pro Cys Asn Gly Val Glu Gly Phe
                165                 170                 175

Asn Cys Tyr Phe Pro Leu Gln Ser Tyr Gly Phe Gln Pro Thr Asn Gly
            180                 185                 190

Val Gly Tyr Gln Pro Tyr Arg Val Val Val Leu Ser Phe Glu Leu Leu
        195                 200                 205

His Ala Pro Ala Thr Val Cys Gly Pro Lys Gly Ser Pro Gly Ser Gly
    210                 215                 220

Ser Gly Ser Gly Tyr Ile Pro Glu Ala Pro Arg Asp Gly Gln Ala Tyr
225                 230                 235                 240

Val Arg Lys Asp Gly Glu Trp Val Leu Leu Ser Thr Phe Leu Gly Arg
                245                 250                 255

Ser Leu Glu Val Leu Phe Gln Gly Pro Gly
            260                 265
```

<210> SEQ ID NO 22
<211> LENGTH: 798
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 22

```
auguuugugu uucuugugcu gcugccucuu gugucuucuc agugugu ggu gagauuucca      60

aauauuacaa aucugugucc auuuggagaa guguuuaaug caacaagauu ugcaucugug    120

uaugcaugga auagaaaaag aauuucuaau uguguggcug auuauucugu gcuguauaau    180

agugcuucuu uuuccacauu uaaauguuau ggagugucuc caacaaaauu aaaugauuua    240

uguuuuacaa auguguaugc ugauucuuuu gugaucagag gugaugaagu gagacagauu    300

gcccccggac agacaggaaa aauugcugau uacaauuaca aacugccuga ugauuuuaca    360

ggauguguga uugcuuggaa uucuaauaau uuagauucua aagugggagg aaauuacaau    420

uaucuguaca gacuguuuag aaaaucaaau cugaaaccuu uugaaagaga uauuucaaca    480

gaaauuuauc aggcuggauc aacaccuugu aauggagugg aaggauuuaa uuguuauuuu    540

ccauuacaga gcuauggauu ucagccaacc aauggugugg gauaucagcc auauagagug    600

guggugcugu cuuuugaacu gcugcaugca ccugcaacag uguguggacc uaaaggcucc    660
```

cccggcuccg gcuccggauc ugguuauauu ccugaagcuc caagagaugg gcaagcuuac 720
guucguaaag auggcgaaug gguauuacuu ucuaccuuuu uaggccgguc ccuggaggug 780
cuguuccagg gccccggc 798

<210> SEQ ID NO 23
<211> LENGTH: 3819
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 23
auguuugugu uucuugugcu gcugccucuu gugucuucuc agugugugaa uuugacaaca 60
agaacacagc ugccaccagc uuauacaaau ucuuuuacca gaggagugua uuauccugau 120
aaaguguuua gaucuucugu gcugcacagc acacaggacc uguuucugcc auuuuuuagc 180
aaugugacau gguuucaugc aauucaugug ucuggaacaa auggaacaaa aagauuugau 240
aauccugugc ugccuuuuaa ugauggagug uauuuugcuu caacagaaaa gucaaauauu 300
auuagaggau ggauuuuugg aacaacacug gauucuaaaa cacagucucu gcugauugug 360
aauaaugcaa caaauguggu gauuaaagug ugugaauuuc aguuuuguaa ugauccuuuu 420
cugggagugu auuaucacaa aaauaauaaa ucuuggaugg aaucugaauu uagaguguau 480
uccucugcaa auaauuguac auuugaauau gugucucagc cuuuucugau ggaucuggaa 540
ggaaaacagg gcaauuuuaa aaaucugaga gaauuugugu uuaaaaauau ugauggauau 600
uuuaaaauuu auucuaaaca cacaccaauu aauuuaguga gagaucugcc ucagggauuu 660
ucugcucugg aaccucuggu ggaucugcca auuggcauua auauuacaag auuucagaca 720
cugcuggcuc ugcacagauc uuaucugaca ccuggagauu cuucuucugg auggacagcc 780
ggagcugcag cuuauuaugu gggcuaucug cagccaagaa cauuucugcu gaaauauaau 840
gaaaauggaa caauuacaga ugcuguggau ugugcucugg auccucuguc ugaaacaaaa 900
uguacauuaa aaucuuuuac aguggaaaaa ggcauuuauc agacaucuaa uuuuagagug 960
cagccaacag aaucuauugu gagauuucca aauauuacaa aucuguguccc auuuggagaa 1020 guguuuaaug caacaagauu ugcaucugug uaugcaugga auagaaaaag aauuucuaau 1080
uguguggcug auuauucugu gcuguauaau agugcuucuu uuuccacauu uaaauguuau 1140
ggagugucuc caacaaaauu aaaugauuua uguuuuacaa auguguaugc ugauucuuuu 1200
gugaucagag gugaugaagu gagacagauu gcccccggac agacaggaaa aauugcugau 1260
uacaauuaca aacugccuga ugauuuuaca ggauguguga uugcuuggaa uucuaauaau 1320
uuagauucua aagugggagg aaauuacaau uaucuguaca gacuguuuag aaaaucaaau 1380
cugaaaccuu uugaaagaga uauuucaaca gaaauuuauc aggcuggauc aacaccuugu 1440
aauggagugg aaggauuuaa uuguuauuuu ccauuacaga gcuauggauu ucagccaacc 1500 aaugguguggg gauaucagcc auauagagug guggugcugu cuuuugaacu gcugcaugca 1560
ccugcaacag ugugugggacc uaaaaaaucu acaaauuuag ugaaaaauaa augugugaau 1620
uuuaauuuua auggauuaac aggaacagga gugcugacag aaucuaauaa aaaauuucug 1680
ccuuuucagc aguuuggcag agauauugca gauaccacag augcagugag agauccucag 1740
acauuagaaa uucuggauau uacaccuugu ucuuuugggg gugugucugu gauuacaccu 1800
ggaacaaaua caucuaauca gguggcugug cuguaucagg augugaauug uacagaagug 1860

```
ccaguggcaa uucaugcaga ucagcugaca ccaacaugga gaguguauuc uacaggaucu   1920

aauguguuuc agacaagagc aggaugucug auuggagcag aacaugugaa uaauucuuau   1980

gaaugugaua uuccaauugg agcaggcauu ugugcaucuu aucagacaca gacaaauucc   2040

ccaaggagag caagaucugu ggcaucucag ucuauuauug cauacaccau gucucuggga   2100

gcagaaaauu cuguggcaua uucuaauaau ucuauugcua uuccaacaaa uuuuaccauu   2160

ucugugacaa cagaaauuuu accugugucu augacaaaaa caucugugga uuguaccaug   2220

uacauuugug gagauucuac agaauguucu aaucugcugc ugcaguaugg aucuuuuugu   2280

acacagcuga auagagcuuu aacaggaauu gcuguggaac aggauaaaaa uacacaggaa   2340

guguuugcuc aggugaaaca gauuuacaaa acaccaccaa uuaaagauuu uggaggauuu   2400

aauuuuagcc agauucugcc ugauccuucu aaaccuucua aaagaucuuu uauugaagau   2460

cugcuguuua auaaagugac acuggcagau gcaggauuua uuaaacagua uggagauugc   2520

cugggugaua uugcugcaag agaucugauu ugugcucaga aauuuaaugg acugacagug   2580

cugccuccuc ugcugacaga ugaaaugauu gcucaguaca caucugcuuu acuggcugga   2640

acaauuacaa gcggauggac auuuggagcu ggagcugcuc ugcagauucc uuuugcaaug   2700

cagauggcuu acagauuuaa uggaauugga gugacacaga auguguuaua ugaaaaucag   2760

aaacugauug caaaucaguu uaauucugca auuggcaaaa uucaggauuc ucugucuucu   2820

acagcuucug cucugggaaa acugcaggau guggugaauc agaaugcaca ggcacugaau   2880

acucugguga aacagcuguc uagcaauuuu ggggcaauuu cuucugugcu gaaugauauu   2940

cugucuagac uggauccucc ugaagcugaa gugcagauug auagacugau cacaggaaga   3000

cugcagucuc ugcagacuua ugugacacag cagcugauua gagcugcuga aauuagagcu   3060

ucugcuaauc uggcugcuac aaaaaugucu gaaugugugc ugggacaguc aaaaagagug   3120

gauuuuugug gaaaaggaua ucaucugaug ucuuuuccac agucugcucc acauggagug   3180

guguuuuuac augugacaua ugugccagca caggaaaaga auuuuaccac agcaccagca   3240

auuugucaug auggaaaagc acauuuucca agagaaggag uguuugugucuaauggaaca   3300

cauugguuug ugacacagag aaauuuuuau gaaccucaga uuauuacaac agauaauaca   3360

uuugugucag gaaauuguga ugugguguau ggaauuguga auaauacagu guaugaucca   3420

cugcagccag aacuggauuc uuuuaaagaa gaacuggaua aauauuuuaa aaaucacaca   3480

ucuccugaug uggauuuagg agauauuucu ggaaucaaug caucuguggu gaauauucag   3540

aaagaaauug auagacugaa ugaaguggcc aaaaaucuga augaaucucu gauugaucug   3600

caggaacuug gaaaauauga acaguacauu aaauggccuu gguacauuug gcuuggauuu   3660

auugcaggau uaauugcaau ugugauggug acaauuaugu uauguuguau gacaucaugu   3720

uguucuuguu uaaaaggaug uuguucuugu ggaagcuguu guaaauuuga ugaagaugau   3780

ucugaaccug uguuaaaagg agugaaauug cauuacaca                         3819
```

<210> SEQ ID NO 24
<211> LENGTH: 3819
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 24
auguucgugu uccuggugcu gcugccucug guguccagcc agugugugaa ccugaccacc 60
agaacacagc ugccuccagc cuacaccaac agcuuuacca gaggcgugua cuaccccgac 120
aagguguuca gauccagcgu gcugcacucu acccaggacc uguuccugcc uuucuucagc 180
aacgugaccu gguuccacgc cauccacgug uccggcacca auggcaccaa gagauucgac 240
aaccccgugc ugcccuucaa cgacggggug uacuuugcca gcaccgagaa guccaacauc 300
aucagaggcu ggaucuucgg caccacacug gacagcaaga cccagagccu gcugaucgug 360
aacaacgcca ccaacguggu caucaaagug ugcgaguucc aguucugcaa cgaccccuuc 420
cugggcgucu acuaccacaa gaacaacaag agcuggaugg aaagcgaguu ccgggguguac 480
agcagcgcca acaacugcac cuucgaguac guguccccagc cuuuccugau ggaccuggaa 540
ggcaagcagg gcaacuucaa gaaccugcgc gaguucgugu uuaagaacau cgacggcuac 600
uucaagaucu acagcaagca caccccuauc aaccucgugc gggaucugcc ucagggcuuc 660
ucugcucugg aaccccuggu ggaucugccc aucggcauca acaucacccg guuucagaca 720
cugcuggccc ugcacagaag cuaccugaca ccuggcgaua gcagcagcgg auggacagcu 780
ggugccgccg cuuacuaugu gggcuaccug cagccuagaa ccuuccugcu gaaguacaac 840
gagaacggca ccaucaccga cgccguggau ugugcucugg auccucugag cgagacaaag 900
ugcacccuga aguccuucac cguggaaaag ggcaucuacc agaccagcaa cuuccgggug 960
cagcccaccg aauccaucgu gcgguucccc aauaucacca aucugugccc cuucggcgag 1020
guguucaaug ccaccagauu cgccucugug uacgccugga accggaagcg gaucagcaau 1080
ugcguggccg acuacuccgu gcuguacaac uccgccagcu ucagcaccuu caagugcuac 1140
ggcguguccc cuaccaagcu gaacgaccug ugcuucacaa acguguacgc cgacagcuuc 1200
gugauccggg gagaugaagu gcggcagauu gccccuggac agacaggcaa gaucgccgac 1260
uacaacuaca agcugcccga cgacuucacc ggcuguguga uugccuggaa cagcaacaac 1320
cuggacucca aagucggcgg caacuacaau uaccuguacc ggcuguuccg gaaguccaau 1380
cugaagcccu ucgagcggga caucuccacc gagaucuauc aggccggcag caccccuugu 1440
aacggcgugg aaggcuucaa cugcuacuuc ccacugcagu ccuacggcuu ucagcccaca 1500
aauggcgugg gcuaucagcc cuacagagug guggugcuga gcuucgaacu gcugcaugcc 1560
ccugccacag ugugcggccc uaagaaaagc accaaucucg ugaagaacaa augcgugaac 1620
uucaacuuca acggccugac cggcaccggc gugcugacag agagcaacaa gaaguuccug 1680
ccauuccagc aguuuggccg ggauaucgcc gauaccacag acgccguuag agaucccccag 1740
acacuggaaa uccuggacau caccccuugc agcuucggcg gagugucugu gaucaccccu 1800
ggcaccaaca ccagcaauca gguggcagug cuguaccagg acgugaacug uaccgaagug 1860
cccguggcca uucacgccga ucagcugaca ccuacauggc ggguguacuc caccggcagc 1920
aauguguuuc agaccagagc cggcugucug aucggagccg agcacgugaa caauagcuac 1980
gagugcgaca uccccaucgg cgcuggaauc ugcgccagcu accagacaca gacaaacagc 2040
ccucggagag ccagaagcgu ggccagccag agcaucauug ccuacacaau gucucugggc 2100
gccgagaaca gcguggccua cuccaacaac ucuaucgcua uccccaccaa cuucaccauc 2160
agcgugacca cagagauccu gccuguguccc augaccaaga ccagcgugga cugcaccaug 2220
uacaucugcg gcgauuccac cgagugcucc aaccugcugc ugcaguacgg cagcuucugc 2280

-continued acccagcuga auagagcccu gacagggauc gccguggaac aggacaagaa cacccaagag 2340
guguucgccc aagugaagca gaucuacaag accccuccua ucaaggacuu cggcggcuuc 2400
aauuucagcc agauucugcc cgauccuagc aagcccagca agcggagcuu caucgaggac 2460
cugcuguuca acaaagugac acuggccgac gccggcuuca ucaagcagua uggcgauugu 2520
cugggcgaca uugccgccag ggaucugauu ugcgcccaga aguuuaacgg acugacagug 2580
cugccuccuc ugcugaccga ugagaugauc gcccaguaca caucugcccu gcuggccggc 2640
acaaucacaa gcggcuggac auuuggagca ggcgccgcuc ugcagauccc cuuugcuaug 2700
cagauggccu accgguucaa cggcaucgga gugacccaga augugcugua cgagaaccag 2760
aagcugaucg ccaaccaguu caacagcgcc aucggcaaga uccaggacag ccugagcagc 2820
acagcaagcg cccugggaaa gcugcaggac guggucaacc agaaugccca ggcacugaac 2880
acccugguca agcagcuguc cuccaacuuc ggcgccauca gcucugugcu gaacgauauc 2940
cugagcagac uggacccucc ugaggccgag gugcagaucg acagacugau cacaggcaga 3000
cugcagagcc uccagacaua cgugacccag cagcugauca gagccgccga gauuagagcc 3060
ucugccaauc uggccgccac caagaugucu gagugugugc ugggccagag caagagagug 3120
gacuuuugcg gcaagggcua ccaccugaug agcuucccuc agucugcccc ucacggcgug 3180
guguuucugc acgugacaua ugugcccgcu caagagaaga auuucaccac cgcuccagcc 3240
aucugccacg acggcaaagc ccacuuuccu agagaaggcg uguucguguc caacggcacc 3300
cauugguucg ugacacagcg gaacuucuac gagccccaga ucaucaccac cgacaacacc 3360
uucgugucug gcaacugcga cgucgugauc ggcauuguga acaauaccgu guacgacccu 3420
cugcagcccg agcuggacag cuucaaagag gaacuggaca aguacuuuaa gaaccacaca 3480
agccccgacg uggaccuggg cgauaucagc ggaaucaaug ccagcgucgu gaacauccag 3540
aaagagaucg accggcugaa cgagguggcc aagaaucuga acgagagccu gaucgaccug 3600
caagaacugg ggaaguacga gcaguacauc aaguggcccu gguacaucug gcugggcuuu 3660
aucgccggac ugauugccau cgugaugguc acaaucaugc uguguugcau gaccagcugc 3720
uguagcugcc ugaagggcug uuguagcugu ggcagcugcu gcaaguucga cgaggacgau 3780
ucugagcccg ugcugaaggg cgugaaacug cacuacaca 3819

<210> SEQ ID NO 25
<211> LENGTH: 41
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

Gly Ser Gly Tyr Ile Pro Glu Ala Pro Arg Asp Gly Gln Ala Tyr Val
1 5 10 15

Arg Lys Asp Gly Glu Trp Val Leu Leu Ser Thr Phe Leu Gly Arg Ser
20 25 30

Leu Glu Val Leu Phe Gln Gly Pro Gly
35 40

<210> SEQ ID NO 26
<211> LENGTH: 123
<212> TYPE: RNA
<213> ORGANISM: Artificial Sequence -continued
<220> FEATURE:
<223> OTHER INFORMATION: Description of Artificial Sequence: Synthetic
      polynucleotide

<400> SEQUENCE: 26
ggaucugguu auauuccuga agcuccaaga gaugggcaag cuuacguucg uaaagauggc     60 gaaugggguau uacuuucuac cuuuuuaggc cggucccugg aggugcuguu ccagggcccc    120
ggc                                                                   123

<210> SEQ ID NO 27
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
aacuaguauu cuucuggucc ccacagacuc agagagaacc cgccacc                   47

<210> SEQ ID NO 28
<211> LENGTH: 4282
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 28
gggcgaacua guauucuucu gguccccaca gacucagaga gaacccgcca ccauguuugu     60
guuucuugug cugcugccuc uugugucuuc ucagugugug aauuugacaa caagaacaca    120
gcugccacca gcuuauacaa auucuuuuac cagaggagug uauuauccug auaaaguguu    180
uagaucuucu gugcugcaca gcacacagga ccuguuucug ccauuuuuua gcaaugugac    240
augguuucau gcaauucaug ugucuggaac aaauggaaca aaaagauuug auaauccugu    300
gcugccuuuu aaugauggag uguauuuugc uucaacagaa aagucaaaua uuauuagagg    360
auggauuuuu ggaacaacac uggauucuaa aacacagucu cugcugauug ugaauaaugc    420
aacaaaugug gugauuaaag ugugugaauu ucaguuuugu aaugauccuu uucugggagu    480
guauuaucac aaaaauaaua aaucuuggau ggaaucugaa uuuagagugu auuccucugc    540
aaauaauugu acauuugaau augugucuca gccuuuucug auggaucugg aaggaaaaca    600
gggcaauuuu aaaaaucuga gagaauuugu guuuaaaaau auugauggau auuuuaaaau    660
uuauucuaaa cacacaccaa uuaauuuagu gagagaucug ccucagggau uuucugcucu    720
ggaaccucug guggaucugc caauuggcau uaauauuaca agauuucaga cacugcuggc    780
ucugcacaga ucuuaucuga caccuggaga uucuucuucu ggauggacag ccggagcugc    840
agcuuauuau gugggcuauc ugcagccaag aacauuucug cugaaauaua augaaaaugg    900
aacaauuaca gaugcugugg auugugcucu ggauccucug ucugaaacaa aauguacauu    960
aaaaucuuuu acaguggaaa aaggcauuua ucagacaucu aauuuuagag ugcagccaac   1020
agaaucuauu gugagauuuc caaauauuac aaaucugugu ccauuuggag aaguguuuaa   1080
ugcaacaaga uuugcaucug uguaugcaug gaauagaaaa agaauuucua auuguguggc   1140
ugauuauucu gugcuguaua auagugcuuc uuuuuccaca uuuaaauguu auggaguguc   1200
uccaacaaaa uuaaaugauu uauguuuuac aaauguguau gcugauucuu uugugaucag   1260
aggugaugaa gugagacaga uugcccccgg acagacagga aaaauugcug auuacaauua   1320

-continued caaacugccu gaugauuuua caggaugugu gauugcuugg aauucuaaua auuuagauuc 1380
uaaaguggga ggaaauuaca auuaucugua cagacuguuu agaaaaucaa aucugaaacc 1440
uuuugaaaga gauauuucaa cagaaauuua ucaggcugga ucaacaccuu guaauggagu 1500
ggaaggauuu aauuguuauu uuccauuaca gagcuaugga uuucagccaa ccaauggugu 1560
gggauaucag ccauauagag ugguggugcu gucuuuugaa cugcugcaug caccugcaac 1620
agugugugga ccuaaaaaau cuacaaauuu agugaaaaau aaauguguga auuuuaauuu 1680
uaauggauua acaggaacag gagugcugac agaaucuaau aaaaaauuuc ugccuuuuca 1740
gcaguuuggc agagauauug cagauaccac agaugcagug agagauccuc agacauuaga 1800
aauucuggau auuacaccuu guucuuuugg gggugugucu gugauuacac cuggaacaaa 1860
uacaucuaau cagguggcug ugcuguauca ggaugugaau uguacagaag ugccaguggc 1920
aauucaugca gaucagcuga caccaacaug gagaguguau ucuacaggau cuaauguguu 1980
ucagacaaga gcaggauguc ugauuggagc agaacaugug aauaauucuu augaauguga 2040
uauuccaauu ggagcaggca uuugugcauc uuaucagaca cagacaaauu ccccaaggag 2100
agcaagaucu guggcaucuc agucuauuau ugcauacacc augucucugg gagcagaaaa 2160
uucuguggca uauucuaaua auucuauugc uauuccaaca aauuuuacca uuucugugac 2220
aacagaaauu uuaccugugu cuaugacaaa aacaucugug gauuguacca uguacauuug 2280
uggagauucu acagaauguu cuaaucugcu gcugcaguau ggaucuuuuu guacacagcu 2340
gaauagagcu uuaacaggaa uugcugugga acaggauaaa aauacacagg aaguguuugc 2400
ucaggugaaa cagauuuaca aaacaccacc aauuaaagau uuuggaggau uuaauuuuag 2460
ccagauucug ccugauccuu cuaaaccuuc uaaaagaucu uuuauugaag aucugcuguu 2520
uaauaaagug acacuggcag augcaggauu uauuaaacag uauggagauu gccugggguga 2580 uauugcugca agagaucuga uuugugcuca gaaauuuaau ggacugacag ugcugccucc 2640
ucugcugaca gaugaaauga uugcucagua cacaucugcu uuacuggcug gaacaauuac 2700
aagcggaugg acauuuggag cuggagcugc ucugcagauu ccuuuugcaa ugcagauggc 2760
uuacagauuu aauggaauug gagugacaca gaauguguua uaugaaaauc agaaacugau 2820
ugcaaaucag uuuaauucug caauuggcaa aauucaggau ucucugucuu cuacagcuuc 2880
ugcucuggga aaacugcagg auguggugaa ucagaaugca caggcacuga auacucuggu 2940
gaaacagcug ucuagcaauu uuggggcaau uucuucugug cugaaugaua uucugucuag 3000
acuggauccu ccugaagcug aagugcagau ugauagacug aucacaggaa gacugcaguc 3060
ucugcagacu uaugugacac agcagcugau uagagcugcu gaaauuagag cuucugcuaa 3120
ucuggcugcu acaaaaaugu cugaaugugu gcugggacag ucaaaaagag uggauuuuug 3180
uggaaaagga uaucaucuga ugucuuuucc acagucugcu ccacauggag uggugguuuu 3240
acaugugaca uaugugccag cacaggaaaa gaauuuuacc acagcaccag caauuuguca 3300
ugauggaaaa gcacauuuuc caagagaagg aguguuugug ucuaauggaa cacauugguu 3360
ugugacacag agaaauuuuu augaaccuca gauuauuaca acagauaaua cauuuguguc 3420
aggaaauugu gaugugguga uuggaauugu gaauaauaca guguaugauc cacugcagcc 3480
agaacuggau ucuuuuaaag aagaacugga uaaauauuuu aaaaaucaca caucuccuga 3540
uguggauuua ggagauauuu cuggaaucaa ugcaucugug gugaauauuc agaaagaaau 3600
ugauagacug aaugaagugg ccaaaaaucu gaaugaaucu cugauugauc ugcaggaacu 3660
uggaaaauau gaacaguaca uuaaauggcc uugguacauu uggcuuggau uuauugcagg 3720
auuaauugca auugugaugg ugacaauuau guuauguugu augacaucau guuguucuug 3780
uuuaaaagga uguuguucuu guggaagcug uuguaaauuu gaugaagaug auucugaacc 3840
uguguuaaaa ggagugaaau ugcauuacac augaugacuc gagcugguac ugcaugcacg 3900
caaugcuagc ugccccuuuc ccguccuggg uaccccgagu cucccccgac cucgggucec 3960 agguaugcuc ccaccuccac cugccccacu caccaccucu gcuaguucca gacaccuccc 4020
aagcacgcag caaugcagcu caaaacgcuu agccuagcca cacccccacg ggaaacagca 4080
gugauuaacc uuuagcaaua aacgaaaguu uaacuaagcu auacuaaccc cagggguuggu 4140 caauuucgug ccagccacac ccuggagcua gcaaaaaaaa aaaaaaaaaa aaaaaaaaaa 4200
aagcauauga cuaaaaaaaa aaaaaaaaaa aaaaaaaaaa aaaaaaaaaa aaaaaaaaaa 4260
aaaaaaaaaa aaaaaaaaaa aa 4282

<210> SEQ ID NO 29
<211> LENGTH: 4282
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 29
gggcgaacua guauucuucu ggucccccaca gacucagaga gaacccgcca ccauguucgu 60
guuccuggug cugcugccuc ugguguccag ccagugugug aaccugacca ccagaacaca 120
gcugccucca gccuacacca acagcuuuac cagaggcgug uacuaccccg acaaggugguu 180 cagauccagc gugcugcacu cuacccagga ccuguuccug ccuuucuuca gcaacgugac 240
cugguuccac gccauccacg uguccggcac caauggcacc aagagauucg acaaccccgu 300
gcugcccuuc aacgacgggg uguacuuugc cagcaccgag aaguccaaca ucaucagagg 360
cuggaucuuc ggcaccacac uggacagcaa gacccagagc cugcugaucg ugaacaacgc 420
caccaacgug gucaucaaag ugugcgaguu ccaguucugc aacgaccccu uccugggcgu 480
cuacuaccac aagaacaaca agagcuggau ggaaagcgag uuccgggugu acagcagcgc 540
caacaacugc accuucgagu acgugaccca gccuuuccug auggaccugg aaggcaagca 600
gggcaacuuc aagaaccugc gcgaguucgu guuuaagaac aucgacggcu acuucaagau 660
cuacagcaag cacaccccua ucaaccucgu gcgggaucug ccucagggcu ucucugcucu 720
ggaaccccug guggaucugc ccaucggcau caacaucacc cgguuucaga cacugcuggc 780
ccugcacaga agcuaccuga caccuggcga uagcagcagc ggauggacag cuggugccgc 840
cgcuuacuau gugggcuacc ugcagccuag aaccuuccug cugaaguaca acgagaacgg 900
caccaucacc gacgccgugg auugugcucu ggauccucug agcgagacaa agugcacccu 960
gaaguccuuc accguggaaa agggcaucua ccagaccagc aacuuccggg ugcagcccac 1020
cgaauccauc gugcgguucc ccaauaucac caaucugugc ccuuucggcg agguguucaa 1080
ugccaccaga uucgccucug uguacgccug gaaccggaag cggaucagca auugcguggc 1140
cgacuacucc gugcuguaca acuccgccag cuucagcacc uucaagugcu acggcguguc 1200
cccuaccaag cugaacgacc ugugcuucac aaacguguac gccgacagcu ucgugauccg 1260
gggagaugaa gugcggcaga uugccccugg acagacaggc aagaucgccg acuacaacua 1320
caagcugccc gacgacuuca ccggcugugu gauugccugg aacagcaaca accuggacuc 1380

-continued

```
caaagucggc ggcaacuaca auuaccugua ccggcuguuc cggaagucca aucugaagcc   1440
cuucgagcgg gacaucucca ccgagaucua ucaggccggc agcaccccuu guaacggcgu   1500
ggaaggcuuc aacugcuacu ucccacugca guccuacggc uuucagccca caaauggcgu   1560
gggcuaucag cccuacagag ugguggugcu gagcuucgaa cugcugcaug ccccugccac   1620
agugugcggc ccuaagaaaa gcaccaaucu cgugaagaac aaaugcguga acuucaacuu   1680
caacggccug accggcaccg gcgugcugac agagagcaac aagaaguucc ugccauucca   1740
gcaguuuggc cgggauaucg ccgauaccac agacgccguu agagaucccc agacacugga   1800
aauccuggac aucaccccuu gcagcuucgg cggagugucu gugaucaccc cuggcaccaa   1860
caccagcaau cagguggcag ugcuguacca ggacgugaac uguaccgaag ugcccguggc   1920
cauucacgcc gaucagcuga caccuacaug gcggguguac uccaccggca gcaauguguu   1980
ucagaccaga gccggcuguc ugaucggagc cgagcacgug aacaauagcu acgagugcga   2040
caucccca uc ggcgcuggaa ucugcgccag cuaccagaca cagacaaaca gcccucggag   2100
agccagaagc guggccagcc agagcaucau ugccuacaca augucucugg gcgccgagaa   2160
cagcguggcc uacuccaaca acucuaucgc uaucccca cc aacuucacca ucagcgugac   2220
cacagagauc cugccugugu ccaugaccaa gaccagcgug gacugcacca uguacaucug   2280
cggcgauucc accgagugcu ccaaccugcu gcugcaguac ggcagcuucu gcacccagcu   2340
gaauagagcc cugacaggga ucgccgugga acaggacaag aacacccaag agguguucgc   2400
ccaagugaag cagaucuaca agaccccucc uaucaaggac uucggcggcu ucaauuucag   2460
ccagauucug cccgauccua gcaagcccag caagcggagc uucaucgagg accugcuguu   2520
caacaaagug acacuggccg acgccggcuu caucaagcag uauggcgauu gucugggcga   2580
cauugccgcc agggaucuga uuugcgccca gaaguuuaac ggacugacag ugcugccucc   2640
ucugcugacc gaugagauga ucgcccagua cacaucugcc cugcuggccg gcacaaucac   2700
aagcggcugg acauuuggag caggcgccgc ucugcagauc cccuuugcua ugcagauggc   2760
cuaccgguuc aacggcaucg gagugaccca gaaugugcug uacgagaacc agaagcugau   2820
cgccaaccag uucaacagcg ccaucggcaa gauccaggac agccugagca gcacagcaag   2880
cgcccuggga aagcugcagg acguggucaa ccagaaugcc caggcacuga acacccuggu   2940
caagcagcug uccuccaacu ucggcgccau cagcucugug cugaacgaua uccugagcag   3000
acuggacccu ccugaggccg aggugcagau cgacagacug aucacaggca gacugcagag   3060
ccuccagaca uacgugaccc agcagcugau cagagccgcc gagauuagag ccucugccaa   3120
ucuggccgcc accaagaugu cugagugugu gcugggccag agcaagagag uggacuuuug   3180
cggcaagggc uaccaccuga ugagcuuccc ucagucugcc ccucacggcg ugguguuucu   3240
gcacgugaca uaugugcccg cucaagagaa gaauuucacc accgcuccag ccaucugcca   3300
cgacggcaaa gcccacuuuc cuagagaagg cguguucgug uccaacggca cccauuggu u   3360
cgugacacag cggaacuucu acgagcccca gaucaucacc accgacaaca ccuucguguc   3420
uggcaacugc gacgucguga ucggcauugu gaacaauacc guguacgacc cucugcagcc   3480
cgagcuggac agcuucaaag aggaacugga caaguacuuu aagaaccaca caagccccga   3540
cguggaccug ggcgauauca gcggaaucaa ugccagcguc gugaacaucc agaaagagau   3600
cgaccggcug aacgaggugg ccaagaaucu gaacgagagc cugaucgacc ugcaagaacu   3660
ggggaaguac gagcaguaca ucaaguggcc cugguacauc uggcugggcu uuaucgccgg   3720
acugauugcc aucgugaugg ucacaaucau gcuguguugc augaccagcu gcuguagcug   3780
```

ccugaagggc uguuguagcu guggcagcug cugcaaguuc gacgaggacg auucugagcc 3840
cgugcugaag ggcgugaaac ugcacuacac augaugacuc gagcugguac ugcaugcacg 3900
caaugcuagc ugccccuuuc ccguccuggg uaccccgagu cucccccgac cucgggucc c 3960 agguaugcuc ccaccuccac cugccccacu caccaccucu gcuaguucca gacaccuccc 4020
aagcacgcag caaugcagcu caaaacgcuu agccuagcca cacccccacg ggaaacagca 4080
gugauuaacc uuuagcaaua aacgaaaguu uaacuaagcu auacuaaccc caggguuggu 4140
caauuucgug ccagccacac ccuggagcua gcaaaaaaaa aaaaaaaaaa aaaaaaaaaa 4200
aagcauauga cuaaaaaaaa aaaaaaaaaa aaaaaaaaaa aaaaaaaaaa aaaaaaaaaa 4260
aaaaaaaaaa aaaaaaaaaa aa 4282

<210> SEQ ID NO 30
<211> LENGTH: 1261
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 30
gggcgaacua guauucuucu ggucccccaca gacucagaga gaacccgcca ccauguuugu 60
guuucuugug cugcugccuc uugugucuuc ucagugugug gugagauuuc caaauauuac 120
aaaucugugu ccauuuggag aaguguuuaa ugcaacaaga uuugcaucug uguaugcaug 180
gaauagaaaa agaauuucua auugugugggc ugauuauucu gugcuguaua auagugcuuc 240
uuuuuccaca uuuaaauguu auggagugc uccaacaaaa uuaaaugauu uauguuuuac 300
aaauguguau gcugauucuu uugugaucag aggugaugaa gugagacaga uugcccccgg 360
acagacagga aaaauugcug auuacaauua caaacugccu gaugauuuua caggaugugu 420
gauugcuugg aauucuaaua auuuagauuc uaaaguggga ggaaauuaca auuaucugua 480
cagacuguuu agaaaaucaa aucugaaacc uuuugaaaga gauauuucaa cagaaauuua 540
ucaggcugga ucaacaccuu guaauggagu ggaaggauuu aauuguuauu uuccauuaca 600
gagcuaugga uuucagccaa ccaauggugu gggauaucag ccauauagag uggugguggcu 660 gucuuuugaa cugcugcaug caccugcaac agugugugga ccuaaaggcu cccccggcuc 720
cggcuccgga ucugguuaua uuccugaagc uccaagagau gggcaagcuu acguucguaa 780
agauggcgaa uggguauuac uuucuaccuu uuuaggccgg ucccuggagg ugcuguucca 840
gggccccggc ugaugacucg agcugguacu gcaugcacgc aaugcuagcu gccccuuucc 900
cguccugggu accccgaguc ucccccgacc ucggguccca gguaugcucc caccuccacc 960
ugccccacuc accaccucug cuaguuccag acaccuccca agcacgcagc aaugcagcuc 1020
aaaacgcuua gccuagccac acccccacgg gaaacagcag ugauuaaccu uuagcaauaa 1080
acgaaaguuu aacuaagcua uacuaacccc aggguugguc aauuucgugc cagccacacc 1140
cuggagcuag caaaaaaaaa aaaaaaaaaa aaaaaaaaaa agcauaugac uaaaaaaaaa 1200
aaaaaaaaaa aaaaaaaaaa aaaaaaaaaa aaaaaaaaaa aaaaaaaaaa aaaaaaaaaa 1260
a 1261

<210> SEQ ID NO 31
<211> LENGTH: 4283
<212> TYPE: RNA
<213> ORGANISM: Artificial Sequence -continued
<220> FEATURE:
<223> OTHER INFORMATION: Description of Artificial Sequence: Synthetic
polynucleotide

<400> SEQUENCE: 31
agaauaaacu aguauucuuc ugguccccac agacucagag agaacccgcc accauguuug 60
uguuucuugu gcugcugccu cuugugucuu cucagugugu gaauuugaca acaagaacac 120
agcugccacc agcuuauaca aauucuuuua ccagaggagu guauuauccu gauaaagugu 180
uuagaucuuc ugugcugcac agcacacagg accuguuucu gccauuuuuu agcaauguga 240
caugguuuca ugcaauucau gugucuggaa caaauggaac aaaaagauuu gauaauccug 300
ugcugccuuu uaaugaugga guguauuuug cuucaacaga aaagucaaau auuauuagag 360
gauggauuuu uggaacaaca cuggauucua aaacacaguc ucugcugauu gugaauaaug 420
caacaaaugu ggugauuaaa gugugugaau uucaguuuug uaaugauccu uuucugggag 480
uguauuauca caaaaauaau aaaucuugga uggaaucuga auuuagagug uauuccucug 540
caaauaauug uacauuugaa uaugugucuc agccuuuucu gauggaucug gaaggaaaac 600
agggcaauuu uaaaaaucug agagaauuug uguuuaaaaa uauugaugga uauuuuaaaa 660
uuuauucuaa acacacacca auuaauuuag ugagagaucu gccucaggga uuuucugcuc 720
uggaaccucu gguggaucug ccaauuggca uuaauauuac aagauuucag acacugcugg 780
cucugcacag aucuuaucug acaccuggag auucuucuuc uggauggaca gccggagcug 840
cagcuuauua ugugggcuau cugcagccaa gaacauuucu gcugaaauau aaugaaaaug 900
gaacaauuac agaugcugug gauugugcuc uggauccucu gucugaaaca aaauguacau 960
uaaaaucuuu uacaguggaa aaaggcauuu aucagacauc uaauuuuaga gugcagccaa 1020
cagaaucuau ugugagauuu ccaaauauua caaaucugug uccauuugga gaaguguuua 1080
augcaacaag auuugcaucu guguaugcau ggaauagaaa aagaauuucu aauugugugg 1140
cugauuauuc ugugcuguau aauagugcuu cuuuuuccac auuuaaaugu uauggagugu 1200
cuccaacaaa auuaaaugau uuauguuuua caaaugugua ugcugauucu uuugugauca 1260
gaggugauga agugagacag auugcccccg gacagacagg aaaaauugcu gauuacaauu 1320
acaaacugcc ugaugauuuu acaggaugug ugauugcuug gaauucuaau aauuuagauu 1380
cuaaaguggg aggaaauuac aauuaucugu acagacuguu uagaaaauca aaucugaaac 1440
cuuuugaaag agauauuuca acagaaauuu aucaggcugg aucaacaccu uguaauggag 1500
uggaaggauu uaauuguuau uuuccauuac agagcuaugg auuucagcca accaauggug 1560
ugggauauca gccauauaga gugguggugc ugucuuuuga acugcugcau gcaccugcaa 1620
cagugugugg accuaaaaaa ucuacaaauu uagugaaaaa uaaaugugug aauuuuaauu 1680
uuaauggauu aacaggaaca ggagugcuga cagaaucuaa uaaaaaauuu cugccuuuuc 1740
agcaguuugg cagagauauu gcagauacca cagaugcagu gagagauccu cagacauuag 1800
aaauucugga uauuacaccu uguucuuuug ggggugugic ugugauuaca ccuggaacaa 1860
auacaucuaa ucagguggcu gugcuguauc aggaugugaa uuguacagaa gugccagugg 1920
caauucaugc agaucagcug acaccaacau ggagagugua uucuacagga ucuaaugugu 1980
uucagacaag agcaggaugu cugauuggag cagaacaugu gaauaauucu uaugaaugug 2040
auauuccaau uggagcaggc auuugugcau cuuaucagac acagacaaau uccccaagga 2100
gagcaagauc uguggcaucu cagucuauua uugcauacac caugucucug ggagcagaaa 2160
auucuguggc auauucuaau aauucuauug cuauuccaac aaauuuuacc auuucuguga 2220
caacagaaau uuuaccugug ucuaugacaa aaacaucugu ggauuguacc auguacauuu 2280
guggagauuc uacagaaugu ucuaaucugc ugcugcagua uggaucuuuu uguacacagc 2340
ugaauagagc uuuaacagga auugcugugg aacaggauaa aaauacacag gaaguguuug 2400
cucaggugaa acagauuuac aaaacaccac caauuaaaga uuuuggagga uuuaauuuua 2460
gccagauucu gccugauccu ucuaaaccuu cuaaaagauc uuuuauugaa gaucugcugu 2520
uuaauaaagu gacacuggca gaugcaggau uuauuaaaca guauggagau ugccugggug 2580
auauugcugc aagagaucug auuugugcuc agaaauuuaa uggacugaca gugcugccuc 2640
cucugcugac agaugaaaug auugcucagu acacaucugc uuuacuggcu ggaacaauua 2700
caagcggaug gacauuugga gcuggagcug cucugcagau uccuuuugca augcagaugg 2760
cuuacagauu uaauggaauu ggagugacac agaauguguu auaugaaaau cagaaacuga 2820
uugcaaauca guuuaauucu gcaauuggca aaauucagga uucucugucu ucuacagcuu 2880
cugcucuggg aaaacugcag gaugugguga aucagaaugc acaggcacug aauacucugg 2940
ugaaacagcu gucuagcaau uuuggggcaa uuucuucugu gcugaaugau auucugucua 3000
gacuggaucc uccugaagcu gaagugcaga uugauagacu gaucacagga agacugcagu 3060
cucugcagac uuaugugaca cagcagcuga uuagagcugc ugaaauuaga gcuucugcua 3120
aucuggcugc uacaaaaaug ucugaaugug ugcugggaca gucaaaaaga guggauuuuu 3180
guggaaaagg auaucaucug augucuuuuc cacagucugc uccacaugga gugguguuuu 3240
uacaugugac auaugugcca gcacaggaaa agaauuuuac cacagcacca gcaauuuguc 3300
augauggaaa agcacauuuu ccaagagaag gaguguuugu gucuaaugga acacauuggu 3360
uugugacaca gagaaauuuu uaugaaccuc agauuauuac aacagauaau acauuugugu 3420
caggaaauug ugauguggug auuggaauug ugaauaauac aguguaugau ccacugcagc 3480
cagaacugga uucuuuuaaa gaagaacugg auaaauauuu uaaaaaucac acaucuccug 3540
auguggauuu aggagauauu ucuggaauca augcaucugu ggugaauauu cagaaagaaa 3600
uugauagacu gaaugaagug gccaaaaauc ugaaugaauc ucugauugau cugcaggaac 3660
uuggaaaaua ugaacaguac auuaaauggc cuugguacau uuggcuugga uuuauugcag 3720
gauuaauugc aauugugaug gugacaauua uguuauguug uaugacauca uguuguucuu 3780
guuuaaaagg auguuguucu uguggaagcu guuguaaauu ugaugaagau gauucugaac 3840
cuguguuaaa aggagugaaa uugcauuaca caugaugacu cgagcuggua cugcaugcac 3900
gcaaugcuag cugccccuuu cccguccugg guaccccgag ucucccccga ccucgggucc 3960
cagguaugcu cccaccucca ccugccccac ucaccaccuc ugcuaguucc agacaccucc 4020
caagcacgca gcaaugcagc ucaaaacgcu uagccuagcc acacccccac gggaaacagc 4080
agugauuaac cuuuagcaau aaacgaaagu uuaacuaagc uauacuaacc ccaggguugg 4140
ucaauuucgu gccagccaca cccuggagcu agcaaaaaaa aaaaaaaaaa aaaaaaaaaa 4200
aaagcauaug acuaaaaaaa aaaaaaaaaa aaaaaaaaaa aaaaaaaaaa aaaaaaaaaa 4260
aaaaaaaaaa aaaaaaaaaa aaa 4283

<210> SEQ ID NO 32
<211> LENGTH: 1262
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 32

```
agaauaaacu aguauucuuc ugguccccac agacucagag agaacccgcc accauguuug     60
uguuucuugu gcugcugccu cuugugucuu cucagugugu ggugagauuu ccaaauauua    120
caaaucugug uccauuugga gaaguguuua augcaacaag auuugcaucu guguaugcau    180
ggaauagaaa aagaauuucu aauugugugg cugauuauuc ugugcuguau aauagugcuu    240
cuuuuuccac auuuaaaugu uauggagugu cuccaacaaa auuaaaugau uuauguuuua    300
caaaugugua ugcugauucu uuugugauca gaggugauga agugagacag auugcccccg    360
gacagacagg aaaaauugcu gauuacaauu acaaacugcc ugaugauuuu acaggaugug    420
ugauugcuug gaauucuaau aauuuagauu cuaaaguggg aggaaauuac aauuaucugu    480
acagacuguu uagaaaauca aaucugaaac cuuuugaaag agauauuuca acagaaauuu    540
aucaggcugg aucaacaccu uguaauggag uggaaggauu uaauuguuau uuuccauuac    600
agagcuaugg auuucagcca accaauggug ugggauauca gccauauaga gugguggugc    660
ugucuuuuga acugcugcau gcaccugcaa cagugugugg accuaaaggc ucccccggcu    720
ccggcuccgg aucugguuau auuccugaag cuccaagaga ugggcaagcu uacguucgua    780
aagauggcga augggu auua cuuucuaccu uuuuaggccg gucccuggag gugcuguucc    840
agggccccgg cugaugacuc gagcugguac ugcaugcacg caaugcuagc ugccccuuuc    900
ccguccuggg uaccccgagu cucccccgac cucgggaccc agguaugcuc ccaccuccac    960
cugccccacu caccaccucu gcuaguucca gacaccuccc aagcacgcag caaugcagcu   1020
caaaacgcuu agccuagcca cacccccacg ggaaacagca gugauuaacc uuuagcaaua   1080
aacgaaaguu uaacuaagcu auacuaaccc caggguuggu caauuucgug ccagccacac   1140
ccuggagcua gcaaaaaaaa aaaaaaaaaa aaaaaaaaaa aagcauauga cuaaaaaaaa   1200
aaaaaaaaaa aaaaaaaaaa aaaaaaaaaa aaaaaaaaaa aaaaaaaaaa aaaaaaaaaa   1260
aa                                                                  1262
```

<210> SEQ ID NO 33
<211> LENGTH: 11917
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 33

```
gaugggcggc gcaugagaga agcccagacc aauuaccuac ccaaaaugga gaaaguucac     60
guugacaucg aggaagacag cccauuccuc agagcuuugc agcggagcuu cccgcaguuu    120
gagguagaag ccaagcaggu cacugauaau gaccaugcua augccagagc guuuucgcau    180
cuggcuucaa aacugaucga aacggaggug gacccauccg acacgauccu ugacauugga    240
agugcgcccg cccgcagaau guauucuaag cacaaguauc auuguaucug uccgaugaga    300
ugugcggaag auccggacag auuguauaag uaugcaacua agcugaagaa aaacuguaag    360
gaaauaacug auaaggaauu ggacaagaaa augaaggagc ucgccgccgu caugagcgac    420
ccugaccugg aaacugagac uaugugccuc cacgacgacg agucgugucg cuacgaaggg    480
caagucgcug uuuaccagga uguauacgcg guugacggac cgacaagucu cuaucaccaa    540
gccaauaagg gaguuagagu cgccuacugg auaggcuuug acaccacccc uuuuauguuu    600
aagaacuugg cuggagcaua uccaucauac ucuaccaacu gggccgacga aaccguguua    660
```

acggcucgua acauaggccu augcagcucu gacguuaugg agcggucacg uagagggaug 720
uccauucuua gaaagaagua uuugaaacca uccaacaaug uucuauucuc uguuggcucg 780
accaucuacc acgaaaagag ggacuuacug aggagcuggc accugccguc uguauuucac 840
uuacguggca agcaaaauua cacaugucgg ugugagacua uaguuaguug cgacggguac 900
gucguuaaaa gaauagcuau caguccaggc cuguauggga agccuucagg cuaugcugcu 960
acgaugcacc gcgagggauu cuugugcugc aaagugacag acacauugaa cggggagagg 1020
gucucuuuuc ccgugugcac guaugugcca gcuacauugu gugaccaaau gacuggcaua 1080
cuggcaacag augucagugc ggacgacgcg caaaaacugc ugguugggcu caaccagcgu 1140
auagucguca acggucgcac ccagagaaac accaauacca ugaaaaauua ccuuuugccc 1200
guaguggccc aggcauuugc uaggugggca aaggaauaua aggaagauca agaagaugaa 1260
aggccacuag gacuacgaga uagacaguua gucaugggggu guuguugggc uuuuagaagg 1320
cacaagauaa caucuauuua uaagcgcccg gauacccaaa ccaucaucaa agugaacagc 1380
gauuuccacu cauucgugcu gcccaggaua ggcaguaaca cauuggagau cgggcugaga 1440
acaagaauca ggaaaauguu agaggagcac aaggagccgu caccucucau uaccgccgag 1500
gacguacaag aagcuaagug cgcagccgau gaggcuaagg aggugcguga agccgaggag 1560
uugcgcgcag cucuaccacc uuuggcagcu gauguugagg agcccacucu ggaagccgau 1620
gucgacuuga uguuacaaga ggcuggggcc ggcucagugg agacaccucg uggcuugaua 1680
aagguuacca gcuacgcugg cgaggacaag aucggcucuu acgcugugcu uucuccgcag 1740
gcuguacuca agagugaaaa auuaucuugc auccacccuc ucgcugaaca agucauagug 1800
auaacacacu cuggccgaaa agggcguuau gccguggaac cauaccaugg uaaaguagug 1860
gugccagagg gacaugcaau acccguccag gacuuucaag cucugaguga aagugccacc 1920
auuguguaca acgaacguga guucguaaac agguaccugc accauauugc cacacaugga 1980
ggagcgcuga acacugauga agaauauuac aaaacuguca agcccagcga gcacgacggc 2040
gaauaccugu acgacaucga caggaaacag ugcgucaaga aagagcuagu cacugggcua 2100
gggcucacag gcgagcuggu cgauccuccc uuccaugaau ucgccuacga gagucugaga 2160
acacgaccag ccgcuccuua ccaaguacca accauagggg uguauggcgu gccaggauca 2220
ggcaagucug gcaucauuaa aagcgcaguc accaaaaaag aucuaguggu gagcgccaag 2280
aaagaaaacu gugcagaaau uauaagggac gucaagaaaa ugaaagggcu ggacgucaau 2340
gccagaacug uggacucagu gcucuugaau ggaugcaaac accccguaga gacccuguau 2400
auugacgagg cuuuugcuug ucaugcaggu acucucagag cgcucauagc cauuauaaga 2460
ccuaaaaagg cagugcucug cggagauccc aaacagugcg guuuuuuuaa caugaugugc 2520
cugaaagugc auuuuaacca cgagauuugc acacaagucu uccacaaaag caucucucgc 2580
cguugcacua aaucugugac uucggucguc ucaaccuugu uuuacgacaa aaaaaugaga 2640
acgacgaauc cgaaagagac uaagauugug auugacacua ccggcaguac caaaccuaag 2700
caggacgauc ucauucucac uuguuucaga gggugggguga agcaguugca aauagauuac 2760
aaaggcaacg aaauaaugac ggcagcugcc ucucaagggc ugacccguaa aggugugu au 2820 gccguucggu acaaggugaa ugaaaauccu cuguacgcac ccaccucaga acaugugaac 2880
guccuacuga cccgcacgga ggaccgcauc guguggaaaa cacuagccgg cgacccaugg 2940 auaaaaaacac ugacugccaa guacccuggg aauuucacug ccacgauaga ggaguggcaa 3000
gcagagcaug augccaucau gaggcacauc uuggagagac cggacccuac cgacgucuuc 3060
cagaauaagg caaacgugug uugggccaag gcuuuagugc cggugcugaa gaccgcuggc 3120
auagacauga ccacugaaca auggaacacu guggauuauu uugaaacgga caaagcucac 3180
ucagcagaga uaguauugaa ccaacuaugc gugagguucu uuggacucga ucuggacucc 3240
ggucuauuuu cugcacccac uguuccguua uccauuagga auaaucacug ggauaacucc 3300
ccgucgccua acauguacgg gcugaauaaa gaaguggucc gucagcucuc ucgcagguac 3360
ccacaacugc cucgggcagu ugccacuggu agagucuaug acaugaacac ugguacacug 3420
cgcaauuaug auccgcgcau aaaccuagua ccuguaaaca gaagacugcc ucaugcuuua 3480
guccuccacc auaaugaaca cccacagagu gacuuuucuu cauucgucag caaauugaag 3540
ggcagaacug uccugguggu cggggaaaag uuguccgucc caggcaaaau gguugacugg 3600
uugucagacc ggccugaggc uaccuucaga gcucggcugg auuuaggcau cccaggugau 3660
gugcccaaau augacauaau auuuguuaau gugaggaccc cauauaaaua ccaucacuau 3720
cagcagugug aagaccaugc cauuaagcua agcauguuga ccaagaaagc augucugcau 3780
cugaaucccg gcggaaccug ugucagcaua gguuaugguu acgcugacag ggccagcgaa 3840
agcaucauug gugcuauagc gcggcaguuc aaguuucccc gaguaugcaa accgaaaucc 3900
ucacuugagg agacggaagu ucuguuugua uucauugggu acgaucgcaa ggcccguacg 3960
cacaauccuu acaagcuauc aucaaccuug accaacauuu auacagguuc cagacuccac 4020
gaagccggau gugcacccuc auaucaugug gugcgagggg auauugccac ggccaccgaa 4080
ggagugauua uaaaugcugc uaacagcaaa ggacaaccug gcggaggggu gugcggagcg 4140
cuguauaaga aauucccgga aaguuucgau uuacagccga ucgaaguagg aaaagcgcga 4200
cuggucaaag gugcagcuaa acauaucauu caugccguag gaccaaacuu caacaaaguu 4260
ucggagguug aaggugacaa acaguuggca gaggcuuaug aguccaucgc uaagauuguc 4320
aacgauaaca auuacaaguc aguagcgauu ccacuguugu ccaccggcau cuuuuccggg 4380
aacaaagauc gacuaaccca aucauugaac cauuugcuga cagcuuuaga caccacugau 4440
gcagauguag ccauauacug cagggacaag aaaugggaaa ugacucucaa ggaagcagug 4500
gcuaggagag aagcagugga ggagauaugc auauccgacg auucuucagu gacagaaccu 4560
gaugcagagc ugguggaggu gcaucccaag aguucuuugg cuggaaggaa gggcuacagc 4620
acaagcgaug gcaaaacuuu cucauauuug gaagggacca aguuucacca ggcggccaag 4680
gauauagcag aaauuaaugc cauguggccc guugcaacgg aggccaauga gcagguaugc 4740
auguauaucc ucggagaaag caugagcagu auuaggucga aaugccccgu cgaggagucg 4800
gaagccucca caccaccuag cacgcugccu ugcuugugca uccaugccau gacuccagaa 4860
agaguacagc gccuaaaagc cucacgucca gaacaaauua cugugugcuc auccuuucca 4920
uugccgaagu auagaaucac uggugugcag aagauccaau gcucccagcc uauauuguuc 4980
ucaccgaaag ugccugcgua uauucaucca aggaaguauc ucguggaaac accaccggua 5040
gacgagacuc cggagccauc ggcagagaac caauccacag aggggacacc ugaacaacca 5100
ccacuuauaa ccgaggauga gaccaggacu agaacgccug agccgaucau caucgaagaa 5160
gaagaagaag auagcauaag uuugcuguca gauggcccga cccaccaggu gcugcaaguc 5220
gaggcagaca uucacgggcc gcccucugua ucuagcucau ccugguccau uccucaugca 5280
uccgacuuug auguggacag uuuauccaua cuugacaccc uggagggagc uagcgugacc 5340
agcggggcaa cgucagccga gacuaacucu uacuucgcaa agaguaugga guuucuggcg 5400
cgaccggugc cugcgccucg aacaguauuc aggaacccuc cacaucccgc uccgcgcaca 5460
agaacaccgu cacuugcacc cagcagggcc ugcuccagaa ccagccuagu uuccaccccg 5520
ccaggcguga auagggugau cacuagagag gagcucgaag cgcuuacccc gucacgcacu 5580
ccuagcaggu cggucuccag aaccagccug gucuccaacc cgccaggcgu aaauagggug 5640
auuacaagag aggaguuuga ggcguucgua gcacaacaac aaugacgguu ugaugcgggu 5700
gcauacaucu uuuccuccga caccggucaa gggcauuuac aacaaaaauc aguaaggcaa 5760
acggugcuau ccgaagugu guuggagagg accgaauugg agauuucgua ugccccgcgc 5820
cucgaccaag aaaaagaaga auuacuacgc aagaaauuac aguuaaaucc cacaccugcu 5880
aacagaagca gauaccaguc caggaaggug gagaacauga aagccauaac agcuagacgu 5940
auucugcaag gccuagggca uuauuugaag gcagaaggaa aaguggagug cuaccgaacc 6000
cugcauccug uuccuuugua uucaucuagu gugaaccgug ccuuuucaag ccccaagguc 6060
gcaguggaag ccuguaacgc cauguugaaa gagaacuuuc cgacuguggc uucuuacugu 6120
auuauuccag aguacgaugc cuauuuggac augguugacg gagcuucaug cugcuuagac 6180
acugccaguu uuugcccugc aaagcugcgc agcuuuccaa agaaacacuc cuauuuggaa 6240
cccacaauac gaucggcagu gccuucagcg auccagaaca cgcuccagaa cguccuggca 6300
gcugccacaa aaagaaauug caaugucacg caaaugagag aauugcccgu auuggauucg 6360
gcggccuuua auguggaaug cuucaagaaa uaugcgugua auaaugaaua uugggaaacg 6420
uuuaaagaaa accccaucag gcuuacugaa gaaaacgugg uaaauuacau uaccaaauua 6480
aaaggaccaa aagcugcugc ucuuuuugcg aagacacaua auuugaauau guugcaggac 6540
auaccaaugg acagguuugu aauggacuua aagagagacg ugaaagugac uccaggaaca 6600
aaacauacug aagaacggcc caagguacag gugauccagg cugccgaucc gcuagcaaca 6660
gcguaucugu gcggaaucca ccgagagcug guuaggagau uaaaugcggu ccugcuuccg 6720
aacauucaua cacuguuuga uaugucggcu gaagacuuug acgcuauuau agccgagcac 6780
uuccagccug gggauugugu ucuggaaacu gacaucgcgu cguuugauaa aagugaggac 6840
gacgccaugg cucugaccgc guuaaugauu cuggaagacu uaggugugga cgcagagcug 6900
uugacgcuga uugaggcggc uuucggcgaa auuucaucaa uacauuugcc cacuaaaacu 6960
aaauuuaaau ucggagccau gaugaaaucu ggaauguucc ucacacuguu ugugaacaca 7020
gucauuaaca uuguaaucgc aagcagagug uugagagaac ggcuaaccgg aucaccaugu 7080
gcagcauuca uuggagauga caauaucgug aaaggaguca aaucggacaa auuaauggca 7140
gacaggugcg ccaccugguu gaauauggaa gucaagauua uagaugcugu ggugggcgag 7200
aaagcgccuu auuucugugg aggguuuauu uugugugacu ccgugaccgg cacagcgugc 7260
cguguggcag acccccuaaa aaggcuguuu aagcuaggca aaccucuggc agcagacgau 7320
gaacaugaug augacaggag aagggcauug caugaggagu caacacgcug gaaccgagug 7380
gguauucuuu cagagcugug caaggcagua gaaucaaggu augaaaccgu aggaacuucc 7440
aucauaguua uggccaugac uacucuagcu agcaguguua aaucauucag cuaccugaga 7500
ggggccccua uaacucucua cggcuaaccu gaauggacua cgacauaguc uaguccgcca 7560
agacuaguau guuuguguuu cuugugcugc ugccucuugu gucuucucag ugugugaauu 7620
ugacaacaag aacacagcug ccaccagcuu auacaaauuc uuuuaccaga ggaguguauu 7680
auccugauaa aguguuuaga ucuucugugc ugcacagcac acaggaccug uuucugccau 7740

-continued uuuuuagcaa ugugacaugg uuucaugcaa uucaugugug uggaacaaau ggaacaaaaa 7800
gauuugauaa uccugugcug ccuuuuaaug auggagugua uuuugcuuca acagaaaagu 7860
caaauauuau uagaggaugg auuuuuggaa caacacugga uucuaaaaca cagucucugc 7920
ugauugugaa uaaugcaaca aaugugguga uuaaagugug ugaauuucag uuuuguaaug 7980
auccuuuucu gggaguguau uaucacaaaa auaauaaauc uuggauggaa ucugaauuua 8040
gaguguauuc cucugcaaau aauuguacau uugaauaugu gucucagccu uuucugaugg 8100
aucuggaagg aaaacagggc aauuuuaaaa aucugagaga auuuguguuu aaaaauauug 8160
auggauauuu uaaaauuuau ucuaaacaca caccaauuaa uuuagugaga gaucugccuc 8220
agggauuuuc ugcucuggaa ccucuggugg aucugccaau uggcauuaau auuacaagau 8280
uucagacacu gcuggcucug cacagaucuu aucugacacc uggagauucu ucuucuggau 8340
ggacagccgg agcugcagcu uauuaugugg gcuaucugca gccaagaaca uuucugcuga 8400
aauauaauga aaauggaaca auuacagaug cuguggauug ugcucuggau ccucugucug 8460
aaacaaaaug uacauuaaaa ucuuuuacag uggaaaaagg cauuuaucag acaucuaauu 8520
uuagagugca gccaacagaa ucuauuguga gauuuccaaa uauuacaaau cuguguccau 8580
uuggagaagu guuuaaugca acaagauuug caucugugua ugcauggaau agaaaaagaa 8640
uuucuaauug uguggcugau uauucugugc uguauaauag ugcuucuuuu uccacauuua 8700
aauguuaugg agugucucca acaaaauuaa augauuuaug uuuuacaaau guguaugcug 8760
auucuuuugu gaucagaggu gaugaaguga gacagauugc ccccggacag acaggaaaaa 8820
uugcugauua caauuacaaa cugccugaug auuuuacagg augugugauu gcuuggaauu 8880
cuaauaauuu agauucuaaa gugggaggaa auuacaauua ucuguacaga cuguuuagaa 8940
aaucaaaucu gaaaccuuuu gaaagagaua uuucaacaga aauuuaucag gcuggaucaa 9000
caccuuguaa uggaguggaa ggauuuaauu guuauuuucc auuacagagc uauggauuuc 9060
agccaaccaa uggugugggga uaucagccau auagaguggu ggugcugucu uuugaacugc 9120
ugcaugcacc ugcaacagug uguggaccua aaaaaucuac aaauuuagug aaaaauaaau 9180
gugugaauuu uaauuuuaau ggauuaacag gaacaggagu gcugacagaa ucuaauaaaa 9240
aauuucugcc uuuucagcag uuuggcagag auauugcaga uaccacagau gcagugagag 9300
auccucagac auuagaaauu cuggauauua caccuuguuc uuuugggggu gugucuguga 9360
uuacaccugg aacaaauaca ucuaaucagg uggcugugcu guaucaggau gugaauugua 9420
cagaagugcc aguggcaauu caugcagauc agcugacacc aacauggaga guguauucua 9480
caggaucuaa uguguuucag acaagagcag gaugucugau uggagcagaa caugugaaua 9540
auucuuauga augugauauu ccaauuggag caggcauuug ugcaucuuau cagacacaga 9600
caaauucccc aaggagagca agaucugugg caucucaguc uauuauugca uacaccaugu 9660
cucugggagc agaaaauucu guggcauauu cuaauaauuc uauugcuauu ccaacaaauu 9720
uuaccauuuc ugugacaaca gaaauuuuac cugugucuau gacaaaaaca ucuguggauu 9780
guaccaugua cauuugugga gauucuacag aauguucuaa ucugcugcug caguauggau 9840
cuuuuuguac acagcugaau agagcuuuaa caggaauugc uguggaacag gauaaaaaua 9900
cacaggaagu guuugcucag gugaaacaga uuuacaaaac accaccaauu aaagauuuug 9960
gaggauuuaa uuuuagccag auucugccug auccuucuaa accuucuaaa agaucuuuua 10020
uugaagaucu gcuguuuaau aaagugacac uggcagaugc aggauuuauu aaacaguaug 10080
gagauugccu gggugauauu gcugcaagag aucugauuug ugcucagaaa uuuaauggac 10140
ugacagugcu gccuccucug cugacagaug aaaugauugc ucaguacaca ucugcuuuac 10200
uggcuggaac aauuacaagc ggauggacau uuggagcugg agcugcucug cagauuccuu 10260
uugcaaugca gauggcuuac agauuuaaug gaauuggagu gacacagaau guguuauaug 10320
aaaaucagaa acugauugca aaucaguuua auucugcaau uggcaaaauu caggauucuc 10380
ugucuucuac agcuucugcu cugggaaaac ugcaggaugu ggugaaucag aaugcacagg 10440
cacugaauac ucuggugaaa cagcugucua gcaauuuugg ggcaauuucu ucugugcuga 10500
augauauucu gucuagacug gauccuccug aagcugaagu gcagauugau agacugauca 10560
caggaagacu gcagucucug cagacuuaug ugacacagca gcugauuaga gcugcugaaa 10620
uuagagcuuc ugcuaaucug gcugcuacaa aaaugucuga augugugcug ggacagucaa 10680
aaagagugga uuuuugugga aaaggauauc aucugauguc uuuuccacag ucugcuccac 10740
auggagugga guuuuuacau gugacauaug ugccagcaca ggaaaagaau uuuaccacag 10800
caccagcaau uugucaugau ggaaaagcac auuuuccaag agaaggagug uuugugucua 10860
auggaacaca uugguuugug acacagagaa auuuuuauga accucagauu auuacaacag 10920
auaauacauu ugugucagga aauugugaug uggugauugg aauugugaau aauacagugu 10980
augauccacu gcagccagaa cuggauucuu uuaaagaaga acuggauaaa uauuuuaaaa 11040
aucacacauc uccugaugug gauuuaggag auauuucugg aaucaaugca ucuguggaga 11100
auauucagaa agaaauugau agacugaaug aaguggccaa aaaucugaau gaaucucuga 11160
uugaucugca ggaacuugga aaauaugaac aguacauuaa auggccuugg uacauuuggc 11220
uuggauuuau ugcaggauua auugcaauug ugauggugac aauuauguua uguuguauga 11280
caucauguug uucuuguuua aaaggauguu guucuugugg aagcuguugu aaauuugaug 11340
aagaugauuc ugaaccugug uuaaaaggag ugaaauugca uuacacauga ugacucgagc 11400
ugguacugca ugcacgcaau gcuagcugcc ccuuucccgu ccuggguacc ccgagucucc 11460
cccgaccucg ggucccaggu augcucccac cuccaccugc cccacucacc accucugcua 11520
guuccagaca ccucccaagc acgcagcaau gcagcucaaa acgcuuagcc uagccacacc 11580
cccacgggaa acagcaguga uuaaccuuua gcaauaaacg aaaguuuaac uaagcuauac 11640
uaaccccagg guuggucaau uucgugccag ccacaccgcg gccgcaugaa uacagcagca 11700
auuggcaagc ugcuuacaua gaacucgcgg cgauuggcau gccgccuuaa aauuuuuauu 11760
uuauuuuuuc uuuucuuuuc cgaaucggau uuuguuuuua auauuucaaa aaaaaaaaaa 11820
aaaaaaaaaa aaaaaaagca uaugacuaaa aaaaaaaaaa aaaaaaaaaa aaaaaaaaaa 11880
aaaaaaaaaa aaaaaaaaaa aaaaaaaaaa aaaaaaa 11917

<210> SEQ ID NO 34
<211> LENGTH: 11917
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 34
gaugggcggc gcaugagaga agcccagacc aauuaccuac ccaaaaugga gaaaguucac 60
guugacaucg aggaagacag cccauuccuc agagcuuugc agcggagcuu cccgcaguuu 120
gagguagaag ccaagcaggu cacugauaau gaccaugcua augccagagc guuuucgcau 180
cuggcuucaa aacugaucga aacggaggug gacccauccg acacgauccu ugacauugga 240
agugcgcccg cccgcagaau guauucuaag cacaaguauc auuguaucug uccgaugaga 300
ugugcggaag auccggacag auuguauaag uaugcaacua agcugaagaa aaacuguaag 360
gaaauaacug auaaggaauu ggacaagaaa augaaggagc ucgccgccgu caugagcgac 420
ccugaccugg aaacugagac uaugugccuc cacgacgacg agucgugucg cuacgaaggg 480
caagucgcug uuuaccagga uguauacgcg guugacggac cgacaagucu cuaucaccaa 540
gccaauaagg gaguuagagu cgccuacugg auaggcuuug acaccacccc uuuuauguuu 600
aagaacuugg cuggagcaua uccaucauac ucuaccaacu gggccgacga aaccguguua 660
acggcucgua acauaggccu augcagcucu gacguuaugg agcggucacg uagagggaug 720
uccauucuua gaaagaagua uuugaaacca uccaacaaug uucuauucuc uguuggcucg 780
accaucuacc acgaaaagag ggacuuacug aggagcuggc accugccguc uguauuucac 840
uuacguggca agcaaaauua cacaugucgg ugugagacua uaguuaguug cgacggguac 900
gucguuaaaa gaauagcuau caguccaggc cuguauggga agccuucagg cuaugcugcu 960
acgaugcacc gcgagggauu cuugugcugc aaagugacag acacauugaa cggggagagg 1020
gucucuuuuc ccgugugcac guaugugcca gcuacauugu gugaccaaau gacuggcaua 1080
cuggcaacag augucagugc ggacgacgcg caaaaacugc ugguugggcu caaccagcgu 1140
auagucguca acggucgcac ccagagaaac accaauacca ugaaaaauua ccuuuugccc 1200
guaguggccc aggcauuugc uaggugggca aaggaauaua aggaagauca agaagaugaa 1260
aggccacuag gacuacgaga uagacaguua gucauggggu guuguugggc uuuuagaagg 1320
cacaagauaa caucuauuua uaagcgcccg gauacccaaa ccaucaucaa agugaacagc 1380
gauuuccacu cauucgugcu gcccaggaua ggcaguaaca cauuggagau cgggcugaga 1440
acaagaauca ggaaaauguu agaggagcac aaggagccgu caccucucau uaccgccgag 1500
gacguacaag aagcuaagug cgcagccgau gaggcuaagg aggugcguga agccgaggag 1560
uugcgcgcag cucuaccacc uuuggcagcu gauguugagg agcccacucu ggaagccgau 1620
gucgacuuga uguuacaaga ggcuggggcc ggcucagugg agacaccucg uggcuugaua 1680
aagguuacca gcuacgcugg cgaggacaag aucggcucuu acgcugugcu uucuccgcag 1740
gcuguacuca agagugaaaa auuaucuugc auccacccuc ucgcugaaca agucauagug 1800
auaacacacu cuggccgaaa agggcguuau gccguggaac cauaccaugg uaaaguagug 1860
gugccagagg gacaugcaau acccguccag gacuuucaag cucugaguga aagugccacc 1920
auuguguaca acgaacguga guucguaaac agguaccugc accauauugc cacacaugga 1980
ggagcgcuga acacugauga agaauauuac aaaacuguca agcccagcga gcacgacggc 2040
gaauaccugu acgacaucga caggaaacag ugcgucaaga aagagcuagu cacugggcua 2100
gggcucacag gcgagcuggu cgauccuccc uuccaugaau ucgccuacga gagucugaga 2160
acacgaccag ccgcuccuua ccaaguacca accauagggg uguauggcgu gccaggauca 2220
ggcaagucug gcaucauuaa aagcgcaguc accaaaaaag aucuaguggu gagcgccaag 2280
aaagaaaacu gugcagaaau uauaagggac gucaagaaaa ugaaagggcu ggacgucaau 2340
gccagaacug uggacucagu gcucuugaau ggaugcaaac accccguaga gacccuguau 2400
auugacgagg cuuuugcuug ucaugcaggu acucucagag cgcucauagc cauuauaaga 2460
ccuaaaaagg cagugcucug cggagauccc aaacagugcg guuuuuuuaa caugaugugc 2520
cugaaagugc auuuuaacca cgagauuugc acacaagucu uccacaaaag caucucucgc 2580

-continued

```
cguugcacua aaucugugac uucggucguc ucaaccuugu uuuacgacaa aaaaaugaga   2640
acgacgaauc cgaaagagac uaagauugug auugacacua ccggcaguac caaaccuaag   2700
caggacgauc ucauucucac uuguuucaga ggguggguga agcaguugca aauagauuac   2760
aaaggcaacg aaauaaugac ggcagcugcc ucucaagggc ugacccguaa aggugugauu   2820
gccguucggu acaaggugaa ugaaaauccu cuguacgcac ccaccucaga acaugugaac   2880
guccuacuga cccgcacgga ggaccgcauc guguggaaaa cacuagccgg cgacccaugg   2940
auaaaaacac ugacugccaa guacccuggg aauuucacug ccacgauaga ggaguggcaa   3000
gcagagcaug augccaucau gaggcacauc uuggagagac cggacccuac cgacgucuuc   3060
cagaauaagg caaacgugug uugggccaag gcuuuagugc cggugcugaa gaccgcuggc   3120
auagacauga ccacugaaca auggaacacu guggauuauu uugaaacgga caaagcucac   3180
ucagcagaga uaguauugaa ccaacuaugc gugagguucu uuggacucga ucuggacucc   3240
ggucuauuuu cugcacccac uguuccguua uccauuagga auaaucacug ggauaacucc   3300
ccgucgccua acauguacgg gcugaauaaa gaaguggucc gucagcucuc ucgcagguac   3360
ccacaacugc cucgggcagu ugccacuggu agagucuaug acaugaacac ugguacacug   3420
cgcaauuaug auccgcgcau aaaccuagua ccuguaaaca gaagacugcc ucaugcuuua   3480
guccuccacc auaaugaaca cccacagagu gacuuuucuu cauucgucag caaauugaag   3540
ggcagaacug uccugguggu cggggaaaag uuguccgucc caggcaaaau gguugacugg   3600
uugucagacc ggccugaggc uaccuucaga gcucggcugg auuuaggcau cccaggugau   3660
gugcccaaau augacauaau auuuguuaau gugaggaccc cauauaaaua ccaucacuau   3720
cagcagugug aagaccaugc cauuaagcua agcauguuga ccaagaaagc augucugcau   3780
cugaaucccg gcggaaccug ugucagcaua gguuaugguu acgcugacag ggccagcgaa   3840
agcaucauug gugcuauagc gcggcaguuc aaguuuuccc gaguaugcaa accgaaaucc   3900
ucacuugagg agacggaagu ucuguuugua uucauugggu acgaucgcaa ggcccguacg   3960
cacaauccuu acaagcuauc aucaaccuug accaacauuu auacagguuc cagacuccac   4020
gaagccggau gugcacccuc auaucaugug gugcgagggg auauugccac ggccaccgaa   4080
ggagugauua uaaaugcugc uaacagcaaa ggacaaccug gcggaggggu gugcggagcg   4140
cuguauaaga aauucccgga aaguuucgau uuacagccga ucgaaguagg aaaagcgcga   4200
cuggucaaag gugcagcuaa acauaucauu caugccguag gaccaaacuu caacaaaguu   4260
ucggagguug aaggugacaa acaguuggca gaggcuuaug aguccaucgc uaagauuguc   4320
aacgauaaca auuacaaguc aguagcgauu ccacuguugu ccaccggcau cuuuuccggg   4380
aacaaagauc gacuaaccca aucauugaac cauuugcuga cagcuuuaga caccacugau   4440
gcagauguag ccauauacug cagggacaag aaaugggaaa ugacucucaa ggaagcagug   4500
gcuaggagag aagcagugga ggagauaugc auauccgacg auucuucagu gacagaaccu   4560
gaugcagagc uggugagggu gcaucccaag aguucuuugg cuggaaggaa gggcuacagc   4620
acaagcgaug gcaaaacuuu cucauauuug gaagggacca aguuucacca ggcggccaag   4680
gauauagcag aaauuaaugc cauguggccc guugcaacgg aggccaauga gcagguaugc   4740
auguauaucc ucggagaaag caugagcagu auuaggucga aaugccccgu cgaggagucg   4800
gaagccucca caccaccuag cacgcugccu ugcuugugca uccaugccau gacuccagaa   4860
agaguacagc gccuaaaagc cucacgucca gaacaaauua cugugugcuc auccuuucca   4920
uugccgaagu auagaaucac uggugugcag aagauccaau gcucccagcc uauauuguuc   4980
```

-continued

```
ucaccgaaag ugccugcgua uauucaucca aggaaguauc ucguggaaac accaccggua   5040
gacgagacuc cggagccauc ggcagagaac caauccacag aggggacacc ugaacaacca   5100
ccacuuauaa ccgaggauga gaccaggacu agaacgccug agccgaucau caucgaagaa   5160
gaagaagaag auagcauaag uuugcuguca gauggcccga cccaccaggu gcugcaaguc   5220
gaggcagaca uucacgggcc gcccucugua ucuagcucau ccugguccau uccucaugca   5280
uccgacuuug auguggacag uuuauccaua cuugacaccc uggagggagc uagcgugacc   5340
agcggggcaa cgucagccga gacuaacucu uacuucgcaa agaguaugga guuucuggcg   5400
cgaccggugc cugcgccucg aacaguauuc aggaacccuc cacaucccgc uccgcgcaca   5460
agaacaccgu cacuugcacc cagcagggcc ugcuccagaa ccagccuagu uuccaccccg   5520
ccaggcguga auagggugau cacuagagag gagcucgaag cgcuuacccc gucacgcacu   5580
ccuagcaggu cggucuccag aaccagccug gucuccaacc cgccaggcgu aaauagggug   5640
auuacaagag aggaguuuga ggcguucgua gcacaacaac aaugacgguu ugaugcgggu   5700
gcauacaucu uuuccuccga caccggucaa gggcauuuac aacaaaaauc aguaaggcaa   5760
acggugcuau ccgaagugu guuggagagg accgaauugg agauuucgua ugccccgcgc   5820
cucgaccaag aaaaagaaga auuacuacgc aagaaauuac aguuaaaucc cacaccugcu   5880
aacagaagca gauaccaguc caggaaggug gagaacauga aagccauaac agcuagacgu   5940
auucugcaag gccuagggca uuauuugaag gcagaaggaa aaguggagug cuaccgaacc   6000
cugcauccug uuccuuugua uucaucuagu gugaaccgug ccuuuucaag ccccaagguc   6060
gcaguggaag ccuguaacgc cauguugaaa gagaacuuuc cgacuguggc uucuuacugu   6120
auuauuccag aguacgaugc cuauuuggac augguugacg gagcuucaug cugcuuagac   6180
acugccaguu uuugcccugc aaagcugcgc agcuuuccaa agaaacacuc cuauuuggaa   6240
cccacaauac gaucggcagu gccuucagcg auccagaaca cgcuccagaa cguccuggca   6300
gcugccacaa aaagaaauug caaugucacg caaaugagag aauugcccgu auuggauucg   6360
gcggccuuua auguggaaug cuucaagaaa uaugcgugua auaaugaaua uugggaaacg   6420
uuuaaagaaa accccaucag gcuuacugaa gaaaacgugg uaaauuacau uaccaaauua   6480
aaaggaccaa aagcugcugc ucuuuuugcg aagacacaua auuugaauau guugcaggac   6540
auaccaaugg acagguuugu aauggacuua aagagagacg ugaaagugac uccaggaaca   6600
aaacauacug aagaacggcc caagguacag gugauccagg cugccgaucc gcuagcaaca   6660
gcguaucugu gcggaaucca ccgagagcug guuaggagau uaaaugcggu ccugcuuccg   6720
aacauucaua cacuguuuga uaugucggcu gaagacuuug acgcuauuau agccgagcac   6780
uuccagccug ggauugugu ucuggaaacu gacaucgcgu cguuugauaa aagugaggac   6840
gacgccaugg cucugaccgc guuaaugauu cuggaagacu uaggugugga cgcagagcug   6900
uugacgcuga uugaggcggc uuucggcgaa auuucaucaa uacauuugcc cacuaaaacu   6960
aaauuuaaau ucggagccau gaugaaaucu ggaauguucc ucacacuguu ugugaacaca   7020
gucauuaaca uuguaaucgc aagcagagug uugagagaac ggcuaaccgg aucaccaugu   7080
gcagcauuca uuggagauga caauaucgug aaaggaguca aaucggacaa auuaauggca   7140
gacaggugcg ccaccugguu gaauauggaa gucaagauua uagaugcugu ggugggcgag   7200
aaagcgccuu auuucugugg aggguuuauu uugugugacu ccgugaccgg cacagcgugc   7260
cguguggcag acccccuaaa aaggcuguuu aagcuaggca aaccucuggc agcagacgau   7320
```

-continued gaacaugaug augacaggag aagggcauug caugaggagu caacacgcug gaaccgagug 7380
gguauucuuu cagagcugug caaggcagua gaaucaaggu augaaaccgu aggaacuucc 7440
aucauaguua uggccaugac uacucuagcu agcaguguua aaucauucag cuaccugaga 7500
ggggccccua uaacucucua cggcuaaccu gaauggacua cgacauaguc uaguccgcca 7560
agacuaguau guucguguuc cuggugcugc ugccucuggu guccagccag ugugugaacc 7620
ugaccaccag aacacagcug ccuccagccu acaccaacag cuuuaccaga ggcguguacu 7680
accccgacaa gguguucaga uccagcgugc ugcacucuac ccaggaccug uuccugccuu 7740
ucuucagcaa cgugaccugg uuccacgcca uccacguguc cggcaccaau ggcaccaaga 7800
gauucgacaa ccccgugcug cccuucaacg acggggugua cuuugccagc accgagaagu 7860
ccaacaucau cagaggcugg aucuucggca ccacacugga cagcaagacc cagagccugc 7920
ugaucgugaa caacgccacc aacgugguca ucaaagugug cgaguuccag uucugcaacg 7980
accccuuccu gggcgucuac uaccacaaga acaacaagag cuggauggaa agcgaguucc 8040
ggguguacag cagcgccaac aacugcaccu ucgaguacgu gucccagccu uuccugaugg 8100
accuggaagg caagcagggc aacuucaaga accugcgcga guucguguuu aagaacaucg 8160
acggcuacuu caagaucuac agcaagcaca ccccuaucaa ccucgugcgg gaucugccuc 8220
agggcuucuc ugcucuggaa ccccuggugg aucugcccau cggcaucaac aucacccggu 8280
uucagacacu gcuggcccug cacagaagcu accugacacc uggcgauagc agcagcggau 8340
ggacagcugg ugccgccgcu uacuaugugg gcuaccugca gccuagaacc uuccugcuga 8400
aguacaacga gaacggcacc aucaccgacg ccguggauug ugcucuggau ccucugagcg 8460
agacaaagug cacccugaag uccuucaccg uggaaaaggg caucuaccag accagcaacu 8520
uccgggugca gcccaccgaa uccaucgugc gguuccccaa uaucaccaau cugugccccu 8580
ucggcgaggu guucaaugcc accagauucg ccucugugua cgccuggaac cggaagcgga 8640
ucagcaauug cguggccgac uacuccgugc uguacaacuc cgccagcuuc agcaccuuca 8700
agugcuacgg cguguccccu accaagcuga acgaccugug cuucacaaac guguacgccg 8760
acagcuucgu gauccgggga gaugaagugc ggcagauugc cccuggacag acaggcaaga 8820
ucgccgacua caacuacaag cugcccgacg acuucaccgg cugugugauu gccuggaaca 8880
gcaacaaccu ggacuccaaa gucggcggca acuacaauua ccuguaccgg cuguuccgga 8940
aguccaaucu gaagcccuuc gagcgggaca ucuccaccga gaucuaucag gccggcagca 9000
ccccuuguaa cggcguggaa ggcuucaacu gcuacuuccc acugcagucc uacggcuuuc 9060
agcccacaaa uggcgugggc uaucagcccu acagaguggu ggugcugagc uucgaacugc 9120
ugcaugcccc ugccacagug ugcggcccua agaaaagcac caaucucgug aagaacaaau 9180
gcgugaacuu caacuucaac ggccugaccg gcaccggcgu gcugacagag agcaacaaga 9240
aguuccugcc auuccagcag uuuggccggg auaucgccga uaccacagac gccguuagag 9300
auccccagac acuggaaauc cuggacauca ccccuugcag cuucggcgga gugucuguga 9360
ucaccccugg caccaacacc agcaaucagg uggcagugcu guaccaggac gugaacugua 9420
ccgaagugcc cguggccauu cacgccgauc agcugacacc uacauggcgg guguacucca 9480
ccggcagcaa uguguuucag accagagccg gcugucugau cggagccgag cacgugaaca 9540
auagcuacga gugcgacauc cccaucggcg cuggaaucug cgccagcuac cagacacaga 9600
caaacagccc ucggagagcc agaagcgugg ccagccagag caucauugcc uacacaaugu 9660
cucugggcgc cgagaacagc guggccuacu ccaacaacuc uaucgcuauc cccaccaacu 9720

-continued

```
ucaccaucag cgugaccaca gagauccugc cuguguccau gaccaagacc agcguggacu   9780
gcaccaugua caucugcggc gauuccaccg agugcuccaa ccugcugcug caguacggca   9840
gcuucugcac ccagcugaau agagcccuga cagggaucgc cguggaacag gacaagaaca   9900
cccaagaggu guucgcccaa gugaagcaga ucuacaagac cccuccuauc aaggacuucg   9960
gcggcuucaa uuucagccag auucugcccg auccuagcaa gcccagcaag cggagcuuca  10020
ucgaggaccu gcuguucaac aaagugacac uggccgacgc cggcuucauc aagcaguaug  10080
gcgauugucu gggcgacauu gccgccaggg aucugauuug cgcccagaag uuuaacggac  10140
ugacagugcu gccuccucug cugaccgaug agaugaucgc ccaguacaca ucugcccugc  10200
uggccggcac aaucacaagc ggcuggacau uuggagcagg cgccgcucug cagaucccccu  10260
uugcuaugca gauggccuac cgguucaacg gcaucggagu gacccagaau gugcuguacg  10320
agaaccagaa gcugaucgcc aaccaguuca acagcgccau cggcaagauc caggacagcc  10380
ugagcagcac agcaagcgcc cugggaaagc ugcaggacgu ggucaaccag aaugcccagg  10440
cacugaacac ccuggucaag cagcuguccu ccaacuucgg cgccaucagc ucugugcuga  10500
acgauauccu gagcagacug gacccuccug aggccgaggu gcagaucgac agacugauca  10560
caggcagacu gcagagccuc cagacauacg ugacccagca gcugaucaga gccgccgaga  10620
uuagagccuc ugccaaucug gccgccacca agaugucuga gugugugcug ggccagagca  10680
agagagugga cuuuugcggc aagggcuacc accugaugag cuucccucag ucugccccuc  10740
acggcguggu guuucugcac gugacauaug ugcccgcuca agagaagaau uucaccaccg  10800
cuccagccau cugccacgac ggcaaagccc acuuuccuag agaaggcgug uucgugucca  10860
acggcaccca uugguucgug acacagcgga acuucuacga gccccagauc aucaccaccg  10920
acaacaccuu cgugucuggc aacugcgacg ucgugaucgg cauugugaac aauaccgugu  10980
acgacccucu gcagcccgag cuggacagcu ucaaagagga acuggacaag uacuuuaaga  11040
accacacaag ccccgacgug gaccugggcg auaucagcgg aaucaaugcc agcgucguga  11100
acauccagaa agagaucgac cggcugaacg agguggccaa gaaucugaac gagagccuga  11160
ucgaccugca agaacugggg aaguacgagc aguacaucaa guggcccugg uacaucuggc  11220
ugggcuuuau cgccggacug auugccaucg ugauggucac aaucaugcug uguugcauga  11280
ccagcugcug uagcugccug aagggcuguu guagcugugg cagcugcugc aaguucgacg  11340
aggacgauuc ugagcccgug cugaagggcg ugaaacugca cuacacauga ugacucgagc  11400
ugguacugca ugcacgcaau gcuagcugcc ccuuucccgu ccuggguacc ccgagucucc  11460
cccgaccucg ggucccaggu augcucccac cuccaccugc cccacucacc accucugcua  11520
guuccagaca ccucccaagc acgcagcaau gcagcucaaa acgcuuagcc uagccacacc  11580
cccacgggaa acagcaguga uuaaccuuua gcaauaaacg aaaguuuaac uaagcuauac  11640
uaaccccagg guuggucaau uucgugccag ccacaccgcg gccgcaugaa uacagcagca  11700
auuggcaagc ugcuuacaua gaacucgcgg cgauuggcau gccgccuuaa aauuuuuauu  11760
uuauuuuuuc uuuucuuuuc cgaaucggau uuuguuuuua auauuucaaa aaaaaaaaaa  11820
aaaaaaaaaa aaaaaaagca uaugacuaaa aaaaaaaaaa aaaaaaaaaa aaaaaaaaaa  11880
aaaaaaaaaa aaaaaaaaaa aaaaaaaaaa aaaaaaa                           11917
```

<210> SEQ ID NO 35
<211> LENGTH: 8896
<212> TYPE: RNA

<213> ORGANISM: Artificial Sequence
<220> FEATURE:
<223> OTHER INFORMATION: Description of Artificial Sequence: Synthetic
polynucleotide

<400> SEQUENCE: 35
gaugggcggc gcaugagaga agcccagacc aauuaccuac ccaaaaugga gaaaguucac 60
guugacaucg aggaagacag cccauuccuc agagcuuugc agcggagcuu cccgcaguuu 120
gagguagaag ccaagcaggu cacugauaau gaccaugcua augccagagc guuuucgcau 180
cuggcuucaa aacugaucga aacggaggug gacccauccg acacgauccu ugacauugga 240
agugcgcccg cccgcagaau guauucuaag cacaaguauc auuguaucug uccgaugaga 300
ugugcggaag auccggacag auuguauaag uaugcaacua agcugaagaa aaacuguaag 360
gaaauaacug auaaggaauu ggacaagaaa augaaggagc ucgccgccgu caugagcgac 420
ccugaccugg aaacugagac uaugugccuc cacgacgacg agucgugucg cuacgaaggg 480
caagucgcug uuuaccagga uguauacgcg guugacggac cgacaagucu cuaucaccaa 540
gccaauaagg gaguuagagu cgccuacugg auaggcuuug acaccacccc uuuuauguuu 600
aagaacuugg cuggagcaua uccaucauac ucuaccaacu gggccgacga aaccguguua 660
acggcucgua acauaggccu augcagcucu gacguuaugg agcggucacg uagagggaug 720
uccauucuua gaaagaagua uuugaaacca uccaacaaug uucuauucuc uguuggcucg 780
accaucuacc acgaaaagag ggacuuacug aggagcuggc accugccguc uguauuucac 840
uuacguggca agcaaaauua cacaugucgg ugugagacua uaguuaguug cgacggguac 900
gucguuaaaa gaauagcuau caguccaggc cuguauggga agccuucagg cuaugcugcu 960
acgaugcacc gcgagggauu cuugugcugc aaagugacag acacauugaa cggggagagg 1020
gucucuuuuc ccgugugcac guaugugcca gcuacauugu gugaccaaau gacuggcaua 1080
cuggcaacag augucagugc ggacgacgcg caaaaacugc ugguugggcu caaccagcgu 1140
auagucguca acggucgcac ccagagaaac accaauacca ugaaaaauua ccuuuugccc 1200
guaguggccc aggcauuugc uaggugggca aaggaauaua aggaagauca agaagaugaa 1260
aggccacuag gacuacgaga uagacaguua gucauggggu guuguugggc uuuuagaagg 1320
cacaagauaa caucuauuua uaagcgcccg gauacccaaa ccaucaucaa agugaacagc 1380
gauuuccacu cauucgugcu gcccaggaua ggcaguaaca cauuggagau cgggcugaga 1440
acaagaauca ggaaaauguu agaggagcac aaggagccgu caccucucau uaccgccgag 1500
gacguacaag aagcuaagug cgcagccgau gaggcuaagg aggugcguga agccgaggag 1560
uugcgcgcag cucuaccacc uuuggcagcu gauguugagg agcccacucu ggaagccgau 1620
gucgacuuga uguuacaaga ggcuggggcc ggcucagugg agacaccucg uggcuugaua 1680
aagguuacca gcuacgcugg cgaggacaag aucggcucuu acgcugugcu uucuccgcag 1740
gcuguacuca agagugaaaa auuaucuugc auccacccuc ucgcugaaca agucauagug 1800
auaacacacu cuggccgaaa agggcguuau gccguggaac cauaccaugg uaaaguagug 1860
gugccagagg gacaugcaau acccguccag gacuuucaag cucugaguga aagugccacc 1920
auuguguaca acgaacguga guucguaaac agguaccugc accauauugc cacacaugga 1980
ggagcgcuga acacugauga agaauauuac aaaacuguca agcccagcga gcacgacggc 2040
gaauaccugu acgacaucga caggaaacag ugcgucaaga aagagcuagu cacugggcua 2100
gggcucacag gcgagcuggu cgauccuccc uuccaugaau ucgccuacga gagucugaga 2160

-continued

```
acacgaccag ccgcuccuua ccaaguacca accauagggg uguauggcgu gccaggauca   2220
ggcaagucug gcaucauuaa aagcgcaguc accaaaaaag aucuaguggu gagcgccaag   2280
aaagaaaacu gugcagaaau uauaagggac gucaagaaaa ugaaagggcu ggacgucaau   2340
gccagaacug uggacucagu gcucuugaau ggaugcaaac accccguaga gacccuguau   2400
auugacgagg cuuuugcuug ucaugcaggu acucucagag cgcucauagc cauuauaaga   2460
ccuaaaaagg cagugcucug cggagauccc aaacagugcg guuuuuuuaa caugaugugc   2520
cugaaagugc auuuuaacca cgagauuugc acacaagucu uccacaaaag caucucucgc   2580
cguugcacua aaucugugac uucggucguc ucaaccuugu uuuacgacaa aaaaaugaga   2640
acgacgaauc cgaaagagac uaagauugug auugacacua ccggcaguac caaaccuaag   2700
caggacgauc ucauucucac uuguuucaga gggugggaga agcaguugca aauagauuac   2760
aaaggcaacg aaauaaugac ggcagcugcc ucucaagggc ugacccguaa aggugugau   2820
gccguucggu acaaggugaa ugaaaauccu cuguacgcac ccaccucaga acaugugaac   2880
guccuacuga cccgcacgga ggaccgcauc guguggaaaa cacuagccgg cgacccaugg   2940
auaaaaacac ugacugccaa guacccuggg aauuucacug ccacgauaga ggaguggcaa   3000
gcagagcaug augccaucau gaggcacauc uuggagagac cggacccuac cgacgucuuc   3060
cagaauaagg caaacgugug uugggccaag gcuuuagugc cggugcugaa gaccgcuggc   3120
auagacauga ccacugaaca auggaacacu guggauuauu uugaaacgga caaagcucac   3180
ucagcagaga uaguauugaa ccaacuaugc gugagguucu uuggacucga ucuggacucc   3240
ggucuauuuu cugcacccac uguuccguua uccauuagga auaaucacug ggauaacucc   3300
ccgucgccua acauguacgg gcugaauaaa gaaguggucc gucagcucuc ucgcagguac   3360
ccacaacugc cucgggcagu ugccacuggu agagucuaug acaugaacac ugguacacug   3420
cgcaauuaug auccgcgcau aaaccuagua ccuguaaaca gaagacugcc ucaugcuuua   3480
guccuccacc auaaugaaca cccacagagu gacuuuucuu cauucgucag caaauugaag   3540
ggcagaacug uccugguggu cggggaaaag uuguccgucc caggcaaaau gguugacugg   3600
uugucagacc ggccugaggc uaccuucaga gcucggcugg auuuaggcau cccaggugau   3660
gugcccaaau augacauaau auuuguuaau gugaggaccc cauauaaaua ccaucacuau   3720
cagcagugug aagaccaugc cauuaagcua agcauguuga ccaagaaagc augucugcau   3780
cugaaucccg gcggaaccug ugucagcaua gguuaugguu acgcugacag ggccagcgaa   3840
agcaucauug gugcuauagc gcggcaguuc aaguuucccc gaguaugcaa accgaaaucc   3900
ucacuugagg agacggaagu ucuguuugua uucauugggu acgaucgcaa ggcccguacg   3960
cacaauccuu acaagcuauc aucaaccuug accaacauuu auacagguuc cagacuccac   4020
gaagccggau gugcacccuc auaucaugug gugcgagggg auauugccac ggccaccgaa   4080
ggagugauua uaaaugcugc uaacagcaaa ggacaaccug gcggaggggu gugcggagcg   4140
cuguauaaga aauucccgga aaguuucgau uuacagccga ucgaaguagg aaaagcgcga   4200
cuggucaaag gugcagcuaa acauaucauu caugccguag gaccaaacuu caacaaaguu   4260
ucggagguug aaggugacaa acaguuggca gaggcuuaug aguccaucgc uaagauuguc   4320
aacgauaaca auuacaaguc aguagcgauu ccacuguugu ccaccggcau cuuuuccggg   4380
aacaaagauc gacuaaccca aucauugaac cauuugcuga cagcuuuaga caccacugau   4440
gcagauguag ccauauacug cagggacaag aaaugggaaa ugacucucaa ggaagcagug   4500
gcuaggagag aagcagugga ggagauaugc auauccgacg auucuucagu gacagaaccu   4560
```

-continued

```
gaugcagagc uggugagggu gcaucccaag aguucuuugg cuggaaggaa gggcuacagc   4620
acaagcgaug gcaaaacuuu cucauauuug gaagggacca aguuucacca ggcggccaag   4680
gauauagcag aaauuaaugc cauguggccc guugcaacgg aggccaauga gcagguaugc   4740
auguauaucc ucggagaaag caugagcagu auuaggucga aaugccccgu cgaggagucg   4800
gaagccucca caccaccuag cacgcugccu ugcuugugca uccaugccau gacuccagaa   4860
agaguacagc gccuaaaagc cucacgucca gaacaaauua cugugugcuc auccuuucca   4920
uugccgaagu auagaaucac uggugugcag aagauccaau gcucccagcc uauauuguuc   4980
ucaccgaaag ugccugcgua uauucaucca aggaaguauc ucguggaaac accaccggua   5040
gacgagacuc cggagccauc ggcagagaac caauccacag aggggacacc ugaacaacca   5100
ccacuuauaa ccgaggauga gaccaggacu agaacgccug agccgaucau caucgaagaa   5160
gaagaagaag auagcauaag uuugcuguca gauggcccga cccaccaggu gcugcaaguc   5220
gaggcagaca uucacgggcc gcccucugua ucuagcucau ccugguccau uccucaugca   5280
uccgacuuug auguggacag uuuauccaua cuugacaccc uggagggagc uagcgugacc   5340
agcggggcaa cgucagccga gacuaacucu uacuucgcaa agaguaugga guuucuggcg   5400
cgaccggugc cugcgccucg aacaguauuc aggaacccuc cacaucccgc uccgcgcaca   5460
agaacaccgu cacuugcacc cagcagggcc ugcuccagaa ccagccuagu uuccaccccg   5520
ccaggcguga auagggugau cacuagagag gagcucgaag cgcuuacccc gucacgcacu   5580
ccuagcaggu cggucuccag aaccagccug gucuccaacc cgccaggcgu aaauagggug   5640
auuacaagag aggaguuuga ggcguucgua gcacaacaac aaugacgguu ugaugcgggu   5700
gcauacaucu uuuccuccga caccggucaa gggcauuuac aacaaaaauc aguaaggcaa   5760
acggugcuau ccgaagugga guuggagagg accgaauugg agauuucgua ugccccgcgc   5820
cucgaccaag aaaaagaaga auuacuacgc aagaaauuac aguuaaaucc cacaccugcu   5880
aacagaagca gauaccaguc caggaaggug gagaacauga aagccauaac agcuagacgu   5940
auucugcaag gccuagggca uuauuugaag gcagaaggaa aaguggagug cuaccgaacc   6000
cugcauccug uuccuuugua uucaucuagu gugaaccgug ccuuuucaag ccccaagguc   6060
gcaguggaag ccuguaacgc cauguugaaa gagaacuuuc cgacuguggc uucuuacugu   6120
auuauuccag aguacgaugc cuauuuggac augguugacg gagcuucaug cugcuuagac   6180
acugccaguu uuugcccugc aaagcugcgc agcuuuccaa agaaacacuc cuauuuggaa   6240
cccacaauac gaucggcagu gccuucagcg auccagaaca cgcuccagaa cguccuggca   6300
gcugccacaa aaagaaauug caaugucacg caaaugagag aauugcccgu auuggauucg   6360
gcggccuuua auguggaaug cuucaagaaa uaugcgugua auaaugaaua uugggaaacg   6420
uuuaaagaaa accccaucag gcuuacugaa gaaaacgugg uaaauuacau uaccaaauua   6480
aaaggaccaa aagcugcugc ucuuuuugcg aagacacaua auuugaauau guugcaggac   6540
auaccaaugg acagguuugu aauggacuua aagagagacg ugaaagugac uccaggaaca   6600
aaacauacug aagaacggcc caagguacag gugauccagg cugccgaucc gcuagcaaca   6660
gcguaucugu gcggaaucca ccgagagcug guuaggagau uaaaugcggu ccugcuuccg   6720
aacauucaua cacuguuuga uaugucggcu gaagacuuug acgcuauuau agccgagcac   6780
uuccagccug ggauugugu ucuggaaacu gacaucgcgu cguuugauaa aagugaggac   6840
gacgccaugg cucugaccgc guuaaugauu cuggaagacu uaggugugga cgcagagcug   6900
```

-continued uugacgcuga uugaggcggc uuucggcgaa auuucaucaa uacauuugcc cacuaaaacu 6960
aaauuuaaau ucggagccau gaugaaaucu ggaauguucc ucacacuguu ugugaacaca 7020
gucauuaaca uuguaaucgc aagcagagug uugagagaac ggcuaaccgg aucaccaugu 7080
gcagcauuca uuggagauga caauaucgug aaaggaguca aaucggacaa auuaauggca 7140
gacaggugcg ccaccugguu gaauauggaa gucaagauua uagaugcugu ggugggcgag 7200
aaagcgccuu auuucugugg aggguuuauu uugugugacu ccgugaccgg cacagcgugc 7260
cguguggcag acccccuaaa aaggcuguuu aagcuaggca aaccucuggc agcagacgau 7320
gaacaugaug augacaggag aagggcauug caugaggagu caacacgcug gaaccgagug 7380
gguauucuuu cagagcugug caaggcagua gaaucaaggu augaaaccgu aggaacuucc 7440
aucauaguua uggccaugac uacucuagcu agcaguguua aaucauucag cuaccugaga 7500
ggggccccua uaacucucua cggcuaaccu gaauggacua cgacauaguc uaguccgcca 7560
agacuaguau guuuguguuu cuugugcugc ugccucuugu gucuucucag ugugugguga 7620
gauuuccaaa uauuacaaau cuguguccau uuggagaagu guuuaaugca acaagauuug 7680
caucugugua ugcauggaau agaaaaagaa uuucuaauug uguggcugau uauucugugc 7740
uguauaauag ugcuucuuuu uccacauuua aauguuaugg agugucucca acaaaauuaa 7800
augauuuaug uuuuacaaau guguaugcug auucuuuugu gaucagaggu gaugaaguga 7860
gacagauugc ccccggacag acaggaaaaa uugcugauua caauuacaaa cugccugaug 7920
auuuuacagg augugugauu gcuuggaauu cuaauaauuu agauucuaaa gugggaggaa 7980
auuacaauua ucuguacaga cuguuuagaa aaucaaaucu gaaaccuuuu gaaagagaua 8040
uuucaacaga aauuuaucag gcuggaucaa caccuuguaa uggaguggaa ggauuuaauu 8100
guuauuuucc auuacagagc uauggauuuc agccaaccaa ugguguggga uaucagccau 8160
auagaguggu ggugcugucu uuugaacugc ugcaugcacc ugcaacagug uguggaccua 8220
aaggcucccc cggcuccggc uccggaucug guuauauucc ugaagcucca agagaugggc 8280
aagcuuacgu ucguaaagau ggcgaauggg uauuacuuuc uaccuuuuua ggccggaccc 8340
uggaggugcu guuccagggc cccggcugau gacucgagcu gguacugcau gcacgcaaug 8400
cuagcugccc cuuucccguc cuggguaccc cgagucuccc ccgaccucgg gucccaggua 8460
ugcucccacc uccaccugcc ccacucacca ccucugcuag uuccagacac cucccaagca 8520
cgcagcaaug cagcucaaaa cgcuuagccu agccacaccc ccacgggaaa cagcagugau 8580
uaaccuuuag caauaaacga aaguuuaacu aagcuauacu aaccccaggg uuggucaauu 8640
ucgugccagc cacaccgcgg ccgcaugaau acagcagcaa uuggcaagcu gcuuacauag 8700
aacucgcggc gauuggcaug ccgccuuaaa auuuuuauuu uauuuuuucu uuucuuuucc 8760
gaaucggauu uuguuuuuaa uauuucaaaa aaaaaaaaaa aaaaaaaaaa aaaaaagcau 8820
augacuaaaa aaaaaaaaaa aaaaaaaaaa aaaaaaaaaa aaaaaaaaaa aaaaaaaaaa 8880
aaaaaaaaaa aaaaaa 8896

<210> SEQ ID NO 36
<211> LENGTH: 9079
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 36
gaugggcggc gcaugagaga agcccagacc aauuaccuac ccaaaaugga gaaaguucac 60
guugacaucg aggaagacag cccauuccuc agagcuuugc agcggagcuu cccgcaguuu 120
gagguagaag ccaagcaggu cacugauaau gaccaugcua augccagagc guuuucgcau 180
cuggcuucaa aacugaucga aacggaggug gacccauccg acacgauccu ugacauugga 240
agugcgcccg cccgcagaau guauucuaag cacaaguauc auuguaucug uccgaugaga 300
ugugcggaag auccggacag auuguauaag uaugcaacua agcugaagaa aaacuguaag 360
gaaauaacug auaaggaauu ggacaagaaa augaaggagc ucgccgccgu caugagcgac 420
ccugaccugg aaacugagac uaugugccuc cacgacgacg agucgugucg cuacgaaggg 480
caagucgcug uuuaccagga uguauacgcg guugacggac cgacaagucu cuaucaccaa 540
gccaauaagg gaguuagagu cgccuacugg auaggcuuug acaccacccc uuuuauguuu 600
aagaacuugg cuggagcaua uccaucauac ucuaccaacu gggccgacga aaccguguua 660
acggcucgua acauaggccu augcagcucu gacguuaugg agcggucacg uagagggaug 720
uccauucuua gaaagaagua uuugaaacca uccaacaaug uucuauucuc uguuggcucg 780
accaucuacc acgaaaagag ggacuuacug aggagcuggc accugccguc uguauuucac 840
uuacguggca agcaaaauua cacaugucgg ugugagacua uaguuaguug cgacggguac 900
gucguuaaaa gaauagcuau caguccaggc cuguauggga agccuucagg cuaugcugcu 960
acgaugcacc gcgagggauu cuugugcugc aaagugacag acacauugaa cggggagagg 1020
gucucuuuuc ccgugugcac guaugugcca gcuacauugu gugaccaaau gacuggcaua 1080
cuggcaacag augucagugc ggacgacgcg caaaaacugc ugguugggcu caaccagcgu 1140
auagucguca acggucgcac ccagagaaac accaauacca ugaaaaauua ccuuuugccc 1200
guaguggccc aggcauuugc uaggugggca aaggaauaua aggaagauca agaagaugaa 1260
aggccacuag gacuacgaga uagacaguua gucaugggggu guuguugggc uuuuagaagg 1320
cacaagauaa caucuauuua uaagcgcccg gauacccaaa ccaucaucaa agugaacagc 1380
gauuuccacu cauucgugcu gcccaggaua ggcaguaaca cauuggagau cgggcugaga 1440
acaagaauca ggaaaauguu agaggagcac aaggagccgu caccucucau uaccgccgag 1500
gacguacaag aagcuaagug cgcagccgau gaggcuaagg aggugcguga agccgaggag 1560
uugcgcgcag cucuaccacc uuuggcagcu gauguugagg agcccacucu ggaagccgau 1620
gucgacuuga uguuacaaga ggcuggggcc ggcucagugg agacaccucg uggcuugaua 1680
aagguuacca gcuacgcugg cgaggacaag aucggcucuu acgcugugcu uucuccgcag 1740
gcuguacuca agagugaaaa auuaucuugc auccacccuc ucgcugaaca agucauagug 1800
auaacacacu cuggccgaaa agggcguuau gccguggaac cauaccaugg uaaaguagug 1860
gugccagagg gacaugcaau acccguccag gacuuucaag cucugaguga aagugccacc 1920
auuguguaca acgaacguga guucguaaac agguaccugc accauauugc cacacaugga 1980
ggagcgcuga acacugauga agaauauuac aaaacuguca agcccagcga gcacgacggc 2040
gaauaccugu acgacaucga caggaaacag ugcgucaaga aagagcuagu cacugggcua 2100
gggcucacag gcgagcuggu cgauccuccc uuccaugaau ucgccuacga gagucugaga 2160
acacgaccag ccgcuccuua ccaaguacca accauagggg uguauggcgu gccaggauca 2220
ggcaagucug gcaucauuaa aagcgcaguc accaaaaaag aucuaguggu gagcgccaag 2280

-continued aaagaaaacu gugcagaaau uauaagggac gucaagaaaa ugaaagggcu ggacgucaau 2340
gccagaacug uggacucagu gcucuugaau ggaugcaaac accccguaga gacccuguau 2400
auugacgagg cuuuugcuug ucaugcaggu acucucagag cgcucauagc cauuauaaga 2460
ccuaaaaagg cagugcucug cggagauccc aaacagugcg guuuuuuuaa caugaugugc 2520
cugaaagugc auuuuaacca cgagauuugc acacaagucu uccacaaaag caucucucgc 2580
cguugcacua aaucugugac uucggucguc ucaaccuugu uuuacgacaa aaaaaugaga 2640
acgacgaauc cgaaagagac uaagauugug auugacacua ccggcaguac caaaccuaag 2700
caggacgauc ucauucucac uuguuucaga gggugggguga agcaguugca aauagauuac 2760
aaaggcaacg aaauaaugac ggcagcugcc ucucaagggc ugacccguaa aggugugau 2820
gccguucggu acaaggugaa ugaaaauccu cuguacgcac ccaccucaga acaugugaac 2880
guccuacuga cccgcacgga ggaccgcauc guguggaaaa cacuagccgg cgacccaugg 2940
auaaaaacac ugacugccaa guacccuggg aauuucacug ccacgauaga ggaguggcaa 3000
gcagagcaug augccaucau gaggcacauc uuggagagac cggacccuac cgacgucuuc 3060
cagaauaagg caaacgugug uugggccaag gcuuuagugc cggugcugaa gaccgcuggc 3120
auagacauga ccacugaaca auggaacacu guggauuauu uugaaacgga caaagcucac 3180
ucagcagaga uaguauugaa ccaacuaugc gugagguucu uuggacucga ucuggacucc 3240
ggucuauuuu cugcacccac uguuccguua uccauuagga auaaucacug ggauaacucc 3300
ccgucgccua acauguacgg gcugaauaaa gaaguggucc gucagcucuc ucgcagguac 3360
ccacaacugc cucgggcagu ugccacuggu agagucuaug acaugaacac ugguacacug 3420
cgcaauuaug auccgcgcau aaaccuagua ccuguaaaca gaagacugcc ucaugcuuua 3480
guccuccacc auaaugaaca cccacagagu gacuuuucuu cauucgucag caaauugaag 3540
ggcagaacug uccugguggu cggggaaaag uuguccgucc caggcaaaau gguugacugg 3600
uugucagacc ggccugaggc uaccuucaga gcucggcugg auuuaggcau cccaggugau 3660
gugcccaaau augacauaau auuuguuaau gugaggaccc cauauaaaua ccaucacuau 3720
cagcagugug aagaccaugc cauuaagcua agcauguuga ccaagaaagc augucugcau 3780
cugaaucccg gcggaaccug ugucagcaua gguuaugguu acgcugacag ggccagcgaa 3840
agcaucauug gugcuauagc gcggcaguuc aaguuucccc gaguaugcaa accgaaaucc 3900
ucacuugagg agacggaagu ucuguuugua uucauugggu acgaucgcaa ggcccguacg 3960
cacaauccuu acaagcuauc aucaaccuug accaacauuu auacagguuc cagacuccac 4020
gaagccggau gugcacccuc auaucaugug gugcgagggg auauugccac ggccaccgaa 4080
ggagugauua uaaaugcugc uaacagcaaa ggacaaccug gcggaggggu gugcggagcg 4140
cuguauaaga aauucccgga aaguuucgau uuacagccga ucgaaguagg aaaagcgcga 4200
cuggucaaag gugcagcuaa acauaucauu caugccguag gaccaaacuu caacaaaguu 4260
ucggagguug aaggugacaa acaguuggca gaggcuuaug aguccaucgc uaagauuguc 4320
aacgauaaca auuacaaguc aguagcgauu ccacuguugu ccaccggcau cuuuuccggg 4380
aacaaagauc gacuaaccca aucauugaac cauuugcuga cagcuuuaga caccacugau 4440
gcagauguag ccauauacug cagggacaag aaaugggaaa ugacucucaa ggaagcagug 4500
gcuaggagag aagcagugga ggagauaugc auauccgacg auucuucagu gacagaaccu 4560
gaugcagagc uggugagggu gcaucccaag aguucuuugg cuggaaggaa gggcuacagc 4620
acaagcgaug gcaaaacuuu cucauauuug gaagggacca aguuucacca ggcggccaag 4680

-continued gauauagcag aaauuaaugc cauguggccc guugcaacgg aggccaauga gcagguaugc 4740
auguauaucc ucggagaaag caugagcagu auuaggucga aaugccccgu cgaggagucg 4800
gaagccucca caccaccuag cacgcugccu ugcuugugca uccaugccau gacuccagaa 4860
agaguacagc gccuaaaagc cucacgucca gaacaaauua cugugugcuc auccuuucca 4920
uugccgaagu auagaaucac uggugugcag aagauccaau gcucccagcc uauauuguuc 4980
ucaccgaaag ugccugcgua uauucaucca aggaaguauc ucguggaaac accaccggua 5040
gacgagacuc cggagccauc ggcagagaac caauccacag aggggacacc ugaacaacca 5100
ccacuuauaa ccgaggauga gaccaggacu agaacgccug agccgaucau caucgaagaa 5160
gaagaagaag auagcauaag uuugcuguca gauggcccga cccaccaggu gcugcaaguc 5220
gaggcagaca uucacgggcc gcccucugua ucuagcucau ccugguccau uccucaugca 5280
uccgacuuug auguggacag uuuauccaua cuugacaccc uggagggagc uagcgugacc 5340
agcggggcaa cgucagccga gacuaacucu uacuucgcaa agaguaugga guuucuggcg 5400
cgaccggugc cugcgccucg aacaguauuc aggaacccuc cacaucccgc uccgcgcaca 5460
agaacaccgu cacuugcacc cagcagggcc ugcuccagaa ccagccuagu uuccaccccg 5520
ccaggcguga auagggugau cacuagagag gagcucgaag cgcuuacccc gucacgcacu 5580
ccuagcaggu cggucuccag aaccagccug gucuccaacc cgccaggcgu aaauagggug 5640
auuacaagag aggaguuuga ggcguucgua gcacaacaac aaugacgguu ugaugcgggu 5700
gcauacaucu uuuccuccga caccggucaa gggcauuuac aacaaaaauc aguaaggcaa 5760
acggugcuau ccgaagugau guuggagagg accgaauugg agauuucgua ugccccgcgc 5820
cucgaccaag aaaaagaaga auuacuacgc aagaaauuac aguuaaaucc cacaccugcu 5880
aacagaagca gauaccaguc caggaaggug gagaacauga aagccauaac agcuagacgu 5940
auucugcaag gccuagggca uuauuugaag gcagaaggaa aaguggagug cuaccgaacc 6000
cugcauccug uuccuuugua uucaucuagu gugaaccgug ccuuuucaag ccccaagguc 6060
gcaguggaag ccuguaacgc cauguugaaa gagaacuuuc cgacuguggc uucuuacugu 6120
auuauuccag aguacgaugc cuauuuggac augguugacg gagcuucaug cugcuuagac 6180
acugccaguu uuugcccugc aaagcugcgc agcuuuccaa agaaacacuc cuauuuggaa 6240
cccacaauac gaucggcagu gccuucagcg auccagaaca cgcuccagaa cguccuggca 6300
gcugccacaa aaagaaauug caaugucacg caaaugagag aauugcccgu auuggauucg 6360
gcggccuuua auguggaaug cuucaagaaa uaugcgugua auaaugaaua uugggaaacg 6420
uuuaaagaaa accccaucag gcuuacugaa gaaaacgugg uaaauuacau uaccaaauua 6480
aaaggaccaa aagcugcugc ucuuuuugcg aagacacaua auuugaauau guugcaggac 6540
auaccaaugg acagguuugu aauggacuua aagagagacg ugaaagugac uccaggaaca 6600
aaacauacug aagaacggcc caagguacag gugauccagg cugccgaucc gcuagcaaca 6660
gcguaucugu gcggaaucca ccgagagcug guuaggagau uaaaugcggu ccugcuuccg 6720
aacauucaua cacuguuuga uaugucggcu gaagacuuug acgcuauuau agccgagcac 6780
uuccagccug ggauugugu ucuggaaacu gacaucgcgu cguuugauaa aagugaggac 6840
gacgccaugg cucugaccgc guuaaugauu cuggaagacu uaggugugga cgcagagcug 6900
uugacgcuga uugaggcggc uuucggcgaa auuucaucaa uacauuugcc cacuaaaacu 6960
aaauuuaaau ucggagccau gaugaaaucu ggaauguucc ucacacuguu ugugaacaca 7020

-continued

```
gucauuaaca uuguaaucgc aagcagagug uugagagaac ggcuaaccgg aucaccaugu   7080

gcagcauuca uuggagauga caauaucgug aaaggaguca aaucggacaa auuaauggca   7140

gacaggugcg ccaccugguu gaauauggaa gucaagauua uagaugcugu ggugggcgag   7200

aaagcgccuu auuucugugg aggguuuauu uugugugacu ccgugaccgg cacagcgugc   7260

cguguggcag acccccuaaa aaggcuguuu aagcuaggca aaccucuggc agcagacgau   7320

gaacaugaug augacaggag aagggcauug caugaggagu caacacgcug gaaccgagug   7380

gguauucuuu cagagcugug caaggcagua gaaucaaggu augaaaccgu aggaacuucc   7440

aucauaguua uggccaugac uacucuagcu agcaguguua aaucauucag cuaccugaga   7500

ggggccccua uaacucucua cggcuaaccu gaauggacua cgacauaguc uaguccgcca   7560

agacuaguau guuuguguuu cuugugcugc ugccucuugu gucuucucag ugugugguga   7620

gauuuccaaa uauuacaaau cuguguccau uuggagaagu guuuaaugca acaagauuug   7680

caucugugua ugcauggaau agaaaaagaa uuucuaauug uguggcugau uauucugugc   7740

uguauaauag ugcuucuuuu uccacauuua aauguuaugg agugucucca acaaaauuaa   7800

augauuuaug uuuuacaaau guguaugcug auucuuuugu gaucagaggu gaugaaguga   7860

gacagauugc ccccggacag acaggaaaaa uugcugauua caauuacaaa cugccugaug   7920

auuuuacagg augugugauu gcuuggaauu cuaauaauuu agauucuaaa gugggaggaa   7980

auuacaauua ucuguacaga cuguuuagaa aaucaaaucu gaaaccuuuu gaaagagaua   8040

uuucaacaga aauuuaucag gcuggaucaa caccuuguaa uggaguggaa ggauuuaauu   8100

guuauuuucc auuacagagc uauggauuuc agccaaccaa ugguguggga uaucagccau   8160

auagaguggu ggugcugucu uuugaacugc ugcaugcacc ugcaacagug uguggaccua   8220

aaggcucccc cggcuccggc uccggaucug guuauauucc ugaagcucca agagaugggc   8280

aagcuuacgu ucguaaagau ggcgaauggg uauuacuuuc uaccuuuuua ggaagcggca   8340

gcggaucuga acaguacauu aaauggccuu gguacauuug gcuuggauuu auugcaggau   8400

uaauugcaau ugugauggug acaauuaugu uauguuguau gacaucaugu uguucuuguu   8460

uaaaaggaug uuguucuugu ggaagcuguu guaaauuuga ugaagaugau ucugaaccug   8520

uguuaaaagg agugaaauug cauuacacau gaugacucga gcugguacug caugcacgca   8580

augcuagcug ccccuuuccc guccugggua ccccgagucu cccccgaccu cgggucccag   8640

guaugcuccc accuccaccu gccccacuca ccaccucugc uaguuccaga caccucccaa   8700

gcacgcagca augcagcuca aaacgcuuag ccuagccaca cccccacggg aaacagcagu   8760

gauuaaccuu uagcaauaaa cgaaaguuua acuaagcuau acuaacccca ggguugguca   8820

auuucgugcc agccacaccg cggccgcaug aauacagcag caauuggcaa gcugcuuaca   8880

uagaacucgc ggcgauuggc augccgccuu aaaauuuuua uuuuauuuuu ucuuuucuuu   8940

uccgaaucgg auuuuguuuu uaauauuuca aaaaaaaaaa aaaaaaaaaa aaaaaaaaag   9000

cauaugacua aaaaaaaaaa aaaaaaaaaa aaaaaaaaaa aaaaaaaaaa aaaaaaaaaa   9060

aaaaaaaaaa aaaaaaaaa                                                9079
```

<210> SEQ ID NO 37
<211> LENGTH: 327
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 37

Met Phe Val Phe Leu Val Leu Leu Pro Leu Val Ser Ser Gln Cys Val
1 5 10 15

Val Arg Phe Pro Asn Ile Thr Asn Leu Cys Pro Phe Gly Glu Val Phe
20 25 30

Asn Ala Thr Arg Phe Ala Ser Val Tyr Ala Trp Asn Arg Lys Arg Ile
35 40 45

Ser Asn Cys Val Ala Asp Tyr Ser Val Leu Tyr Asn Ser Ala Ser Phe
50 55 60

Ser Thr Phe Lys Cys Tyr Gly Val Ser Pro Thr Lys Leu Asn Asp Leu
65 70 75 80

Cys Phe Thr Asn Val Tyr Ala Asp Ser Phe Val Ile Arg Gly Asp Glu
85 90 95

Val Arg Gln Ile Ala Pro Gly Gln Thr Gly Lys Ile Ala Asp Tyr Asn
100 105 110

Tyr Lys Leu Pro Asp Asp Phe Thr Gly Cys Val Ile Ala Trp Asn Ser
115 120 125

Asn Asn Leu Asp Ser Lys Val Gly Gly Asn Tyr Asn Tyr Leu Tyr Arg
130 135 140

Leu Phe Arg Lys Ser Asn Leu Lys Pro Phe Glu Arg Asp Ile Ser Thr
145 150 155 160

Glu Ile Tyr Gln Ala Gly Ser Thr Pro Cys Asn Gly Val Glu Gly Phe
165 170 175

Asn Cys Tyr Phe Pro Leu Gln Ser Tyr Gly Phe Gln Pro Thr Asn Gly
180 185 190

Val Gly Tyr Gln Pro Tyr Arg Val Val Val Leu Ser Phe Glu Leu Leu
195 200 205

His Ala Pro Ala Thr Val Cys Gly Pro Lys Gly Ser Pro Gly Ser Gly
210 215 220

Ser Gly Ser Gly Tyr Ile Pro Glu Ala Pro Arg Asp Gly Gln Ala Tyr
225 230 235 240

Val Arg Lys Asp Gly Glu Trp Val Leu Leu Ser Thr Phe Leu Gly Ser
245 250 255

Gly Ser Gly Ser Glu Gln Tyr Ile Lys Trp Pro Trp Tyr Ile Trp Leu
260 265 270

Gly Phe Ile Ala Gly Leu Ile Ala Ile Val Met Val Thr Ile Met Leu
275 280 285

Cys Cys Met Thr Ser Cys Cys Ser Cys Leu Lys Gly Cys Cys Ser Cys
290 295 300

Gly Ser Cys Cys Lys Phe Asp Glu Asp Asp Ser Glu Pro Val Leu Lys
305 310 315 320

Gly Val Lys Leu His Tyr Thr
325

<210> SEQ ID NO 38
<211> LENGTH: 311
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 38

Met Phe Val Phe Leu Val Leu Leu Pro Leu Val Ser Ser Gln Cys Val
1 5 10 15

-continued

```
Asn Leu Thr Val Arg Phe Pro Asn Ile Thr Asn Leu Cys Pro Phe Gly
            20                  25                  30

Glu Val Phe Asn Ala Thr Arg Phe Ala Ser Val Tyr Ala Trp Asn Arg
        35                  40                  45

Lys Arg Ile Ser Asn Cys Val Ala Asp Tyr Ser Val Leu Tyr Asn Ser
    50                  55                  60

Ala Ser Phe Ser Thr Phe Lys Cys Tyr Gly Val Ser Pro Thr Lys Leu
65                  70                  75                  80

Asn Asp Leu Cys Phe Thr Asn Val Tyr Ala Asp Ser Phe Val Ile Arg
                85                  90                  95

Gly Asp Glu Val Arg Gln Ile Ala Pro Gly Gln Thr Gly Lys Ile Ala
            100                 105                 110

Asp Tyr Asn Tyr Lys Leu Pro Asp Asp Phe Thr Gly Cys Val Ile Ala
        115                 120                 125

Trp Asn Ser Asn Asn Leu Asp Ser Lys Val Gly Gly Asn Tyr Asn Tyr
    130                 135                 140

Leu Tyr Arg Leu Phe Arg Lys Ser Asn Leu Lys Pro Phe Glu Arg Asp
145                 150                 155                 160

Ile Ser Thr Glu Ile Tyr Gln Ala Gly Ser Thr Pro Cys Asn Gly Val
                165                 170                 175

Glu Gly Phe Asn Cys Tyr Phe Pro Leu Gln Ser Tyr Gly Phe Gln Pro
            180                 185                 190

Thr Asn Gly Val Gly Tyr Gln Pro Tyr Arg Val Val Val Leu Ser Phe
        195                 200                 205

Glu Leu Leu His Ala Pro Ala Thr Val Cys Gly Pro Lys Gly Ser Pro
    210                 215                 220

Gly Ser Gly Ser Gly Ser Gly Tyr Ile Pro Glu Ala Pro Arg Asp Gly
225                 230                 235                 240

Gln Ala Tyr Val Arg Lys Asp Gly Glu Trp Val Leu Leu Ser Thr Phe
                245                 250                 255

Leu Gly Ser Gly Ser Gly Ser Glu Gln Tyr Ile Lys Trp Pro Trp Tyr
            260                 265                 270

Ile Trp Leu Gly Phe Ile Ala Gly Leu Ile Ala Ile Val Met Val Thr
        275                 280                 285

Ile Met Leu Cys Cys Met Thr Ser Cys Cys Ser Cys Leu Lys Gly Cys
    290                 295                 300

Cys Ser Cys Gly Ser Cys Cys
305                 310
```

<210> SEQ ID NO 39
<211> LENGTH: 1397
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 39

```
agaauaaacu aguauucuuc ugguccccac agacucagag agaacccgcc accauguuug      60

uguuucuugu gcugcugccu cuugugucuu cucagugugu gaauuugaca gugagauuuc     120

caaauauuac aaaucugugu ccauuuggag aaguguuuaa ugcaacaaga uuugcaucug     180

uguaugcaug gaauagaaaa agaauuucua auugugugc ugauuauucu gugcuguaua     240

auagugcuuc uuuuuccaca uuuaaauguu auggagugc uccaacaaaa uuaaaugauu     300

uauguuuuac aaauguguau gcugauucuu uugugaucag aggugaugaa gugagacaga     360
```

```
uugcccccgg acagacagga aaaauugcug auuacaauua caaacugccu gaugauuuua    420

caggaugugu gauugcuugg aauucuaaua auuuagauuc uaaaguggga ggaaauuaca    480

auuaucugua cagacuguuu agaaaaucaa aucugaaacc uuuugaaaga gauauuucaa    540

cagaaauuua ucaggcugga ucaacaccuu guaauggagu ggaaggauuu aauuguuauu    600

uuccauuaca gagcuaugga uuucagccaa ccaauggugu gggauaucag ccauauagag    660

ugguggugcu gucuuuugaa cugcugcaug caccugcaac agugugugga ccuaaaggcu    720

cccccggcuc cggcuccgga ucugguuaua uuccugaagc uccaagagau gggcaagcuu    780

acguucguaa agauggcgaa uggguauuac uuucuaccuu uuuaggaagc ggcagcggau    840

cugaacagua cauuaaaugg ccuugguaca uuuggcuugg auuuauugca ggauuaauug    900

caauugugau ggugacaauu auguuauguu guaugacauc auguuguucu uguuuaaaag    960

gauguuguuc uuguggaagc uguuguugau gacucgagcu gguacugcau gcacgcaaug   1020

cuagcugccc cuuucccguc cuggguaccc cgagucuccc ccgaccucgg gucccaggua   1080

ugcucccacc uccaccugcc ccacucacca ccucugcuag uuccagacac cucccaagca   1140

cgcagcaaug cagcucaaaa cgcuuagccu agccacaccc ccacgggaaa cagcagugau   1200

uaaccuuuag caauaaacga aaguuuaacu aagcuauacu aaccccaggg uuggucaauu   1260

ucgugccagc cacacccugg agcuagcaaa aaaaaaaaaa aaaaaaaaaa aaaaaaagca   1320

uaugacuaaa aaaaaaaaaa aaaaaaaaaa aaaaaaaaaa aaaaaaaaaa aaaaaaaaaa   1380

aaaaaaaaaa aaaaaaa                                                  1397
```

```
<210> SEQ ID NO 40
<211> LENGTH: 314
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Asp Trp Ile Trp Arg Ile Leu Phe Leu Val Gly Ala Ala Thr Gly
1               5                   10                  15

Ala His Ser Gln Met Gln Val Arg Phe Pro Asn Ile Thr Asn Leu Cys
            20                  25                  30

Pro Phe Gly Glu Val Phe Asn Ala Thr Arg Phe Ala Ser Val Tyr Ala
        35                  40                  45

Trp Asn Arg Lys Arg Ile Ser Asn Cys Val Ala Asp Tyr Ser Val Leu
    50                  55                  60

Tyr Asn Ser Ala Ser Phe Ser Thr Phe Lys Cys Tyr Gly Val Ser Pro
65                  70                  75                  80

Thr Lys Leu Asn Asp Leu Cys Phe Thr Asn Val Tyr Ala Asp Ser Phe
                85                  90                  95

Val Ile Arg Gly Asp Glu Val Arg Gln Ile Ala Pro Gly Gln Thr Gly
            100                 105                 110

Lys Ile Ala Asp Tyr Asn Tyr Lys Leu Pro Asp Asp Phe Thr Gly Cys
        115                 120                 125

Val Ile Ala Trp Asn Ser Asn Asn Leu Asp Ser Lys Val Gly Gly Asn
    130                 135                 140

Tyr Asn Tyr Leu Tyr Arg Leu Phe Arg Lys Ser Asn Leu Lys Pro Phe
145                 150                 155                 160
```

```
Glu Arg Asp Ile Ser Thr Glu Ile Tyr Gln Ala Gly Ser Thr Pro Cys
                165                 170                 175

Asn Gly Val Glu Gly Phe Asn Cys Tyr Phe Pro Leu Gln Ser Tyr Gly
            180                 185                 190

Phe Gln Pro Thr Asn Gly Val Gly Tyr Gln Pro Tyr Arg Val Val Val
        195                 200                 205

Leu Ser Phe Glu Leu Leu His Ala Pro Ala Thr Val Cys Gly Pro Lys
    210                 215                 220

Gly Ser Pro Gly Ser Gly Ser Gly Ser Gly Tyr Ile Pro Glu Ala Pro
225                 230                 235                 240

Arg Asp Gly Gln Ala Tyr Val Arg Lys Asp Gly Glu Trp Val Leu Leu
                245                 250                 255

Ser Thr Phe Leu Gly Ser Gly Ser Gly Ser Glu Gln Tyr Ile Lys Trp
            260                 265                 270

Pro Trp Tyr Ile Trp Leu Gly Phe Ile Ala Gly Leu Ile Ala Ile Val
        275                 280                 285

Met Val Thr Ile Met Leu Cys Cys Met Thr Ser Cys Cys Ser Cys Leu
    290                 295                 300

Lys Gly Cys Cys Ser Cys Gly Ser Cys Cys
305                 310
```

<210> SEQ ID NO 41
<211> LENGTH: 1406
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 41

```
agaauaaacu aguauucuuc ugguccccac agacucagag agaacccgcc accauggauu     60

ggauuuggag aauccuguuc cucgugggag ccgcuacagg agcccacucc cagaugcagg    120

ugagauuucc aaauauuaca aaucuguguc cauuuggaga aguguuuaau gcaacaagau    180

uugcaucugu guaugcaugg aauagaaaaa gaauuucuaa uuguguggcu gauuauucug    240

ugcuguauaa uagugcuucu uuuuccacau uuaaauguua uggagugucu ccaacaaaau    300

uaaaugauuu auguuuuaca aauguguaug cugauucuuu ugugaucaga ggugaugaag    360

ugagacagau ugcccccgga cagacaggaa aaauugcuga uuacaauuac aaacugccug    420

augauuuuac aggaugugug auugcuugga auucuaauaa uuuagauucu aaagugggag    480

gaaauuacaa uuaucuguac agacuguuua gaaaaucaaa ucugaaaccu uuugaaagag    540

auauuucaac agaaauuuau caggcuggau caacaccuug uaauggagug gaaggauuua    600

auuguuauuu uccauuacag agcuauggau uucagccaac caauggugug ggauaucagc    660

cauauagagu gguggugcug ucuuuugaac ugcugcaugc accugcaaca gugugugggac    720

cuaaaggcuc ccccggcucc ggcuccggau cugguuauau uccugaagcu ccaagagaug    780

ggcaagcuua cguucguaaa gauggcgaau ggguauuacu uucuaccuuu uuaggaagcg    840

gcagcggauc ugaacaguac auuaaauggc cuugguacau uuggcuugga uuuauugcag    900

gauuaauugc aauugugaug gugacaauua uguuauguug uaugacauca uguuguucuu    960

guuuaaaagg auguuguucu uguggaagcu guuguugaug acucgagcug guacugcaug   1020

cacgcaaugc uagcugcccc uuucccgucc uggguacccc gagucucccc cgaccucggg   1080

ucccagguau gcucccaccu ccaccugccc cacucaccac cucugcuagu uccagacacc   1140
```

-continued ucccaagcac gcagcaaugc agcucaaaac gcuuagccua gccacacccc cacgggaaac 1200
agcagugauu aaccuuuagc aauaaacgaa aguuuaacua agcuauacua accccagggu 1260
uggucaauuu cgugccagcc acacccugga gcuagcaaaa aaaaaaaaaa aaaaaaaaaa 1320
aaaaaagcau augacuaaaa aaaaaaaaaa aaaaaaaaaa aaaaaaaaaa aaaaaaaaaa 1380
aaaaaaaaaa aaaaaaaaaa aaaaaa 1406

<210> SEQ ID NO 42
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 42
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa 100

<210> SEQ ID NO 43
<211> LENGTH: 55
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 43
agacgaacta gtattcttct ggtccccaca gactcagaga gaacccgcca ccaug 55

<210> SEQ ID NO 44
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 44
gcuagccgcg ucgcu 15

<210> SEQ ID NO 45
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 45
auuuacgaac gauagcaug 19

<210> SEQ ID NO 46
<211> LENGTH: 56
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide -continued

```
<400> SEQUENCE: 46

agcacgcagc aatgcagcuc aaaacgcuua gccuagccac acccccacgg gaaaca         56


<210> SEQ ID NO 47
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47

gagucgcuag ccgcgucgcu                                                 20
```

UNITED STATES PATENT AND TRADEMARK OFFICE
CERTIFICATE OF CORRECTION

PATENT NO. : 11,779,659 B2
APPLICATION NO. : 17/565842
DATED : October 10, 2023
INVENTOR(S) : Ugur Sahin et al.

It is certified that error appears in the above-identified patent and that said Letters Patent is hereby corrected as shown below:

On the Title Page

(30) Foreign Application Priority Data, insert --Jan. 26, 2021 (WO) ................ PCT/EP2021/051772-- therefor

(30) Foreign Application Priority Data, delete "Jan. 26, 2021 (WO) ................ PCT/EP2021/052572" and insert --Feb. 3, 2021 (WO)................PCT/EP2021/052572-- therefor In the Claims Claim 1, Line 33, delete "m7(3' OMeG)(5')ppp(5)" and insert --m7(3'OMeG)(5')ppp(5')-- therefor Claim 1, Line 35, delete "G2" and insert --$G_2$-- therefor Claim 10, Line 43, delete "m7(3' OMeG)(5')ppp(5)" and insert --m7(3'OMeG)(5')ppp(5')-- therefor Claim 10, Line 45, delete "G2" and insert --$G_2$-- therefor Claim 18, Line 8, delete "(m1 )" and insert --(m1Ψ)-- therefor Claim 22, Line 18, delete "nucleoside"

Signed and Sealed this
Ninth Day of January, 2024

*Katherine Kelly Vidal*

Katherine Kelly Vidal
*Director of the United States Patent and Trademark Office*